(12) United States Patent
Kim et al.

(10) Patent No.: US 6,900,193 B1
(45) Date of Patent: May 31, 2005

(54) STRUCTURAL MODIFICATION OF 19-NORPROGESTERONE I: 17-α-SUBSTITUTED-11-β-SUBSTITUTED-4-ARYL AND 21-SUBSTITUTED 19-NORPREGNADIENEDIONE AS NEW ANTIPROGESTATIONAL AGENTS

(75) Inventors: Hyun K. Kim, Bethesda, MD (US); Richard P. Blye, Highland, MD (US); Pemmaraju N. Rao, San Antonio, TX (US); James W. Cessac, San Antonio, TX (US); Carmie K. Acosta, San Antonio, TX (US); Anne Marie Simmons, San Antonio, TX (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/526,855

(22) Filed: Mar. 17, 2000

Related U.S. Application Data

(63) Continuation-in-part of application No. 09/180,132, filed on May 24, 1999.
(60) Provisional application No. 60/016,628, filed on May 1, 1996.

(51) Int. Cl.[7] ........................ A61K 31/56; A61K 31/58; C07J 5/00; C07J 9/00; C07J 43/00
(52) U.S. Cl. ........................ 514/179; 514/176; 514/177; 514/182; 514/841; 540/107; 552/556; 552/595; 552/598; 552/602; 552/608
(58) Field of Search ................................. 552/595, 602; 514/177, 179

(56) References Cited

U.S. PATENT DOCUMENTS

| | | | | |
|---|---|---|---|---|
| 5,073,548 A | * | 12/1991 | Cook et al. | 514/169 |
| 5,244,886 A | * | 9/1993 | Scholz et al. | 514/175 |
| 5,741,787 A | * | 4/1998 | Peeters | 514/177 |

FOREIGN PATENT DOCUMENTS

| | | | |
|---|---|---|---|
| EP | 0129499 | * | 6/1984 |

OTHER PUBLICATIONS

Acosta et al., "Oxidative Demethylation of 4–Substituted N,N–Dimethylanilines with Iodine and Calcium Oxide in the Presence of Methanol.", J. Chem. Soc., Chem. Commun., (17), pp. 1985–1986, 1994.*

* cited by examiner

Primary Examiner—Barbara P. Badio
(74) Attorney, Agent, or Firm—Townsend & Townsend & Crew LLP

(57) ABSTRACT

The present invention relates, inter alia, to compounds having the general formula:

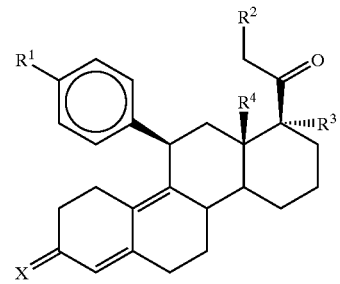

I in which: $R^1$ is a member selected from the group consisting of —$OCH_3$, —$SCH_3$, —$N(CH_3)_2$, —$NHCH_3$, —$NC_4H_8$, —$NC_5H_{10}$, —$NC_4H_8O$, —CHO, —$CH(OH)CH_3$, —$C(O)CH_3$, —$O(CH_2)_2N(CH_3)_2$, and —$O(CH_2)_2NC_5H_{10}$; $R^2$ is a member selected from the group consisting of hydrogen, halogen, alkyl, acyl, hydroxy, alkoxy (e.g., methoxy, ethoxy, vinyloxy, ethynyloxy, cyclopropyloxy, etc.), acyloxy (e.g., acetoxy, glycinate, etc.), alkylcarbonate, cypionyloxy, S-alkyl, —SCN, S-acyl and —$OC(O)R^6$, wherein $R^6$ is a functional group including, but not limited to, alkyl (e.g., methyl, ethyl, etc.), alkoxy ester (e.g., —$CH_2OCH_3$) and alkoxy (—$OCH_3$); $R^3$ is a member selected from the group consisting of alkyl, hydroxy, alkoxy and acyloxy; $R^4$ is a member selected from the group consisting of hydrogen and alkyl; and X is a member selected from the group consisting of =O and =N—$OR^5$, wherein $R^5$ is a member selected from the group consisting of hydrogen and alkyl.

In addition to providing the compounds of Formula I, the present invention provides methods wherein the compounds of Formula I are advantageously used, inter alia, to antagonize endogenous progesterone; to induce menses; to treat endometriosis; to treat dysmenorrhea; to treat endocrine hormone-dependent tumors; to treat meningiomas; to treat uterine leiomyomas; to treat uterine fibroids; to inhibit uterine endometrial proliferation; to induce cervical ripening; to induce labor; and for contraception.

56 Claims, 13 Drawing Sheets

* Cyp = 3-Cyclopentylpropionyl-

*Yield from 83 to 86 is 37%     Figure 5

STRUCTURAL MODIFICATION OF 19-NORPROGESTERONE I: 17-α-SUBSTITUTED-11-β-SUBSTITUTED-4-ARYL AND 21-SUBSTITUTED 19-NORPREGNADIENEDIONE AS NEW ANTIPROGESTATIONAL AGENTS

CROSS-REFERENCES TO RELATED APPLICATIONS

This patent application is a continuation-in-part of U.S. patent application Ser. No. 09/180,132, filed May 24, 1999, which is a 371 of PCT/US97/07373, filed Apr. 30, 1997, and which claims the benefit of U.S. Provisional Patent Application Ser. No. 60/016,628, filed May 1, 1996.

FIELD OF THE INVENTION

The present invention relates generally to the field of steroids and, in particular, to novel 17-α-substituted, 11-β-substituted-4-aryl and 21-substituted 19-norpregnadienedione analogs which possess potent antiprogestational activity with minimal antiglucocorticoid activity.

BACKGROUND OF THE INVENTION

There have been numerous attempts over the past few decades to prepare steroids with antihormonal activity. These have been reasonably successful where antiestrogens and antiandrogens are concerned. However, the discovery of effective antiprogestational and antiglucocorticoid steroids has proved to be a formidable task for the steroid chemist. It has been generally recognized for some years, however, that antiprogestational steroids would find wide applicability in population control, while antiglucocorticoids would be extremely valuable in the treatment of, for example, Cushing's syndrome and other conditions characterized by excessive endogenous production of cortisone. In the last decade, largely through the efforts of Teutsch, et al. of the Roussel-Uclaf group in France, a new series of 19-nortestosterone derivatives has been synthesized with strong affinity for the progesterone and glucocorticoid receptors and with marked antiprogestational and antiglucocorticoid activity in vivo. This important discovery revealed the existence of a pocket in the progesterone/glucocorticoid receptors that is able to accommodate a large 11β-substituent on selected 19-nortestosterone derivatives. By suitable selection of such a substituent, steroids with antihormonal properties were obtained.

The pioneering studies of Teutsch, et al. on the synthesis of antiprogestational and antiglucocorticoid steroids is summarized in a recent review article (G. Teutsch in *Adrenal Steroid Antagonism*. Ed. M. K. Agarwal, Walter de Gruyter and Co., Berlin, 1984. pp. 43–75) describing the work leading to the discovery of RU-38,486, the first steroid of this type selected for clinical development. RU-38,486 or mifepristone was found to be an effective antiprogestational/contragestative agent when administered during the early stages of pregnancy (IPPF Medical Bulletin 20; No. 5, 1986). In addition to these antiprogestational properties, mifepristone has very significant antiglucocorticoid activity and was successfully used by Nieman, et al., *J. Clin. Endocrinology Metab.*, 61:536, (1985)) in the treatment of Cushing's syndrome. In common with the vast majority of steroidal hormone analogs, mifepristone additionally exhibits a range of biological properties. Thus, for example, it exhibits growth-inhibitory properties towards estrogen-insensitive T47Dco human breast cancer cells (Horwitz, *Endocrinology*, 116:2236, 1985). Experimental evidence suggests that the metabolic products derived from mifepristone contribute to its antiprogestational and antiglucocorticoid properties (Heikinheimo, et al., *J. Steroid Biochem*, 26:279 (1987)).

Ideally, for purposes of contraception, it would be advantageous to have compounds which possess antiprogestational activity without (or with minimal) antiglucocorticoid activity. Although there have been a number of attempts to modify the mifepristone structure in order to obtain separation of the antiprogestational activity from the antiglucocorticoid activity, this goal has not yet been fully achieved. As such, there remains a need in the art for the development of new steroids which possess antiprogestational activity with minimal antiglucocorticoid activity.

SUMMARY OF THE INVENTION

The present invention provides new steroids which possess potent antiprogestational activity with minimal antiglucocorticoid activity. More particularly, the present invention provides compounds having the general formula:

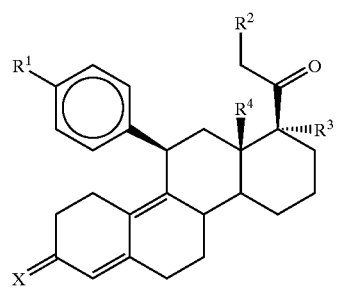

I wherein: $R^1$ is a functional group including, but not limited to, —$OCH_3$, —$SCH_3$, —$N(CH_3)_2$, —$NHCH_3$, —$NC_4H_8$, —$NC_5H_{10}$, —$NC_4H_8O$, —CHO, —$CH(OH)CH_3$, $C(O)CH_3$, —$O(CH_2)_2N(CH_3)_2$, —$O(CH_2)_2NC_4H_8$ and —$O(CH_2)_2NC_5H_{10}$; $R^2$ is a functional group including, but not limited to, hydrogen, halogen, alkyl, acyl, hydroxy, alkoxy (e.g., methoxy, ethoxy, vinyloxy, ethynyloxy, cyclopropyloxy, etc.), acyloxy (e.g., formyloxy, acetoxy, priopionyloxy, heptanoyloxy, glycinate, etc.), alkylcarbonate, cypionyloxy, S-alkyl, —SCN, S-acyl and —OC(O)$R^6$, wherein $R^6$ is a functional group including, but not limited to, alkyl (e.g., methyl, ethyl, etc.), alkoxyalkyl (e.g., —$CH_2OCH_3$) and alkoxy (—$OCH_3$); $R^3$ is a functional group including, but not limited to, alkyl (e.g., methyl, methoxymethyl, etc.), hydroxy, alkoxy (e.g., methoxy, ethoxy, methoxyethoxy, vinyloxy, etc.), and acyloxy; $R^4$ is a functional group including, but not limited to, hydrogen and alkyl; and X is a functional group including, but not limited to, =O and =N—$OR^5$, wherein $R^5$ is a member selected from the group consisting of hydrogen and alkyl.

As explained above, the compounds of the present invention possess potent antiprogestational activity with minimal antiglucocorticoid activity and, thus, they are suitable for long term use in the treatment of human endocrinologies or other conditions in steroid-sensitive tissues. Specific conditions for treatment include, but are not limited to, endometriosis (Kettel, L. M., et al., *Fertil Steril*, 56:402–407; Murphy, A. A., et al., *Fertil Steril*, 6:3761–766; Grow, D. R., et al., *J. Clin. Endocrinol. Metab.*, 81:1933–1939.) uterine leiomyoma (Murphy, A. A., et al., Ibid.; Murphy, A. A., et al., *J. Clin. Endocrinol. Metab.*, 76:513–517), uterine fibroid (Brogden, R. N., et al., *Drugs*, 45:384:409), meningioma (Brogden, R. N., et al., Ibid.; Poisson, M., et al., *J. Neurooncol.*, 1:179–189; Carroll, R. S., et al., *Cancer Res.*, 53:1312–1316; Mahajan, D. K. and London, S. N., *Fertil Steril*, 68:967–976 (1997)), and metastatic breast cancer (Brogden, R. N., et al., Id.; Rochefort, H., *Trends in Pharmacol. Sci.*, 8:126–128; Horwitz, K. B., *Endocr. Rev.*, 13:146–163 (1992) Mahajan, D. K. and London. S. N., Id.). Other uses include, but are not limited to, contraception (Wood, A. J. J., N. engl. *J. Med.*, 329:404–412 (1993); Ulmann, A., et al., *Sci. Amer.*, 262:42–48 (1990)), emergency postcoital contraceptive (Reel, J. R., et al., *Contraception*, 58:129–136 (1998)) and inducement of cervical ripening.

As such, in addition to providing compounds of Formula 1, the present invention provides methods wherein the compounds of Formula I are advantageously used, inter alia, to antagonize endogenous progesterone; to induce menses; to treat endometriosis; to treat dysmenorrhea; to treat endocrine hormone-dependent tumors (e.g., breast cancer, uterine leiomyomas, etc.); to treat meningiomas; to treat uterine fibroids; to inhibit uterine endometrial proliferation; to induce cervical ripening; to induce labor; and for a contraception.

Other features, objects and advantages of the invention and its preferred embodiments will become apparent from the detailed description which follows.

DETAILED DESCRIPTION OF THE INVENTION AND PREFERRED EMBODIMENTS

Figure 1A:
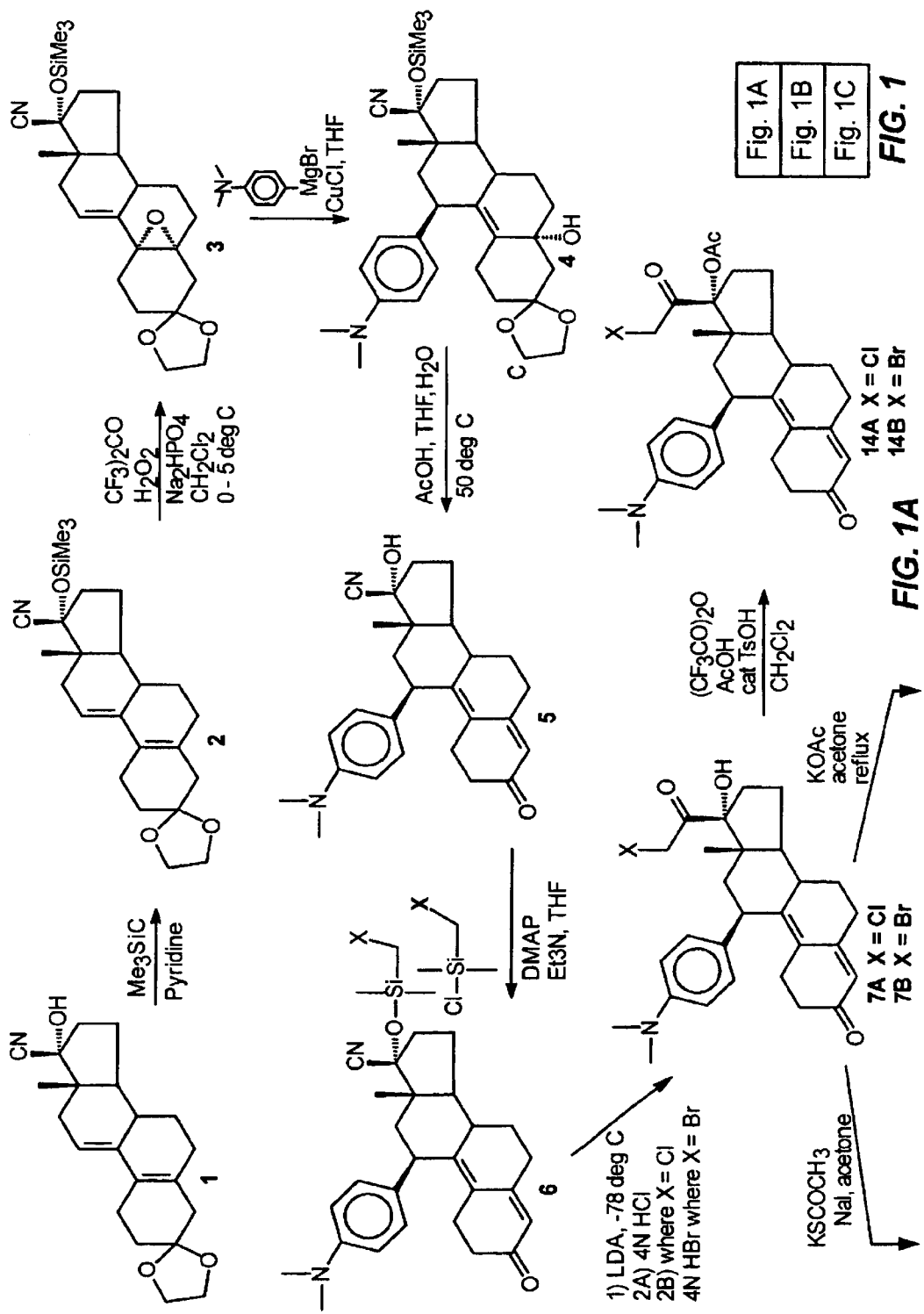
FIGS. 1 (1A, 1B and 1C) through 11 illustrate the synthetic schemes used to prepare the compounds of Formula I.

In one aspect, the present invention provides compounds having the following general formula:

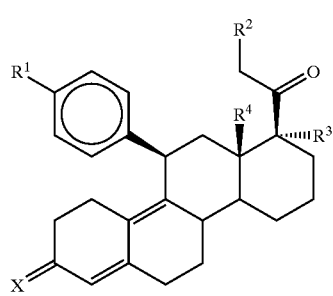

In Formula I, $R^1$ is a functional group including, but not limited to, $-OCH_3$, $-SCH_3$, $-N(CH_3)_2$, $-NHCH_3$, $-NC_4H_8$, $-NC_5H_{10}$, $-NC_4H_8O$, $-CHO$, $-CH(OH)CH_3$, $-C(O)CH_3$, $-O(CH_2)_2$, $-N(CH_3)_2$, $-O(CH_2)_2NC_4H_8$, and $-O(CH_2)_2NC_5H_{10}$. $R^2$ is a functional group including, but not limited to, hydrogen, halogen, alkyl, acyl, hydroxy, alkoxy (e.g., methoxy, ethoxy, vinyloxy, ethynyloxy, cyclopropyloxy, etc.), acyloxy (e.g., formyloxy, acetoxy, priopionyloxy, heptanoyloxy, glycinate, etc.), alkylcarbonate, cypionyloxy, S-alkyl, $-SCN$, S-acyl and $-OC(O)R^6$, wherein $R^6$ is a functional group including, but not limited to, alkyl (e.g., methyl, ethyl, etc.), alkoxyalkyl (e.g., $-CH_2OCH_3$) and alkoxy ($-OCH_3$). $R^1$ is a functional group including, but not limited to, alkyl, hydroxy, alkoxy and acyloxy. $R^4$ is a functional group including, but not limited to, hydrogen and alkyl. Finally, X is a functional group including, but not limited to, $=O$ and $=N-OR^5$, wherein $R^5$ is a member selected from the group consisting of hydrogen and alkyl. In a preferred embodiment, $R^1$, $R^2$, $R^3$, $R^4$ and X are selected with the proviso that if $R^1$ is $-N(CH_3)_2$, $R^3$ is acetoxy; $R^4$ is methyl and X is $=O$, then $R^2$ is not hydrogen.

The term "alkyl" is used herein to refer to a branched or unbranched, saturated or unsaturated, monovalent hydrocarbon radical having from 1–12 carbons and, preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term alkyl encompasses "substituted alkyls." Substituted alkyl refers to alkyl as just described including one or more functional groups such as lower alkyl, aryl, aralkyl, acyl, halogen (i.e., alkylhalos, e.g., $CF_3$), hydroxy (e.g., hydroxymethyl), amino, alkylamino, acylamino, acyloxy, alkoxy (e.g., methoxymethyl), mercapto and the like. These groups may be attached to any carbon atom of the lower alkyl moiety.

The term "alkoxy" is used herein to refer to the $-OR$ group, where R is a lower alkyl, substituted lower alkyl, aryl, substituted aryl, aralkyl or substituted aralkyl. Suitable alkoxy radicals include, for example, methoxy, ethoxy, phenoxy, t-butoxy (e.g., methoxyethoxy, methoxymethoxy, etc.), etc.

The term "acyloxy" is used herein to refer to an organic radical derived from an organic acid by the removal of a hydrogen. The organic radical can be further substituted with one or more functional groups such as alkyl, aryl, aralkyl, acyl, halogen, amino, thiol, hydroxy, alkoxy, etc. An example of such a substituted organic radical is glycinate (e.g., $-OC(O)CH_2NH_2$). Suitable acyloxy groups include, for example, acetoxy, i.e., $CH_3COO-$, which is derived from acetic acid, formyloxy, i.e., $H.CO.O-$, which is derived from formic acid and cypionyloxy, which is derived from 3-cyclopentylpropionic acid.

The term "halogen" is used herein to refer to fluorine, bromine, chlorine and iodine atoms.

The term "hydroxy" is used herein to refer to the group $-OH$.

The term "acyl" denotes groups $-C(O)R$, where R is alkyl or substituted alkyl, aryl or substituted aryl as defined herein.

The term "aryl" is used herein to refer to an aromatic substituent which may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical which would otherwise be occupied by a hydrogen atom (such as 2-pyridyl, 3-pyridyl and 4-pyridyl).

The term "alkyl carbonate" is used herein to refer to the group $-OC(O)OR$, where R is alkyl, substituted alkyl, aryl, or substituted aryl as defined herein.

The term "S-alkyl" is used herein to refer to the group $-SR$, where R is lower alkyl or substituted lower alkyl.

The term "S-acyl" is used herein to refer to a thioester derived from the reaction of a thiol group with an acylating agent. Suitable S-acyls include, for example, S-acetyl, S-propionyl and S-pivaloyl. Those of skill in the art will know that S-acyl refers to such thioesters regardless of their method of preparation.

The terms "N-oxime" and "N-alkyloxime" are used herein to refer to the group =N—OR$^5$, wherein R$^5$ is, for example, hydrogen (N-oxime) or alkyl (N-alkyloxime). Those of skill in the art will know that the oximes can consist of the syn-isomer, the anti-isomer or a mixture of both the syn- and anti-isomers.

Within Formula I, certain embodiments are preferred, namely those in which R$^1$ is —N(CH$_3$)$_2$; those in which R$^2$ is halogen or alkoxy; those in which R$^3$ is acyloxy; those in which R$^4$ is alkyl (e.g., methyl and ethyl); and those is which X is =O and =N—OR$^5$, wherein R$^5$ is hydrogen or alkyl. More particularly, compounds which are preferred are those in which R$^1$ is —N(CH$_3$)$_2$; R$^2$ is halogen; R$^3$ is acyloxy; and R$^4$ is alkyl. Within this embodiment, compounds which are particularly preferred are those in which R$^2$ is F, Br or Cl; and R$^4$ is methyl. Also preferred are compounds in which R$^1$ is —N(CH$_3$)$_2$; R$^2$ is alkyl; R$^3$ is acyloxy; R$^4$ is alkyl; and X is =O. Also preferred are compounds in which R$^1$ is —N(CH$_3$)$_2$; R$^2$ is alkoxy; R$^3$ is acyloxy; R$^4$ is alkyl; and X is =O. Within this embodiment, compounds which are particularly preferred are those in which R$^2$ is methoxy or ethoxy; and R$^3$ is acetoxy or methoxy. Also preferred are compounds in which R$^1$ is —N(CH$_3$); R$^2$ is hydroxy; R$^3$ is acyloxy; R$^4$ is alkyl; and X is =O. Also preferred are compounds in which R$^1$ is —N(CH$_3$)$_2$; R$^2$ and R$^3$ are both acyloxy; R$^4$ is alkyl; and X is =O. Within this embodiment, compounds which are particularly preferred are those in which R$^2$ and R$^3$ are both acetoxy. Also preferred are compounds in which R$^1$ is —N(CH$_3$)$_2$; R$^2$ is S-acyl; R$^3$ is hydroxy or acyloxy; R$^4$ is alkyl; and X is =O. Also preferred are compounds in which R$^1$ is —N(CH$_3$)$_2$; R$^2$ is cypionyloxy; R$^3$ is acetoxy; R$^4$ is alkyl; and X is =O. Also preferred are to compounds in which R$^1$ is —N(CH$_3$)$_2$; R$^2$ is methoxy; R$^3$ is acetoxy; R$^4$ is alkyl; and X is =O and =N—OR$^5$, wherein R$^5$ is, for example, hydrogen or alkyl (e.g., methyl, ethyl, etc.). Also preferred are compounds in which R$^1$ is —N(CH$_3$)$_2$; R$^2$ and R$^3$ are both acetoxy; R$^4$ is alkyl; and X is =O and =N—OR$^5$, wherein R$^5$ is, for example, hydrogen or alkyl (e.g., methyl, ethyl, etc.).

Exemplar compounds falling within the above preferred embodiments include, but are not limited to, 17α-acetoxy-21-fluoro-11β-N,N-dimethylaminophenyl)-19-norpregna-4, 9-diene-3,20-dione, 17α-acetoxy-21-chloro-11β-(4-N,N-dimethylaminophenyl)-19-norpregna-4,9-diene-3,20-dione, 17α-acetoxy-21-bromoro-11β-(4-N,N-dimethylaminophenyl)-19-norpregna-4,9-diene-3,20-dione, 17-,21-diacetoxy-11β-(4-N,N-dimethylaminophenyl) 19-norpregna-4,9-diene-3,20-dione, 17α-hydroxy-21-acetylthio-11β-(4-N,N-dimethylaminophenyl)-19-norpregna-4,9-diene-3,20-dione, 17α-acetoxy-21-acetylthio-11β-(4-N,N-dimethylaminophenyl)-19-norpregna-4,9-diene-3,20-dione, 17α-acetoxy-21-ethoxy-11β-(4N,N-dimethylaminophenyl)-19-norpregna-4,9-diene-3,20-dione, 17α-acetoxy-21-methyl-11β-(4-N,N-dimethylamino-phenyl)-19-norpregna-4,9-diene-3,20-dione, 17α-acetoxy-21-methoxy-11β-N,N-dimethylaminophenyl)-19-norpregna-4,9-diene-3,20-dione, 17α-acetoxy-21-ethoxy-11β-(4-N,N-dimethylaminophenyl)-19-norpregna-4,9-diene-3,20-dione, 17α-acetoxy-21-(3'-cyclopentylpropionyloxy) 11β-(4-N,N-dimethylaminophenyl)-19-norpregna-4,9-diene-3,20-dione, 17α-acetoxy-21-hydroxy-11β-(4-N,N-dimethylaminophenyl)-19-norpregna-4,9-diene-3,20-dione, 17α,21-diacetoxy-11β-(4-N,N-dimethylaminophenyl) 9-norpregna-4,9-diene-3,20-dione 3-oxime, 17α-acetoxy-21-methoxy-11β-(4-N,N-dimethylaminophenyl)-19-norpregna-4,9-diene-3,2-dione 3-oxime, 17α-acetoxy-11β-[4-(N-methylamino)phenyl]-19-norpregna-4,9-diene-3,20-dione, and 17α,21-diacetoxy-11β-[4-(N-methylamino) phenyl]-19-norpregna-4,9-diene-3,20-dione.

In addition to the foregoing, certain other embodiments are preferred, namely those in which R$^1$ is —N(CH$_3$)$_2$, —NC$_4$H$_8$, —NC$_4$H$_{10}$, —NC$_4$H$_8$O, —C(O)CH$_3$, —O(CH$_2$)$_2$N(CH$_3$)$_2$, —O(CH$_2$)$_2$NC$_4$H$_8$, —O(CH$_2$)$_2$NC$_3$H$_{10}$, and —O(CH$_2$)$_2$NC$_5$H$_{10}$; those in which R$^2$ is hydrogen, alkyloxy, alkoxy, —SAc, —SCN, —OC(O)CH$_2$N(CH$_3$)$_2$, and —OC(O)R$^6$, wherein R$^6$ is a functional group including, but not limited to, alkyls (e.g., —CH$_2$CH$_3$), alkoxy esters (e.g., —CH$_2$OMe) and alkoxys (e.g., —OCH$_3$); those in which R$^3$ is alkyl, alkoxy, acyloxy and hydroxy; those in which R$^4$ is alkyl (e.g., methyl and ethyl); and those is which X is =O or =N—OR$^5$, wherein R$^5$ is hydrogen or alkyl. Also preferred are compounds in which R$^1$ is —N(CH$_3$)$_2$; R$^2$ is hydrogen; R$^3$ is methoxymethyl; R$^4$ is methyl; and X is =O. Also preferred are compounds in which R$^1$ is —N(CH$_3$)$_2$; R$^2$ is hydrogen; R$^3$ is —OC(O)H, —OC(O)CH$_2$CH$_3$ or —OC(O)C$_6$H$_{13}$; R$^4$ is methyl; and X is =O. Also preferred are compounds in which R$^1$ is —NC$_4$Hs, —NC$_5$H$_{10}$, —NC$_4$H$_8$O, —C(O)CH$_3$ or —SCH$_3$; R$^2$ is hydrogen; R$^3$ is acetoxy; R$^4$ is methyl; and X is =O. Also preferred are compounds in which R$^1$ is —N(CH$_3$)$_2$ or —NC$_5$H$_{10}$; R$^2$ is hydrogen; R$^3$ is methoxy; R$^4$ is methyl; and X is =O. Also preferred are compounds in which R$^1$ is —NC$_5$H$_{10}$ or —C(O)CH$_3$; R$^2$ and R$^3$ are both acetoxy; R$^4$ is methyl; and X is =O. Also preferred are compounds in which R$^1$ is —C(O)CH$_3$; R$^2$ is —SAc; R$^3$ is acetoxy; R$^4$ is methyl; and X is =O. Also preferred are compounds in which R$^1$ is —C(O)CH$_3$, —N(CH$_3$)$_2$, —NC$_4$H; or —NC$_5$H$_{10}$; R$^2$ and R$^3$ are both methoxy; R$^4$ is methyl; and X is =O. Also preferred are compounds in which R$^1$ is —NC$_5$H$_{10}$, —C(O)CH$_3$ or —O(CH$_2$)$_2$N(CH$_3$)$_2$; R$^2$ is methoxy; R$^3$ is acetoxy; R$^4$ is methyl; and X is =O. Also preferred are compounds in which R$^1$ is —N(CH$_3$)$_2$; R$^2$ is —OC(O)CH$_2$CH$_3$, —OC(O)OCH$_3$, —OC(O)OCH$_2$OCH$_3$, —OCH=CH$_2$, —OC(O)CH$_2$N(CH$_3$)$_2$ or —SCN; R$^3$ is acetoxy; R$^4$ is methyl; and X is =O. Also preferred are compounds in which R$^1$ is —N(CH$_3$)$_2$; R$^2$ is —OC(O)H; R$^3$ is —OC(O)H; R$^4$ is methyl; and X is =O. Also preferred are compounds in which R$^1$ is —N(CH$_3$)$_2$; R$^2$ is —OC(O)H; R$^3$ is hydroxy; R$^4$ is methyl; and X is =O. Also preferred are compounds in which R$^1$ is —NC$_5$H$_{10}$; R$^2$ is hydrogen; R$^3$ is acetoxy; R$^4$ is methyl; and X is =N—OR$^5$, wherein R$^5$ is hydrogen. Also preferred are compounds in which R$^1$ is —N(CH$_3$)$_2$ or —NC$_5$H$_{10}$; R$^2$ is hydrogen or methoxy; R$^3$ is methoxy or ethoxy; R$^4$ is methyl; and X is =N—OR$^5$, wherein R$^5$ is hydrogen.

Exemplar compounds falling within the above preferred embodiments include, but are not limited to, 17α-formyloxy-11β-[4-(N,N-diethylamino)phenyl]-19-norpregna-4,9-diene-3,20-dione; 17α-propionoxy-11β-[4-(N,N-dimethylamino)phenyl]-19-norpregna-4,9-diene-3, 20-dione; 17α-heptanoyloxy-11β-[4-(N,N-dimethylamino) phenyl]-19-norpregna-4,9-diene-3,20-dione; 17α-methoxymethyl-11β-[4-N,N-dimethylamino)phenyl]-19-norpregna-4,9-diene-3,20-dione; 17α-acetoxy-11β-(4-N-pyrrolidinophenyl)-19-norpregna-4,9-diene-3,20-dione; 17α-acetoxy-11β-(4-N-piperidinophenyl)-19-norpregna-4, 9-diene-3,20-dione; 17α-acetoxy-11β-(4-N-morpholinophenyl)-19-norpregna-4,9-diene-3,20-dione; 17α-acetoxy 11β-(4-acetylphenyl)-19-norpregna-4,9-diene-3,20-dione; 17α-acetoxy-11β-(4-methylthiophenyl)-19-norpregna-4,9-diene-3,20-dione; 17α-methoxy-11β-[4-(N, N-dimethylamino)phenyl]-19-norpregna-4,9-diene-3,20-dione; 17α-methoxy-11β-(4-N-piperidinophenyl)-19- norpregna-4,9-diene-3,20-dione; 17α,21-diacetoxy-11β-(4-N-piperidinophenyl)-19-norpregna-4,9-diene-3,20-dione; 17α,21-diacetoxy-11β-(4-acetylphenyl)19-norpregna-4,9-diene-3,20-dione; 17α-acetoxy-11β-(4-acetylphenyl)-21-thioacetoxy-19-norpregna-4,9-diene-3,20-dione; 17α,21-dimethoxy-11β-[4-(N,N-dimethylamino)phenyl]-19-norpregna-4,9-diene-3,20-dione; 17α,21-dimethoxy-11β-(4-N-pyrrolidinophenyl)-19-norpregna-4,9-diene-3,20-dione; 17α,21-dimethoxy-11β-(4-N-piperidinophenyl)19-norpregna-4,9-diene-3,20-dione; 17α,21-dimethoxy-11β-(4-acetylphenyl)-19-norpregna-4,9-diene-3,20-dione; 17α-acetoxy-11β-(4-acetylphenyl)21-methoxy-19-norpregna-4,9-diene-3,20-dione; 17α-acetoxy-11β-{4-[2'-(N,N-dimethylamino)ethoxy]phenyl}-21-methoxy-19-norpregna-4,9-diene-3,20-dione; 17α,21-diformyloxy-11β-[4-(N,N-dimethylamino)phenyl]-19-norpregna-4,9-diene-3,20-dione; 17α-acetoxy-11β-[4-(N,N-dimethylamino)phenyl]-21-propionyloxy-19-norpregna-4,9-diene-3,20-dione; 17α-acetoxy-11β-[4-(N,N-dimethylamino)phenyl]-21-(2'-methoxyacetyl)oxy-19-norpregna-4,9-diene-3,20-dione; 17α-acetoxy-21-hydroxy-11β-[4-(N,N-dimethylamino)phenyl]-19-norpregna-4,9-diene-3,20-dione-21-methyl carbonate; 17α-acetoxy-11β-[4-(N,N-dimethylamino)phenyl]-21-(1'-ethenyloxy)-19-norpregna-4,9-diene-3,20-dione; 17α-acetoxy-11β-[4-(N,N-dimethylamino)phenyl]-21-(2'-N,N-dimethylamino)acetoxy-19-norpregna-4,9-diene-3,20-dione; 17α-acetoxy-11β-[4-(N,N-dimethylamino)phenyl]-21-thiocyanato-19-norpregna-4,9-diene-3,20-dione; 17α-acetoxy-11β-(4-N-piperidinophenyl)-19-norpregna-4,9-diene-3,20-dione 3-oxime; 17α-methoxy-11β-[4-(N,N-dimethylamino)phenyl]-19-norpregna-4,9-diene-3,20-dione 3-oxime; 17α-methoxy-11β-(4-N-piperidinophenyl)-19-norpregna-4,9-diene-3,20-dione 3-oxime; and 17α,21-dimethoxy-11β-[4-(N,N-dimethylamino)phenyl]-19-norpregna-4,9-diene-3,20-dione 3-oxime.

The compounds of the present invention can readily be synthesized in a variety of ways using modern synthetic organic chemistry techniques. Typically, the compounds of the present invention are prepared using the synthetic schemes set forth in FIGS. 1–11. In general, there are five strategic steps that are useful in the synthesis of the antiprogestational agents of the present invention. They are: (1) C21-substitution; (2) construction of the 17α-hydroxy-20-ketone pregnane side chain with the natural configuration via the SNAP reaction; (3) modification of the 17α-hydroxy moiety; (4) regiospecific synthesis of the epoxide and 1,4-conjugate grignard addition of a variety of 4-substituted aryl compounds; and (5) deketalization at C3 and 20 and concomitant dehydratration at C5. Each of these five strategic steps is described in greater detail hereinbelow. Moreover, a more detailed description of the synthetic protocols used to prepare the compounds of the present invention is set forth in the Example Section. It will be readily apparent to those of skill in the art that the particular steps, or combination of steps, used will vary depending on the compound being synthesized.

1. 21-Substitution

Figure 1B:
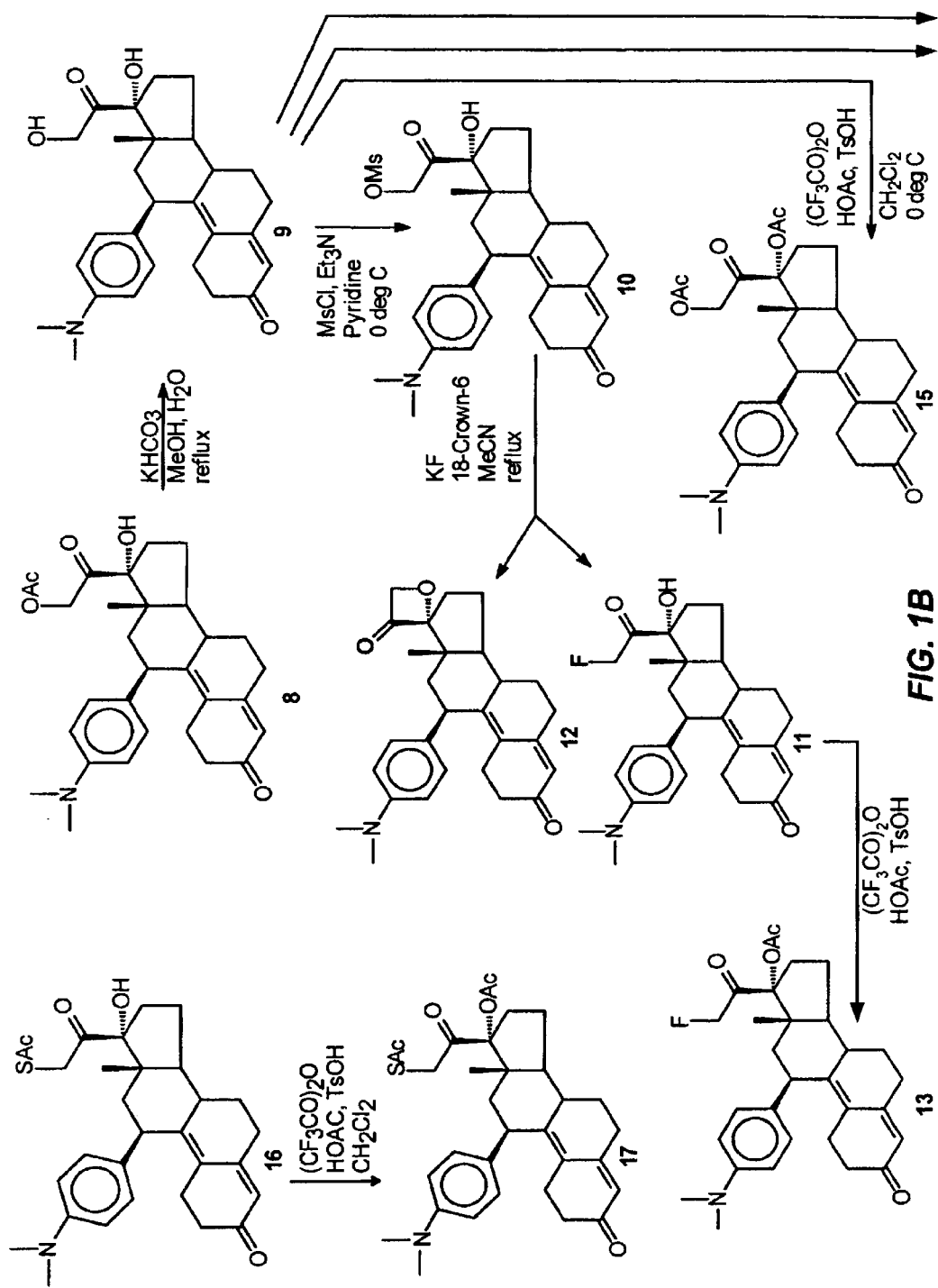
Figure 1C:
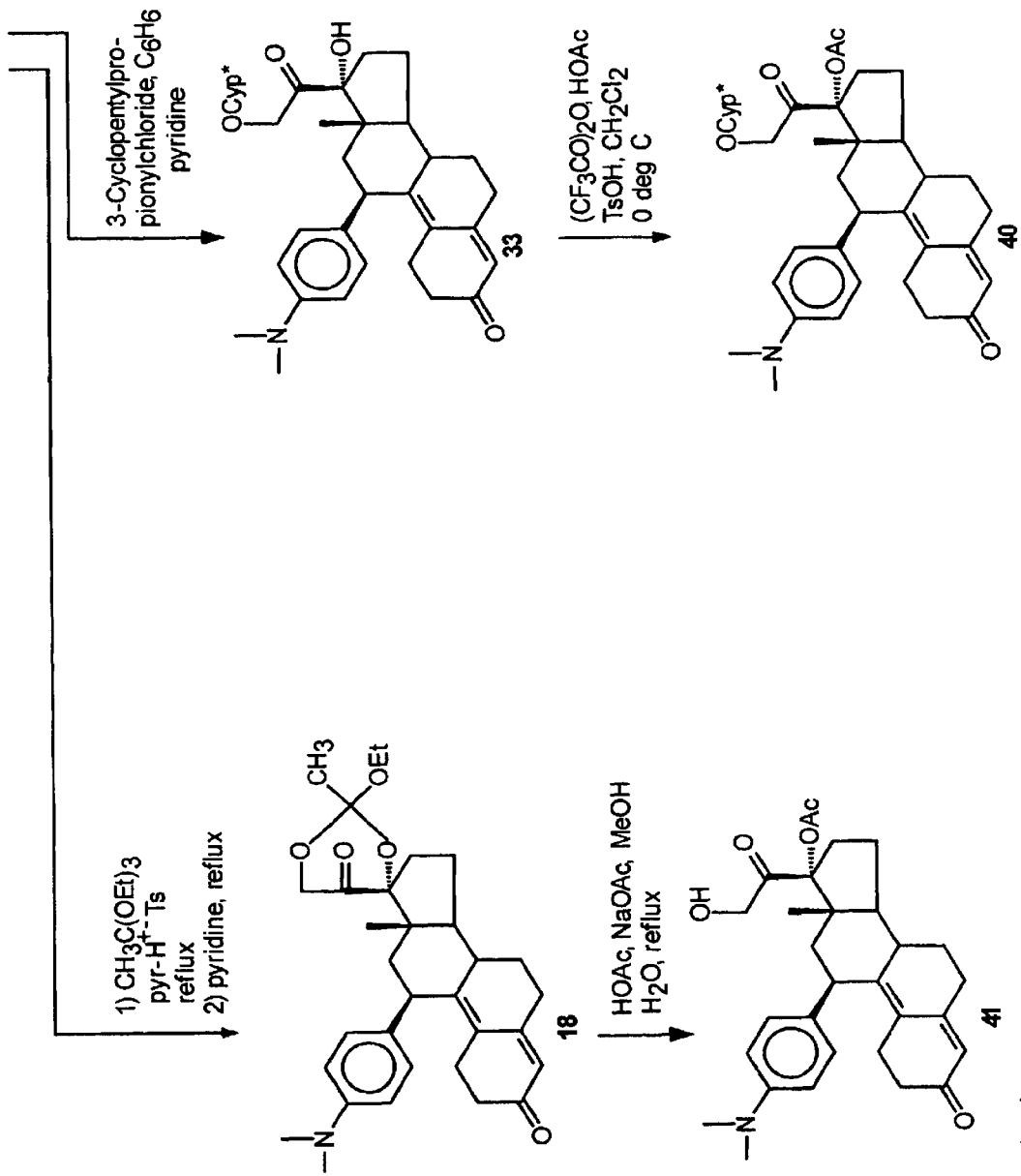
Figure 2:
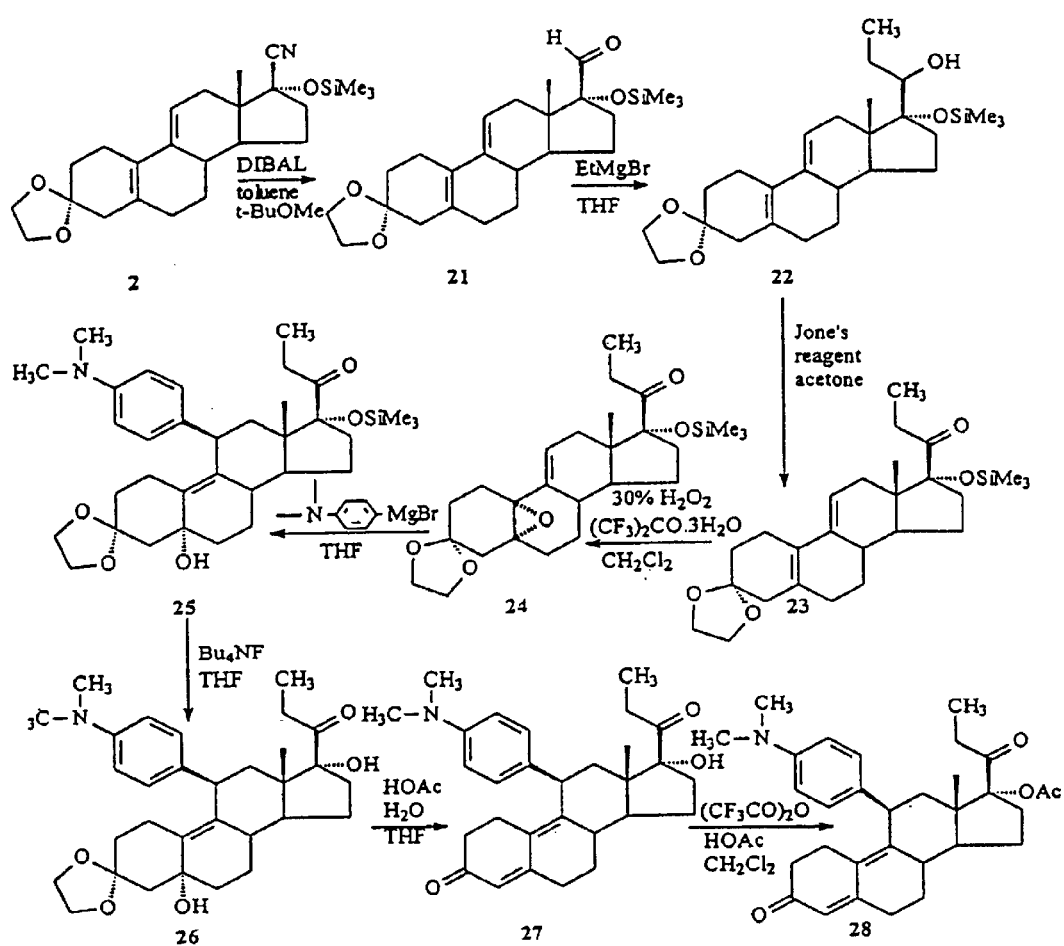
Figure 3:
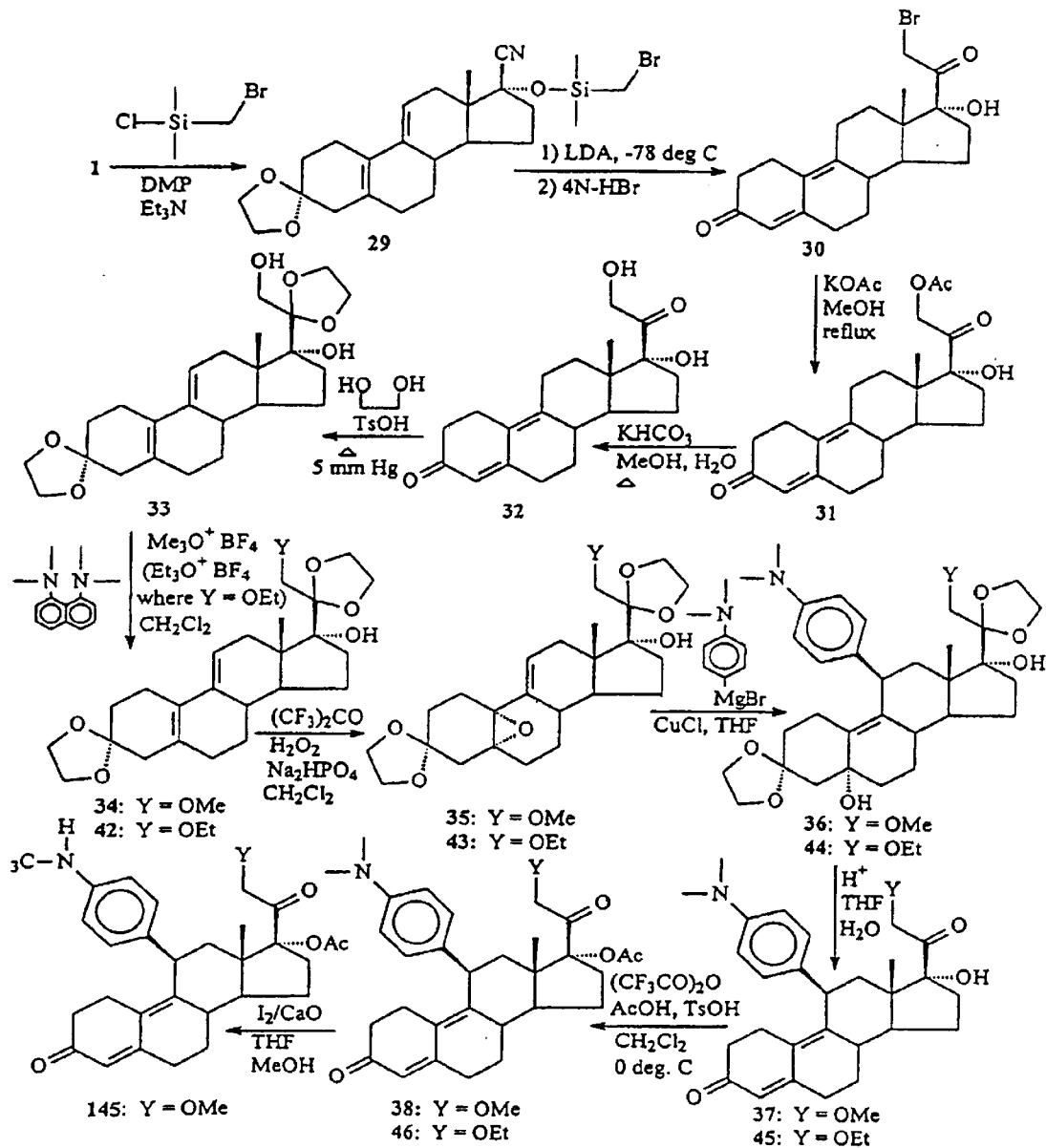

In particular embodiments of the present invention, a number of different functional groups, such as F, Cl, Br, Me, hydroxy, alkoxy (e.g., methoxy, ethoxy, etc.), acyloxy (i.e., formyloxy, acetoxy, propionyloxy, etc.), cypionyloxy, methoxyacetoxy, and acylthio, have been introduced at C-21 of lead compound 17α-acetoxy-11β-(4-N,N-dimethylaminophenyl)-19-norpregna-4,9-diene-3,20-dione (CDB-2914 or C-21H or 69B) using the synthetic schemes set forth in FIGS. 1, 2 and 3. For instance, a Silicon Nucleophilic Annulation Process (SNAP) on 17β-cyanohydrin (5) was used to prepare all of the 21-halogenated compounds with the exception of the 21-fluoro compound. This compound, however, was readily obtained by reacting the 21-mesylate with KF in acetonitrile in the presence of a crown ether. In addition, the 17α-acetoxy-21-ol compound (41) was obtained selectively from the ethoxyethylidenedioxy derivative (18) by means of buffered hydrolysis, whereas the 17α-ol-21-acetate derivative (8) was prepared from reacting the 21-halo compound with KOAc. It is interesting to note that both the 21-acetate and the 17α-acetate produced the 17α,21-diol (9) by a base catalyzed methanolysis. Thereafter, this 17α,21-diol was readily converted to the 17α,21-diacetate (15) by a mixed anhydride procedure. With regard to the synthesis of 17α-acetoxy-21-cypionate (40), the hydroxyl group at C-21 of the 17α,21-diol (9) was first converted to the corresponding cypionate (39) and then the 17α-OH group was acetylated. The 17α-acetoxy-21-thioacetate (17) was obtained by reaction of the 21-iodo compound generated in situ from the corresponding bromo compound (7B), with potassium thioacetate followed by acetylation of the 17α-alcohol as shown in the synthetic scheme set forth in FIG. 1.

Moreover, the 21-methyl analog (28) was prepared following the synthetic route set forth in FIG. 2. The key reactions in this scheme are (1) the conversion of the 17α-cyanohydrin to the 17α-trimethylsilyloxy, 17α-aldehyde, and (2) the creation of the 21-methylprogesterone skeleton (21→22).

In addition, the 21-methoxy analog (38) was obtained following the synthetic scheme set forth in FIG. 3. The key step in this scheme is the reaction of the 17α,21-diol protected at C-3 and C-20 with Meerwein's trimethyloxonium tetrafluoroborate salt in the presence of the sterically more hindered, less nucleophilic base, 1,8-bis(dimethylamino)naphthalene, as the proton sponge to selectively methylate the less-hindered 21-hydroxyl group. The subsequent epoxidation of the crude 21-methoxy compound (34) produced a 2:1 mixture of α and β epoxides as evidenced by $^1$H NMR. The crude epoxide (35) was subjected directly to the copper (I) catalyzed conjugate Grignard addition, assuming 66% of the crude epoxide was the desired-epoxide, hydrolysis and acetylation gave the 21-methoxy compound (38) with a purity of 98%. Following similar procedures, the 21-ethoxy compound (46) was obtained using triethyloxonium tetrafluoroborate salt. Treatment of the 21-acetete (15) and 21-methoxy compound (38) with hydroxylamine HCl followed by adjustment of the pH to pH 7 provided the desired 3-oximes, 47 and 48, respectively, as a mixture of syn- and anti-isomers. Under these conditions, the sterically hindered C-20 ketone was intact as evidenced by IR spectroscopy.

Figure 10:
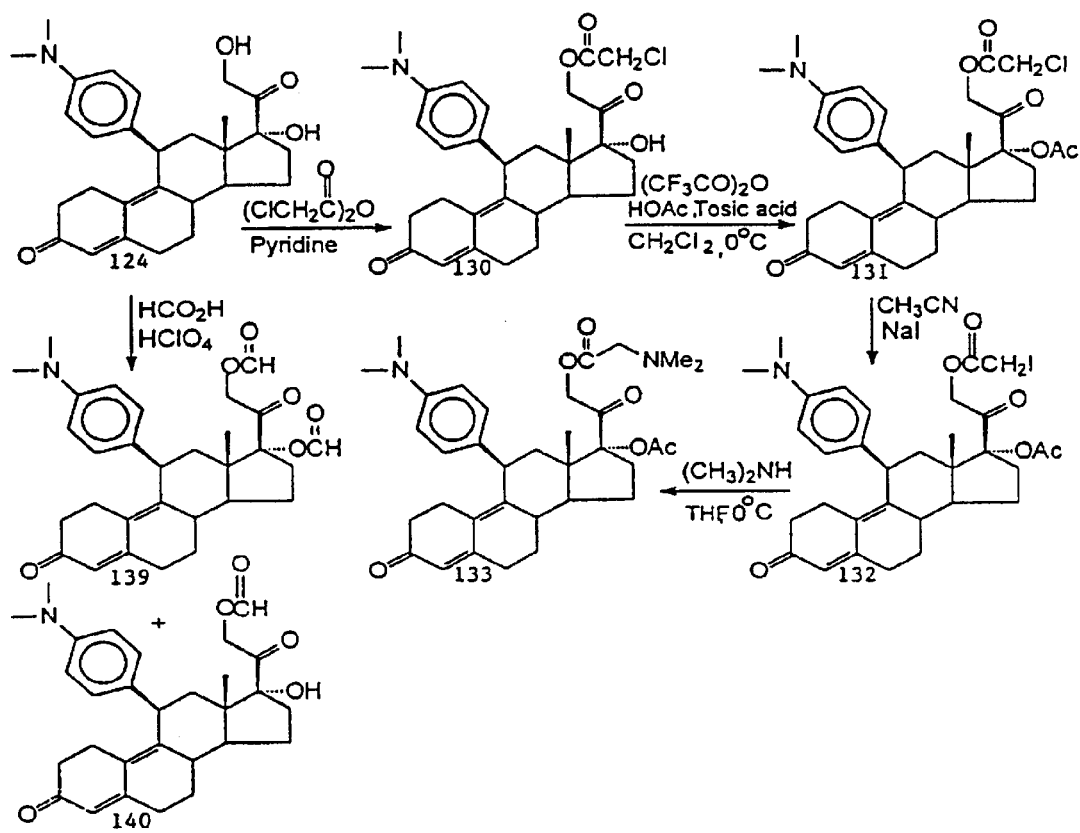
Figure 11:
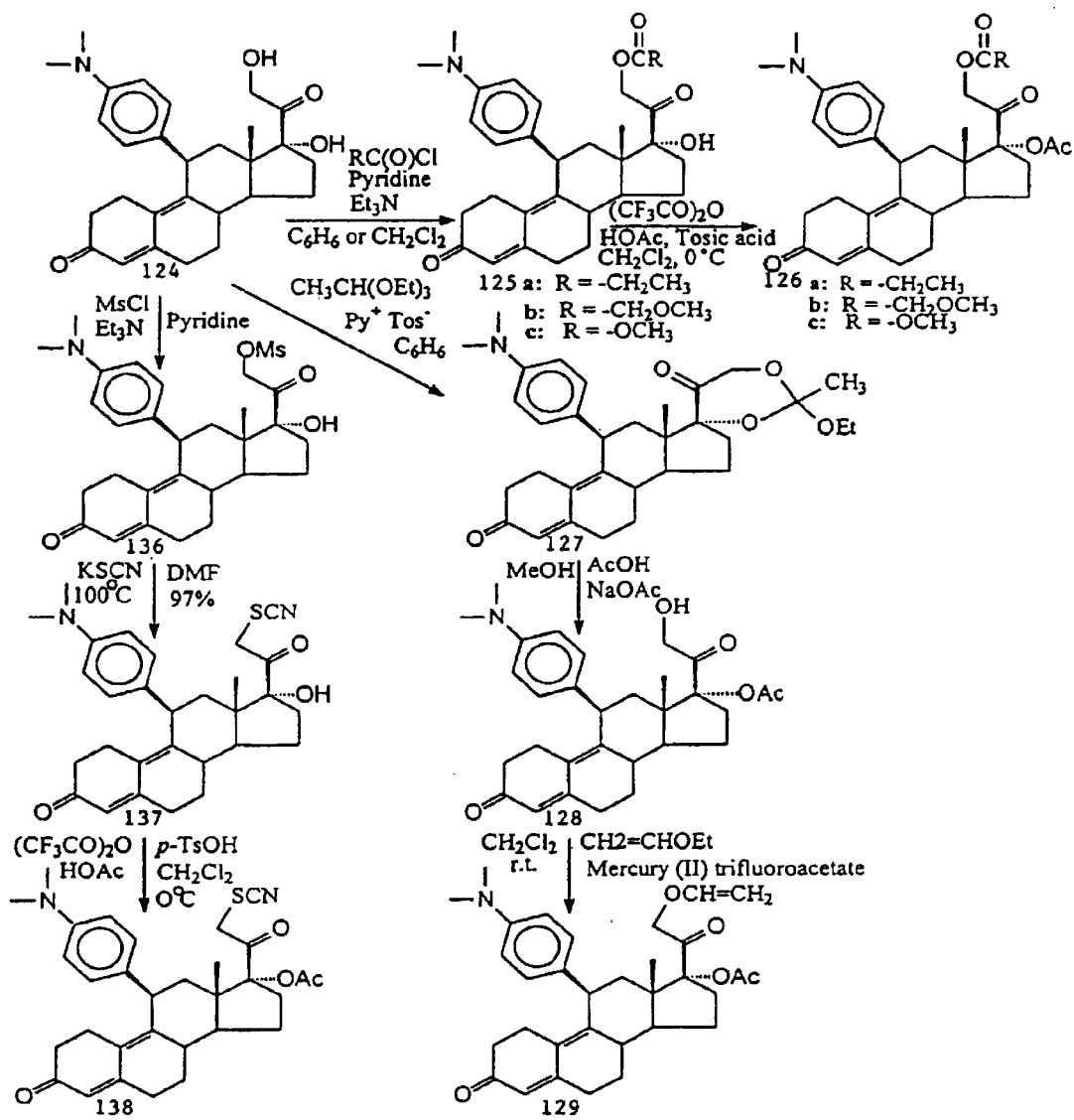

In addition, using methods similar to those described above, additional functional groups, such as propionyloxy—(126a), 2-methoxyacetoxy—(126b), methylcarbonate (126c), 2{N,N-dimethylamino)acetoxy (133), and thiocyanato (138) were readily synthesized (see, e.g., FIGS. 10 and 11). Their synthetic methodology is straightforward. All of these compounds were derived from the previously prepared 17α,21-dihydroxy-11β-[4-(N,N-dimethylamino)phenyl]-19-norpregna-4,9-diene-3,20-dione (9 in FIG. 1 or 124 in FIG. 11). The C21-(1-ethenyl)oxy analog (129) was obtained from the C17α-acetoxy-21-ol (128) by reaction with ethyl vinyl ether in the presence of mercury(II) trifluoroacetate. Compound 128 was, in turn, obtained from hydrolysis of the 17α,21-cyclic ortho ester (18 in FIG. 1 or 127 in FIG. 11). Reaction of the C17α,21-diol (9 in FIG. 1 or 124 in FIG. 11) with methyl chloroformate in pyridine gave the methyl carbonate at C21 (125c). Subsequent acetylation at C17 led to the target compound 126c (see, FIG. 11). Treatment of the C17α,21-diol (9 or 124) with methoxyacetyl chloride, followed by acetylation, provided 126b (see, FIG. 11). The synthesis of the 21-thiocyanato analog (138), which is illustrated in FIG. 11, involved the preparation of the 21-mesylate (136), followed by thiocyanation at C21 (137) using the modified procedure of Abramson, H. N., et al. (*J. Pharm. Sci.* 65:765–768 (1976)). Subsequent acetylation at C17 led to the target compound (138). The 21N, N-dimethylamino)acetoxy (133) analog was obtained by preparing the 21-chloroacetate (130), acetylation of the 17α-OH (131) and converting the latter to the 21-iodoacetate (132) followed by the reaction of 132 with dimethylamine (see, FIG. 10). This order of sequence did not result in hydrolysis of the 21-ester group. It is pointed out that an attempt to prepare the 21-iodoacetate (132) directly from the diol (124) was not as successful.

The 17α,21-diformate (139), which is illustrated in FIG. 10, was synthesized by perchloric acid catalyzed formylation of the 17α,21-diol (124) following the procedure of Oliveto, E. P., et al. (*J. Am. Chem. Soc.,* 77:3564–3567 (1955)). NMR analysis of this material indicated a 55:45 mixture of the 17α,21 diformate (139) resonating at 8.029 (s, C17-OCHO) and 8.165 ppm (s, C21-OCHO), respectively, and the 21-monoformate (140) at 8.172 ppm (s, C21-OCHO). Therefore, chromatographic separation was essential to obtain the pure 17α,21-diformate (139).

Syntheses of the 17α,21-dimethoxy derivatives (113a, 113b, 133c and 133d) were achieved via oxidation at C-21 to afford the 21-hydroxy derivative (107) of the 17α-methoxy compound (94) following a modification of the procedure reported by Moriarty, R. M. et al., *J. Chem. Soc. Chem. Commun.,* 641–642 (1981), and Velerio, et al., *Steroids,* 60:268–271 (1995). Subsequent O-methylation provided the key 17α,21-dimethoxy intermediate (108) (see, FIG. 8). Reduction of the 20-ketone (108) to the 20ξ-ol (109) followed by epoxidation at C5 and C10, copper (I) catalyzed conjugate Grignard addition to the 5α,10α-epoxide (110), selective oxidation of the secondary alcohol, 20ξ-ol (111) using IBX to the 20-ketone (112), hydrolysis and acetylation, led to the target 17α,21-dimethoxy derivatives (113).

2. Silicon Nucleophilic Annelation Process (SNAP)

As described herein silylation of β-cyanohydrin ketal with halomethyldimethylsilyl chloride afforded the chloro- or bromomethyldimethylsilyl ether. The reductive SNAP reaction provided the 17α-hydroxy-20-ketopregnane side chain with the natural configuration at C17 (Livingston, D. A., et al., *J. Am. Chem. Soc.,* 112:6449–6450 (1990); Livingston, D. A., *Adv. Med. Chem.,* 1:137–174 (1992); U.S. Pat. No. 4,092,693, which issued to Livingston, D. A., et al. (May 1, 1990); U.S. Pat. No. 4,977,255, which issued to Livingston, D. A., et al. (Dec. 11, 1990). Alternatively, the formation of the halomethyldimethylsilyl ether, followed by treatment with lithium diisopropyl amide, provided the 21-substituted-17α-hydroxy-20-ketopregnanes.

3. 17α-Substitution

All 17α-esters illustrated in FIGS. 4–11 were prepared from their 17α-hydroxy precursors. With the exception of the 17α-formate (69A) and the 17α,21-diformate (139), all 17α-esters were also obtained via a mixed anhydride procedure (Carruthers, N. I. et al., *J. Org. Chem.,* 57:961–965 (1992)).

17α-methoxy steroid (93) became available in large quantities from the 17α-hydroxydienedione (92) leading to a new series of antiprogestational agents, such as compounds 97 and 113. Methylation of 17α-hydroxy group was most efficiently carried out using methyl iodide and silver oxide with acetonitrile as a cosolvent as described in the general procedure of Finch, et al. (*J. Org. Chem.,* 40:206–215 (1975)). Other syntheses of 17α-methoxy steroids have been reported in the literature (see, e.g. Numazawa, M. and Nagaoka, M., *J. Chem. Soc. Commun.,* 127–128 (1983); Numazawa, M. and Nagaoka, M., *J. Org. Chem.,* 50:81–84 (1985); Glazier, E. R., J. Org. Chem., 27:4397–4393 (1962).

Figure 5:
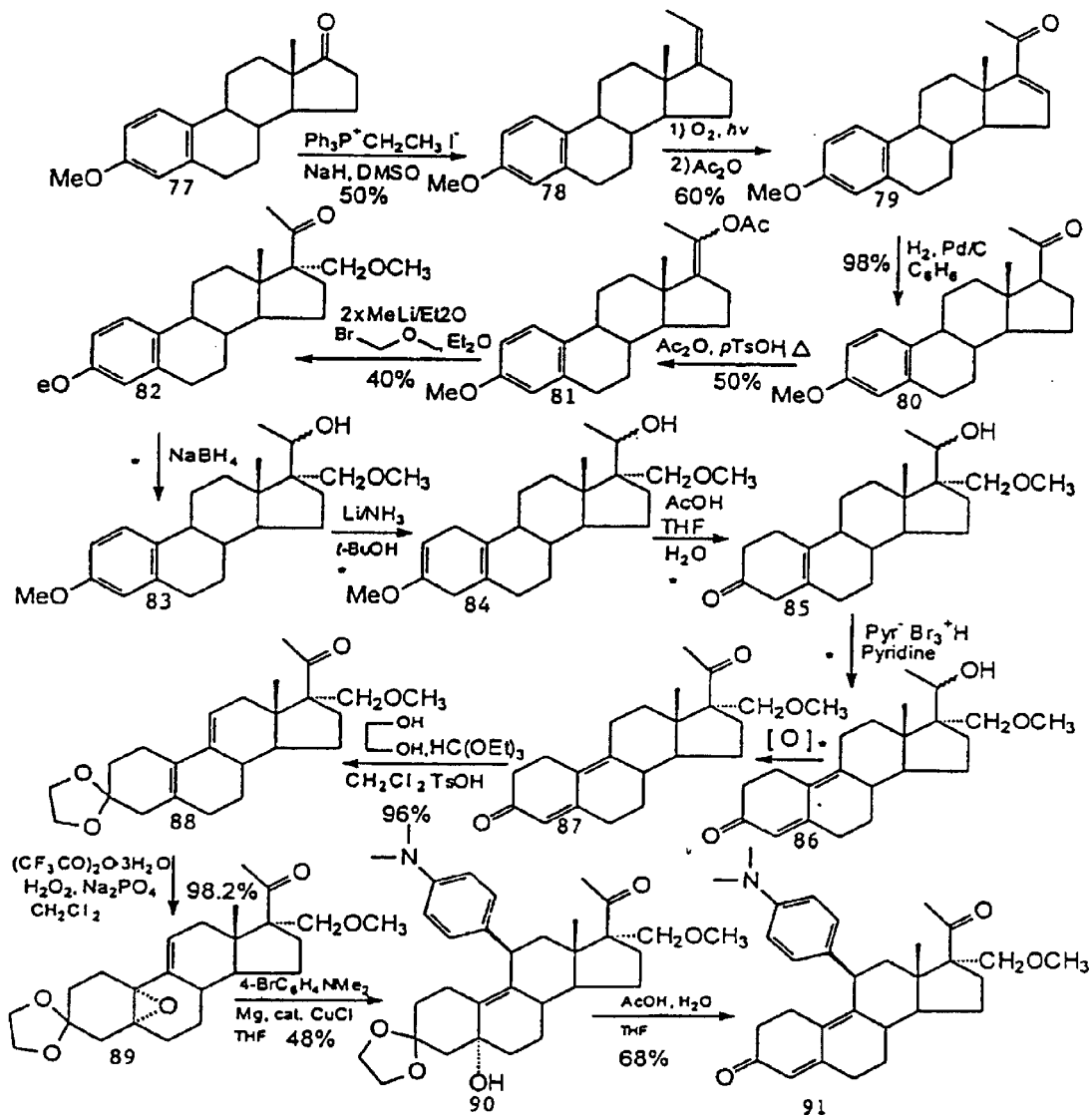

The 17α-methoxymethyl compound (91) was obtained in 0.7% overall yield via the 14-step sequence illustrated in FIG. 5 starting from estrone methyl ether (77). No attempts were made to optimize the yield. The general strategy involved: (1) Construction of the 20-ketopregnane side chain; (2) Formation of the 17,20-enol acetate and subsequent alkylation with bromomethyl methyl ether; (3) Elaboration of the 3-ketal-5(10),9(11)-diene; (4) Epoxidation; (5) Conjugate Grignard addition; and (6) Hydrolysis.

4. 11β-Aryl-4-Substitution

The introduction of a variety of 4-substituted phenyl group at C11β into 19-norprogesterone requires the 5α,10α-epoxide. Epoxidation of 2, 23, 34, 42, 50, 88, 94, 99, 109 and 119 has been known to be problematic (see, Wiechert, R. and Neef, G., *J. Steroid Biochem.,* 27:851–858 (1987)). The procedure developed by Teutsch, G., et al. (*Adrenal Steroid Antagonism* (Agarwal, M. K., ed.), 43–75, Walter de Gruyter & Co., Berlin, N.Y. (1984)), i.e., $H_2O_2$ and hexachloro or fluoroacetone, proved to be regioselective, but not highly stereoselective. A mixture of 5α,10α-epoxide and the corresponding 5β,10β-isomer was formed in approximately a 3:1 ratio. However, reduction of the C20-ketone (108) to the C20-ol (109) prior to epoxidation, resulted in a 9:1 ratio of the desired 5α,10α-epoxide.

Treatment of the 5α,10α-epoxides with 3–5 equivalents of Grignard reagents prepared from various 4-substituted aryl bromides (see, Yur'ev, Y. K., et al., *Izvest. Akad. Nauk S.S.S.R., Otdel Khim Nauk,* 166–171 (CA 45: 10236f, (1951)); Wolfe, J. P. and Buchwald, S. L., *J. Org. Chem.,* 62:6066–6068 (1997); Veradro, G., et al., *Synthesis,* 447–450 (1991); Jones, D. H., *J. Chem. Soc.* (C), 132–137 (1971); Detty et al., *J. Am. Chem. Soc.,* 105:875–882 (1983), and Rao, P. N. et al., *Steroids,* 63:523–550 (1998)) in the presence of copper (I) chloride as a catalyst provided the desired 11β-substituted phenyl steroids. It is noted that 4-bromothioanisole was purchased from the Aldrich Chemical Co. (Milwaukee, Wis.). Evidence of the 11β-orientation of the 4-substituted phenyl substituent was shown by the upfiled shift of the C18 methyl group (δ=0.273–0.484 ppm in $CDCl_3$), which is in agreement with Teutsch's observations (see, Teutsch, G. and Belanger, A., *Tetrahedron Lett.,* 2051–2054 (1979)).

The presence of an unprotected 20-ketone resulted in low yields or in undesirable Grignard product mixtures. This was circumvented by reduction of the 20-ketone (analysis of this material by NMR indicated a single isomer, no further work was done for identification of this single isomer) prior to epoxidation and subsequent oxidation of the 20-alcohol by use of iodoxybenzoic acid (IBX) (Dess, D. B. and Martin, J. C., *J. Org. Chem.,* 48:4155–4156 (1983); Frigerio, M. and Santagostino, M., *Tetrahedron Letters,* 35:8019–8022 (1994); and Frigerio, M. et al., *J. Org. Chem.,* 60:7272–7276) after Grignard addition (see, FIG. 8).

Figure 6:
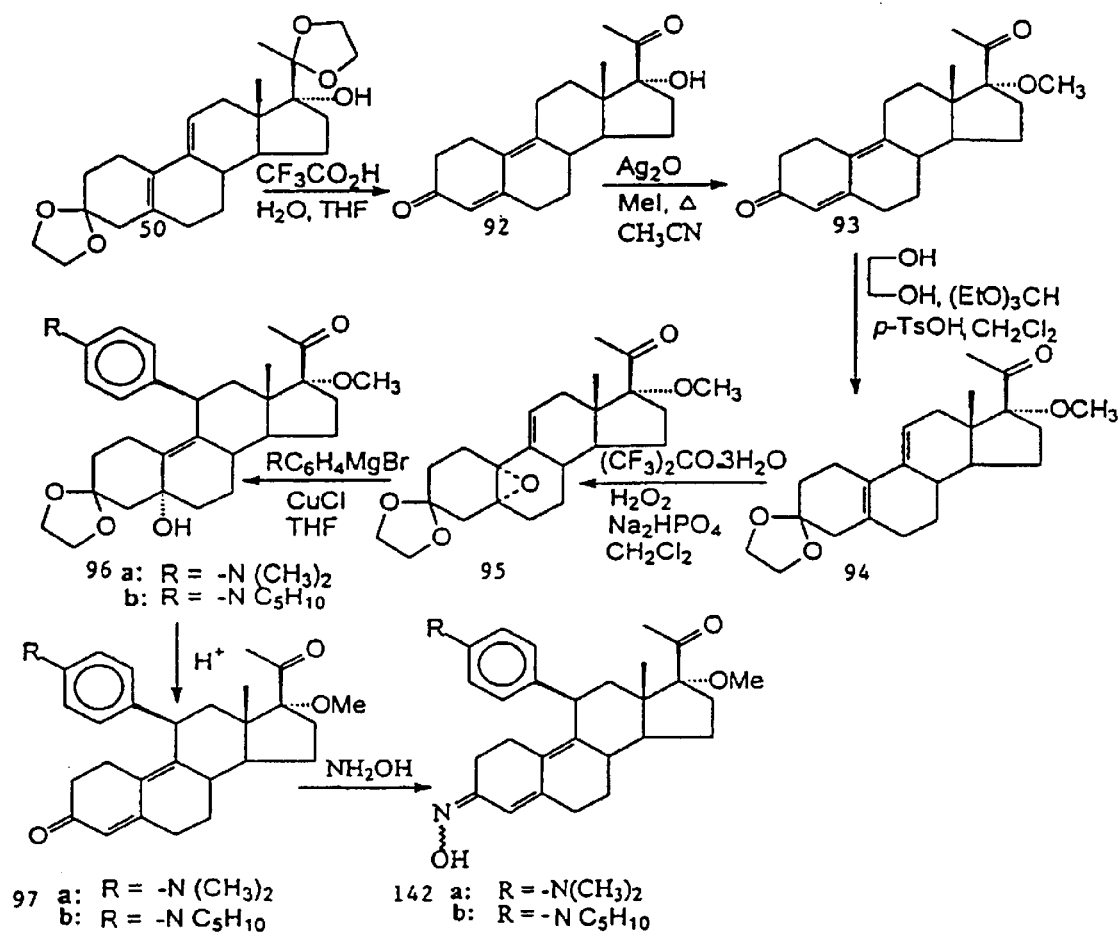
Figure 7:
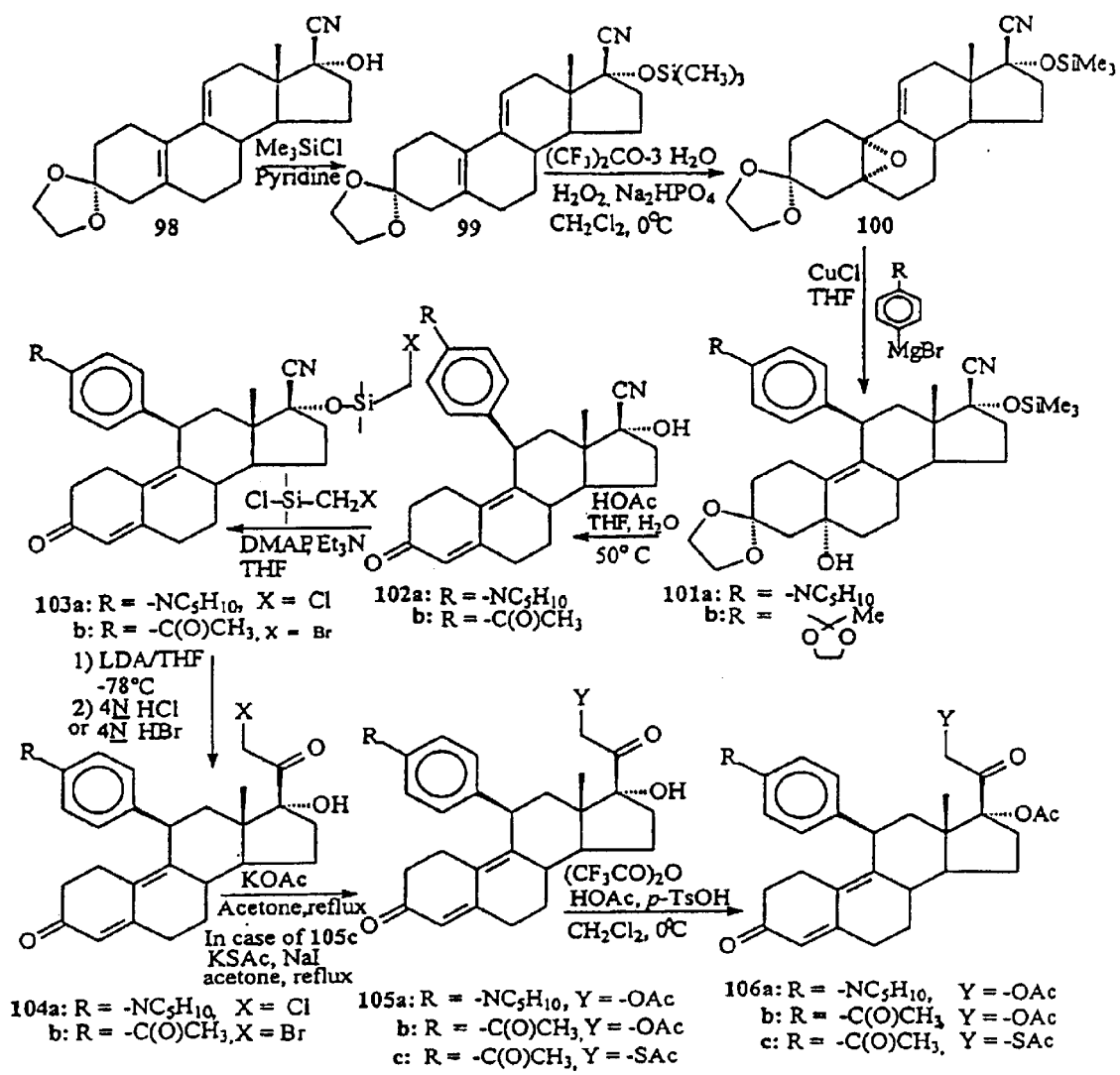
Figure 8:
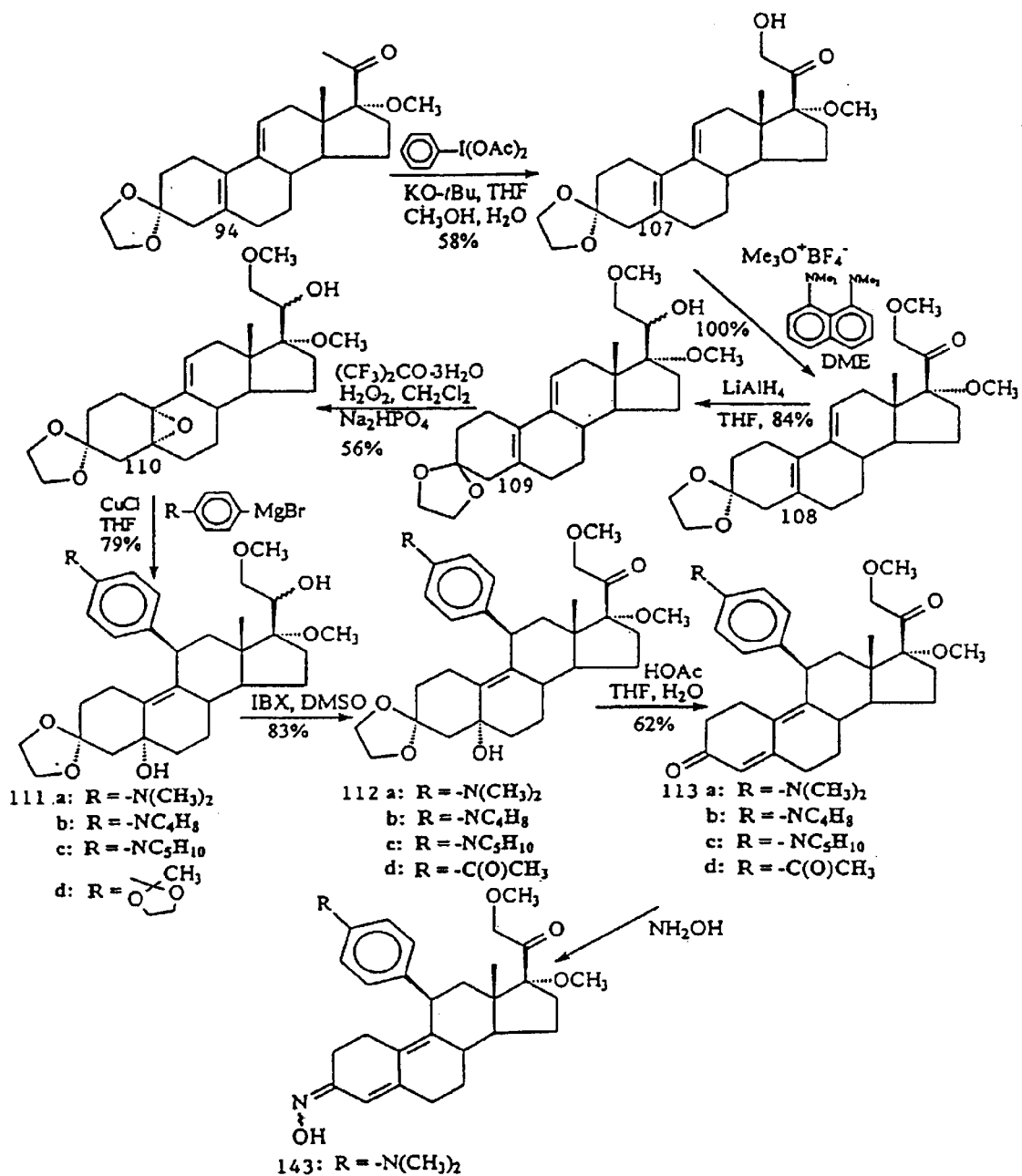
Figure 9:
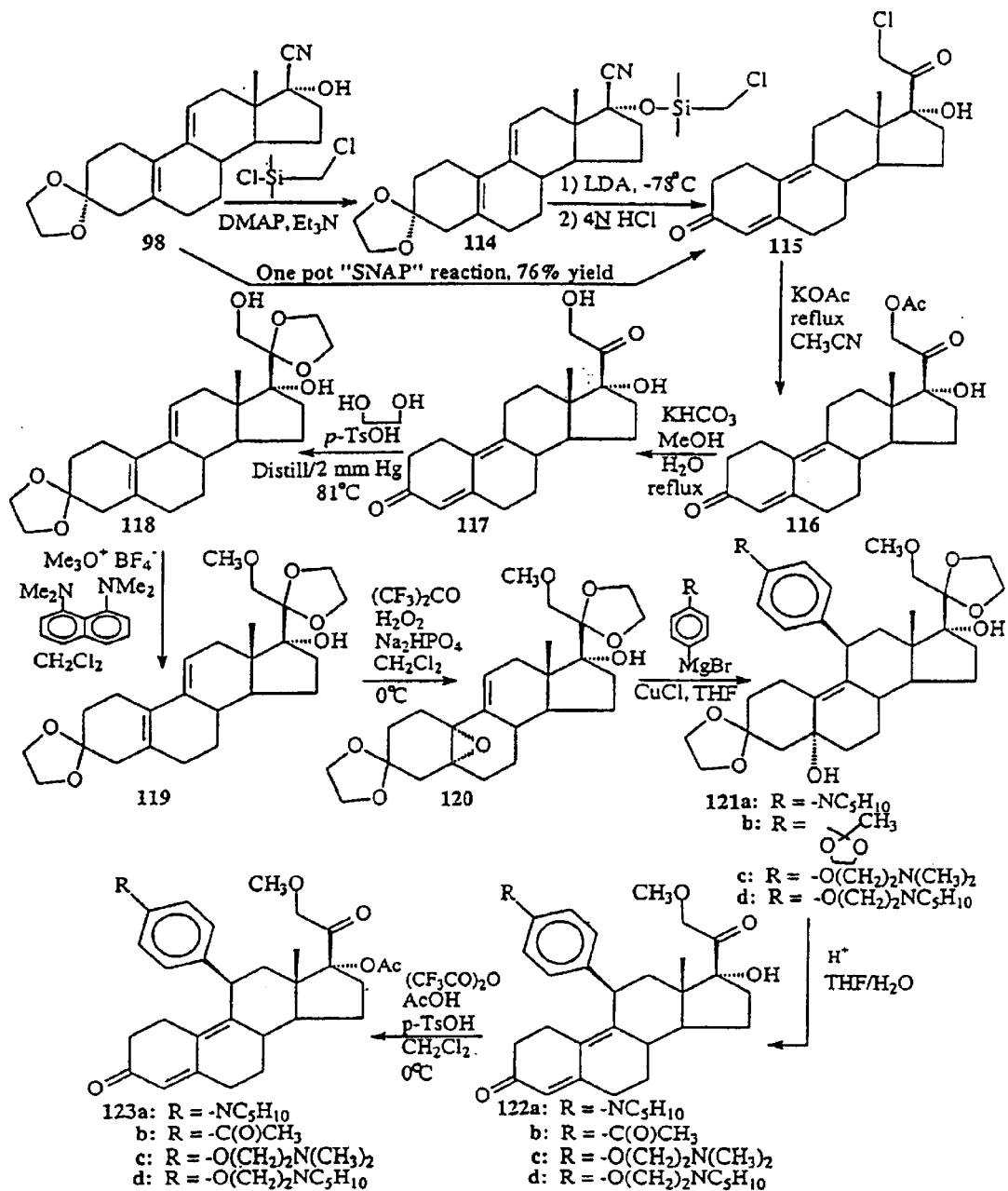

In case of FIGS. 5 and 6, the C3-ketone group was protected as a monoethyleneketal, and the C20-ketone was found to be intact when the Grignard reaction was followed during the multi-step procedures. For the syntheses of the 17α,21-diacetoxy derivatives (FIG. 7), the strategy was to accomplish the conjugate addition prior to the SNAP reaction using the multi-step process described herein.

5. Deketalization

Deketalization with concomitant dehydration at C-5 in acidic media proceeded smoothly to provide the 4,9-diene-3,20-dione.

Quite surprisingly, the compounds of Formula I possess potent antiprogestational activity with minimal antiglucocorticoid activity. As a result of their antiprogestational activity, the compounds of Formula I can advantageously be used, inter alia, to antagonize endogenous progesterone; to induce menses; to treat endometriosis; to treat dysmenorrhea; to treat endocrine hormone-dependent tumors; to treat meningioma; to treat uterine leiomyonas, to treat uterine fibroids; to inhibit uterine endometrial proliferation; to induce labor; to induce cervical ripening, for hormone therapy; and for contraception.

More particularly, compounds having antiprogestational activity are characterized by antagonizing the effects of progesterone. As such, the compounds of the present invention are of particular value in the control of hormonal irregularities in the menstrual cycle, for controlling endometriosis and dysmenorrhea, and for inducing menses. In addition, the compounds of the present invention can be used as a method of providing hormone therapy either alone or in combination with estrogenic substances in postmenopausal women, or in women whose ovarian hormone production is otherwise compromised.

Moreover, the compounds of the present invention can be used for control of fertility during the whole of the reproductive cycle. For long-term contraception, the compounds of the present invention can be administered either continuously or periodically depending on the dose. In addition, the compounds of the present invention are of particular value as postcoital contraceptives, for rendering the uterus inimical to implantation, and as "once a month" contraceptive agents.

A further important utility for the compounds of the present invention lies in their ability to slow down growth of hormone-dependent tumors and/or tumors present in hormone-responsive tissues. Such tumors include, but are not limited to, kidney, breast, endometrial, ovarian, and prostate tumors, e.g., cancers, which are characterized by possessing progesterone receptors and can be expected to respond to the compounds of this invention. In addition, such tumors include meningiomas. Other utilities of the compounds of the present invention include the treatment of fibrocystic disease of the breast and uterine.

Compounds suitable for use in the above method of the present invention can readily be identified using in vitro and in vivo screening assays known to and used by those of skill in the art. For instance, a given compound can readily be screened for its antiprogestational properties using, for example, the anti-McGinty test and/or the anti-Clauberg test described in the examples. In addition, a given compound can readily be screened for its ability to bind to the progesterone and/or glucocorticoid receptors or to inhibit ovulation using the assays described in the examples. Moreover, a given compound can readily be screened for its ability to inhibit tumor cell growth (e.g., malignant tumor growth, i.e., cancer) or to abolish tumorigenicity of malignant cells in vitro or in vivo. For instance, tumor cell lines can be exposed to varying concentrations of a compound of interest, and the viability of the cells can be measured at set time points using, for example, the alamar Blue® assay (commercially available from BioSource, International of Camarillo, Calif.). Other assays known to and used by those of skill in the art can be employed to identify compounds useful in the methods of the present invention.

The compounds according to the present invention can be administered to any warm-blooded mammal such as humans, domestic pets, and farm animals. Domestic pets include dogs, cats, etc. Farm animals include cows, horses, pigs, sheep goats, etc.

The amount of active ingredient that can be combined with a carrier material to produce a single dosage form will vary depending upon the disease treated, the mammalian species, and the particular mode of administration. For example, a unit dose of the steroid can preferably contain between 0.1 milligram and 1 gram of the active ingredient. A more preferred unit dose is between 0.001 and 0.5 grams. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

The compounds of the present invention can be administered by a variety of methods. Thus, those products of the invention that are active by the oral route can be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration can be administered to by depot injection, implants including Silastic™ and biodegradable implants, intramuscular and intravenous injections.

Compositions can be prepared according to any method known to the art for the manufacture of pharmaceutical compositions and such compositions can contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients can be, for example, inert diluents, such as calcium carbonate, sodium carbonate, lactose, calcium phosphate or sodium phosphate, granulating and disintegrating agents, such as maize starch, or alginic acid; binding agents, such as starch, gelatin or acacia; and lubricating agents, such as magnesium stearate, stearic acid and talc. Tablets can be uncoated or, alternatively, they can be coated by known methods to delay disintegration and adsorption in the gastrointestinal tract and thereby provide a sustained action over a longer period. For example, a time delay such as glyceryl monostearate or glyceryl distearate alone or with a wax can be employed.

Formulations for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (erg., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g. polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmolarity.

Oil suspensions can be formulated by suspending the active ingredient in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These compositions can be preserved by the addition of an antioxidant such as ascorbic acid.

Dispersible powders and granules of the invention suitable for preparation of an aqueous suspension by the addition of water can be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical compositions of the invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion can also contain sweetening and flavoring agents.

Syrups and elixirs can be formulated with sweetening agents, such as glycerol, sorbitol or sucrose. Such formulations can also contain a demulcent, a preservative, a flavoring or a coloring agent.

The pharmaceutical compositions of the invention can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, such as a solution of 1,3-butanediol. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The compounds of this invention can also be administered in the form of suppositories for rectal administration of the drug. These compositions can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

They can also be administered by in intranasal, intraocular, intravaginal, and intrarectal routes including suppositories, insufflation, powders and aerosol formulations.

Products of the invention which are preferably administered by the topical route can be administered as applicator sticks, solutions, suspensions, emulsions, gels, creams, ointments, pastes, jellies, paints, powders, and aerosols.

The invention will be described in greater detail by way of specific examples. The following examples are offered for illustrative purposes, and are intended neither to limit or define the invention in any manner.

EXAMPLES

Preparation of the Compounds of Formula I

Example 1

This example illustrates the preparation and properties of 17α-acetoxy-21-fluoro-11β-[4-(N,N-dimethylamino)phenyl]-19-norpregna-4,9-diene-3,20-dione (13) via the Silicon Nucleophilic Annulation Process (SNAP) of 5.

Step 1. 3,3-Ethylenedioxy-17β-cyano-17α-trimethylsilyloxyestra-5(10),9(11)-diene (2):

Under nitrogen, a solution of the cyanohydrin ketal (1, 15 g, 43.9 mmol) in pyridine (85 mL) was treated with chlorotrimethylsilane (28 mL=27.11 g, 221 mmol) and the mixture was stirred at room temperature for 5 hours. The reaction was monitored by Thin Layer Chromatography (TLC) in 2% acetone in $CH_2Cl_2$. The reaction mixture was poured into a 50:50 mixture of ice/saturated sodium bicarbonate solution (1 L), stirred until the ice was melted, and extracted with hexanes (3×). The organic extracts were washed with water (2×), brine (1×), combined, dried over $Na_2SO_4$, and concentrated in vacuo. The remaining pyridine was azeotropically removed in vacuo with heptane to give 18 g of the crude product as a foam. Crystallization from ether/hexanes gave 16.35 g of the pure silyl ether (2) as a white solid in 90% yield; m.p.=100–102° C. FTIR (KBr, diffuse reflectance) $v_{max}$ 2880, 2232 and 1254 $cm^{-1}$.

NMR ($CDCl_3$) δ 0.11 (s, 9H, $OSiMe_3$), 0.73 (s, 3H, $C18-CH_3$), 3.83 (s, 4H, —$OCH_2CH_2O$—) and 5.49 (br s, 1H, 11β-H).

Step 2. 3,3-Ethylenedioxy-5α,10α-epoxy-17β-cyano-17α-trimethylsilyloxyestra-9(11)-ene (3):

Hydrogen peroxide (30%, 6 mL, 58.6 mmol) was added to a vigorously stirred mixture of hexafluoroacetone trihydrate (11.8 g, 53.6 mmol) and $Na_2HPO_4$ (6.8 g, 47.9 mmol) in $CH_2Cl_2$ (150 mL) cooled to 0° C. in an ice bath. After stirring at 0° C. for 30 minutes, a solution of the silyl ether (2, 16 g, 38.7 mmol) in $CH_2Cl_2$ (10 mL), pre-cooled to 0° C. was added. The mixture was then stirred at 0° C. for 8 hr. At that time TLC in 5% acetone/$CH_2Cl_2$ indicated incomplete reaction and the mixture was then stirred overnight at 4° C. The reaction mixture was diluted with $CH_2Cl_2$ (200 mL) and washed with 10% sodium sulfite solution (2×), saturated sodium bicarbonate solution (1×) and brine (1×). The organic layers were combined, dried over $Na_2SO_4$, filtered and concentrated in vacuo to give 16.8 g of the crude epoxide mixture which consists of a 70:30 mixture of the 5α,10α-epoxide and 5β,10β-epoxide. Crystallization of the crude mixture from ether/hexanes afforded 8.5 g of the pure 5β,10β-epoxide (3) as a white solid in 51% yield; m.p.= 164–165° C. FTIR (KBr, diffuse reflectance) $v_{max}$ 2940, 2872, 2228 and 1252 cm$^{-1}$. NMR (CDCl$_3$) δ 0.23 (s, 9H, OSiMe$_3$), 0.91 (s, 3H, C18-CH$_3$), 3.91 (s, 4H, OCH$_2$CH$_2$O) and 6.12 (br s, 1H, C11-CH=).

Step 3. 3,3-Ethylenedioxy-5α-hydroxy-11β-[4-(N,N-dimethylamino)phenyl]-17β-cyano-17α-trimethylsilyloxyestr-9(10)-ene (4):

Magnesium (2.6 g, 107 mmol) was added to a 1.0 L, 3-neck flask equipped with a magnetic stir bar, addition funnel and a condenser. A crystal of iodine was added followed by dry THF (100 mL) and a few drops of 1,2-dibromoethane. The mixture was stirred under nitrogen and heated in a warm water bath until evidence of reaction was observed. A solution of 4-bromo-N,N-dimethylaniline (19.6 g, 98 mmol) in dry THF (100 mL) was then added dropwise over a period of 20 min. and the mixture stirred for an additional 1.5 hours. Solid copper (I) chloride (1 g, 10.1 mmol) was added followed 30 minutes later by a solution of the 5α-,10α-epoxide (3, 8.4 g, 19.55 mmol) in dry THF (10 mL). The mixture was stirred at room temperature for 1 hr., then quenched by the addition of saturated NH$_4$Cl solution (100 mL). With vigorous stirring, air was drawn through the reaction mixture for 30 minutes. The mixture was diluted with ether (250 mL) and the layers allowed to separate. The THF/ether solution was washed with 10% NH$_4$Cl solution (3×), 2 N NH$_4$OH solution (3×) and brine (1×). The organic layers were combined, dried over Na$_2$SO$_4$, filtered and concentrated in vacuo to give the crude product. Crystallization of the crude product from ether gave 8.6 g of the pure product 4 as a white solid in 80% yield; m.p.=222–224° C. dec. FTIR (KBr, diffuse reflectance) $v_{max}$ 3221, 2951, 2232, 1613, 1517 and 1253 cm$^{-1}$. NMR (CDCl$_3$) δ 0.20 (s, 9H, OSiMe$_3$), 0.5 (s, 3H, C18-CH$_3$), 2.83 (s, 6H, NMe$_2$), 3.9 (m, 4H, OCH$_2$CH$_2$O), 4.3 (m, 1H, C11α-CH), 6.63 (d, J=9 Hz, 2H, 3',5' aromatic-CH's) and 7.03 (d, J=9 Hz, 2',6' aromatic-CH's).

Step 4. 11β-[4N,N-Dimethylamino)phenyl]-17βcyano-17α-hydroxyestra-4,9-dien-3-one (5):

A solution of the Grignard adduct (4, 8.5 g, 15.4 mmol) was dissolved in THF (50 mL) and the system was flushed with nitrogen. Glacial acetic acid (150 mL) and water (50 mL) were added and the mixture was heated at 50° C. for 4 hrs. The volatile substances were removed in vacuo under a stream of nitrogen and the residual acid neutralized with NH$_4$OH. The mixture was extracted with CH$_2$Cl$_2$ (3×). The organic fractions were washed with water (2×), brine (1×), combined, dried over Na$_2$SO$_4$, filtered and concentrated in vacuo. Crystallization of the residue from ether gave 3.1 g of cyanohydrin (5) as a pale yellow solid. Chromatography of the mother liquors eluting with 50% EtOAc in hexanes followed by crystallization gave 1.8 g of an additional product. Total yield of the cyanohydrin 5, was 4.9 g in 76.2% yield; m.p.=152–154° C.; FTIR (KBr, diffuse reflectance) $v_{max}$ 3384, 2950, 2231, 1646, 1606 and 1520 cm$^{-1}$. NMR (CDCl$_3$) δ 0.67 (s, 3 H, C18-CH$_3$), 2.97 (s, 6H, NMe$_2$), 4.38 (br s, 1 H, C11α-CH), 5.83 (s, 1H, C4-CH=), 6.7 (d, J=9 Hz, 2H, 3',5' aromatic-CH's) and 7.1 (d, J=9 Hz, 2H, 2',6' aromatic-CH's).

Step 5. 11β-[4-(N,N-Dimethylamino)phenyl]-17β-cyano-17α-bromomethyldimethylsilyloxyestra-4,9-dien-3-one (6):

Under nitrogen, a solution of cyanohydrin (5) (4.8 g, 11.52 mmol), triethylamine (2.5 mL, 17.8 mmol) and dimethylaminopyridine (DMAP) (0.4 g, 3.3 mmol) in dry THF (50 mL) was treated with bromomethyldimethylsilyl chloride (2 mL, 14.66 mmol). The mixture was stirred overnight at room temperature, diluted with hexanes, filtered through Celite and concentrated in vacuo. Flash chromatography of the residue using 40% EtOAc in hexanes gave 4.8 g of the pure silyl ether (6) as a white solid in 73.4% yield; m.p.= 176–177° C. FTIR (KBr, diffuse reflectance) $v_{max}$ 2950, 2882, 2229, 1660, 1613 and 1519 cm$^{-1}$. NMR (CDCl$_3$) δ 0.41 (s, 6 H, OSi(CH$_3$)$_2$), 0.6 (s, 3 H, C18-CH$_3$), 2.61 (s, 2H, —SiCH$_2$Br), 2.91 (s, 6 H, NMe$_2$), 4.4 (br m, 1 H, C18-CH), 5.77 (s, 1 H, C4-CH=), 6.66 (d, J=9 Hz, 2H, 3',5' aromatic-CH's) and 7.05 (d, J=9 Hz, 2',6' aromatic-CH's).

Step 6A. 17α-Hydroxy-21-chloro-11β-[4-(N,N-dimethylamino)phenyl]-19-norpregna-4,9-diene-3,20-dione (7A):

Under anhydrous conditions and using a mechanical stirrer, a solution of the silyl ether (6) (370 mg, 0.71 mmol) in dry THF (7.0 mL) was cooled to −78° C. and treated dropwise with a 1.5 M solution of lithium diisopropylamide in cyclohexane (1.2 mL, 1.77 mmol). The reaction mixture was stirred at −78° C. for 45 min. and then warmed to −40° C. The reaction was quenched by addition of 4 N HCl (10 mL) and allowed to warm to room temperature. The excess acid was neutralized with the cautious addition of saturated NaHCO$_3$ solution. The mixture was extracted with EtOAc. The organic extracts were washed with H$_2$O, and brine, combined, and dried over Na$_2$SO$_4$. Evaporation of the solvent gave 378 mg of the crude product. The material was chromatographed eluting with 7.5% acetone/CH$_2$Cl$_2$ to afford 179 mg of the 21-chloro ketone (7A) as a stable foam in 54% yield. MS (EI) m/z (relative intensity) 467 (M$^+$, 70), 431 (M$^+$ −36, 8), 134(18) and 121 (100) FTIR (KBr, diffuse reflectance) $v_{max}$ 3363, 2940, 1727, 1641 and 1517 cm$^{-1}$. NMR (CDCl$_3$) δ 0.37 (s, 3H, C18-CH$_3$), 2.90 (s, 6 H, NMe$_2$), 4.40 (br. d, 1 H, C11α-CH), 4.5 (dd., 2 H, J=15 Hz, J'=12 Hz, C21-CH$_2$Cl), 5.77 (s, 1H, C4-CH=), 6.67 and 7.0 (d, 4 H, aromatic-CH's).

Generation of (7A) from (5): "One Pot" (Step 5 and 6) Chloromethyldimethylsilylation/LDA Reaction:

A solution of cyanohydrin (5) (2.25 g, 5.4 mmol), TEA (1.02 mL, 7.29 mmol) and DMAP (165 mg, 1.35 mmol) in THF (20 mL) was treated with chloromethyl dimethylsilyl-chloride (0.82 mL, 6.21 mmol). The reaction was stirred overnight and diluted with THF (30 mL). The mixture was chilled to −78° C. and treated dropwise with LDA (1.5 M/C$_6$H$_{12}$, 14.4 mL). The mixture was stirred at −78° C. for 45 min. and then warmed to −40° C. The reaction was quenched by addition of 4N HCl and allowed to warm to room temperature. The excess acid was neutralized with saturated NaHCO$_3$ solution and diluted with water. The aqueous mixture was extracted with methylene chloride. The organic extracts were washed with H$_2$O, brine, combined and dried over Na$_2$SO$_4$. Evaporation of the solvent gave 3.24 g of the residue. The material was chromatographed eluting with 7.5% acetone/CH$_2$Cl$_2$) to afford 1.13 g of 7A in 45% yield, which was identical in all respects to the 21-chloroketone (7A) obtained from the previously described two step procedure.

Step 6B. 17α-Hydroxy-21-bromo-11β-[4-N,N-dimethylamino)phenyl]-19-norpregna-4,9-diene-3,20-dione (7B):

Under anhydrous conditions and using a mechanical stirrer, a solution of the silyl ether 6 (2.9 g, 5.11 mmol) in dry THF (80 mL) was cooled to −78° C. and treated dropwise with a 1.5 M solution of lithium diisopropylamide (LDA) in cyclohexane (10.2 mL, 15.3 mmol). After 1 hr., the reaction mixture became very viscous, i.e., almost a gel. The reaction was quenched at −78° C. by addition of 4 N HBr (50 mL, 200 mmol) and the mixture allowed to warm to room temperature. The excess acid was neutralized by slow addition of concentrated $NH_4OH$ solution (15 mL) and the mixture was poured into water (100 mL) and extracted with $CH_2Cl_2$ (3×). The organic extracts were washed with water (3×), combined, filtered through $Na_2SO_4$ and concentrated in vacuo to give 3.1 g of the crude product as a foam. Purification via Flash chromatography gave a 94:6 mixture of the 21-bromo (7B) and 21-chloro (7A) derivative evidenced by a reverse phase HPLC on a NovaPak column eluting with $MeOH/H_2O/Et_3N$ (70:30:0.033) at a flow rate of 1.0 mL/min at λ=302 nm. MS(EI) m/z (relative intensity): 513 ($M^+$+2, 10), 512 ($M^+$, 20), 431 (18) and 121 (100). FTIR (KBr, diffuse reflectance) $v_{max}$ 3327, 2948, 1723, 1660, 1611 and 1518 $cm^{-1}$. NMR ($CDCl_3$) δ 0.3 (s, 3H, C18-$CH_3$), 2.80 (s, 6H, $NMe_2$), 4.3 (br m, 3H, C11α-CH and C21-$CH_2Br$), 5.65 (s, 1H, C4-CH=), 6.55 (d, J=9 Hz, 2H, 3',5' aromatic-CH's) and 6.9 (d, J=9 Hz, 2',6' aromatic-CH's). This mixture was used for the subsequent reaction without further purification.

Step 7. 17α-Hydroxy-21-acetoxy-11β-[4-N,N-dimethylamino)phenyl]-19-norpregna-4,9-diene-3,20-dione (8):

Under nitrogen, a solution of a 94:6 mixture of the 21-halogenated steroid (7A and 7B) (1.8 g, 3.5 mmol) and potassium acetate (10 g, 102 mmol) in acetone was refluxed for 2 hrs. At the end of that time, TLC (10% acetone/$CH_2Cl_2$) indicated no presence of starting material. The reaction mixture was cooled to room temperature, filtered, concentrated in vacuo, diluted with water (200 mL) and extracted with $CH_2Cl_2$ (3×). The organic extracts were washed with water (2×), combined, filtered through $Na_2SO_4$ and concentrated in vacuo to give 1.6 g of the crude acetate (8) as a foam in 93% yield. A small portion of the pure acetate (8) was solidified by trituration with ether for characterization. This solid did not have a proper melting point and remained a solid when heated to 300° C. MS (EI) m/z (relative intensity): 491 ($M^+$, 72), 431 (6), 314(17) and 121 (100). FTIR (KBr, diffuse reflectance) $v_{max}$ 3326, 2949, 1752, 1733, 1639, 1613, 1588 and 1519 $cm^{-1}$. NMR ($CDCl_3$) δ 0.43 (s, 3H, C18-$CH_3$), 2.27 (s, 3H, OAc), 3.0 (s, 6H, $NMe_2$), 4.5 (br. d, 1H, C11α-CH), 5.25 (dd, $J_1$=29.7 Hz, $J_2$=24 Hz, 2H, $CH_2OAc$), 5.87 (s, 1H, C4-CH=), 6.77 (d, =9 Hz, 2H, 3',5' aromatic-CH's) and 7.17 (d, J=8.7 Hz, 2H, 2',6' aromatic-CH's). Anal. Calcd. for $C_{30}H_{37}NO_5 \cdot \frac{1}{2}H_2O$: C, 71.97; H, 7.65; N, 2.80. Found: C, 72.16; H, 7.48; N, 2.90.

Step 8. 17α,21-Dihydroxy-11β-[4-(N,N-dimethylamino)phenyl]-19-norpregna-4,9-diene-3,20-dione (9):

A solution of the 21-acetate (8) (1.6 g, 3.25 mmol) in MeOH (100 mL) was deoxygenated by bubbling through it a slow stream of nitrogen for 30 minutes. A similarly deoxygenated 0.5 M solution of $KHCO_3$ in deionized water (10 mL, 5 mmol) was added and the mixture heated to reflux under nitrogen and monitored by TLC (5% i-PrOH/$CH_2Cl_2$) which indicated a complete reaction after 2 hr. The mixture was neutralized with 1M AcOH solution and the methanol removed in vacuo under a stream of nitrogen. The residue was taken up in $CH_2Cl_2$ and washed with water (3×). The organic layers were combined, dried over $Na_2SO_4$, filtered and concentrated in vacuo to give 1.6 g of the residue. This material was purified by Flash chromatography using 3% i-PrOH/$CH_2Cl_2$) followed by precipitation from methanol with water to give 1.1 g of the diol (9) as a yellow amorphous solid in 75% yield; m.p.=softens at 130° C. FTIR (KBr, diffuse reflectance) $v_{max}$ 3391, 2946, 1712, 1654, 1612 and 1518 $cm^{-1}$. NMR ($CDCl_3$) δ 0.35 (s, 3H, C18-$CH_3$), 2.91 (s, 6H, $NMe_2$), 4.5 (m, 3H, C11α-CH and $CH_2$-OH), 5.77 (s, 1H, C4-CH=), 6.67 (d, J=9 Hz, 2H, 3',5' aromatic-CH's) and 7.0 (d, J=8.7 Hz, 2H, 2',6' aromatic-CH's). MS (EI) m/z (relative intensity): 449($M^+$, 51), 431 (14), 419(9), 389(27), 3432(9) and 121 (100). Anal. Calcd. for $C_{28}H_{35}NO_4 \cdot \frac{1}{2}H_2O$: C, 73.33; H, 7.91; N, 3.05. Found: C, 73.52; H, 7.70; N, 3.06.

Step 9. 17α-Hydroxy-21-methyloxy-11β-[4-N,N-Dimethylamino)phenyl]-19-norpregna-4,9-diene-3,20-dione (10):

Under nitrogen, a solution of the diol (9) (0.5 g, 1.11 mmol) and triethylamine (0.25 mL, 1.8 mmol) in dry pyridine (10 mL) was cooled to 0° C. in an ice bath and treated with methanesulfonyl chloride (0.125 mL, 1.615 mmol). After stirring at 0° C. for 1 hr., TLC (10% acetone/$CH_2Cl_2$) of a quenched (EtOAc/$H_2O$) aliquot indicated complete reaction. Cold water (50 mL) was added and the mixture extracted with $CH_2Cl_2$ (3×). The organic layers were washed with water (3×), combined, dried over $Na_2SO_4$, filtered and concentrated in vacuo. Azeotropic in vacuo removal of trace pyridine using heptane gave 0.62 g of the residue. Purification via Flash chromatography using 10% acetone/$CH_2Cl_2$ followed by trituration with $Et_2O$ gave 0.46 g of the pure 21-mesylate (10) as a yellow solid in 78.4% yield; m.p.= 146–149° C. FTIR (KBr, diffuse reflectance) $v_{max}$ 3298, 2947, 2738, 1630, 1614, 1518 and 1174 $cm^{-1}$. NMR ($CDCl_3$) δ 0.39 (s, 3H, C18-$CH_3$), 2.91 (s, 6H, $NMe_2$), 3.2 (s, 3H, $OSO_2CH_3$), 4.4 (br d, 1H, C11α-CH), 5.27 (dd, $J_1$=27 Hz, $J_2$=18 Hz, 2H, C21-$CH_2O$ Ms), 5.79 (s, 1H, C4-CH=), 6.69 (d, J=9 Hz, 2H, 3',5' aromatic-CH's) and 7.07 (d, J=9 Hz, 2H, 2',6' aromatic-CH's).

Step 10. 17α-Hydroxy-21-fluoro-11β-[4-(N,N-dimethylamino)phenyl]-19-norpregna-4,9-diene-3,20 dione (11) and 17-Spirooxetano-3'-oxo-11β-[4-(N,N-dimethylamino)phenyl]-19-norpregna-4,9-dien-3-one (12):

Under nitrogen, a mixture of the 21-mesylate (10) (0.4 g, 0.758 mmol), potassium fluoride (0.5 g, 8.6 mmol) and 18-Crown-6 (0.5 g, 1.9 mmol) in anhydrous $CH_3CN$ (15 mL) was heated to reflux and monitored by TLC (6% acetone/$CH_2Cl_2$) which indicated consumption of starting material and formation of two major products after 1 hr. The reaction mixture was cooled to room temperature, diluted with water (150 mL) and extracted with $CH_2Cl_2$ (3×). The organic extracts were washed with water (3×), combined, dried over $Na_2SO_4$, filtered and concentrated in vacuo. The mixture was separated via flash chromatography using 6% acetone/$CH_2Cl_2$ to give 0.158 g of the 21-fluoro compound (11) as a pale yellow solid in 46% yield; m.p. 132–135° C. FTIR (KBr, diffuse reflectance) $v_{max}$ 3492–3303, 2948, 1733, 1652, 1610 and 1519 $cm^{-1}$. NMR ($CDCl_3$) δ 0.40 (s, 3H, C18-$CH_3$), 2.90 (s, 6H, $NMe_2$), 4.4 (br d, 1H, C11α-CH), 5.26 (dd, $J_{HF}$=48.6 Hz, $J_1$=16.2 Hz, $J_2$=22 Hz, 2H, $CH_2F$), 5.77 (s, 1H, C4-CH=), 6.67 (d, J=9 Hz, 2H, 3',5' aromatic-CH's) and 7.01 (d, J=9 Hz, 2H, 2',6' aromatic-CH's). MS(EI) m/z (relative intensity): 451 ($M^+$, 33) and 121 (100). In addition to the aforementioned compound 11, 0.177 g of the oxetan-3'-one (12) was obtained as an off-white amorphous powder in 54.1% yield; m.p.=softens at 95° C. MS (EI): m/z (relative intensity) 431 ($M^+$, 38), 134(14) and 121 (100) FTIR (KBr, diffuse reflectance) $v_{max}$ 2941, 1809, 1663, 1613 and 1519 $cm^{-1}$. Analysis by a reverse phase HPLC on a NovaPak $C_{18}$ column eluted with $CH_3CN/H_2O/Et_3N$ (50:50:0.033) at a flow rate of 1 mL/min and at λ=302 nm indicated this material to be of 97% purity whose retention time ($t_R$) is 13.39 min. NMR ($CDCl_3$) δ 0.55

(s, 3H, C18-CH$_3$), 2.91 (s, 6H, NMe$_2$), 4.45 (br d, J=6.7 Hz, 1H, C11α-CH), 5.03 (dd, J$_{1=17.1}$ Hz, J$_2$=15.3 Hz, 2H, C21-CH$_2$), 5.79 (s, 1H, C4-CH═), 6.69 (d, J=9 Hz, 2H, 3',5' aromatic-CH's), 7.03 (d, J=9 Hz, 2H, 2',6' aromatic-CH's). Anal. Calcd. for C$_{29}$H$_{33}$NO$_3$: C, 77.93; H, 7.71; N, 3.25. Found: C, 77.80; H, 7.62; N, 3.11.

Step 11. 17α-Acetoxy-21-fluoro-11β-[4-(N,N-dimethylamino)phenyl]-19-norpregna-4,9-diene-3,20-dione (13):

Under nitrogen, trifluoroacetic anhydride (1.75 mL, 12.39 mmol), glacial acetic acid (0.7 mL, 12.14 mmol) and dry CH$_2$Cl$_2$ (10 mL) were combined and stirred at room temperature for ½ hr. The mixture was cooled to 0° C. in an ice bath and toluenesulfonic acid monohydrate (0.1 g, 0.53 mmol) was added. A solution of the 21-fluoro-17α-alcohol (11) (0.28 g, 0.62 mmol) in dry CH$_2$Cl$_2$ was then introduced via syringe and the mixture stirred at 0° C. for 6.5 hrs. After that time, TLC (10% acetone/CH$_2$Cl$_2$) indicated a complete reaction. The mixture was diluted with water (3×), neutralized with concentrated NH$_4$OH solution and extracted with CH$_2$Cl$_2$ (3×). The organic extracts were washed with water (3×), combined, filtered through Na$_2$SO$_4$ and concentrated in vacuo to give 0.32 g of the crude product as a foam. Purification via flash chromatography (5% acetone/CH$_2$Cl$_2$) followed by trituration with heptane and pentane gave 0.18 g of the pure 21-fluoro-17α-acetate (13) as a white amorphous solid in 58.8% yield; m.p. 169–173°. Analysis by a reverse phase HPLC on a NovaPak C18 column eluted with MeOH/H$_2$O/Et$_3$N (70:30:0.033) at a flow rate of 1 mL/min and at λ=302 nm indicated this material to be of 98.9% purity which has a retention time of t$_R$5.97 min. MS(EI), m/z (relative intensity): 493(M$^+$, 32), 134 (14), 122(13) and 121 (100). FTIR (KBr, diffuse reflectance) ν$_{max}$ 2946, 1739, 1662, 1612 and 1510 cm$^{-1}$.

NMR (CDCl$_3$) δ 0.40 (s, 3H, C18-CH$_3$), 2.10 (s, 3H, OAc), 2.90 (s, 6H, NMe$_2$), 4.4 (br d, 1H, C11α-CH), 4.95 (dq, J$_{HF}$=48 Hz, J$_1$=16 Hz, J$_2$=22 Hz, 2H, CH$_2$F), 5.80 (s, 1H, C4-CH═), 6.67 (d, J=9 Hz, 2H, 3',5' aromatic-CH's) and 7.03 (d, J=9 Hz, 2H, 2',6' aromatic-CH's). Anal. Calcd. for C$_{30}$H$_{36}$FNO$_4$: C, 73.00; H, 7.35; N, 2.84. Found: C, 72.96; H, 7.47; N, 2.84.

Example 2

This example illustrates the preparation and properties of 17α-acetoxy-21-chloro-11β-[4-N,N-dimethylamino)phenyl]-19-norpregna-4,9-diene-3,20-dione (14A).

A solution of trifluoroacetic anhydride (2.2 mL, 15.56 mmol) in CH$_2$Cl$_2$ (25 mL) was treated with acetic acid (0.89 mL, 15.56 mmol). The mixture was stirred at room temperature for 30 min. and p-toluenesulfonic acid (137 mg, 0.72 mmol) was added. The mixture was chilled to 0° C. and a solution of 7A (364 mg, 0.78 mmol) in CH$_2$Cl$_2$ (2.0 mL) was added. The mixture was stirred for 2 hrs. and quenched with cautious addition of saturated NaHCO$_3$ solution. The mixture was extracted with CH$_2$Cl$_2$. The organic extracts were washed with H$_2$O and brine, combined and dried over Na$_2$SO$_4$. Evaporation of the solvent gave 412 mg of a stable foam. The material was chromatographed eluting with 5% acetone in CH$_2$Cl$_2$ to afford 210 mg of 14A in 53% yield as an amorphous foam which persisted recrystallization from a variety of solvents. Analysis by a reverse phase HPLC on a NovaPak C$_{18}$ column, eluted with 30% aq. MeOH with 0.033% TEA at a flow rate of 1.0 mL/min at λ=260 nm showed the material to be approximately 95% pure. Therefore, the material was purified by preparative HPLC on a Whatman Magnum Partisil 10-ODS-3 column eluted with aqueous MeOH with 0.033% TEA at a flow rate of 10 mL per minute at λ=325 nm to afford 158 mg of 14A as an amorphous yellow foam in 48% yield. FTIR (KBr, diffuse reflectance) ν$_{max}$ 2947, 1731, 1660, 1610 and 1518 cm$^{-1}$. NMR (CDCl$_3$) δ 0.40 (s, 3H, C18-CH$_3$), 2.13 (s, 3H, C17α-OAc), 2.90 (s, 6H, N(CH$_3$)$_2$), 4.23 (dd, J=15 Hz, J'=9 Hz, 2H, C21-CH$_2$Cl), 4.4 (br d, 1H, C11α-CH), 5.72 (s, 1H, C4-CH═), 6.67 and 7.0 (d, 4H, aromatic-CH). MS (EI) m/z (relative intensity): 510(M$^+$, 6), 509 (M$^+$–1, 16), 134 and 121 (100). Anal. Calcd. for C$_{30}$H$_{36}$NO$_4$Cl: C, 70.64; H, 7.11; N, 2.75. Found: C, 70.46; H, 7.10; N, 2.76.

Example 3

This example illustrates the preparation and properties of 17α-acetoxy-21-bromo-11β-[4-(N,N-dimethylamino)phenyl]-19-norpregna-4,9-diene-3,20-dione (14B).

Step 1. Purification of 7B

The pure 21-bromo compound (7B) was isolated from a 90:10 mixture of the 21-halo product (7B:7A) by means of Waters Prep LC system on a NovaPak C$_{18}$ column (40×100 mm) eluted with 30% aq. MeOH and 0.03% Et$_3$N at a flow rate of 35 mL/min and at λ=334 nm. A total amount of 0.75 g of a 90:10 mixture (7B:7A) was chromatographed in 10 runs of 75 mg each to give of 0.5 g of the pure 21-bromo compound (7B) as a pale yellow solid in 67% yield. This material was >99% pure by analytical HPLC. FTIR (KBr, diffuse reflectance) ν$_{max}$ 3327, 2948, 1723, 1660, 1611 and 1518 cm$^{-1}$. NMR (CDCl$_3$) δ 0.3 (s, 3H, C18-CH$_3$), 2.80 (s, 6H, NMe$_2$), 4.33 (dd, J$_1$=12 Hz, J$_2$=9 Hz, 2H, C21-CH$_2$Br), 4.40 (br d, 1H, C11α-CH), 5.65 (s, 1H, C4-CH═), 6.55 (d, J=9 Hz, 2H, 3',5' aromatic-CH's), 6.9 (d, J=9 Hz, 2',6' aromatic-CH's).

Step 2. Preparation of the Target Compound (14B)

Under nitrogen, a mixture of trifluoroacetic anhydride (1.64 mL, 11.68 mmol), glacial acetic acid (0.67 mL, 11.62 mmol) and dry CH$_2$Cl$_2$ (10 mL) was stirred at room temperature for 30 min and then cooled to 0° C. in an ice bath. p-Toluenesulfonic acid monohydrate (0.1 g, 0.52 mmol) was added followed by a solution of the 21-bromo alcohol (7B) (0.3 g, 0.59 mmol) in dry CH$_2$Cl$_2$ (2 mL). The reaction mixture was stirred at 0° C. and monitored by TLC (10% acetone/CH$_2$Cl$_2$) which indicated a complete reaction in 2 hrs. The mixture was diluted with water (10 mL), neutralized with concentrated NH$_4$OH solution and extracted with CH$_2$Cl$_2$ (3×). The organic extracts were washed with H$_2$O (3×), combined, filtered through Na$_2$SO$_4$ and concentrated in vacuo to give 0.35 g of the residue as a foam. This material was purified by flash chromatography using 5% acetone/CH$_2$Cl$_2$ followed by crystallization from Et$_2$O/hexanes to give 0.24 g of the 21-bromo acetate (14B). Analysis by NMR indicated a significant amount of ether as solvent of crystallization. This material was then dissolved in CH$_2$Cl$_2$ (3 mL) and the solvent blown down to give an oil. Trituration with heptane followed by washing with pentane and drying in vacuo gave 0.16 g of the pure 21-bromo compound (14B) as a white crystalline solid in 49% yield: m.p.=141–145° C. MS (EI) m/z (relative intensity): 555 (M$^+$+2, 82), 553 (M$^+$, 76), 475(13), 414(8), 372(13), 134 (15) and 121 (100). FTIR (KBr, diffuse reflectance) ν$_{max}$ 2933, 1730, 1664, 1613, 1596 and 1519 cm$^{-1}$. NMR (CDCl$_3$) δ 0.40 (s, 3H, C18-CH$_3$), 2.13 (s, 3H, OAc), 2.80 (s, 6H, NMe$_2$), 4.07 (dd, J$_1$=14 Hz, J$_2$=7 Hz, 2H, C21-CH$_2$Br), 4.40 (br d, 1H, C11α-CH), 5.83 (s, 1H, C4-CH═), 6.67 (d, J=9 Hz, 2H, 3',5' aromatic-CH's), 7.07 (d, J=9 Hz, 2H, 2',6' aromatic-CH's). Anal. Calcd. for C$_{30}$H$_{36}$BrNO$_4$·⅕H$_2$O: C, 64.98; H, 6.54; Br, 14.41; N, 2.53. Found: C, 64.82; H, 6.62; N, 2.27.

Example 4

This example illustrates the preparation and properties of 17α,21-diacetoxy-11β-[4-(N,N-dimethylamino)phenyl]-19-norpregna-4,9-diene-3,20-dione (15).

Under nitrogen, a mixture of trifluoroacetic anhydride (4.0 mL, 28.3 mmol), glacial acetic acid (1.6 mL, 27.7 mmol) and dry $CH_2Cl_2$ (10 mL) was stirred at room temperature for 30 min. and then cooled to 0° C. in an ice bath. p-Toluenesulfonic acid monohydrate (0.1 g, 0.53 mmol) was added followed by a solution of the 17α,21-diol (9, 0.345 g, 0.77 mmol) in dry $CH_2Cl_2$ (2 mL). The reaction mixture was stirred at 0° C. and monitored by TLC (0% acetone/$CH_2Cl_2$) which indicated a complete reaction in two hrs. The mixture was diluted with $H_2O$ (10 mL), neutralized with concentrated $NH_4OH$ solution and extracted with $CH_2Cl_2$ (3×). The organic layers were washed with $H_2O$ (3×), combined, filtered through $Na_2SO_4$ and concentrated in vacuo to give 0.4 g of the residue as a foam. This material was purified by flash chromatography using 5% acetone/$CH_2Cl_2$ followed by trituration with heptane and pentane to give 0.24 g of the 17α,21-diacetate (15) as a yellow amorphous solid in 58.4% yield: m.p.=128–134° C. Analysis by a reverse phase HPLC on a NovaPak $C_{12}$ column eluted with $CH_3CN:H_2O:Et_3N$ (1:1:0.033) at a flow rate of 1 mL/min and at λ=302 nm indicated 15 to be of >98% purity which has a retention time of 12 min. MS (EI) m/z (relative intensity): 533 ($M^+$, 24), 134 (14), 122 (11) and 121 (100). FTIR (KBr, diffuse reflectance) $v_{max}$ 2942, 1738, 1663, 1611, 1518 and 1233 $cm^{-1}$. NMR ($CDCl_3$) δ 0.33 (s, 3H, C18-$CH_3$), 2.10 (s, 3H, C17α-OAc), 2.13 (s, 3H, C21-OAc), 2.90 (s, 6H, $NMe_2$), 4.43 (br d, 1H, C11α-CH), 4.84 (dd, $J_1$=29.7 Hz, $J_2$=18 Hz, 2H C21-$CH_2$Br), 5.80 (s, 1H, C4-CH=), 6.67 (d, J=9 Hz, 2H, 3',5' aromatic-CH's), 7.05 (d, J=9 Hz, 2H, 2',6' aromatic-CH's). Anal. Calcd. for $C_{32}H_{39}NO_6 \cdot \frac{1}{3}H_2O$: C, 71.22; H, 7.41; N, 2.60. Found: C, 71.27; H, 7.35; N, 2.61.

Example 5

This example illustrates the preparation and properties of 17α-acetoxy-21-acetylthio-11β-[4-(N,N-dimethylamino)phenyl]-19-norpregna-4,9-diene-3,20-dione (17).

Step 1. 17α-Hydroxy-21-acetylthio-11β-[4-N,N-dimethylamino)phenyl]-19-norpregna-4,9-diene-3,20-dione (16):

The 17α-Hydroxy-21-bromo compound (7B) (2.79 g, 5.44 mmol) dissolved in acetone (150 mL) was refluxed with sodium iodide (8.16 g, 54.4 mmol) for 1 hr in an atmosphere of nitrogen and then filtered directly into a suspension of potassium thioacetate (6.2 g, 54.4 mmol) in acetone (150 mL). After refluxing for an additional 2.5 hrs, the reaction mixture was cooled to room temperature, filtered, concentrated in vacuo, diluted with $H_2O$ and extracted with $CH_2Cl_2$. The organic fractions were washed with $H_2O$ and brine, combined and dried over sodium sulfate. The filtrate was evaporated and the residue was purified via flash silica gel column (6% acetone/$CH_2Cl_2$) to afford 1.99 g of 16 as a yellow foam in 72.1% yield. Crystallization of the foam from EtOAc/hexanes gave yellow crystals with m.p. 197–198° C. FTIR (KBr, diffuse reflectance) $v_{max}$ 3483, 2943, 1722, 1696, 1642, 1615, 1585 and 1520 $cm^{-1}$. NMR ($CDCl_3$) δ 0.40 (s, 3H, C18-$CH_3$), 2.41 (s, 3H, Ac), 2.93 (s, 6H, $NMe_2$), 3.32 (s, 1H, C17α-OH), 3.65 and 4.31 (AB-System, J=16.5 Hz, 2H, C21-$CH_2$), 4.36 (br d, 1H, C11α-CH), 5.73 (s, 1H, C4-CH=), 6.66 (d, J=9 Hz, 2H, 3',5' aromatic-CH's) and 7.07 (d, J=9 Hz, 2H, 2',6' aromatic-CH's). MS(EI) m/z (relative intensity): 507 ($M^+$). Anal. Calcd. for $C_{30}H_{37}O_4NS$: C, 70.79; H, 7.35; N, 2.76; S, 6.31. Found: C, 70.97; H, 2.75; N, 2.76; S, 6.29.

Step 2. Preparation of the Target Compound (17):

Under nitrogen, trifluoroacetic anhydride (8.5 mL, 61.95 mmol), glacial acetic acid (3.5 mL, 60.7 mmol) and dry $CH_2Cl_2$ (100 mL) were combined and stirred at room temperature for 20 min. The mixture was cooled to 0° C. in an ice bath and p-toluenesulfonic acid monohydrate (0.5 g, 2.65 mmol) was added. A solution of the 17α-alcohol (16) (1.99 g, 3.99 mmol) in dry $CH_2Cl_2$ was added and the mixture stirred at 0–5° C. for 10 hr. The mixture was neutralized with saturated $NaHCO_3$ solution and extracted with $CH_2Cl_2$ (3×). The organic fractions were washed with $H_2O$ (3×), combined and dried over $Na_2SO_4$. The filtrate was evaporated and the residue was purified via flash silica gel column (4.6% acetone/$CH_2Cl_2$) to afford 1.73 g of 17 as a yellow foam in 80.4% yield: m.p.=123–124° C. MS(EI) m/z (relative intensity): 549 ($M^+$). FTIR (KBr, diffuse reflectance) $v_{max}$ 2946, 1736, 1692, 1663, 1611 and 1518 $cm^{-1}$. NMR ($CDCl_3$) δ 0.39 (s, 3H, C18-$CH_3$), 2.18 (s, 3H, OAc), 2.38 (s, 3H, SAc), 2.92 (s, 6H, $NMe_2$), 3.91 (s, 2H, 21-$CH_2$), 4.44 (br d, 1H, C11α-CH), 5.78 (s, 1H, C4-CH=), 6.67 (d, J=9 Hz, 2H, 3',5' aromatic-CH's) and 7.08 (d, J=9 Hz, 2H, 2',6' aromatic-CH's). Anal. Calcd. for $C_{32}H_{39}NO_5S$: C, 69.92; H, 7.15; N, 2.55; S, 5.83. Found: C, 69.66; H, 7.12; N, 2.58; S, 5.59.

Example 6

This example illustrates the preparation and properties of 17α-acetoxy-21-methyl-11β-[4-(N,N-dimethylamino)phenyl]-19-norpregna-4,9-diene-3,20-dione (28):

Step 1. 3,3-Ethylenedioxy-17α-trimethylsilyloxyestra-5(10),9(11)-dien-17α-aldehyde (21).

The cyano trimethylsilyl ether (2) (16 g, 38.7 mmol) was dissolved in THF (30 mL, distilled from lithium aluminum hydride (LAH)) in oven-dried glassware, and t-butyl methyl ether (300 mL) was added. The mixture was cooled to 0° C. in an ice bath. diisobutylaluminum hydride (DIBAL-H) (75 mL, 1 M in toluene) was added to the mixture over 30 min. using an addition funnel. The reaction mixture was stirred under nitrogen at room temperature and monitored by HPLC (on a NovaPak $C_{18}$ column eluted with $CH_3CN/H_2O/75:25$). The reaction was complete after 4 hr. It was cooled to 0° C. in an ice bath and aq. acetic acid (40 mL, 50%) was added. The mixture was diluted with $H_2O$ and extracted with ether (3×). The ether extracts were washed with 10% acetic acid, $H_2O$, saturated $NaHCO_3$ solution, $H_2O$ and brine. The combined organic layers were dried over $Na_2SO_4$ and concentrated in vacuo to yield 15.11 g of the crude aldehyde (21). Flash chromatography using 1% THF/$CH_2Cl_2$ gave 10.6 g of the pure product as a white solid in 65% yield; m.p.=105–109° C. MS(EI) m/z (relative intensity): 416 ($M^+$, 30), 270(47), 169 (44), 129(47), 99(73), 86 (31) and 73 (100). FTIR (KBr, diffuse reflectance) $v_{max}$ 2910 and 1731 $cm^{-1}$. NMR ($CDCl_3$) δ 0.11 (s, 9H, $Si(CH_3)_3$), 0.67 (s, 3H, C18-$CH_3$), 3.98 (s, 4H, $OCH_2CH_2O$), 5.60 (br s, 1H, C11-CH=) and 9.67 (s, 1H, C17β-CHO). Anal. Calcd. for $C_{24}H_{36}O_4Si \cdot \frac{1}{6}hexane$ ($C_6H_{14}$): C, 69.67; H, 8.60. Found: C, 69.07; H, 8.79.

Step 2. 3,3-Ethylenedioxy-17α-trimethylsilyloxy-20ξ-hydroxy-21-methyl-19-norpregna-5(10),9(11)-diene (22).

In oven-dried glassware, the crude aldehyde (21) (30.35 g, 72.8 mmol) was dissolved in THF (432 mL, distilled from LAH) and cooled to 0° C. under nitrogen. Ethyl magnesium bromide (37 mL, 3 M in ether) was transferred via double-tipped needles to an additional funnel and then slowly added to the reaction mixture. The mixture was stirred at room temperature and monitored by TLC (2% acetone/$CH_2Cl_2$).

Reaction was complete in 3 hr, so mixture was cooled to 0° C. and saturated NH$_4$Cl solution (310 mL) was added slowly. THF was evaporated in vacuo. The mixture was extracted with ether (3×) and brine, and dried over Na$_2$SO$_4$. The solvent was evaporated, yielding 31.03 g of the crude 20-hydroxy product (22) as a foam in 95% yield. This material was directly used-without further purification in the subsequent reaction. FTIR (KBr, diffuse reflectance) $v_{max}$ 3503 and 2951 cm$^{-1}$. NMR (CDCl$_3$) δ 0.16 (s, 9H, Si(CH$_3$)$_3$), 0.75, 0.78 (2s, C18-CH$_3$ for 20α- and 20β-isomers), 1.01 (t, J=6 Hz, 3H, C21-CH$_3$), 3.98 (s, 4H, 3-OCH$_2$CH$_2$O) and 5.60 (br s, 1H, C11-CH=). MS (I) m/z (relative intensity): 447(M$^+$, 4.2), 418(17), 387(32), 356 (70) and 297 (100).

Step 3. 3,3-Ethylenedioxy-17α-trimethylsilyloxy-21-methyl-19-norpregna-5(10), 9(11)-dien-20-one (23):

The C-20 alcohol (22) (25.34 g, 56.7 mmol) was dissolved in acetone and stirred at 0° C. in an ice bath. Jones' reagent (42 mL) was added slowly to the above solution until the reaction mixture remained an orange color. Then isopropanol was added until the green color persisted. Ice H$_2$O (2 L) was added and stirred well. The mixture was extracted with EtOAc (3×), washed with H$_2$O (2×), saturated NaHCO$_3$, H$_2$O and brine. The combined organic layers were dried over Na$_2$SO$_4$ and concentrated in vacuo to give 18.83 g of the crude ketone (23). Flash chromatography using 1% ether/CH$_2$Cl$_2$ gave 7.3 g of the purified product as a foam in 29% yield. NMR (CDCl$_3$) δ 0.10 (s, 9H, Si(CH$_3$)$_3$), 0.51 (s, 3H, C18-CH$_3$), 1.04 (t, J=7 Hz, 3H, C21-CH$_3$), 3.99 (s, 4H, C3-ketal) and 5.61 (br s, 1 H, C11-CH=).

Step 4. 3,3-Ethylenedioxy-5α,10α-epoxy-17α-trimethylsilyloxy-21-methyl-19-norpregna-9(11)-en-20-one (24):

Hexafluoroacetone trihydrate (2.20 g, 10 mmol) and CH$_2$Cl$_2$ (23 mL) were stirred vigorously under nitrogen in an ice bath. Solid Na$_2$HPO$_4$ (0.78 g, 6.5 mmol) was added. 30% Hydrogen peroxide (1.50 mL) was poured into the mixture. It was stirred 30 min. A chilled solution of the C-20 ketone (23) (3.00 g, 6.75 mmol) in CH$_2$Cl$_2$ (23 mL) was added slowly with a pipette. The reaction mixture was stirred overnight in the cold room at 4° C. TLC (2% acetone/CH$_2$Cl$_2$) showed reaction complete in the morning. CH$_2$Cl$_2$ was added to the reaction mixture and it was washed with Na$_2$SO$_3$ (2×), saturated NaHCO$_3$, and brine. Organic extracts were dried over Na$_2$SO$_4$ and concentrated to give 2.98 g of a 77:25 mixture of the crude a: β-epoxide (24) according to NMR in 95% yield. This mixture was directly used in the subsequent reaction without further purification. NMR (CDCl$_3$) δ 0.10 (s, 9H, Si(CH$_3$)$_3$), 0.51 (s, 3H, C18-CH$_3$), 1.05 (t, J=6 Hz, 3H, C21-CH$_3$), 3.94 (s, 4H, 3-OCH$_2$CH$_2$O—), 5.90 (br s, 1H, C11-CH= for β-epoxide) and 6.09 (br s, 1H, C11-CH= for α-epoxide).

Step 5. 3,3-Ethylenedioxy-5α-hydroxy-11β-[4-(N,N-dimethylamino)phenyl]-17α-trimethylsilyloxy-21-methyl-19-norpregn-9(10)-en-20-one (25):

Mg (2.80 g, 116.2 mmol), which was washed with 0.1 N HCl, then H$_2$O and acetone and dried in vacuo, was weighed into dry round-bottomed flask equipped with a reflux condenser. A small crystal of iodine was added and the system was flushed with nitrogen and flame-dried. The flask was cooled to room temperature and 68.5 mL of THF distilled from LAH was added via syringe. 1,2-Dibromoethane (approx. 0.5 mL) was added and the mixture was stirred at room temperature. After bubbling began and the color of I$_2$ disappeared, a solution of 4-bromo-N,N-dimethylaniline (20.43 g, 102.1 mmol) in THF (34 mL) was added via syringe. The mixture was stirred until most the Mg had reacted. Copper (I) chloride (1.13 g, 114.2 mmol) was added as a solid and stirred for 20 min. The crude epoxide (24) (7.33 g, 15.91 mmol) in THF (49 mL) was then added using a syringe. The reaction mixture was stirred at room temperature for 30 min, at which time the reaction was complete by TLC (2% acetone/CH$_2$Cl$_2$). Saturated NH$_4$Cl solution (25 mL) was added and stirred for 30 min while air was pulled through by slight vacuum. The mixture was diluted with H$_2$O, extracted with CH$_2$Cl$_2$ (3×), washed with H$_2$O (2×) and brine, dried over Na$_2$SO$_4$, and evaporated under reduced pressure. The residue was purified by flash chromatography using 3% acetone/CH$_2$Cl$_2$) to afford 4.27 g of the pure product (25) in 46.1% yield. IR (KBr, diffuse reflectance) $v_{max}$ 3531, 2940, 1708, 1614, and 1518 cm$^{-1}$. NMR (CDCl$_3$) δ 0.09 (s, 9H, Si(CH$_3$)$_3$), 0.19 (s, 3H, C18-CH$_3$), 1.02 (t, J=7 Hz, 3H, C21-CH$_3$), 2.88 (s, 6H, N(CH$_3$)$_2$), 3.99 (m, 4H, C3-OCH$_2$CH$_2$O—), 4.26 (br d, 1 H, C11α-CH), 6.85 (dd, J=41 Hz, J'=10 Hz, 4H, aromatic-CH). MS (EI) m/z (relative intensity): 581 (M$^+$, 46), 563(34), 391 (37), 134(65) and 121 (100).

Step 6. 3,3-Ethylenedioxy-5α,17α-dihydroxy-11β-(4-N,N-methylaminophenyl)-21-methyl-19-norpregn-9(10)-en-20-one (26):

Tetrabutylammonium fluoride (18.1 mL, 1 M in THF) was stirred with molecular sieves under nitrogen for approx. 1 hr. The 17α-trimethylsilyloxy compound (25) (3.50 g, 6.0 mmol) in THF (21 mL) which was distilled from LAH, was added to the mixture and stirred at room temperature for 1 hr. H$_2$O was added and the THF was removed in vacuo. EtOAc was added to the mixture and was filtered through Celite. The product was extracted with EtOAc, washed with H$_2$O and brine, and dried over Na$_2$SO$_4$. Evaporation of the solvent gave 3.19 g of the crude 5α,17α-dihydroxy compound (26) in quantitative yield. This material was directly used without further purification in the subsequent reaction. IR (KBr, diffuse reflectance) $v_{max}$ 3506, 2934, 1704, 1613 and 1518 cm$^{-1}$. NMR (CDCl$_3$) δ 0.36 (s, 3H, C18-CH$_3$), 1.03 (t, J=7 Hz, 3H, C21-CH$_3$), 2.84 (s, 6H, N(CH$_3$)$_2$), 4.00 (s, 4H, C3-OCH$_2$CH$_2$O—), 4.16 (d, 1H, C11α-CH) and 6.85 (dd, J=29 Hz, J'=10 Hz 4H, aromatic-CH's). MS (EI) m/z (relative intensity): 509 (M$^+$, 20), 491 (11), 134(27) and 121 (100)

Step 7. 17α-Hydroxy-21-methyl-11β-[4-(N,N-dimethylamino)phenyl]-19-norpregna-4,9-diene-3,20-dione (27):

The 5α,17α-dihydroxy compound (26) (3.19 g, 6.26 mmol) was dissolved in THF (25 mL). Glacial acetic acid (75 mL) was added, followed by H$_2$O (25 mL). The mixture was stirred overnight at room temperature at which time TLC (10% acetone/CH$_2$Cl$_2$) showed reaction complete in the morning. The THF and acetic acid were removed under high vacuum and the residue was extracted with EtOAc (3×) and washed with saturated NaHCO$_3$ solution, H$_2$O and brine. The combined organic extracts were dried over Na$_2$SO$_4$ and concentrated in vacuo to afford 2.81 g of the crude diene dione 17-alcohol (27) as a foam in 100% yield. IR (KBr, diffuse reflectance) $v_{max}$ 3419, 2942, 1705, 1655, 1612 and 1581 cm$^{-1}$. NMR (CDCl$_3$) δ 0.40 (s, 3H, C18-CH$_3$), 1.02 (t, J=7 Hz, 3H, C21-CH$_3$), 2.88 (s, 6H, N(CH$_3$)$_3$), 4.37 (br d, 1H, C11α-CH), 5.76 (s, 1H, C4-CH=F) and 6.85 (dd, J=24 Hz, J'=9 Hz, 4H, aromatic-CH's), MS (EI) m/z (relative intensity): 447 (M$^+$, 25), 211 (4), 134(23) and 121 (100).

Step 8 Preparation of the Target Compound (28):

In oven-dried glassware, trifluoroacetic anhydride (18.75 mL) and glacial acetic acid (7.2 mL) were added to CH$_2$Cl$_2$ (50 mL) and stirred for 30 min. under nitrogen at room temperature. Solid p-toluenesulfonic acid monohydrate (1.19 g) was added and the mixture was cooled to 0° C. in an ice bath. The 17-alcohol (27) (2.77 g, 6.17 mmol) in $CH_2Cl_2$ (22 mL) was added and the reaction mixture was stirred at 0° C. for 1.5 hr. Saturated $K_2CO_3$ was carefully added dropwise until the bubbling of $CO_2$ ceased. The mixture was diluted with $H_2O$, extracted with $CH_2Cl_2$ (3×), and washed with $H_2O$ (2×) and brine. The organic layers were filtered through $Na_2SO_4$ and concentrated under reduced pressure to yield 3.12 g of the crude product (28). The crude acetate was purified by flash chromatography using 3.5% acetone/$CH_2Cl_2$ and fractions >98% pure by HPLC (70% MeOH/30% $H_2O$/0.03% TEA) were triturated in heptane to form 600 mg of a pale yellow amorphous solid in 20% yield. Analysis of the solid by HPLC using the same eluent at A=260 nm indicated it to be 100% purity: m.p.= 125–133° C.; $[\alpha]^{27}D$=+163.16° (c=1.0, $CHCl_3$). FTIR (KBr, diffuse reflectance) $v_{max}$ 1732, 1713 and 1662 $cm^{-1}$. MS (EI) m/z (relative intensity): 489 ($M^+$, 27), 372(4), 251 (4), 134(14) and 121 (100). NMR ($CDCl_3$), δ 0.330 (s, 3H, C18-$CH_3$), 1.039 (t, 3=7.2 Hz, 3H, C21-$CH_3$), 2.112 (s, 3H, C17α-OAc), 2.904 (s, 6H, N($CH_3$>), 4.380 (d, J=6.6 Hz, 1H, C11α-CH), 5.773 (s, 1H, C4-CH=), 6.635 (d, J=8.4 Hz, 2H, 3',5' aromatic-CH's) and 6.978 (d, J=8.7 Hz, 2H, 2',6' aromatic-CH's). Anal. Calcd. for $C_{31}H_{39}O_4N$: C, 76.04; H, 8.03; N, 2.86. Found: C, 76.03; H, 8.05; N, 2.91.

Example 7

This example illustrates the preparation and properties of 17α-acetoxy-21-hydroxy-11β-[4-(N,N-dimethylamino)phenyl]-19-norpregna-4,9-diene-3,20-dione (41).

Step 1. Synthesis of 17α,21-(1-Ethoxyethylidenedioxy)-11β-[4-(N,N-dimethylamino)phenyl]-19-norpregna-4,9-diene-3,20-dione (18):

A solution of the 17α,21-diol (9) (1.0 g, 1.11 mmol), triethyl orthoacetate (2 mL, 10.9 mmol) and pyridinium p-toluenesulfonate (0.1 g, 0.4 mmol) in benzene (50 mL) was heated to reflux under nitrogen in a system equipped with a Dean-Stark trap for removal of water. After 1 hr of reflux, monitoring by TLC (5% acetone/$CH_2Cl_2$) indicated a complete reaction. Pyridine (1 mL, 12.4 mmol) was added and the reaction mixture concentrated in vacuo under a stream of nitrogen at 40–50° C. The residue was diluted with water (approx. 100 mL) and extracted with $CH_2Cl_2$ (3×). The combined organic extracts were washed with $H_2O$ (2×) and brine (1×), filtered through $Na_2SO_4$ and concentrated in vacuo. Purification of the residue via Flash chromatography (3% acetone/$CH_2Cl_2$) followed by crystallization from ether/pentane gave 0.81 g of the intermediate ethoxyethylidenedioxy compound (18) as a white amorphous solid in 70% yield. FTIR (KBr, diffuse reflectance) $v_{max}$ 2947, 1716, 1660, 1614, 1599 and 1518 $cm^{-1}$. MS(FI) m/z (relative intensity): 519 ($M^+$, 65), 308 (23), 134(31) and 121 (100).

NMR ($CDCl_3$) δ 0.33 (s, 3H, C18-$CH_3$), 1.13 (t, J=7.5 Hz, 3H, $OCH_2CH_3$), 1.60 (s, 3H, ethylidenedioxy $CH_3$), 2.90 (s, 6H, $NMe_2$), 3.59 (q, J=7.5 Hz, 2H, $OCH_2CH_3$), 4.13 (dd, $J_1$=25.8, $J_2$=17.4 Hz, 2H, C21-$CH_2$), 4.43 (br. d, J=8.4 Hz, 1H, C11α-CH), 5.80 (s, 1H, C4-CH=), 6.67 (d, J=9 Hz, 2H, 3'. 5' aromatic-CH's) and 7.07 (d, J=9 Hz, 2H, 2',6' aromatic-CH's). Anal. Calcd. for $C_{32}H_{41}NO_5$: C, 73.96; H, 7.95; N, 2.70. Found: C, 73.70; H, 7.89; N, 2.73.

Step 2. Preparation of the Target Compound (41):

Under nitrogen, a mixture of the crude ethoxyethylidenedioxy compound (18, 0.56 g., 1.11 mmol), 0.2 M NaOAc (3 mL, 0.3 mmol) in methanol (30 mL) was heated to reflux. Monitoring by TLC (5% acetone/$CH_2Cl_2$) indicated a complete reaction in 3.5 hours. The methanol was removed in vacuo under a stream of nitrogen, the residue diluted with water (~50 mL) and extracted with $CH_2Cl_2$ (3×). The organic fractions were combined, washed with $H_2O$ (2×) and brine (1×), dried over $Na_2SO_4$, filtered and concentrated in vacuo to give 0.56 g of the crude 21-ol, 17α-acetate (41) as a foam. Purification of this material via flash chromatography (7.5% acetone/$CH_2Cl_2$) followed by trituration with ether/pentane gave 0.32 g of the target compound, 21-OH, 17α-acetate as an off-white solid in 84% yield; m.p.= 205–210° C. The NMR indicated this product contains 5.3% of the 17α-OH, 21-OAc (8) isomer as a contaminant. Compound 41 is extremely labile to base, rapidly converting to compound 8 under the reverse-phase conditions (MeOH/$H_2O$/$Et_3N$) normally employed for HPLC analysis of related compounds. This transesterification occurs at an appreciate rate even when the solvent system is buffered at pH 7.0 with phosphoric acid. The purity of the acetate mixture (8 and 41) was ascertained at >99% by normal phase HPLC analysis (Waters Associates μPorasil Silica using $CH_3CN$/$CH_2Cl_2$ (40:60) with a flow rate of 2 mL/min at λ=302 nm). Under these conditions, the two acetates have an identical retention time of 4.69 min. MS (EI) m/z (relative intensity): 491 ($M^+$, 45), 431 (32), 134 (7) and 121 (100). FTIR (KBr, diffuse reflectance) $v_{max}$ 3362, 2949, 2886, 1730, 1656, 1611, 1597 and 1518 $cm^{-1}$. NMR (300 MHz, $CDCl_3$) δ 0.37 (s, 3H, C18-$CH_3$), 2.11 (s, 3H, C17α-OAc), 2.90 (s, 6H, $NMe_2$), 4.23 (d, J=17.4, 1H, C21-$CH_2$), 4.36 (d, J=17.4 Hz, 1H, C21-$CH_2$), 4.39 (d, J=6 Hz, 1H, C11α-CH), 5.78 (s, 1H, C4-CH=), 6.63 (d, J=8.7 Hz, 2H, 3',5' aromatic-CH's), 6.97 (d, J=8.7 Hz, 2',6' aromatic-CH's). The presence of the 17α-OH, 21-OAc isomer (8) to the extent of 5.3% could be detected by the appearance of two doublets, one at 4.88 and the other at 5.11, both with J=18.3 Hz.

Example 8

This example illustrates the preparation and properties of 17α-acetoxy-21-(3'-cyclopentylpropionyloxy)-11β-[4-(N,N-dimethylamino)phenyl]-19-norpregnadiene-3,20 dione (40).

Step 1. 17α-Hydroxy-21-(3'-cyclopentylpropionyloxy)-11β-[4-(N,N-dimethylamino)phenyl]-19-norpregna-4,9-diene-3,20-dione (39):

Under nitrogen, a solution of the diol (9, 0.5 g, 1.11 mmol) in dry benzene (20 mL) and pyridine (1 mL, 12.4 mmol) was treated with 3-cyclopentylpropionyl chloride (0.2 mL, 1.31 mmol). The reaction mixture was stirred at room temperature and monitored by TLC (10% acetone/$CH_2Cl_2$) which indicated about a 50% reaction after 1 hr. Additional cypionyl chloride (0.2 mL, 1.31 mmol) was introduced and the reaction was stirred a further 1 hr. at room temperature. Analysis by TLC at that time indicated a complete reaction. The reaction mixture was concentrated in vacuo under a stream of nitrogen and the residue was diluted with water. The mixture was extracted with $CH_2Cl_2$ (3×). The organic fractions were combined, and washed with $H_2O$ (2×), brine (1×), dried ($Na_2SO_4$), filtered and concentrated in vacuo to give 0.63 g of the residue as an oil. Purification of this material by flash chromatography using 7% acetone/$CH_2Cl_2$ gave 0.51 g of the 17αhydroxy 21-cypionate (39) as an oil. Trituration of this material with ether afforded 0.43 g of a pure solid (39) in 67% yield; m.p.=137–140° C. MS (EI) m/z relative intensity: 573 ($M^+$, 46), 431 (11), 134 (15) and 121 (100). FTIR (KBr, diffuse reflectance) $v_{max}$ 3509, 2944, 1726, 1643, 1613 and 1520 $cm^{-1}$. NMR ($CDCl_3$) δ 0.38 (s, 3H, C18-$CH_3$), 2.90 (s, 6H $NMe_2$), 4.4 (br d, J=6 Hz, C11α-CH), 5.03 (dd, $J_1$=31.5 Hz, $J_2$=18 Hz, 2H, C21-CH$_2$—), 5.76 (s, 1H, C4-CH=), 6:67 (d, J=9 Hz, 2H, 3',5' aromatic-CH's) and 7.07 (d, J=9 Hz, 2H, 2',6' aromatic-CH's).

Step 2. Preparation of the Target Compound (40):

Under nitrogen, trifluoroacetic anhydride (2.0 mL, 14.2 mmol), glacial acetic acid (0.8 mL, 13.99 mmol) and dry CH$_2$Cl$_2$ (10 mL) were combined and stirred at room temperature for ½ hr. The mixture was cooled to 0° C. in an ice bath and p-toluenesulfonic acid monohydrate (1 g, 0.53 mmol) was added to it. A solution of the 17α-hydroxy-21-cypionate (39, 0.4 g, 0.7 mmol) in dry CH$_2$Cl$_2$ was then introduced and the reaction mixture stirred at 0° C. and monitored by TLC (5% acetone/CH$_2$Cl$_2$). After 2 hr. at 0° C. it became apparent that this particular reaction was proceeding at a much slower rate than observed for other 17α-acetylations. The ice-bath was removed and the reaction was then stirred and monitored by TLC at room temperature. After 6 hr. at room temperature, TLC indicated ~75% conversion. The reaction mixture was then diluted with H$_2$O (10 mL), neutralized with concentrated NH$_4$OH solution and extracted with CH$_2$Cl$_2$ (3×). The organic fractions were combined, washed with H$_2$O (2×), brine (1×), filtered through Na$_2$SO$_4$ and concentrated in vacuo to give 0.53 g of the residue as an oil. Purification via flash chromatography (5% acetone/CH$_2$Cl$_2$) gave 0.21 g of the pure 17-acetate (40) as a foam. This material was dissolved in EtOH (~2 mL) and precipitated as a yellow amorphous solid upon dilution with H$_2$O, sonication and cooling to give 0.21 g of the pure solid (40) in 28% yield: m.p. softens at 96° C. MS (EI) m/z (relative intensity): 615 (M$^+$, 80), 555 (10), 372 (18), 134 (14) and 120 (100) FTIR (KBr, diffuse reflectance) $v_{max}$ 2950, 2868, 1737, 1664, 1612 and 1519 cm$^{-1}$. NMR (CDCl$_3$) δ 0.43 (s, 3H, C18-CH$_3$), 2.11 (s, 3H, OAc), 2.91 (s, 6H, NMe$_2$), 4.42 (br d, J=6 Hz, C11α-CH), 4.84 (dd, $J_1$=29 Hz, $J_2$=17 Hz, 2H, 21-CH$_2$-OCyp), 5.80 (s, 1H, C4-CH=), 6.70 (d, J=9 Hz, 2H, 3',5' aromatic-CH's) and 7.07 (d, 9 Hz, 2H, 2',6' aromatic-CH's). Anal. Calcd. for C$_{38}$H$_{49}$NO$_6$·¼C$_5$H$_{12}$: C, 74.38; H, 8.27; N, 2.21. Found: C, 74.39; H, 8.28; N, 2.20.

Example 9

This example illustrates the preparation and properties of 17α-acetoxy-21-methoxy-11β-(4-N,N-dimethylaminophenyl)-19-norpregna-4,9-diene-3,20-dione (38).

Step 1. 17α-Bromomethyldimethylsilylol-17β-cyano-3,3-ethylenedioxyestra-5(10),9(11)-diene (29):

Under nitrogen and anhydrous conditions, a solution of the cyanohydrin ketal (1, 35.45 g (104 mmol)), dimethylaminopyridine (6.33 g, 52 mmol) and dry Et$_3$N (21.7 mL, 155 mmol) in dry THF (300 mL) was stirred at room temperature overnight. After that time, TLC using 2% acetone/CH$_2$Cl$_2$ indicated approximately 95% completion of reaction. The mixture was diluted with hexanes (~250 mL), stirred at 10 minutes, filtered through Celite and concentrated in vacuo to give the residue (46.38 g) evidenced by TLC to consist of a mixture of the expected product (29) plus DMAP hydrochloride salt. This material was purified via silica flash chromatography using ether as eluent to give the silyl ether (29, 35.53 g, 69.5%). This material was used directly in the subsequent reaction without further purification or characterization.

Step 2. 17α-Hydroxy-21-bromo-19-norpregna-4,9-diene-3,20-dione (30):

Under nitrogen, a solution of the crude 17α-bromo compound (29, 35.53 g, 72 mmol) in dry THF (1200 mL) was cooled to −78° C. in a dry ice/isopropanol bath and treated dropwise with a 1.5 M solution of lithium diisopropylamide in cyclohexane (105 mL, 157.5 mmol) over a period of ~15 minutes. This mixture was stirred at −78° C. for 1 hr. Aqueous HBr (4.45 M, 350 mL, 1.56 mol) was added slowly and the mixture allowed to warm to room temperature, and stirred for 30 min. A TLC using 5% acetone/CH$_2$Cl$_2$ taken at that time indicated an incomplete reaction (3 products). The mixture was then stirred again at room temperature overnight. Analysis by TLC at that time indicated formation of 1 major product. The reaction mixture was then cooled in an ice bath, carefully neutralized with concentrated NH$_4$OH solution (105 mL) and extracted with EtOAc (3×). The organic fractions were washed with H$_2$O (2×), combined, dried over Na$_2$SO$_4$ and concentrated in vacuo. Trituration of the solid residue with ether gave the 17α-hydroxy-21-bromo compound (30, 17.14 g) in 60.4% yield as an off-white powder. FTIR (KBr, diffuse reflectance) $v_{max}$ 3476, 2948, 1726, 1644, 1598 and 1572 cm$^{-1}$. NMR (DMSO-d$_6$+CDCl$_3$) δ 0.70 (s, 3H, C18-CH$_3$), 4.43 (dd $J_1$=27 Hz, $J_2$=15 Hz, 2H, C21-FU CH$_2$Br) and 5.60 (s, 1H, C4-CH=). MS (EI) m/z (relative intensity): 392(M$^+$, 11), 313 (100), 159 (77) and 91 (71).

Step 3. 17α-hydroxy-21-acetoxy-19-norpregna-4,9-diene-3,20-dione (31):

The 21-bromo-17α-hydroxy compound (30, 6.57 g, 16.7 mmol) was added to a 3-neck 1 L flask which had been purged with nitrogen, equipped with a condenser and a magnetic stir bar. Acetone (500 mL) was added, followed by potassium acetate (17.3 g, 176.2 mmol). The suspension was stirred magnetically and brought to reflux under nitrogen. Several minutes after reaching reflux, a solution formed. After ½ hr, the reaction was examined by TLC (silica: 5% acetone in CH$_2$Cl$_2$). All starting material had been converted to the product. The reaction was allowed to cool to room temperature, precipitated KBr was removed by filtration, and the solution evaporated in vacuo. The crude product (6.63 g) was obtained, taken up in CH$_2$Cl$_2$ and washed with H$_2$O (2×), followed by brine (1×). The combined organic extracts were filtered through Na$_2$SO$_4$ and evaporated in vacuo to obtain 6.41 g of the 21-acetoxy-17α-hydroxy compound (31) in 99% yield. FTIR (KBr, diffuse reflectance) $v_{max}$ 3474, 2946, 1744, 1720, 1645 and 1607 cm$^{-1}$. NMR (CDCl$_3$) δ 0.80 (s, 3H, C18-CH$_3$), 2.13 (s, 3H, C21-OAc), 5.0 (dd, 2H C21-CH$_2$, $J_1$=24 Hz, $J_2$=9 Hz) and 5.68 (s, 1H, C4-CH=). MS (EI) m/z (relative intensity): 372 (M$^+$, 55), 312 (68), 271 (69), 253 (97) and 213 (100).

Step 4. 17α,21-Dihydroxy-19-norpregna-4,9-diene-3,20-dione (32):

A suspension of the 21-acetoxy-17α-hydroxy compound (31, 9.43 g, 25.32 mmol) in MeOH (800 mL) was deoxygenated by purging with nitrogen for ½ hr. A similarly deoxygenated 0.5 M solution of KHCO$_3$ (78 mL, 39 mmol) was added to the suspension and the mixture brought to reflux under nitrogen. Almost immediately after addition of KHCO$_3$, a solution formed. After ⅔ hr at reflux, the reaction mixture was examined by TLC (silica; 5% isopropanol in CH$_2$Cl$_2$). The reaction was >95% complete. The reaction was allowed to cool to room temperature, then neutralized by addition of 2.24 mL (39 mmol) of glacial acetic acid. CH$_3$OH was evaporated in vacuo. The residue was taken up in 500 mL of CH$_2$Cl$_2$ and washed with H$_2$O (3×). Combined organic extracts were dried by filtration through Na$_2$SO$_4$, and evaporated in vacuo to recover an amorphous yellow material (32, 8.50 g) in 100% yield. This material was readily crystallized from hot acetone (100 mL). The crystals were collected on a Buchner funnel, triturated well with ether, and air dried. It gave 4.82 g of 32 in 57.6% yield. Additional material was obtained by chromatography of the mother liquors. FTIR (KBr, diffuse reflectance) $v_{max}$ 3517, 2944, 1714, 1657, 1598 and 1578 cm$^{-1}$. NMR (CDCl$_3$) δ 0.82 (s, 3H, C18-CH$_3$), 4.53 (dd, 2H, C21-CH$_2$—, J$_1$=42H, J$_2$=21 Hz), 5.72 (s, 1H, C4-CH=). MS (EI) m/z (relative intensity): 330 (M$^+$, 100), 253 (83), 228 (98), 213 (95) and 91 (91).

Step 5. 3,20-bis-Ethylenedioxy-17α,21-dihydroxy-19-norpregna-5(10),9(11)-diene (33):

A quantity of 3.8 g (11.5 mmol) of the 17α,21-dihydroxy compound (32, 200 mg, 1.05 mmol) of p-toluenesulfonic acid, and 300 mL of ethylene glycol were placed in a 500 mL of round bottom flask equipped with a vacuum distillation head. The mixture was heated in an oil bath and the temperature was maintained at 100–105° C. Ethylene glycol was distilled in vacuo (5 mm Hg), at a temperature of 75° C. The reaction continued for 3 hr. and was allowed to cool to room temperature. Saturated NaHCO$_3$ solution was added and the mixture extracted with CH$_2$Cl$_2$. The organic extract was washed with H$_2$O (1×) and brine (1×). The organic extracts were dried by filtration through Na$_2$SO$_4$ and evaporated in vacuo. Crude diketal (6.2 g) was obtained. Examination of this material by TLC (silica; 5% isopropanol in CH$_2$Cl$_2$) indicated almost all starting material had been converted to the diketal as a major product with R$_f$=0.38, an intermediate product as a minor product with R$_f$=0.63, or a third material with R$_f$=0.63 which increases if the reaction is allowed to go too long. The crude material was crystallized from 30 mL of hot CH$_2$Cl$_2$. The crystals were collected on a Buchner funnel triturated well with ether and air dried to give 3.01 g of 33 in 62.5% yield. This product was considered sufficiently pure to be carried out on the next reaction. Highly pure material was obtained by flash column chromatography using 5% isopropanol in CH$_2$Cl$_2$. FTIR (KBr, diffuse reflectance) $v_{max}$ 3418 and 2896 cm$^{-1}$; no evidence of any absorptions in the CO region. NMR (CDCl$_3$) δ 0.8 (s, 3H, C18-CH$_3$), 3.88 (m, 10H, C3- and C20-OCH$_2$CH$_2$O, C21-CH$_2$), 4.0 (s, 4H, C3-OCH$_2$CH$_2$O—), 5.58 (br s, 1H, C11-CH=). MS (EI) m/z (relative intensity): 418 (M$^+$, 2), 387(1.4), 297 (3) and 103 (100).

Step 6. 3,20-bis(Ethylenedioxy)-17α-hydroxy-21-methoxy-19-norpregna-5(10),9(11)-diene (34):

To a solution of the 17α,21-dihydroxy diketal (33, 2.0 g, 4.78 mmol) in CH$_2$Cl$_2$ (250 mL) was added 7.20 g (33.6 mmol) of solid 1,8-bis(dimethylamino)naphthalene ("proton sponge") followed by 4.97 g (33.6 mmol) of trimethyloxonium tetrafluoroborate. The heterogeneous mixture was stirred in an ice bath under nitrogen, and allowed to come to room temperature as the bath melted. After 2.5 hr., TLC (silica; 5% isopropanol in CH$_2$Cl$_2$) indicated the reaction was complete. The mixture was transferred to a separatory funnel and washed with ice cold 1N HCl (250 mL), saturated NaHCO$_3$ solution and H$_2$O. The combined organic extracts (3×) were dried by filtration through solid Na$_2$SO$_4$ and evaporated in vacuo. Examination by TLC indicated the resulting yellow oil was heavily contaminated with a base. The oil was taken up in CH$_2$Cl$_2$ (75 mL) and stirred vigorously with Dowex 50×8–200 (80 mL, dry volume) for 15 minutes. This effectively removed all the remaining proton sponge. The mixture was filtered and the Dowex washed well with CH$_2$Cl$_2$. Methylene chloride was evaporated in vacuo and the residue dried overnight under high vacuum to give a pale foam, 1.63 g in 79% yield. This material was sufficiently pure to carry on to the next reaction. Highly pure material was obtained by flash column chromatography eluting with 20% EtOAc in CH$_2$Cl$_2$, followed by crystallization from a small amount of methanol with water. FTIR (KBr, diffuse reflectance) $v_{max}$ 3510, 2898, 1720, 1450 and 1370 cm$^{-1}$. NMR (CDCl$_3$) δ 0.8 (s, 3H, C18-CH$_3$), 3.43 (s, 3H, C21-OCH$_3$), 3.67 (dd, 2H, C21-CH$_2$, J$_1$=18 Hz, J$_2$=10.5 Hz), 4.0 (s, 4H, C3-OCH$_2$CH$_2$O), 4.09 (m, 8H, C3- and C20-OCH$_2$CH$_2$O) and 5.58 (br s, 1H, C11-CH=). MS (EI) m/z (relative intensity): 432 (M$^+$, 1.4), 387 (3), 297 (2.6) and 117 (100).

Step 7. 3,20-bis-(Ethylenedioxy)-5α,10α-epoxy-17α-hydroxy-21-methoxy-19-norpregn-9(11)-ene (35):

Solid Na$_2$HPO$_4$ (0.45 g, 3.14 mmol) and 30% H$_2$O$_2$ (0.84 mL) were added to a vigorously stirred solution of hexafluoroacetone trihydrate (1.24 g, 0.79 mL, 5.7 mmol) in CH$_2$Cl$_2$ (13 mL). The mixture was stirred under nitrogen in an ice bath for ½ hr. A chilled solution of the 21-methoxy-17α-hydroxy compound (34, 1.63 g, 3.77 mmol) in CH$_2$Cl$_2$ (13 mL) was added slowly via pipette. The reaction was transferred to the cold room and allowed to stir overnight at 4° C. The next morning, examination by TLC (silica; 25% EtOAc in CH$_2$Cl$_2$) indicated all starting material had been converted to a mixture of two more polar components. Methylene chloride (25 mL) was added and the mixture washed with 10% Na$_2$SO$_3$ (2×), saturated NaHCO$_3$ solution and H$_2$O; The combined organic extracts (3×) were dried by filtration through Na$_2$SO$_4$, evaporated in vacuo and dried several hours under high vacuum to give 1.86 g of an amorphous solid in quantitative yield, which consists of at least, 4 epoxides evidenced by $^1$H NMR.

NMR (CDCl$_3$) δ 0.77 (s, 3H, C18-CH$_3$), 3.40 (s, 0.3H, C21-OCH$_3$), 3.60 (dd, C21-CH$_2$, J$_1$=15 Hz, J$_2$=9 Hz), 3.9 (s, C3-OCH$_2$CH$_2$O), 4.0 (m, C3- and C20-OCH$_2$CH$_2$O), 5.83 (br s, C11-CH= of β-epoxide) and 6.03 (br s, C11-CH= of α-epoxide).

Step 8. 3,20-bis-(Ethylenedioxy)-5α,17α-dihydroxy-11β-[4N,N-dimethylamino)phenyl]-21-methoxy-19-norpregn-9(10)-ene (36):

A 100 mL round bottom flask was equipped with a magnetic stirrer, a reflux condenser and a rubber septum and flame dried under a stream of N$_2$. Magnesium (0.50 g, 20.7 mmol) was added, followed by a crystal of iodine, dry THF (20 mL) and 1–2 drops of dibromoethane. The mixture was heated in a warm H$_2$O bath under N$_2$ for approximately ½ hr, but there were no observable change. A solution of 4-bromo-N,N-dimethylaniline (3.77 g, 18.85 mmol) in THF (10 mL) was added via syringe over a period of several minutes and rinsed with an additional THF (10 mL). There was evidence of reaction immediately as the magnesium turned dark. After stirring for 1.5 hr., solid copper(I) chloride (0.21 g, 2.07 mmol), was added and the reaction mixture stirred another ½ hr. Crude epoxide (assumed 3.77 mmol from the previous reaction) was added as a solution in THF (5 mL) and rinsed in with an additional THF (5 mL). The reaction was allowed to stir 1 hr at room temperature and then quenched by the addition of saturated ammonium chloride (50 mL). Air was drawn through the mixture with vigorous stirring for ½ hr. Ether was added and the layers allowed to separate. The organic solution was washed with 10% NH$_4$Cl (2×), 2 N NH$_4$OH (3×) and brine (1×). Organic fractions were combined, dried over Na$_2$SO$_4$, filtered and evaporated in vacuo to obtain 3.37 g of crude material. Analysis by TLC (silica; 20% acetone in CH$_2$Cl$_2$) indicated formation of a new more polar compound. Flash column chromatography (silica; 20% acetone in CH$_2$Cl$_2$), yielded 0.890 g of the pure product in 63% yield, assuming 66% of the starting material was the desired 5α,10α-epoxide). FTIR (KBr, diffuse reflectance) $v_{max}$ 3494, 2936, 1612 and 1518 cm$^{-1}$. NMR (CDCl$_3$) δ 0.47 (s, 3H, C18-CH$_3$), 2.90 (s, 6H, —N(CH$_3$)$_2$), 3.43 (s, 3H, C21-OCH$_3$), 4.03 (m, 10H, C3- and C20-OCH$_2$CH$_2$O— and C21-CH$_2$), 6.67 (d, 2H, aromatic-CH's, J=9 Hz), and 7.10 (d, 2H, aromatic-CH's, J=9 Hz). MS (EI) m/z (relative intensity): 569 (M$^+$, 4), 551 (11), 506 (4), 134 (27), 121 (49) and 117 (100). Anal. Calcd. for C$_{33}$H$_{47}$O$_7$N: C, 69.57; H, 8.31; N, 2.46. Found: C, 69.40; H, 8.19; N, 2.53.

Step 9. 17α-Hydroxy-21-methoxy-11β-[4-(N,N-dimethylamino)phenyl-19-norpregna-4,9-diene-3,20-done (37):

The diketal (36, 1.81 g, 3.18 mmol) was dissolved in THF (20 mL) and the solution stirred magnetically at room temperature under nitrogen. Trifluoroacetic acid (60 mL) was added followed by H$_2$O (20 mL). After 1 hr., the reaction was examined by TLC (silica; 20% acetone in CH$_2$Cl$_2$; neutralized with conc. NH$_4$OH before developing). All starting material had been converted to the product. The reaction was neutralized by the careful addition of conc. NH$_4$OH (55 mL). Enough additional NH$_4$OH was added to bring the pH between 6 and 7. The product was extracted by CH$_2$Cl$_2$ (3×). The organic extracts were combined, washed with H$_2$O (1×) and dried by filtration through Na$_2$SO$_4$. Evaporation in vacuo followed by drying overnight under high vacuum gave 37 as an amber glass (1.42 g, 96.3%). The resulting oil was crystallized by trituration with H$_2$O and scratching and sonicating to produce a fine bright yellow powder. FTIR (KBr, diffuse reflectance) $v_{max}$ 3408, 2943, 1722, 1663, 1612 and 1518 cm$^{-1}$. NMR (CDCl$_3$) δ 0.37 (s, 3H, C18-CH$_3$), 2.90 (s, 6H, —N(CH$_3$)$_2$), 3.43 (s, 3H, C21-OCH$_3$), 4.43 (dd, 2H, C21-CH$_2$, J$_1$=27 Hz, J$_2$=18 Hz), 5.77 (s, 1H, C4-CH=), 6.65 (d, 2H, aromatic-CH's, J=9 Hz) and 7.03 (d, 2H, aromatic-CH's, J=9 Hz). MS (EI) m/z (relative intensity): 463 (M$^+$, 20), 134 (21) and 121 (100). Anal. Calcd. for C$_{29}$H$_{37}$O$_4$N.⅔H$_2$O: C, 73.23; H, 8.12; N, 2.94. Found: C, 73.09; H, 7.88; N, 2.97.

Step 10. Preparation of the Target Compound (38):

A mixture of CH$_2$Cl$_2$ (35 mL), trifluoroacetic anhydride (6.0 mL) and glacial acetic acid (2.43 mL) was allowed to stir at room temperature under nitrogen. After ½ hr, the mixture was cooled to 0° C. in an ice water bath and p-toluenesulfonic acid (350 mg) was added. A solution of the 17α-hydroxy-21-methoxy compound (37, 730 mg, 1.57 mmol) was added in CH$_2$Cl$_2$ (4 mL) and rinsed in with CH$_2$Cl$_2$ (2×4 mL). After stirring 1.5 hr at 0° C., examination by TLC (silica; 10% acetone in CH$_2$Cl$_2$, after neutralization by NH$_4$OH) indicated the reaction was >95% complete. The reaction mixture was diluted with H$_2$O (35 mL) and neutralized with concentrated NH$_4$OH. The product was extracted by CH$_2$Cl$_2$ (3×) and brine (1×). The combined organic extracts were dried by filtration through Na$_2$SO$_4$ and evaporated in vacuo to give 0.91 g of the crude product. Flash column chromatography on silica using 10% acetone in CH$_2$Cl$_2$ followed by evaporation in vacuo and drying under high vacuum produced 38 as a pure pale yellow foam (0.6 g, 75.8%). Treatment with pentane followed by sonicating produced a fine powder: m.p. softens at 116° C. HPLC analysis on a NovaPak C$_{18}$ column eluted with 70% CH$_3$OH in H$_2$O with 0.03% Et$_3$N at a flow rate of 1 mL per min at A=302 indicated the product 38 to be 98.06% pure with a retention time of $t_R$=5.08 min. FTIR (diffuse reflectance, KBr) $v_{max}$ 2940, 1734, 1663, 1612, 1518, 1446, 1370, 1235, and 1124 cm$^{-1}$. NMR (CDCl$_3$) δ 0.38 (s, 3H, C18-CH$_3$), 2.08 (s, 3H, OAc), 2.90 (s, 6H, NMe$_2$), 3.42 (s, 3H, C21-OCH$_3$), 4.20 (dd, 2H, C21-CH$_2$, J$_1$=24 Hz, J$_2$=15 Hz), 5.80 (s, 1H, C4-CH=), 6.67 (d, 2H, aromatic-CH's, J=9 Hz) and 7.0 (d, 2H, aromatic-CH's, J=9 Hz). MS (EI) m/z (relative intensity): 505 (M$^+$, 75), 445 (1.1), 430 (8%), 372(2.7), 134 (16) and 121 (100). Anal. Calcd. for C$_{31}$H$_{39}$O$_5$N: C, 73.64; H, 7.77; N, 2.77. Found: C, 73.34; H, 7.74; N, 2.70.

Example 10

This example illustrates the preparation and properties of 17α-acetoxy-21-ethoxy-11β-[4-(N,N-dimethylamino)phenyl]-9-norpregna-4,9-diene-3,20-dione (46).

Step 1. 3,20-bis-(Ethylenedioxy)-17α-hydroxy-21-ethoxy-19-norpregna-5(10),9(11)-diene (42):

To a cold solution of the 17α,21-dihydroxy diketal (33, 5.66 g, 13.53 mmol) in CH$_2$Cl$_2$ (700 mL) in an ice bath under nitrogen was added 20.3 g (94.7 mmol) of solid 1,8-bis-(dimethylamino)naphthalene ("proton sponge"), followed by triethyloxonium tetrafluoroborate (18.0 g, 94.7 mmol). The reaction mixture was allowed to gradually warm to room temperature as the ice bath melted. After 1 hr, TLC (silica; 5% isopropanol in CH$_2$Cl$_2$) indicated the reaction was >95% complete. The reaction was quenched after a total time of 2 hr by the addition of H$_2$O. The mixture was transferred to a separatory funnel and washed with H$_2$O (2×). The combined organic fractions were dried by filtration through Na$_2$SO$_4$ and evaporated in vacuo. The resulting residue was taken up in EtOAc and washed with ice cold 1 N HCl (2×), saturated NaHCO$_3$ and H$_2$O. Combined organic fractions were filtered through Na$_2$SO$_4$ and evaporated in vacuo to recover 6.86 g of an oil. Purification of this oil by flash column chromatography on silica using 5% acetone in CH$_2$Cl$_2$ gave 4.37 g of a colorless foam in 72.4% yield: m.p.=softens at 62° C. FTIR (KBr, diffuse reflectance) $v_{max}$ 3485, 2889, 2738, 1440, 1371, 1216, 1120 and 1058 cm$^{-1}$. NMR (300 MHz, CDCl$_3$) δ 0.8 (s, 3H, C18-CH$_3$), 1.22 (t, 3H, C21-OCH$_2$CH$_3$, J=6.9 Hz), 3.0 (s, 1H, C17α-OH), 3.46–3.82 (m, 4H, C21-CH$_2$ and C21-OCH$_2$CH$_3$), 3.98 (s, 4H, C3-OCH$_2$CH$_2$O), 3.84–4.28 (m, 8H, C3- and C20-CH$_2$CH$_2$O), and 5.55 (br s, 1 H, C11-CH=). MS (EI) m/z (relative intensity): 446(M$^+$, 2), 400 (0.9), 387 (6.6), 369 (2.8), 297(5.5) and 131 (100).

Step 2. 3,20-bis-(Ethylenedioxy)-5α,10α-epoxy-17α-hydroxy-21-ethoxy-19-norpregn-9(11)-ene (43):

To a solution of hexafluoroacetone trihydrate (2.05 mL, 14.7 mmol) in CH$_2$Cl$_2$ (35 mL), was added solid Na$_2$HPO$_4$ (1.17 g, 8.24 mmol) followed by 30% H$_2$O$_2$ (2.2 mL). The mixture was stirred vigorously in an ice bath under nitrogen for ½ hr. A chilled solution of the 21-ethoxy-17α-hydroxy compound (42, 4.37 g, 9.79 mmol) in CH$_2$Cl$_2$ (35 mL) was added slowly via pipette. The reaction was transferred to the cold room and allowed to stir overnight at 4° C. The next morning, examination of the reaction mixture by TLC (silica; 5% acetone in CH$_2$Cl$_2$) indicated all of the starting material had been converted to two more polar components in approximately a 2:1 ratio. The reaction mixture was transferred to a separatory funnel and washed with 10% Na$_2$SO$_3$ (2×), saturated NaHCO$_3$, H$_2$O and brine. The combined organic fractions were filtered through Na$_2$SO$_4$ and evaporated in vacuo to recover 4.84 g of a colorless foam. Trituration of this crude product with Et$_2$O produced a white solid. The solid was collected on a Buchner funnel and dried overnight in vacuo to give 1.73 g of white crystals in 38.1% yield. Examination of this material by TLC and NMR indicated it was pure 5α,10α-epoxide (43). Purification of the mother liquors by flash column chromatography on silica eluting with 7% acetone in CH$_2$Cl$_2$ gave an additional 0.6 g of 5α,10 epoxide (43). Total yield of purified 5α,10α-epoxide (43) was 2.33 g (51.3%): m.p.=

154–166° C. (dec). FTIR (KBr, diffuse reflectance) $v_{max}$ 3566, 2934, 2890, 2441, 1375, 1212, 1118, 1064 and 1044 cm$^{-1}$. NMR (CDCl$_3$) δ 0.78 (s, 3H, C18-CH$_3$), 1.2 (t, 3H, C21-OCH$_2$CH$_3$, J=6 Hz), 2.88 (s, 1H, C17α-OH), 3.33–3.73 (m, 4H, C21-CH$_2$ and C21-OCH$_2$CH$_3$), 3.93 (s, 4H, C3-OCH$_2$CH$_2$O—), 3.73–4.27 (m, 8H, C3- and C20-OCH$_2$CH$_2$O), 6.03 (br, s, 1H, C11-CH=). MS (EI) m/z (relative intensity): 462 (M$^+$, 1.1), 403 (8.9), 385 (5.9), 131 (100) and 87 (32).

Step 3. 3,20-bis-(Ethylenedioxy)-5α,17α-dihydroxy-11β-[4-N,N-dimethylamino)phenyl]-21-ethoxy-19-norpregn-9(10)-ene (44):

A three-neck round bottom flask (250 mL) was equipped with a magnetic fan stirrer, a condenser, a glass stopper and a rubber septum and flame dried under a stream of nitrogen. Magnesium was added (655 mg, 24.5 mmol), followed by a crystal of iodine, 25 mL of dry THF, and 1–2 drops of dibromoethane. After heating in a warm water bath for approximately ½ hr under nitrogen, no observable change occurred. A solution of 4-bromo-N,N-dimethylaniline (4.9 g, 24.5 mmol) in 13 mL of dry THF was added via syringe over a period of several minutes and rinsed in with an additional 13 mL of THF. A reaction occurred almost immediately as the THF began to reflux and the surface of the magnesium turned dark. Approximately 10 min. after the addition of the 4-bromo-N,N-dimethylaniline, heating was discontinued, but the reaction was allowed to remain in the bath. After stirring for 1.5 hr, copper (I) chloride (267 mg, 2.7 mmol) was added as a solid and stirring continued for another ½ hr. The 5α,10α-epoxide (43, 2.27 g, 4.9 mmol) was added via syringe as a solution in 6.5 mL of dry THF and rinsed in with 6.5 mL of THF. After 2 hr, examination of the reaction mixture by TLC on silica (20% acetone in CH$_2$Cl$_2$; quenched with saturated NH$_4$Cl before developing) indicated all epoxide had been converted to a new more polar material. The reaction was quenched by the addition of saturated NH$_4$Cl (65 mL) and air was drawn through the mixture for ½ hr with vigorous stirring. The reaction mixture was transferred to a separatory funnel, ether added, and the layers allowed to separate. The organic fraction was washed with 10% NH$_4$Cl (1×), 2 N NH$_4$OH (1×) and brine (1×). The combined organic fractions (3×) were filtered through Na$_2$SO$_4$ and evaporated in vacuo to obtain 5.62 g of crude material. This crude product was purified by flash column chromatography on silica. The column was first washed with CH$_2$Cl$_2$ to remove impurities with high Rr before eluting the product with 20% acetone in CH$_2$Cl$_2$. Appropriate fractions were combined and evaporated in vacuo to give a crystallizing oil. Crystallization of this material from a minimum amount of hot ether afforded 2.09 g of a pale blue powder (44) in 73% yield; m.p.=199–201° C. (dec). FTIR (KBr, diffuse reflectance) $v_{max}$ 3591, 3529, 3421, 2971, 2882, 1615, 1562, 1519, 1443, 1354, 1190, 1122 and 1053 cm$^{-1}$. NMR (CDCl$_3$) δ 0.47 (s, 3H, C18-CH$_3$), 1.23 (t, 3H, C21-OCH$_2$CH$_3$, J=6 Hz), 2.90 (s, 6H, —N(CH$_3$)$_2$), 3.43–3.80 (m, 4H, C21-CH$_2$ and C21-OCH$_2$CH$_3$), 3.80–4.33 (m, 9H, C3- and C20-OCH$_2$CH$_2$O—, and C11α-CH), 6.67 (d, 2H, aromatic-CH's, J=9 Hz), 7.10 (d, 2H, aromatic-CH's, J=9 Hz). MS (EI) m/z (relative intensity): 538 (M$^+$, 14), 565(19), 506 (13) and 131 (100). Anal. Calcd. for C$_3$H$_{907}$N: C, 69.96; H, 8.46; N, 2.40. Found: C, 69.78; H, 8.37; N, 2.35.

Step 4. 17α-Hydroxy-21-ethoxy-11β-[4-(N,N-dimethylamino)phenyl]-19-norpregna-4,9-diene-3,20-dione (45):

The dihydroxy diketal (44, 2.0 g, 3.43 mmol) was dissolved in THF (20 mL) and stirred magnetically at room temperature under nitrogen. Trifluoroacetic acid (60 mL) was added followed by H$_2$O (20 mL). After 40 min, TLC (20% acetone in CH$_2$Cl$_2$, neutralized with conc. NH$_4$OH before developing) indicated the reaction had gone to completion. The reaction was allowed to continue another hour before neutralizing by the careful addition of conc. NH$_4$OH (55 mL). Additional NH$_4$OH was added to bring the pH to 6–7, CH$_2$Cl$_2$ was added, the mixture transferred to a separatory funnel, and the layers allowed to separate. The organic phase was washed again with H$_2$O (1×), and brine (1×). Combined CH$_2$Cl$_2$ extracts (3×) were filtered through Na$_2$SO$_4$ and evaporated in vacuo to give 1.73 g of an amber foam. Purification by flash column chromatography on silica eluting with 20% acetone in CH$_2$Cl$_2$ afforded 1.28 g of pure 45 as a bright yellow foam in 78% yield: m.p.=softens at 96° C. FTIR (KBr, diffuse reflectance) $v_{max}$ 3440, 2944, 2880, 1721, 1658, 1612, 1518, 1443, 1347, 1211 and 1136 cm$^-$. NMR (CDCl$_3$)80.40 (s, 3H, C18-CH$_3$), 1.3 (t, 3H, C21-OCH$_2$CH$_3$, J=6 Hz), 2.93 (s, 6H, —N(CH$_3$)$_2$), 3.43.8 (m, 3H, C21-OCH$_2$CH$_3$ and C17α-OH), 4.13–4.63 (m, 3H, C21-CH$_2$ and C11α-CH), 5.80 (s, 1H, C4-CH=), 6.68 (d, 2H, aromatic-CH's, 3=0.9 Hz), 7.05 (d, 2H, aromatic-CH's, J=9 Hz). MS (EI) m/z (relative intensity): 477 (M$^+$, 42), 280 (14), 134 (26) and 121 (100). Anal. Calcd. for C$_{30}$H$_{39}$O$_4$N—H$_2$O: C, 74.50; H, 8.21; N, 2.90. Found: C, 74.46; H, 8.21; N, 2.93.

Step 5. Preparation of the Target Compound (46):

A mixture of trifluoroacetic anhydride (9.77 mL), and glacial acetic acid (3.9 mL) in CH$_2$Cl$_2$ (50 mL) was allowed to stir ½ hr under nitrogen at room temperature. The mixture was cooled to 0° C. in an ice bath and toluenesulfonic acid monohydrate (0.57 g, 3 mmol) was added. A solution of the 17α-hydroxy-21-ethoxy compound (45, 1.22 g, 2.55 mmol) in CH$_2$Cl$_2$ (10 mL) was added to the above mixture, and then rinsed in with 10 mL of CH$_2$Cl$_2$. After stirring 2 hr at 0° C., the reaction was examined by TLC (silica; 10% acetone in CH$_2$Cl$_2$, neutralized with conc. NH$_4$OH before developing) and was found to be >95% complete. The reaction mixture was diluted with H$_2$O (50 mL) and neutralized by the careful addition of conc. NH$_4$OH. More CH$_2$Cl$_2$ and H$_2$O were added, the mixture was transferred to a separatory funnel, and the layers allowed to separate. The organic fraction was washed again with H$_2$O and brine. Combined CH$_2$Cl$_2$ extracts (3×) were filtered through Na$_2$SO$_4$ and evaporated in vacuo to give 1.35 g of an amber foam. This crude product was purified twice by flash column chromatography on silica eluting with 8% acetone in CH$_2$Cl$_2$. Appropriate fractions were combined, evaporated in vacuo, chased with ether to obtain 0.81 g of a foam. Treatment with pentane produced a pale yellow powder. The powder was dried overnight in vacuo at 58° C. to remove all traces of solvent. Total yield of pure 46 was 491 mg in 37%; m.p.=softens at 104° C. HPLC analysis on Phenomenex Prodigy 5 ODS-2 column (150×4.6 mm) eluted with 30% H$_2$O with 0.03% triethylammonium phosphate (pH 7.0) in CH$_3$OH at a flow rate of 1 mL per min at λ=302 indicated the product 46 to be 98.76% pure with a retention time (t$_R$) of 16.64 min. FTIR (KBR, diffuse reflectance) $v_{max}$ 2945, 2890, 1734, 1663, 1612, 1562, 1518, 1446, 1368 and 1235 cm$^{-1}$. NMR (CDCl$_3$) δ 0.43 (s, 3H, C18-CH$_3$), 1.28 (t, 3H, C21-OCH$_2$CH$_3$, J=6 Hz), 2.15 (s, 3H, C17α-OAc), 2.95 (s, 6H, —N(CH$_3$)$_2$), 3.63 (q, 2H, C21-OCH$_2$CH$_3$, J=6 Hz), 4.03–4.60 (m, 3H, C21-CH$_2$ and C11α-CH), 5.87 (s, 1H, C4-CH=), 6.72 (d, 2H, aromatic-CH's, J=9 Hz) and 7.08 (d, 2H, aromatic-CH's, J=9 Hz). MS (EI) m/z (relative intensity): 519 (M$^+$, 34), 459 (4.5), 372 (7.4), 134 (18) and 121 (100). Anal. Calcd. for C$_{32}$H$_{41}$O$_5$N: C, 73.95; H, 7.96; N, 2.70. Found: C, 73.84; H, 8.20; N, 2.65.

Example 11

This example illustrates the preparation and properties of 17α,21-diacetoxy-11-[4-(N,N-dimethylamino)phenyl]-19-norpregna-4,9-diene-3,20-dione 3-oxime as a mixture of syn and anti-isomers (47):

A solution of the diacetate (15, 0.5 g, 0.937 mmol) and hydroxylamine hydrochloride (0.651 g, 937 mmol) in absolute ethanol (25 mL) was stirred at room temperature under nitrogen. After 2.5 hr, TLC (10% acetone in $CH_2Cl_2$) indicated a complete reaction. The reaction mixture was diluted with $H_2O$ (200 mL), adjusted to a pH 7 with saturated $NaHCO_3$ solution, and extracted with $CH_2Cl_2$ (3×). The organic fractions were washed with $H_2O$ (2×) and brine (1×), combined, dried ($Na_2SO_4$), filtered and concentrated in vacuo to give 0.56 g of residue as a foam. Purification by flash chromatography (5% acetone/$CH_2Cl_2$) followed by precipitation from ether solution with pentane gave 0.3 g of the oxime (47) in 58% as an off-white amorphous powder. Analysis by HPLC on a NovaPak $C_{18}$ column eluted with $CH_3CN:H_2O:Et_3N$ 45:55:0.033 at a flow rate of 2 mL per min at λ=274 nm indicated approximately 98% purity consisting of a 32:68 mixture of the syn- and anti-isomers. Analysis by NMR indicated a syn: anti ratio of 43:57: m.p.=sinters at 151° C., and then decomposes. FTIR (KBr, diffuse reflectance) $v_{max}$ 2946, 1737, 1612 and 1518 $cm^{-1}$. NMR ($CDCl_3$) δ 0.40 (s, 3H, C18-$CH_3$), 3.93 (s, 6H, $NMe_2$), 4.40 (br. s, 1H, C11α-CH), 4.87 (dd, $J_1$=29.7 Hz, $J_2$=18 Hz, 2H, C21-$CH_2OAc$), 5.97 (s, 0.57H, C4-CH= for anti-isomer), 6.63 (s, 0.43H, C4-CH= for syn-isomer), 6.70 (d, 2H, J=9 Hz, 3',5' aromatic-CH's) and 7.10 (d, 2H, J=9 Hz, 2',6' aromatic-CH's). MS (EI) m/z (relative intensity): 549((M+H)$^+$, 63) and 275 (100).

Example 12

This example illustrates the preparation and properties of 17α-acetoxy-21-methoxy-11β-[4-(N,N-dimethylamino)phenyl]-19-norpregna-4,9-diene-3,20-dione 3-oxime as a mixture of syn and anti-isomers (48):

A solution of the 21-methoxy compound (38, 0.1 g, 0.2 mmol) and hydroxylamine hydrochloride (0.139 g, 2 mmol) in absolute ethanol (5 mL) was stirred at room temperature under nitrogen. After 1 hr, TLC (10% acetone in $CH_2Cl_2$) indicated a complete reaction. The reaction mixture was diluted with $H_2O$, adjusted to a pH of 7 with saturated $NaHCO_3$ solution, and extracted with $CH_2Cl_2$ (3×). The organic fractions were washed with $H_2O$ (2×) and brine (1×), combined, dried over $Na_2SO_4$ filtered and concentrated in vacuo to give the crude product as a foam. This material was combined with 0.12 g additional crude product in a previous batch and the total amount (0.21 g) was purified by flash chromatography (15% acetone/$CH_2Cl_2$) followed by trituration with pentane to give 0.12 g of the oxime (48) in 58% yield as a white amorphous powder. Analysis by HPLC on a NovaPak $C_{18}$ column eluted with $MeOH:H_2O:Et_3N$ 65:35:0.0033 at a flow rate of 1 mL/min at λ=276 nm indicated approximately 97% purity of a mixture of the syn- and anti-isomers. The retention times of the two isomers were too close together ($t_R$=8.8 and 9.2 min) to give an accurate integration ratio. Analysis by NMR indicated a syn:anti ratio of 26:74; m.p.=sinters at 142° C. and melts at 146–162° C. FTIR (KBr, diffuse reflectance) $v_{max}$ 2938, 1733, 1613 and 1517 $cm^{-1}$. NMR (300 MHZ, $CDCl_3$) δ 0.36 (s, 3H, C18-$CH_3$), 2.10 (s, 3H, 17α-OAc), 2.89 (s, 6H, $NMe_2$), 3.41 (s, 3H, $OCH_3$), 4.10 (d, 1H, C21-$CH_2$, J=16.8 Hz), 4.30 (m, 2H, 11α-H plus 21-$CH_2$), 5.88 (s, 0.74H, C4-CH= for anti-isomer), 6.53 (s, 0.26H, C4-CH= for syn-isomer), 6.62 (d, 2H, 3',5' aromatic-CH's), J=8.7 (Hz) and 6.99 (d, 2H, 2',6' aromatic-CH's, J=8.7 Hz). MS (EI) m/z (relative intensity): 521 (M$^+$, 100) and 261 (67).

Example 13

This example illustrates the preparation and properties of 17α-formyloxy-11β-[4-(N,N-dimethylamino)phenyl]-19-norpregna-4,9-diene-3,20-dione (69A) (FIG. 4). 17α-Hydroxy-11β-[4-(N,N-dimethylamino)phenyl]-19-norpregna-4,9-diene-3,20-dione (61, 140 mg, 0.323 mmol) was dissolved in 96% formic acid (2.44 g, 50.9 mmol) in an argon atmosphere and cooled to 0° C. in an ice bath (Oliveto, E. P., et al., *J. Am. Chem. Soc.*, 77:3564–3567 (1955)). $P_2O_5$ (500 mg, 1.76 mmol) was added as a solid and after stirring five minutes, the reaction mixture was allowed to warm to room temperature. After 1.5 hr, saturated $NaHCO_3$ was added carefully to neutralize the mixture. The mixture was extracted with EtOAc (3×) and washed with $H_2O$ and brine and dried over $Na_2SO_4$. Another similar reaction was run starting with 500 mg (1.15 mmol) of the 17α-hydroxy compound (61). Two products from the above two reactions were combined and chromatographed on dry column silica gel using $CH_2Cl_2:CH_3C(O)CH_3$ (9:1) to afford the crude product as a yellow foam (69A), which was indicated by HPLC to be 97% pure. This material was rechromatographed using the same solvent system to give 185 mg of the good product (69A) as an amorphous off-white solid. Analysis by HPLC indicated 98.8% purity. The yield was 28%; and m.p.=softens at 115° C. FTIR (KBr, diffuse reflectance) $v_{max}$ 2941, 1722, 1664, 1611 and 1518 $cm^{-1}$. NMR ($CDCl_3$): δ 0.3.8 (s, 3H, C18-Me), 2.13 (s, 3H, C21-Me), 2.91 (s, 6H, $N(CH_3)_2$), 4.44 (d, 1H, C11α-CH), 5.8 (br s, 1H, C4-CH=), 6.68 and 7.06 (dd, 4H, aromatic-CH's) and 8.11 (br s, 1H, C17α-HC=O). MS (EI) m/z (relative intensity): 461 (M$^+$, 36.2), 400 (2.1), 134 (15.4), 121 (100), and 91 (3.0). Anal. Calcd. for $C_{29}H_{35}NO_4 \cdot \frac{1}{4}H_2O$: C, 74.73; H, 7.68; N, 3.01. Found: C, 74.64; H, 7.65; N, 3.05.

Example 14

Figure 4:
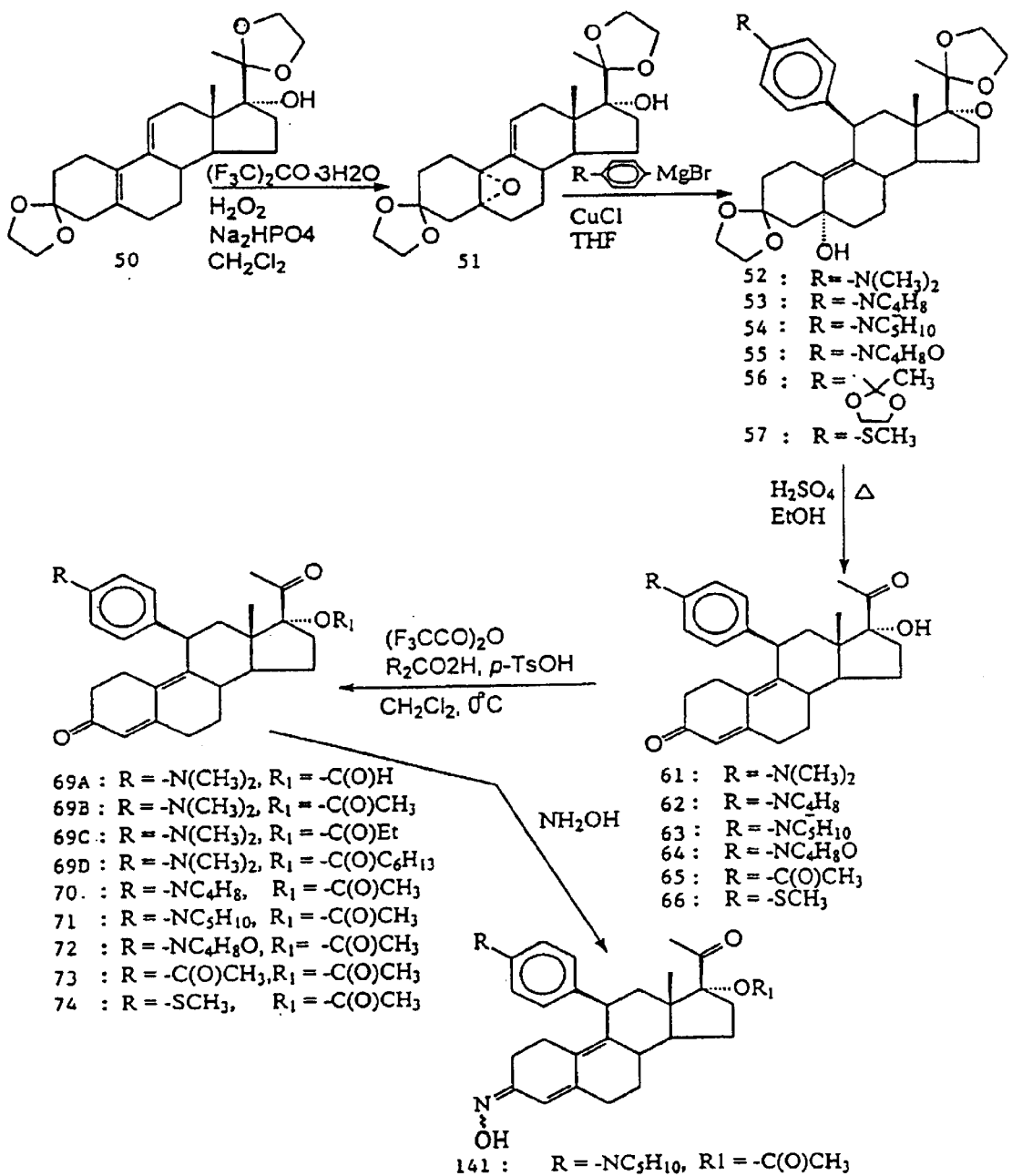

This example illustrates the preparation and properties of 17α-Propionoxy-11β-[4-(N,N-dimethylamino)phenyl]-19-norpregna-4,9-diene-3,20-dione (69C) (FIG. 4). Trifluoroacetic anhydride (0.48 g, 4.29 mmol) and propionic acid (0.61 g, 4.29 mmol) were added to benzene, and p-toluenesulfonic acid monohydrate (0.186 g, 1.31 mmol) as a solid was added to the mixture. The mixture was stirred at room temperature for ½ hr. The 17α-hydroxy steroid (61, 581 mg, 1.34 mmol) was dissolved in benzene and added to the above mixture. The mixture was stirred at room temperature for 6 hr. The mixture was poured into ice cold sodium $NaHCO_3$ solution and extracted with EtOAc. The EtOAc extracts were washed with $H_2O$, brine and dried over $Na_2SO_4$, and evaporated in vacuo. The product obtained was purified by flash column chromatography using EtOAc: hexane (4:6) as solvent. The product was crystallized from isopropanol to give 145 mg of crude 69C as white crystals. In checking this material by reverse phase HPLC, it was found that an impurity was present which could not be separated from the desired product by chromatography on silica gel. The mother liquor was concentrated in vacuo, and the ester was purified by chromatography on an ODS-3 10/50 Whatman column using $MeOH:H_2O$ (9:1) as a solvent and monitoring the separation using a Waters Model 481 variable wavelength detector at 365 nm and at a flow rate of 9 mL/min. Fractions were collected and similar fractions were combined. Good material from the above two was combined and recrystallized from isopropanol to give 299 mg of 69C as white crystals in 80% yield; m.p.=125–126° C. FTIR (KBr, diffuse reflectance): $v_{max}$ 2946, 2882, 1730, 1662, 1610, 1596 and 1516 cm$^{-1}$. NMR (CDCl$_3$): δ 0.363 (s, 3H, C18-Me), 2.086 (s, 3H, C21-Me), 2.905 (s, 6H, —NMe$_2$), 4.386 (d, 1H, C11α-CH), 5.775 (s, 1H, C4-CH═), 6.634 and 6.979 (d, 4H, aromatic-CH's). MS (EI) m/z (relative intensity): 489 (M$^+$, 42.2), 400 (6.5), 372 (6.7), 134 (20.2), 121 (100), and 57 (11.7). Anal. Calcd. for C$_{31}$H$_{39}$NO$_4$.½C$_3$H$_8$O: C, 75.14; H, 8.29; N, 2.70. Found: C, 75.03; H, 8.43; N, 2.83.

Example 15

This example illustrates the preparation and properties of 17α-Heptanoyloxy-11β-[4-(N,N-dimethylamino)phenyl]-19-norpregna-4,9-diene-3,20-dione (69D) (FIG. 4). The above procedure was followed using heptanoic acid (0.56 g, 4.29 mmol) instead of propionic acid on the 17α-hydroxy compound (61, 581 mg, 1.34 mmol). The reaction was run at room temperature for 17 hr. After workup, the crude product was purified by flash chromatography using EtOAc:hexane (4:6). The slightly impure product was chromatographed on an ODS-3 10/50 column using CH$_3$OH at a flow rate of 9 mL per min, monitored at 365 nm. This afforded 335 mg of an oil (69D) in 48.5% yield. This oil was solidified on standing at room temperature as an off-white solid; m.p.=softens at 68° C. FTIR (KBr, diffuse reflectance): $v_{max}$ 2943, 1731, 1664, 1612 and 1518 cm$^{-1}$. NMR (CDCl$_3$): δ 0.36 (s, 3H, C18-CH$_3$), 2.1 (s, 3H, C21-CH$_3$), 2.93 (s, 6H, N(CH$_3$)$_2$), 4.44 (br d, 1H, C11α-CH), 5.82 (br s, 1H, C4-CH═), 6.68 and 7.04 (d, 4H, aromatic-CH's). MS (EI) m/z (relative intensity): 545 (M$^+$, 37.4), 400 (7.7), 372 (7.4), 134 (18.6) and 121 (100). Anal. Calcd. for C$_{35}$H$_4$NO$_4$.½H$_2$O: C, 75.81; H, 8.66; N, 2.53. Found: C, 75.89; H, 8.55; N, 2.71.

Example 16

This example illustrates the preparation and properties of 17α-Methoxymethyl-11β-[4-(N,N-methylamino)phenyl]-19-norpregna-4,9-diene-3,20-dione (91) (FIG. 5).

Step 1. 3-Methoxy-19-norpregna-1,3,5(10), 17(20)-tetraene (78):

Sodium hydride (50% in mineral oil, 14.72 g, 306.6 mmol) was weighed into a dry 3-neck flask and the oil was removed by washing with dry pentane (3×). The residual pentane was removed under a stream of nitrogen. DMSO (255 mL) freshly distilled from CaH$_2$ was added. The mixture was stirred and heated at 60–65° C. until gas evolution had ceased and the mixture was homogeneous. The dimsyl anion solution was cooled to room temperature and a solution of ethyl triphenylphosphonium iodide (135.0 g, 306.6 mmol) in DMSO (510 mL) was added to give a brick-red solution of the ylide. A solution of estrone methyl ether (77, 19.5 g, 68.6 mmol) in benzene (freshly distilled from sodium, 39.0 mL) was added to the DMSO solution and the mixture was stirred at 60° C. for 18 hr. The solution was cooled to room temperature and poured into ice/water (1000 mL). The aqueous mixture was extracted with hexanes (3×). The hexane extracts were washed with H$_2$O (3×) and brine (1×). The combined hexane extracts were dried over Na$_2$SO$_4$ and evaporation of the solvent gave 19.17 g of an oily material. This material was dissolved in petroleum ether and percolated through a column of neutral alumina. Evaporation of the solvent gave a solid (78). The material was crystallized from methanol/ether to afford 10.95 g of 78 in 54% yield as a white crystalline solid; m.p.=70–75° C.

(Lit m.p.=76.5–77.5° C.: Kribner, et al., J. Org. Chem., 31:24–26 (1966)). Elution of the alumina column with EtOAc allowed for the recovery of 8.0 g of 77. NMR (CDCl$_3$): δ 0.9 (s, 3H, C18-CH$_3$), 1.70 (d, J=6 Hz, C21-CH$_3$), 3.80 (s, 3H, C3-OCH$_3$), 5.2 (m, 1H, C20-CH═), 6.8 (m, 2H, 2',4'-aromatic-CH's), and 7.27 (d, 1H, J=8 Hz, 1'-aromatic-CH).

Step 2. 3-Methoxy-19-norpregna-1,3,5(10), 16-tetraene-20-one (79).

A fine stream of oxygen was bubbled through a solution of the 17-ethylidene compound (78, 4.0 g, 13.5 mmol) in pyridine (100 mL) containing hematoporphyrine (80 mg, 1 mol %) for 16 hr while being illuminated with six 15 watt fluorescent lights. Acetic anhydride (20 mL) was added to the pyridine solution and the mixture was stirred for 2.5 hr. The mixture was poured into cold H$_2$O and extracted with CH$_2$Cl$_2$ (3×). The metylene chloride extracts were sequentially washed with 5.0 N HCl (3×), H$_2$O (1×), saturated NaHCO$_3$ (1×) and brine (1×). The combined methylene chloride extracts were dried over Na$_2$SO$_4$ and evaporation of the solvent gave a black solid. The material was dissolved in hot EtOAc, treated with charcoal, and filtered through Celite. Evaporation of the solvent gave 4.15 g of a yellow solid. Crystallization of this yellow solid from EtOAc afforded 2.45 g of 79 in 58.5% yield; m.p.=182–185° C. (Lit m.p. 186–188° C.: Kribner, et al., J. Org. Chem., 34:3502–3505 (1969)).

Step 3. 3-Methoxy-19-norpregna-1,3,5(10)-trien-20-one (80):

A solution of the enone (79, 4.0 g, 12.89 mmol) in benzene (160 mL) containing 10% Pd/C (400 mg, 3 mol %) was hydrogenated at atmospheric pressure. The reaction was allowed to stir for 16 hr. The mixture was filtered through Celite under nitrogen. Evaporation of the solvent gave 3.96 g of the 20-ketone (80) (Kribner, et al, J. Org. Chem., 34:3502–3505 (1969)) as a light yellow solid in 98% yield. NM (CDCl$_3$): δ 0.63 (s, 3H, C18-CH$_3$), 2.15 (s, 3H, C21-CH$_3$), 3.80 (s, 3H, C3-OCH$_3$), 6.70 (m, 2H, 2',4' aromatic-CH's) and 7.2 (d, 2H, J=8 Hz, 1' aromatic-CH).

Step 4. 3-Methoxy-20-acetoxy-19-norpregna-1,3,5(10), 17(20)tetraene (81):

A mixture of the 20-ketone (80, 3.0 g, 9.60 mmol) and p-toluenesulfonic acid (1.13 g, 5.94 mmol) in acetic anhydride (200 mL) was heated at 150° C. in an oil bath while the solvent was slowly distilled through a short path column (Temp. Head 130–134° C.) over 5 hr. The remaining solvent was removed at reduced pressure. The residue was partitioned between cold ether and cold saturated NaHCO$_3$ solution. The layers were separated and the aqueous layer was extracted with Et$_2$O (2×). The Et$_2$O layers were washed with H$_2$O, brine, combined and dried over sodium sulfate. Evaporation of the solvent gave 3.67 g of the enol acetate (81) (Krubiner, A. M. et al., J. Org. Chem., 34:3502–3505 (1969)), a stable yellow foam. This product was purified via flash chromatography eluting with 20% EtOAc/hexane to afford 1.78 g of 81 in 52% yield as a mixture of E and Z isomers. NMR (CDCl$_3$): δ 0.87 and 0.92 (s, C18-CH$_3$), 1.80 (br s, 3H, C21-CH$_3$), 2.13 (s, 3H, C21-OCOCH$_3$), 6.80 (m, 2H, 2',4' aromatic-CH's) and 7.20 (d, J=8 Hz, 1H, 1' aromatic-CH). MS (EI) m/z (relative intensity): 354 (M$^+$), 312, 297(100), 173, 147 and 123.

Step 5. 3-Methoxy-17α-methoxymethyl-19-norpregna-1, 3,5(10)-triene-20-one (82):

A solution of the enol-acetate (81, 1.7 g, 4.8 mmol) in ether (70 mL) was added dropwise over ½ hr to a cold (0° C.) ether solution of methyl lithium (8.3 mL of a 1.3 M solution, 10.8 mmol). After ½ hr, a sodium bicarbonate-quenched aliquot showed very little enol-acetate remaining. Bromomethyl methyl ether (7.2 mL of a 2.0 M/ether solution, 14.4 mmol) was added to the above lithium enolate solution. The mixture was stirred at 0° C. for ½ hr, then allowed to warm to room temperature over 1 hr. The mixture was poured into ice/water and extracted with $Et_2O$. The ether layers were washed with $H_2O$ and brine, combined and dried over anhydrous $Na_2SO_4$. Evaporation of the solvent gave 1.78 g of 82. The product was isolated by flash chromatography eluted with 17.5% EtOAc/hexane to afford 600 mg of 82 as a yellow foam in 35% yield. NMR (300 MHz, $CDCl_3$): δ 0.672 (s, 3H, C18-$CH_3$), 2.171 (s, 3H, C21-$CH_3$), 3.310 (s, 3H, 17α-$CH_2OCH_3$), 3.40 and 3.90 (d, 2H, J=8.4 Hz, 17α-$CH_2OCH_3$), 3.761 (s, 3H, C3-$OCH_3$), 6.82 (m, 2H, 2',4' aromatic-CH's), and 7.20 (d, 1H, J=8 Hz, 1' aromatic-CH). MS (EI) m/z (relative intensity): 356 ($M^+$), 227 (100), 173, 147 and 115.

Step 6. 3-Methoxy-17α-methoxymethyl-19-norpregna-1,3,5(10)-trien-20-ol (83):

A solution of the 20 ketone (82, 600 mg, 1.68 mmol) in THF/EtOH was treated with $NaBH_4$ (135 mg, 3.5 mmol) dissolved in cold $H_2O$ (3 mL). The mixture was stirred at 50° C. for 5 hr. The mixture was chilled in an ice bath and excess NaBH was destroyed with the cautious addition of acetic acid. The mixture was diluted with $H_2O$ and extracted with $CH_2Cl_2$. The $CH_2Cl_2$ extracts were washed with $H_2O$ and brine, combined and dried over $Na_2SO_4$. Evaporation of the solvent gave 580 mg of 83 as a mixture of 20α-(minor) and 20β-(major) epimers as a light yellow oil. Flash chromatography eluting with 2% acetone/$CH_2Cl_2$ of a small sample allowed for the isolation of the 20α-epimer with $R_f$=0.35 and the 20β-epimer with $R_f$=0.50. Their assignments were based on 300 MHz NMR analysis. NMR ($CDCl_3$) for 20α-OH: δ 0.797 (s, 3H, C18-$CH_3$), 1.254 (d, 3H, J=6.3 Hz, C21-$CH_3$), 3.376 (s, 3H, C17α-$CH_2OCH_3$), 3.435 and 3.875 (d, 2H, J=8.7 Hz, C17α-$CH_2OCH_3$), 3.769 (s, 3H, C3-$OCH_3$), 6.85 (m, 2H, 2',4' aromatic-CH's), and 7.165 (d, 1H, J=8.4 Hz, 1' aromatic-CH). NMR ($CDCl_3$) for 20β-OH: δ 0.998 (s, 3H, C18-$CH_3$), 1.218 (d, 3H, J=6.3 Hz, C21-$CH_3$), 3.311 (s, 3H, C17α-$CH_2OCH_3$), 3.371 and 3.612-(d, 2H, J=8.7 Hz, C17α-$CH_2$ $OCH_3$), 3.755 (s, 3H, C3-$OCH_3$), 6.85 (m, 2H, 2',4' aromatic-CH's) 7.165 (d, 1H, J=8.4 Hz, 1' aromatic-CH). MS (EI) m/z (relative intensity): 358 ($M^+$), 282, 227, 174 (100) and 147.

Step 7. 3-Methoxy-17α-methoxymethyl-19-norpregna-2,5(10)-dien-20-ol (84):

A solution of the 20-alcohol (83, 760 mg, 2.12 mmol) in THF/t-BuOH (1:1, 50 mL) was added to redistilled ammonia (50 mL). While stirring vigorously, lithium metal (294 mg, 42.2 mmol), cut into small pieces, was added. Within 2 min, the mixture turned blue and was stirred at ammonia reflux (−35° C.) for 5 hr. The reaction was quenched through the addition of methanol (15 mL). The ammonia was evaporated under a stream of nitrogen. The residue was diluted with $H_2O$ and extracted with $CH_2Cl_2$. The $CH_2Cl_2$ extracts were washed with $H_2O$ and brine, combined and dried over $Na_2SO_4$. Evaporation of the solvent gave 874 mg of 84 (14.4% over theoretical yield) as a stable yellow foam. This 1,4-dihydro derivative (84) was used without further purification in the next reaction. NMR ($CDCl_3$): δ 1.0 (s, 3H, C18-$CH_3$), 1.20 (d, 3H, J=6.3 Hz, C21-$CH_3$), 3.3 (s, 3H, 17α-$CH_2OCH_3$), 3.56 (s, 3H, C3-$OCH_3$) and 4.67 (br, m, 1H, C2-CH=). FTIR (KBr, diffuse reflectance) $v_{max}$ 1666 and 1694 $cm^{−1}$.

Step 8. 17α-Methoxymethyl-19-norpregna-5(10)-en-3-on-20-ol (85):

A solution of the 1,4-dihydro derivative (84, 710 mg, 1.97 mmol) in acetic acid, THF, $H_2O$ (3:1:1, 50 mL) was stirred at 4045° C. Within 45 minutes, TLC analysis indicated complete consumption of the starting material. The solvent was removed in vacuo and the residue was taken up in $H_2O$ and the aqueous mixture was extracted with $CH_2Cl_2$. The $CH_2Cl_2$ extracts were washed with $H_2O$ and brine, combined and dried over $Na_2SO_4$. Evaporation of the solvent afforded 684 mg of 85 in 96% yield as a stable light yellow foam. NMR ($CDCl_3$): δ 1.0 (s, 3H, C18-$CH_3$), 1.21 (d, 3H, J=6.3 Hz, C21-$CH_3$), 3.31 (s, 3H, C17α-$CH_2OCH_3$), 3.35 and 3.72 (d, 2H, J=8.4 Hz, C17α-$CH_2OCH_3$).

Step 9. 17α-Methoxymethyl-19-norpregna-4,9-dien-3-on-20-ol (86):

A solution of 85 (584 mg, 1.69 mmol) in pyridine (2.5 mL) was added to a pyridine (5.2 mL) solution of pyridinium bromide perbromide (594 mg, 1.86 mmol) preheated to 80° C. The mixture was heated at 80–90° C. for 1 hr. The mixture was poured into cold 2.5 N HCl (50 mL). The aqueous mixture was extracted with EtOAc.

The EtOAc extracts were washed with 2.5 N HCl (50 mL), saturated $NaHCO_3$ solution and brine. The combined EtOAc extracts were dried over $Na_2SO_4$. Evaporation of the solvent gave 540 mg of 86 as a yellow foam in 92.2% yield. The material was used without further purification in the following reaction. NMR ($CDCl_3$): δ 3.33 (s, 3H, C17α-$CH_2OCH_3$), 5.67 (br s, 1H, C4-CH=).

Step 10. 17α-Methoxymethyl-19-norpregna-4,9-diene-3,20-dione (87):

A solution of the mixture of 20a and 20β-ol (86, 540 mg, 1.57 mmol) in acetone (15 mL) was chilled in an ice bath and treated dropwise with Jones reagent until the orange color of $Cr^{VI}$ persisted. The mixture was stirred at 0° C. for 10 min, then the excess $Cr^{VI}$ was destroyed with the addition of 2-propanol until the green color of $Cr^{IV}$ persisted. The mixture was diluted with $H_2O$ and the aqueous mixture was extracted with EtOAc. The EtOAc extracts were washed with $H_2O$ and brine, combined and dried over $Na_2SO_4$. Evaporation of the solvent gave 540 mg of a stable foam. Flash chromatography, eluting with 5% acetone/$CH_2Cl_2$, gave 202 mg of the 3,20-diketone (87) in 37.6% yield as a stable yellow foam. NMR ($CDCl_3$): δ 0.83 (s, 3H, C18-$CH_3$), 2.19 (s, 3H, C21-$CH_3$), 3.30 (s, 3H, C17α-$CH_2OCH_3$), 3.36 and 3.85 (d, 2H, J=8.7 Hz, C17α-$CH_2OCH_3$), and 5.72 (br s, 1H, C4-CH=). FTIR (KBr, diffuse reflectance) $v_{max}$ 1703, 1662 and 1605 $cm^{−1}$.

Step 11. 3,3-Ethylenedioxy-17α-methoxymethyl-19-norpregna-5(10),9(11)-dien-20-one (88):

A solution of the 3,20-diketone (87, 202 mg, 0.59 mmol) in $CH_2Cl_2$ (16 mL) was treated with triethyl-orthoformate (123 μL, 0.74 mmol), ethylene glycol (81.4 μL, 1.46 mmol) and p-toluenesulfonic acid (ca. 1.0 mg). The mixture was stirred for ½ hr, chilled in an ice bath, and diluted with saturated $NaHCO_3$. The aqueous mixture was extracted with $CH_2Cl_2$. The $CH_2Cl_2$ extracts were washed with $H_2O$ and brine, combined, and dried over $Na_2SO_4$. Evaporation of the solvent gave 219 mg of the ketal (88) as a in yellow foam in 96% yield. NMR ($CDCl_3$): δ 0.63 (s, 3H, C18-$CH_3$), 2.17 (s, 3H, C21-$CH_3$), 3.30 (s, 3H, C17α-$CH_2OCH_3$), 3.37 and 3.82 (d, 2H, J=8.7 Hz, C17α-$CH_2OCH_3$), 4.0 (s, 4H, C3-$OCH_2CH_2O$—), and 5.57 (br m, 1H, C11-CH=).

Step 12. 3,3-Ethylenedioxy-5α,10α-epoxy-17α-methoxymethyl-19-norpregna-9(11)-en-20-one (89):

A mixture of hexafluoroacetone trihydrate (148.44 mg, 0.67 mmol), 30% hydrogen peroxide (76 μL, 0.67 mmol)

and disodium hydrogen phosphate (52.5 mg, 0.37 mmol) in $CH_2Cl_2$ (2.0 mL) was stirred at 0° C. for ½ hr. A solution of the ketal (88, 200 mg, 0.52 mmol) in $CH_2Cl_2$ was added to the above mixture and the mixture was stirred at 4° C. for 18 hr. The mixture was diluted with a 10% sodium sulfite solution and was extracted with $CH_2Cl_2$. The $CH_2Cl_2$ extracts were washed with $H_2O$ and brine, combined and dried over $Na_2SO_4$. Evaporation of the solvent gave 200 mg of the epoxide (89) as a mixture of 5α,10α- and 5β,10β-epoxides as a yellow foam in 95.5% yield. NMR ($CDCl_3$): δ 0.67 (s, 3H, C18-$CH_3$), 2.17 (s, 3H, C21-$CH_3$), 3.33 (s, 3H, C17α-$CH_2OCH_3$), 3.94 (br s, 4H, C3-$OCH_2$—$CH_2O$—), 5.85 (br m, C11-CH= of 5β,10β-epoxide), and 6.05 (br m, C11-CH= of 5α,10α-epoxide).

Step 13. 3-Ethylenedioxy-5α-hydroxy-11β-[4-(N,N-dimethylamino)phenyl]-17α-methoxymethyl-19-norpregn-9-en-20-one (90):

Magnesium (604.6 mg, 24.88 mmol) was added to an oven-dried flask while hot. Under an atmosphere of nitrogen, a single crystal of iodine was added and the magnesium was agitated to evenly coat the magnesium. After cooling to room temperature, one drop of dibromoethane was added, followed by the addition of THF (10 mL). While the mixture was rapidly stirred, a solution of 4-bromo-N,N-dimethylaniline (2.1 g, 10.5 mmol) in THF (10 mL) was added slowly. During the addition, the mixture was warmed to 50–60° C. Within 15 min, the iodine color quenched and the mixture maintained reflux without external heating. The reaction mixture was stirred for 1½ hr and allowed to cool to room temperature. Copper (I) chloride (249.5 mg, 2.52 mmol) was added and the mixture was stirred for ½ hr. From the above mixture, 2.0 mL (1.0 mmol, 2 eq.) was removed via syringe and placed into a dry flask. A solution of the epoxide (89, 200 mg, 0.5 mmol) was added to the Grignard reagent prepared above. After ½ hr stirring, TLC analysis using a solvent system of 5% acetone/$CH_2Cl_2$ indicated the reaction was incomplete. Therefore, 2.0 mL additional Grignard reagent was added. Within ½ hr, TLC indicated complete consumption of the starting material. The reaction mixture was diluted with saturated $NH_4Cl$ solution and the mixture was stirred for ½ hr while air was bubbled through the mixture. The aqueous mixture was extracted with $CH_2Cl_2$. The $CH_2Cl_2$ extracts were washed with saturated $NH_4Cl$ solution, $H_2O$ and brine. The combined $CH_2Cl_2$ extracts were dried over $Na_2SO_4$. Evaporation of the solvent gave 350 mg of the crude product. Following chromatography, 126 mg of 90 was obtained as a stable yellow foam in 48% yield NMR ($CDCl_3$): δ 0.28 (s, 3H, C18-$CH_3$), 2.10 (s, 3H, C21-$CH_3$), 2.87 (s, 6H, —N($CH_3$)$_2$), 3.27 (s, 3H, C17α-$CH_2OCH_3$), 3.90 (br m, 4H, C3-$OCH_2$—$CH_2O$—), 4.25 (br m, 1H, C11α-CH), 6.61 and 7.05 (d, 4H, J=9 Hz, aromatic-CH's).

Step 14. Preparation of the Target Compound 91:

A solution of 90 (126 mg, 0.24 mmol) in acetic acid/THF/$H_2O$ (3:1:1, 5.0 mL) was heated at reflux for ½ hr. The solvent was removed in vacuo and the residue was diluted with saturated $NaHCO_3$ solution. The aqueous mixture was extracted with $CH_2Cl_2$. The $CH_2Cl_2$ extracts were washed with $H_2O$ and brine, combined, and dried over $Na_2SO_4$. Evaporation of the solvent gave 111 mg of a stable foam. Flash chromatography eluted with 7% acetone/$CH_2Cl_2$ gave 75 mg of 91 in 68% yield as a stable foam. The material resisted crystallization from a variety of solvents and HPLC analysis on NovaPak $C_{18}$ column, eluted with 30% aq. MeOH with 0.033% TEA at a flow rate of 1.0 ml per min at λ=302 nm showed this material to be only 95% pure. Therefore, this material was purified via preparative HPLC on Nova Pak $C_{18}$ column (40×100 mm RCM) eluted with 30% aq. MeOH with 0.033% TEA at a flow rate of 1.0 mL per min and at λ=330 nm to afford 47 mg of 91 as a stable off-white foam with a purity of 98.8%; m.p.=softens at 110° C. and melts at 115–117° C. FTIR (KBr, diffuse reflectance) $v_{max}$ 2940, 2074, 1868, 1704, 1663, 1612, 1560 and 1518 cm$^{-1}$. NMR (300 MHz, $CDCl_3$): δ 0.356 (s, 3H, C18-$CH_3$), 2.148 (s, 3H, C21-$CH_3$), 2.905 (s, 6H, —N($CH_3$)$_2$), 3.300 (s, 3H, C17α-$CH_2OCH_3$), 3.339 and 3.858 (d, 2H, J=8.1 Hz, C17α-$CH_2OCH_3$), 4.335 (d, 1H, J=6.3 Hz, C11α-CH), 5.758 (s, 1H, C4-CH=) and 6.638 & 6.992 (d, 4H, J=8.4 Hz, aromatic-CH's). MS(EI) m/z (relative intensity): 461 (M$^+$, 36.6), 134 (25.4) and 121 (100). Anal. Calcd. for $C_{30}H_{39}NO_3$: C, 78.05; H, 8.52; N, 3.03. Found: C, 77.29; H, 8.40; N, 2.97.

Example 17

This example illustrates the preparation and properties of 17α-Acetoxy-11β-[4-(N-pyrrolidino)phenyl]-19-norpregna-4,9-diene-3,20-dione (70) (FIG. 4).

Step 1. 3,20-bis-Ethylenedioxy-17α-hydroxy-19-norpregna-5(10),9(11)-diene (50):

A mixture of 17α-hydroxy-19-norpregna-4,9-diene-3,20-dione (92, 10 g, 31.8 mmol), ethylene glycol (11.10 g, 178.7 mmol), freshly distilled triethyl orthoformate (14 g, 94.1 mmol) and toluenesulfonic acid monohydrate (0.3 g, 1.58 mmol) in $CH_2Cl_2$ (150 mL) was stirred at room temperature under nitrogen overnight. Analysis by TLC (5% acetone in $CH_2Cl_2$) at that time indicated a complete reaction. Solid $NaHCO_3$ (~1 g) was added and the mixture was diluted with $CH_2Cl_2$ (~100 mL) and poured into $H_2O$. The mixture was extracted with $CH_2Cl_2$ (3×). The organic fractions were washed with $H_2O$ (3×), filtered through sodium sulfate, combined and concentrated in vacuo to give 12 g of the crude product 50 as a yellow foam. Crystallization of this crude material from $CH_2Cl_2$/MeOH containing a trace of pyridine gave 9.8 g of the pure diketal 50 as a light yellow solid in 77% yield; m.p. 169–171° C. FTIR (KBr, diffuse reflectance) $v_{max}$ 3484 and 2912 cm$^{-1}$. NMR (300 MHz, $CDCl_3$): δ 0.792 (s, 3H, C18-$CH_3$), 1.378 (s, 3H, C21-$CH_3$), 3.816 and 4.047 (m, 4H, C20-ketal), 3.983 (s, 4H, C3-ketal) and 5.555 (m, 1H, C11-CH=). MS (EI) m/z (relative intensity): 402 (M$^+$, 100.0), 366 (2.5), 340 (20.8) 270 (59.9) and 99 (50.1).

Step 2. 3,20-bis-Ethylenedioxy-17α-hydroxy-5α,10α-epoxy-19-norpregna-9(11)-ene (51):

Hydrogen peroxide (30%, 3.3 mL, 32.31 mmol) was added to a solution of hexafluoroacetone trihydrate (3.34 g, 16.17 mmol) in $CH_2Cl_2$ (53 mL) cooled to 0° C. Solid $Na_2HPO_4$ (1.48 g, 10.43 mmol) was added and the mixture stirred at 0° C. for ½ hr. A solution of the 3,20-diketal (50, 6.0 g, 14.9 mmol) in $CH_2Cl_2$ (45 mL), precooled to 0° C., was added over a period of 10 min and the reaction mixture was stirred overnight at 5° C. Analysis by TLC (5% acetone in $CH_2Cl_2$) at that point indicated absence of the starting material. The reaction mixture was diluted with $CH_2Cl_2$ (~100 mL) and washed with 10% $Na_2SO_3$ solution (2×) and saturated $NaHCO_3$ solution (2×). The organic fractions were filtered through $Na_2SO_4$, combined and concentrated in vacuo to give 7 g of 51 of a white foam. Trituration of the epoxide mixture (a and 0) with ether afforded 3.05 g of the pure 5α,10α-epoxide 51 as a white solid in 48.9% yield; m.p.=172–173° C. FTIR (KBr, diffuse reflectance) $v_{max}$ 3439, 2950, 1705, 1642 and 1593 cm$^{-1}$. NMR (300 MHz, $CDCl_3$) δ 0.789 (s, 3H, C18-$CH_3$), 1.365 (s, 3H, C21-$CH_3$), 3.810–4.094 (m, 8H, C3- and C20-ketals) and 6.013 (m, 1H, C11-CH=). MS (EI) m/z (relative intensity): 418 (M⁺, 0.5), 400 (1.4), 293 (0.9), 131 (2.5), 99 (4.3) and 87 (100.00).

Step 3. 3,20-bis-Ethylenedioxy-5α,17α-dihydro-11β-[4-(N-pyrrolinino)phenyl]-19-norpregn-9-ene (53):

Magnesium (0.98 g, 40.31 mmol) was added to a 250 mL, 3-neck flask with a magnetic stirrer and a reflux condenser. A crystal of iodine was added, followed by dry THF (20 mL) and a few drops of 1,2-dibromoethane. A solution of N-(4-bromophenyl)pyrrolidine (Yur'e v Y K et al., *Izvest Akad Nauk S.S.S.R., Otdel Khim Nauk*, 166–171 (1951): CA, 45:10236f (1951)) (8.3 g., 36.71 mmol) in dry THF was then added and the mixture was stirred under nitrogen and heated to reflux. After heating for 45 min, most of the magnesium had reacted. The reaction was cooled to room temperature and solid copper (I) chloride (0.36 g, 3.62 mmol) was added followed ½ hr later by a solution of the 5α,10α-epoxide (51, 3.05 g, 7.29 mmol) in dry THF (20 mL). The reaction mixture was stirred at room temperature for 1 hr, then cooled to 0° C. in an ice bath and quenched by the addition of saturated $NH_4Cl$ (~15 mL). With vigorous stirring, air was drawn through the reaction mixture for ±2 hr to oxidize Cu(I) to Cu(II). The mixture was diluted with $H_2O$ (~100 mL) and extracted with $CH_2Cl_2$ (3x). The organic fractions were washed with $H_2O$ (3x), combined, dried over $Na_2SO_4$, filtered and concentrated in vacuo to give 8.36 g of residue. Trituration of this material with pentane followed by decanting the mother liquors removed the phenylpyrrolidine by-product. Trituration of 4 g of the residue with ether gave the Grignard adduct (53, 3.66 g) as blue-grey solid in 88.8% yield. A small amount of this material was purified by flash chromatography using 10% acetone in $CH_2Cl_2$ followed by crystallization from $CH_2Cl_2$/ether for purposes of characterization: m.p.=251–254° C. (dec.). FTIR (KBr, diffuse reflectance) $\mu_{max}$ 3580, 3537, 2948, 2871, 2822, 1614 and 1517 cm⁻¹. NMR (CDCl₃) δ 0.484 (s, 3H, C18-CH₃), 1.383 (s, 3H, C21-CH₃), 1.977 (m, 4H, pyrrolidine β-CH₂), 3.245 (m, 4H, pyrrolidine α-CH₂), 3.765–4.038 (m, 8H, C3-ketal and C20-ketal), 4.186 (d, 1H, J=6.3 Hz, C11α-CH), 6.461 (d, 2H, J=8.4 Hz, 3',5' aromatic-CH's) and 7.047 (d, 2H, J=8.7 Hz, 2',6' aromatic-CH's). MS (EI) m/z (relative intensity): 565 (M⁺, 23.2), 547 (20.5), 160 (14.2), 147 (61.5) and 87 (100.00). Anal. Calcd. for $C_{34}H_{47}NO_6 \cdot {}^{1}/_{10}H_2O$: C, 71.75; H, 8.38; N, 2.47. Found: C, 71.98; H, 8.47; N, 2.52.

Step 4. 17α-Hydroxy-11β-[4-(N-pyrrolidino)phenyl]-19-norpregna-4,9-diene-3,20-dione (62):

A suspension of the Grignard adduct (53, 3.45 g, 6.1 mmol) in EtOH (110 mL) was deoxygenated by bubbling nitrogen through it for ~½ hr. A similarly deoxygenated 8.5% $H_2SO_4$ solution (11 mL, 17.53 mmol) was added and the resulting clear solution was heated to reflux under nitrogen. After 25 min., TLC (20% acetone/$CH_2Cl_2$; overspotted with concentrated $NH_4OH$) indicated a complete reaction. The reaction mixture was cooled to 0° C. in an ice bath, diluted with $H_2O$ (100 mL) and adjusted to a pH of ~8.0 using concentrated $NH_4OH$ solution.

The resulting suspension was extracted with $CH_2Cl_2$ (3x). The organic fractions were washed with $H_2O$ (2x), filtered through $Na_2SO_4$, combined and concentrated in vacuo to give 2.53 g of crude product which was purified by flash chromatography (10% acetone/$CH_2Cl_2$) followed by trituration with ether to give 2.24 g of the pure 17α-hydroxy derivative (62) as an off-white solid in 80% yield; m.p.= softens at 130° C. FTIR (KBr, diffuse reflectance) $v_{max}$ 3457, 2946, 2892, 2834, 1706, 1662, 1616 and 1518 cm⁻¹. NMR (CDCl₃) δ 0.490 (s, 3H, C18-CH₃), 1.978 (m, 4H, pyrrolidine β-CH₂'s), 2.254 (s, 3H, C21-CH₃), 3.243 (m, 4H, pyrrolidine α-CH₂'s), 4.361 (d, 1H, J=6.9 Hz, C11α-CH), 5.752 (s, 1H, C4-CH=), 6.465 (d, 2H, J=8.4 Hz, 3',5' aromatic-CH's), and 6.93 (d, 2H, J=8.4 Hz, 2',6' aromatic-CH's). MS (EI) m/z (relative intensity): 459 (M⁺, 45.5), 160 (10.8), 147 (100.0) and 91 (3.5). Anal. Calcd. for $C_{30}H_{37}NO_3 \cdot {}^{2}/_{5}H_2O$: C, 77.19; H, 8.16; N, 3.00. Found: C, 77.27; H, 8.15; N, 3.12.

Step 5 Preparation of the Target Compound 70:

Under nitrogen, trifluoroacetic anhydride (19.37 g, 92.22 mmol), glacial acetic acid (5.67 g, 94.42 mmol) and dry $CH_2Cl_2$ (10 mL) were combined and stirred at room temperature for 1 hr. Toluenesulfonic acid monohydrate (0.9 g, 4.73 mmol) in $CH_2Cl_2$ (30 mL) was added and the mixture cooled to 0° C. in an ice bath. A solution of the 17α-hydroxy compound (62, 2.12 g, 4.61 mmol) in dry $CH_2Cl_2$ (5 mL) was added and the reaction mixture was stirred at 0° C. and monitored by TLC (20% acetone/$CH_2Cl_2$, 110 overspotted with concentrated $NH_4OH$) which indicated a complete reaction after 1 hr. The mixture was diluted with $H_2O$ (~10 mL), stirred at 0° C. for another 15 min, then carefully adjusted to a pH of ~8 using pH paper with dropwise addition of concentrated $NH_4OH$ solution (~16 mL). The mixture was diluted with $H_2O$ (~200 mL) and extracted with $CH_2Cl_2$ (3x). The organic fractions were washed with $H_2O$ (3x), filtered through sodium sulfate, combined and concentrated in vacuo to give 2.3 g of crude product as a yellow foam. This material was purified by flash chromatography (5% acetone/$CH_2Cl_2$) followed by crystallization from 90% EtOH to give 1.87 g of the pure 17α-acetate as a light yellow solid in 80.7% yield; m.p.=149–154° C. Reverse phase HPLC on Waters NovaPak $C_{18}$ column eluted with 0.05 M $KH_2PO_4$ buffer [pH=3.0]/$CH_3CN$, (40:60) at a flow rate of 1 mL/min and at λ=302 nm indicated this material to be >99% pure with a retention time ($t_R$) of 8.98 min. FTIR (KBr, diffuse reflectance) $v_{max}$ 2946, 2880, 1734, 1715, 1665, 1614 and 1518 cm⁻¹. NMR (CDCl₃) δ 0.376 (s, 3H, C18-CH₃), 1.978 (m, 4H, pyrrolidine P—CH₂'s), 2.091 (s, 3H, C17α-OAc), 2.132 (s, 3H, C21-CH₃), 3.241 (m, 4H, pyrrolidine α-CH₂'s), 4.386 (d, 1H, J=7.2 Hz, C11α-CH), 5.771 (s, 1H, C4-CH=), 6.465 (d, 2H, J=8.4 Hz, 3',5' aromatic-CH's) and 7.030 (d, 2H, J=8.4 Hz, 2',6' aromatic-CH's). MS (EI) m/z (relative intensity): 501 (M⁺, 33.80), 426 (2.3), 160 (10.7) and 147(100.0). Anal. Calcd. for $C_{32}H_{39}NO_4 \cdot {}^{3}/_{4}H_2O$: C, 74.61; H, 7.92; N, 2.72. Found: C, 74.58; H, 7.69; N, 2.87.

Example 18

This example illustrates the preparation and properties of 17α-Acetoxy-11β-[4(N-Piperidino)phenyl]-19-norpregna-4,9-diene-3,20-dione (71) (FIG. 4).

Step 1. 3,20-bis-Ethylenedioxy-5α,17α-dihydroxy-11β-[4-(N-piperidino)phenyl]-19-norpregn-9-ene (54):

Magnesium (1.74 g, 71.7 mmoll) was weighed into a 250 mL round bottom two-neck flask equipped with a reflux condenser, a magnetic stirring bar and a rubber septum. A small crystal of iodine was added and the system was flushed with dry nitrogen. The system plus contents were flame dried under nitrogen. The system was cooled to room temperature and freshly distilled THF (60 mL) was added via syringe. A small amount (~0.1 mL) of dry dibromoethane was added and the mixture stirred at room temperature. After evidence of reaction was observed (disappearnance of $I_2$, color, bubble formation on the surface of magnesium), a solution of N-(4-bromophenyl)piperidine (Wolfe, J. P. and Buchwald, S. L., *J. Org. Chem.*, 62:6066–6068 (1997); and Veradro, G. et al., *Synthesis*, 447–450 (1991)) (17.21 g, 71.7 mmol) in dry THF (40 mL) was added via syringe. The mixture was then stirred in a hot water bath for 3.5 hr, after which time the majority of the magnesium metal had reacted. The mixture was cooled to room temperature and copper (I) chloride (710 mg, 7.17 mmol) was added as a solid, and the mixture was then stirred in a hot water bath for 3.5 hr, after which time the majority of the magnesium metal had reacted. The mixture was cooled to room temperature and copper (I) chloride (710 mg, 7.17 mmol) was added as a solid and the mixture stirred at room temperature for ½ hr. The 5α,10α-epoxide (51, 6.0 g, 14.3 mmol) in dry THF (40 mL) was added via syringe and the mixture stirred at room temperature for ½ hr. At this time, a small aliquot of the reaction mixture was withdrawn, quenched with saturated $NH_4Cl$ solution, and extracted with a small amount of EtOAc. A TLC (10% acetone in $CH_2Cl_2$) of the organic layer indicated the absence of the starting material. Saturated $NH_4Cl$ solution (~100 mL) was added to the reaction mixture, and the mixture was stirred at room temperature for ½ hr while air was drawn through the reaction mixture (to oxidize copper) via a 6 inch needle inserted through the rubber septum by applying a partial vacuum to the top of the condenser. The contents of the flask was diluted with $H_2O$ (~250 mL) and extracted with $CH_2Cl_2$ (3×). The organic fractions were washed with saturated $NH_4Cl$ solution (1×), $H_2O$ (1×), brine (1×) and then dried over anhydrous $Na_2SO_4$. The organic fraction was filtered and concentrated in vacuo to yield 26.8 g of an oil. The material was placed on a flash column and eluted and using 10% acetone in $CH_2Cl_2$ yielding 5.25 g of 54 as an off-white solid in 63.87% yield; m.p.=211–214° C. (sealed tube). FTIR (KBr, diffuse reflectance) $v_{max}$ 3508, 2933, 2790, 1609, 1511, 1441, 1365 and 1234 cm$^{-1}$. NMR (CDCl$_3$) δ 0.45 (s, 3H, C18-CH$_3$), 1.38 (s, 3H, C21-CH$_3$), 3.05–3.2 (m, 4H, —N—(CH$_2$)$_2$—), 3.8–4.05 (m, 8H, 3- and 20-ketals), 4.1 (d, 1H, C11α-CH) and 6.8–7.1 (dd, 4H, aromatic-CH's). Anal. Calcd. for $C_{35}H_{45}O_6N$: C, 72.51; H, 8.52; N, 2.41. Found: C, 71.84; H, 8.60; N, 0.46. MS (EI) m/z (relative intensity): 579 (M$^+$).

Step 2. 17α-Hydroxy-11β-[4-(N-Piperidino)phenyl]-19-norpregna-4,9-diene-3,20-dione (63):

Nitrogen was bubbled through a mixture of EtOH (120 mL) and $H_2SO_4$ (8.5%, 15 mL) for ½ hr to remove oxygen. The Grignard adduct (54, 4.0 g, 6.89 mmol) was added as a solid with stirring. The mixture was put into an oil bath preheated to 95° C. for ½ hr. The mixture was cooled in an ice bath and quenched with saturated $K_2CO_3$ (pH=~10). The reaction mixture was diluted with $H_2O$ (250 mL) and extracted with $CH_2Cl_2$ (3×). The organic fractions were washed with saturated NaHCO$_3$ (1×), $H_2O$ (1×), brine (1×), combined, dried over anhydrous $Na_2SO_4$ and concentrated in vacuo to give 3.35 g of a foam. This material was purified by flash column chromatography using 10% acetone in $CH_2Cl_2$ to yield 2.95 g of a crude product (63) which was crystallized from $CH_2Cl_2$ and ether to yield 2.45 g of an off-white crystalline product (63) in two crops in 61.4% yield; m.p.=219–221° C. FTIR (KBr, diffuse reflectance) $v_{max}$ 3433, 2942, 1708, 1654, 1605, 1512 and 1234 cm$^{-1}$. NMR (CDCl$_3$) δ 0.45 (s, 3H, C18-Me), 2.25 (s, 3H, C21-Me), 3.05–3.2 (m, 4H, —N—(CH$_2$)$_2$—), 4.35 (d, 1H, C11α-CH), 5.75 (s, 1H, C4-CH=), 6.8–7.0 (dd, 4H, aromatic-CH). MS (EI) m/z (relative intensity): 161 (100), 174 (11.43) and 473 (75.71, M$^+$). Anal. Calcd. for $C_{31}H_{39}O_3N$: C, 78.61; H, 8.30; N, 2.96. Found: C, 77.59; H, 8.29; N, 3.03.

Step 3. Preparation of the Target Compound 71:

The diketone (63, 1.7 g, 3.59 mmol) was dissolved in $CH_2Cl_2$ (50 mL) and cooled to 0° C. in an ice bath. In a separate round bottom flask, trifluoroacetic anhydride (15.11 g, 71.78 mmol) and acetic acid (4.75 g, 71.78 mmol) were added to $CH_2Cl_2$ (100 mL), flushed with dry nitrogen and stirred at room temperature for ½ hr. This mixed anhydride was then placed in an ice bath and cooled to 0° C. The cold mixed anhydride solution was then added to the steroid solution and treated with p-toluenesulfonic acid (628 mg, 3.3 mmol). The reaction mixture was stirred for 2 hr at 0° C. The reaction was quenched with saturated $K_2CO_3$ (pH=~10), diluted with $H_2O$ and extracted with $CH_2$—$Cl_2$ (3×). The organic layers were washed with $H_2O$ (2×) and brine (1×), dried over $Na_2SO_4$, filtered and concentrated to yield 3.38 g of crude material. A flash column using 10% acetone in $CH_2Cl_2$ yielded 1.66 g of 71 as an off-white solid in 54.1% yield. The crude product 71 was recrystallized from $CH_2Cl_2$ and Et$_2$O. The material retained $CH_2Cl_2$ and was dried in a heating pistol in vacuo over refluxing benzene for 5 days to afford 895 mg of 71 as an off-white solid in 48.4% yield; m.p.=175–183° C. (sealed tube). FTIR (KBr, diffuse reflectance) $v_{max}$ 2936, 1733, 1717, 1654, 1609, 1512, 1450, 1372, 1259 and 1235 cm$^{-1}$. NMR (300 MHz, CDCl$_3$) δ 0.340 (s, 3H, C18-Me), 2.091 (s, 3H, C17-OAc), 2.131 (s, 3H, C21-CH$_3$), 3.120 (m, 4H, —N—(CH$_2$)$_2$—), 4.370 (m, 1H, C11α-CH), 5.778 (s, 1H, C4-CH=) and 6.810–7.000 (m, 4H, aromatic-CH's). MS(EI) m/z (relative intensity): 161 (100), 174(11.11) and 515 (M$^+$, 59.72).

Reverse-phase HPLC analysis on Waters NovaPak C$_8$ column eluted with MeOH:H$_2$O in the ratio of 70:30 with 0.05% TEA at a flow rate of 1 mL/min and at 260 run indicated it to be 99.5% pure. Anal. Calcd. for $C_3H_{41}O_4N.½EtOH$: C, 76.86; H, 8.01; N, 2.72. Found: C, 76.64; H, 8.06; N, 2.69.

Example 19

This example illustrates the preparation and properties of 17α-Acetoxy-11β-[4-(N-Morpholino)phenyl]-19-norpregna-4,9-diene-3,20-dione (72) (FIG. 4):

Step 1. 3,20-bis-Ethylenedioxy-5α,17α-dihydroxy-11β-(N-morpholino)phenyl]-19-norpregn-9-ene (55):

Magnesium (0.90 g, 37.02 mmol) was added to a 250 mL 3-neck flask equipped with a magnetic stirrer and a reflux condenser. A crystal of iodine was added followed by dry THF (20 mL) and a few drops of 1,2-dibromoethatne. A solution of N-(4 bromophenyl)morpholine (Jones, D. H., *J. Chem. Soc.* (C), 132–137 (1971)) (7.8 g, 32.21 mmol) in dry THF (30 mL) was then added and the mixture was stirred under nitrogen and heated to reflux. After 45 min of stirring, most of the magensium had reacted. The reaction was cooled to room temperature, and solid copper (I) chloride (0.32 g, 32.3 mmol) was added followed ½ hr later by a solution of the 5α,10α-epoxide (51, 2.7 g, 6.45 mmol) in dry THF (20 mL). The reaction mixture was stirred at room temperature for 1 hr, then cooled to 0° C. in an ice bath and quenched by the addition of saturated $NH_4Cl$ solution (~10 mL). With vigorous stirring, air was drawn through the reaction mixture for ½ hr to oxidize Cu(I) to Cu(II). The mixture was extracted with $CH_2Cl_2$ (3×) and the organic factions washed with $H_2O$ (3×). The organic fractions were combined, dried over sodium sulfate, filtered and concentrated in vacuo to give 8 g of residue. Trituration of this material with ether gave the pure adduct (55, 2.1 g) as an off-white solid. The mother liquors were concentrated in vacuo and the residue purified by flash chromatography (20% acetone/$CH_2Cl_2$) to give an additional 0.6 g of the product (55). Total yield of 55 was 2.7 g in 72% yield; m.p.=243–245° C. FTIR (KBr, diffuse reflectance) $v_{max}$ 3578, 3539, 2978, 2949, 2887, 2868, 2821, 1610 and 1511 cm$^{-1}$. NMR (CDCl$_3$) δ 0.450 (s, 3H, C18-CH$_3$), 1.377 (s, 3H, C21-CH$_3$), 3.110 (m, 4H, morpholine—O—CH$_2$CH$_2$N)—), 3.789–4.039 (m, 10H, C3-ketal, C20-ketal and morpholine —O—CH$_2$CH$_2$N), 4.202 (d, 1H, J=6.9 Hz, C11α-CH), 6.791 (d, 2H, J=8.7, 3',5' aromatic-CH's) and 7.107 (d, 2H, J=2',6' aromatic-CH's). MS(EI) m/z (relative intensity): 581 (M$^+$, 11.0), 563 (8.6), 366 (2.5), 163 (18.5) and 87 (100.0). Anal. Calcd. for C$_3$H$_7$NO$_7$.⅔H$_2$O: C, 68.79; H, 8.20; N, 2.36. Found: C, 68.84; H, 8.01; N, 2.36.

Step 2. 17α-Hydroxy-11β-[4-(N-morpholino)phenyl]-19-norprena-4,9-diene-3,20-dione (64):

A suspension of the Grignard adduct (55, 2.56 g, 4.4 mmol) in EtOH (80 mL) was deoxygenated by bubbling nitrogen through it for ~½ hr. A similarly deoxygenated 8.5% H$_2$SO$_4$ solution (8 mL, 12.75 mmol) was added, and the resulting clear solution was heated to reflux under nitrogen. After 25 min, TLC (20% acetone/CH$_2$Cl$_2$, overspotted with concentrated NH$_4$OH) indicated a complete reaction. The reaction mixture was cooled to 0° C. in an ice bath, diluted with H$_2$O (~100 mL) and adjusted to a pH of ~8.0 using concentrated NH$_4$OH solution. The resulting suspension was extracted with CH$_2$Cl$_2$ (3×). The organic factions were washed with H$_2$O (2×), filtered through Na$_2$SO$_4$, combined and concentrated in vacuo to give 2.2 g of a yellow foam. Trituration of this material with ether gave the pure 17α-hydroxy compound (64, 1.8 g) as a white solid in 86% yield; m.p.=218–220° C. FTIR (KBr, diffuse reflectance) $v_{max}$ 3426, 2950, 2852, 1710, 1652, 1580 and 1511 cm$^{-1}$. NMR (CDCl$_3$) δ 0.450 (s, 3H, C18-CH$_3$), 2.255 (s, 3H, C21-CH$_3$), 3.115 (m, 4H, morpholine —OCH$_2$CH$_2$N—), 3.843 (m, 4H, morpholine-OCH$_2$CH$_2$N), 4.373 (d, 1H, J=7.2 Hz, C11α-CH), 5.763 (s, 3H, C4-CH=), 6.804 (d, 2H, J=8.7 Hz, 3',5' aromatic-CH's) and 7.028 (d, 2H, J=8.7 Hz, 2',6' aromatic-CH's). MS (EI) m/z (relative intensity): 475 (M$^+$, 58.5), 374 (4.9), 322 (5.4), 176 (14.2) and 163 (100.0). Anal. Calcd. for C$_{30}$H$_{37}$NO$_4$.¹⁄₁₀H$_2$O: C, 75.47; H, 7.85; N, 2.93. Found: C, 75.46; H, 7.90; N, 3.04.

Step 3. Preparation of the Target Compound 72:

Under nitrogen, trifluoroacetic anhydride (14.9 g, 70.94 mmol), glacial acetic acid (4.31 g, 71.7 mmol) and dry CH$_2$Cl$_2$ (25 mL) were combined and stirred at room temperature for 1 hr. Toluenesulfonic acid monohydrate (0.7 g, 3.68 mmol) was added and the mixture cooled to 0° C. in an ice bath. A solution of the 17α-hydroxy compound (64, 1.66 g, 3.49 mmol) in dry CH$_2$Cl$_2$ (5 mL) was added and the reaction mixture was stirred at 0° C. and monitored by TLC (20% acetone CH$_2$Cl$_2$, overspotted with NH$_4$OH) which indicated a complete reaction after 1 hr. The mixture wad diluted with H$_2$O (~10 mL), stirred at 0° C. for another 15 min, then carefully adjusted to a pH of ~8 (with pH paper) with dropwise addition of concentrated NH$_4$OH solution (~16 mL). The mixture was diluted with H$_2$O (~200 mL) and extracted with CH$_2$Cl$_2$ (3×). The organic fractions were washed with water (3×), filtered through Na$_2$SO$_4$, combined and concentrated in vacuo to give 1.8 g of the residue as a yellow foam. This material was purified via flash chromatography (10% acetone/CH$_2$Cl$_2$), followed by trituration with ether to afford 1.2 g of the pure 17α-acetate (72) as an off-white solid in 67.5% yield. Analysis by NMR indicated this material retained a large amount of ether which could be removed by drying in vacuo at 153° C.; m.p.=194–196° C. FTIR (KBr, diffuse reflectance) $v_{max}$ 2950, 2885, 1738, 1710, 1663, 1608 and 1513 cm$^{-1}$. NMR (CDCl$_3$) δ 0.342 (s, 3H, C18-CH$_3$), 2.096 (s, 3H, C21-CH$_3$), 2.132 (s, 3H, C17α-OAc), 3.116 (m, 4H, morpholine-OCH$_2$CH$_2$N), 3.847 (m, 4H, morpholine-OCH$_2$CH$_2$N), 4.398 (d, 1H, J=6.9 Hz, C11α-CH), 5.785 (s, 1H, C4-CH=), 6.810 (d, 2H, J=8.7 Hz, 3',5' aromatic-CH's) and 7.030 (d, 2H, J=8.7 Hz, 2',6' aromatic-CH's). MS (EI) m/z (relative intensity): 517 (M$^+$, 51.2), 442(5.1), 414 (6.6), 176 (16.0) and 163 (100.0). Anal. Calcd. for C$_{32}$H$_{39}$NO$_5$.½H$_2$O: C, 74.04; H, 7.60; N, 2.70. Found: C, 74.04; H, 7.60; N, 2.84.

Analysis by HPLC on a Waters NovaPak, C$_{18}$ eluted with 0.05 M KH$_2$PO$_4$ buffer, pH=3.0/CH$_3$CN (55:45) at a flow rate of 1 mL/min and and at λ=302 nm indicated this material to be >99% pure with a retention time ($t_R$) of 8.7 m.

Example 20

This example illustrates the preparation and properties of 17α-Acetoxy-11β-(4-acetylphenyl)-19-norpregna-4,9-diene-3,20-dione (73) (FIG. 4).

Step 1 3,20-bis-Ethylenedioxy-5α,17α-dihydroxy-11β-[4-(2-methyl-1,3-dioxolan-2-yl)phenyl]-49-norpregn-9-ene (56):

Magnesium turnings (435 mg, 17.9 mmol) were weighed into a 100 mL round bottom two-neck flask equipped with a reflux condenser, a magnetic stirrer and a rubber septum. A small crystal of iodine was added and the system was flushed with dry nitrogen and flame dried. After the system had cooled to room temperature, freshly distilled THF (20 mL) was introduced via syringe followed by a small amount of dry dibromoethane (~0.1 mL). After evidence of reaction was observed (disappearance of 12 color, bubble formation on metal), a solution of the ketal of 4-bromoacetophenone (see, Detty, M. R., et al., J. Am. Chem. Soc., 105:875–882 (1983); and Rao, P. N., et al., Steroids, 63:523–530 (1998)) (4.35 g, 17.9 mmol) in dry THF (10 mL) was added via syringe. The mixture was then stirred in a hot water bath for 2 hr. (After 35 min, an additional 10 mL of THF was added as a white precipitate formed and the reaction mixture thickened). The reaction was cooled to room temperature and copper (I) chloride (177 mg, 1.79 mmol) was added and the mixutre stirred at room temperature for ½ hr (the precipitate went back into solution with the addition of the copper chloride). The 5α,10α-epoxide (51, 1.5 g, 3.58 mmol) in dry THF (10 mL) was added via syringe and the reaction mixture stirred at room temperature for 45 min. At this time, TLC (10% acetone in CH$_2$Cl$_2$) showed no starting material. Saturated NH$_4$Cl solution (20 mL) was added and the mixture stirred at room temperature for ½ hr while air was drawn through the reaction mixture to oxidize the copper. The contents of the flask were diluted with H$_2$O (100 mL) and extracted with CH$_2$Cl$_2$ (3×). The organic fractions were washed with saturated NH$_4$Cl solution (1×), H$_2$O (1×), and brine (1×), and then dried over anhydrous Na$_2$SO$_4$, filtered and concentrated in vacuo to yield an oil. The oil was purified on a flash column (10% acetone in CH$_2$Cl$_2$) yielding 1.3 g of a stable white foam. The material was crystallized from ether to yield 880 mg of 56 as a white crystalline solid in 42.3% yield; m.p.=185–188° C. FTIR (KBr, diffuse reflectance) $v_{max}$ 3501, 2940, 1609, 1443, 1371, 1181 and 1042 cm$^{-1}$. NMR (CDCl$_3$) δ 0.45 (s, 3H, C18-CH$_3$), 1.4 (s, 3H, CH$_3$ from ethylene ketal of acetophenone at C$_{11}$β-), 1.6 (s, 3H, C21-CH$_3$), 3.6–4.2 (br m, 12H, C3- and C20-ketals and ketal of acetophenone at C11β-), 4.3 (br d, 1H, C11α-CH), and 7.05–7.47 (dd, 4H, aromatic-CH's). MS(EI) m/z (relative intensity): 582 (M$^+$). Anal. Calcd. for C$_{34}$H$_{46}$O$_8$: C, 70.08; H, 7.96. Found: C, 70.00; H, 8.05.

Step 2. 17α-Hydroxy-11β-(4-Acetylphenyl)-19-norpregna-4,9-diene-3,20-one (65):

Nitrogen was bubbled through a mixture of EtOH (25 mL) and 8.5% H$_2$SO$_4$ (2.5 mL) for ½ hr to remove oxygen. The Grignard adduct (57, 750 mg, 1.28 mmol) was added as a solid with stirring. The mixture was put into an oil bath preheated to 95° C. for 1 hr. The mixture was cooled in an ice bath and quenched with saturated $K_2CO_3$ to bring the pH to 10. The mixture was diluted with $H_2O$ (125 mL) and extracted with $CH_2Cl_2$ (3×). The organic fractions were washed with saturated $NaHCO_3$ (1×), $H_2O$ (1×), brine (1×), combined and dried over anhydrous $Na_2SO_4$. This material was concentrated in vacuo to give 600 mg of 65 as an oil. The material was purified on a flash column (10% acetone in $CH_2Cl_2$) to yield 560 mg of 65. This material was crystallized from $CH_2Cl_2$ and ether to give 475 mg of 65 as a white solid in 85.9% yield; m.p.=foams/honeycombs at 112–115° C. FTIR (KBr, diffuse reflectance) $v_{max}$ 3390, 2976, 1709, 1679, 1655, 1601, 1360 and 1275 $cm^{-1}$. NMR ($CDCl_3$) δ 0.4 (s, 3H, C18-$CH_3$), 2.25 (s, 3H, C21-$CH_3$), 2.6 (s, 3H, 11β-4-phenylacetyl $CH_3$), 3.25 (s, 1H, C17α-OH), 4.5 (br d, 1H, C11α-CE), 5.8 (s, 1H, C4-CH=) and 7.2–8.0 (dd, 4H, aromatic-CH's). MS (EI) m/z (relative intensity): 432($M^+$, 88.7), 414 (11.3), 389 (25.4), 371 (21.1), 346 (100.0), 331 (46.5), 319 (22.5), 280 (15.5), 235 (16.9), 200 (14.1), 147(18.3), 133 (18.3), 115 (12.7), 105 (15.5) and 91 (21.1)

Step 3. Preparation of the Target Compound 73:

The triketone (65, 375 mg, 0.87 mmol) was dissolved in $CH_2Cl_2$ (10 mL) and cooled to 0° C. in an ice bath. In a separate round bottom flask, trifluoroacetic anhydride (3.65 g, 17.3 mmol) and acetic acid (1.14 g, 17.3 mmol) were added to $CH_2Cl_2$ (10 mL), flushed with dry nitrogen and stirred at room temperature for ½ hr. The mixed anhydride was then placed in an ice bath and cooled to 0° C. The cold mixed anhydride solution was then added to the triketone (65) solution and treated with p-toluenesulfonic acid (I 52 mg, 0.79 mmol). The reaction mixture was stirred for 45 min at 0° C. The reaction was quenched with saturated $K_2CO_3$ (pH=10), diluted with $H_2O$ and extracted with $CH_2Cl_2$ (3×). The organic layers were combined, washed with $H_2O$ (2×), brine (1×), dried over sodium sulfate, filtered and concentrated to yield 425 mg of crude 73. The crude product 73 was purified on a flash column (10% acetone in $CH_2Cl_2$) to yield 340 mg of compound 73. Crystallization from $CH_2Cl_2$ and ether afforded 305 mg of 73 as a white solid in 73.96% yield; m.p.=243–246° C.

Analysis by reverse phase HPLC on a Waters Nova Pak $C_{18}$ column eluted with MeOH:$H_2O$ in the ratio of 70:30 at a flow rate of 1 mL/min and at λ=260 nm indicated it to be 99.6% pure. FTIR (KBr, diffuse reflectance) $v_{max}$ 2791, 1729, 1712, 1681, 1595, 1362, and 1257 $cm^{-1}$. No ($CDCl_3$) δ 0.3 (s, 3H, C18-Me), 2.10 (s, 3H, C17α-OAc), 2.15 (s, 3H, C21-$CH_3$), 2.55 (s, 3H, 11β-4-phenylacetyl $CH_3$), 4.5 (br d, 4H, C11α-CH), 5.8 (s, 1H, C4-CH=) and 7.2–8.0 (dd, 4H, aromatic-CH's). MS (EI) m/z (relative intensity): 474($M^+$, 2.8), 414 (36.6), 399 (14.0), 389 (8.5) and 371 (100). Anal. Calcd. for $C_{30}H_{34}O_5$ ½$Et_2O$: C, 74.85; H, 7.44. Found: C, 74.94; H, 7.19.

Example 21

This example illustrates the preparation and properties of 17α-Acetoxy-1-(4-methylthiophenyl)-19-norpregna-4,9-diene-3,20-dione (74) (FIG. 4).

Step 1. 3,20-bis-(Ethylenedio)-5α,17α-dihydroxy-11β-(4-methylthiophenyl)-19-norpregn-9-ene (57):

Magnesium (290 mg, 11.9 mmol) was weighed into a 100 mL round bottom two-necked flask equipped with a reflux condenser, a magnetic stirrer and a rubber septum. A small crystal of iodine was added and the system was flushed with dry nitrogen. The system plus contents were flame dried under nitrogen. The system was cooled to room temperature and freshly distilled THF (20 mL) was added via syringe. A small amount (0.1 mL) of dry dibromoethane was added and the mixture stirred at room temperature. After evidence of reaction was observed (disappearance of $I_2$ color, bubble formation on the surface of magnesium), a solution of 4-bromothioanisole (available from Aldrich Chemical Co. (Milwaukee, Wis.)) (2.43 g, 11.9 mmol) in dry THF (10 mL) was added via syringe. The mixture was then stirred in a hot water bath for 1.5 hr, after which time the majority of the magnesium metal had reacted. The mixture was cooled to room temperature and copper (I) chloride (118 mg, 1.19 mmol) was added as a solid and the mixture stirred at room temperature for ½ hr. The 5α,10α-epoxide (51, 1.0 g, 2.38 mmol) in dry THF (10 mL) was added via syringe and the mixture stirred at room temperature for 1 hr. At this time, a small aliquot of the reaction mixture was withdrawn, quenched with saturated $NH_4Cl$ solution, and extracted with a small amount of EtOAc. A TLC (10% acetone in $CH_2Cl_2$) of the organic layer indicated absence of starting material. Saturated $NH_4Cl$ solution (20 mL) was added to the reaction mixture and the mixture was stirred at room temperature for ½ hr while air was drawn through the reaction mixture (to oxidize copper) via a 6-inch needle inserted through the rubber septum by applying a partial vacuum to the top of the condenser. The contents of the flask were diluted with $H_2O$ (~100 mL) and extracted with $CH_2Cl_2$ (3×). The organic fractions were washed with saturated $NH_4Cl$ solution (1×), $H_2O$ (1×), brine (1×), then dried over anhydrous sodium sulfate. The organic fractions was filtered and concentrated in vacuo to yield 5.75 g of 57 as an oil. This oil was placed on a flash column and eluted with 10% acetone in $CH_2Cl_2$ yielding 850 mg of 57 as a white stable foam. The foam was crystallized from ether to yield 675 mg of 57 as a white solid; m.p.=158–159° C. FTIR (KBr, diffuse reflectance) $v_{max}$ 3571, 3539, 2944, 1490, 1447, 1190 and 1076 $cm^{-1}$. NMR ($CDCl_3$) δ 0.45 (s, 3H, C18-$CH_3$), 1.36 (s, 3H, C21-$CH_3$), 2.45 (s, 3H, 11β-4-$CH_3$S-phenyl), 3.8–4.1 (br m, 8H, C3- and C20-ketals), 4.25 (br d, 1H, C11α-CH) and 7.17 (s, 4H, aromatic-CH's). MS (EI) m/z (relative intensity): 542 ($M^+$). Anal. Calcd. for $C_{31}H_{42}O_6S$: C, 68.60; H, 7.80; S, 5.91. Found: C, 68.52; H, 7.76; S, 5.84.

Step 2. 17α-Hydroxy-11β-(4-methylthiophenyl)-19-norpregna-4,9-diene-3,20-dione (66):

Nitrogen was bubbled through a mixture of EtOH (20 mL) and 8.5% $H_2SO_4$ (2.0 mL) for ½ hr to remove oxygen. The Grignard adduct (57, 500 mg, 0.92 mmol) was added as a solid with stirring. The mixture was put into an oil bath preheated to 95° C. for ½ hr. The mixture was cooled in an ice bath and quenched with saturated $K_2CO_3$ (pH=10). The reaction mixture was diluted with $H_2O$ (125 mL) and extracted with $CH_2Cl_2$ (3×). The organic fractions were washed with saturated $NaHCO_3$ (1×), $H_2O$ (1×), brine (1×), combined and then dried over anhydrous $Na_2SO_4$. It was concentrated in vacuo to give 500 mg of 66 as an oil. This oil was purified by flash chromatography (10% acetone in $CH_2Cl_2$) to yield 350 mg of the crude 66. Crystallized from $CH_2Cl_2$ and ether gave 330 mg of 66 as a white crystalline product; m.p.=foams/honeycombs at 102–106° C. FTIR (KBr, diffuse reflectance) $v_{max}$ 3409, 2975, 2887, 1707, 1650, 1608, 1493 and 1207 $cm^{-1}$. NMR ($CDCl_3$) δ 0.45 (s, 3H, C18-$CH_3$), 2.25 (s, 3H, C21-$CH_3$), 2.5 (s, 3H, 11β-4-$CH_3$S-phenyl), 3.1 (s, 1H, C17α-OH), 4.4 (br d, 1H, C11α-CH), 5.8 (s, 1H, C4-CH=) and 6.95–7.3 (dd, 4H, aromatic-CH's). MS (EI)/z (relative intensity): 436 ($M^+$, 100), 418 (14.1), 350 (76.1), 335 (35.2), 323 (16.9), 296 (14.1), 281 (16.9), 249 (16.9), 235 (39.4), 211 (18.3), 137 (87.3) and 91

(19.7). Anal. Calcd for $C_{27}H_{32}O_3S$: C, 74.28; H, 7.39. Found: C, 73.01; H, 8.27.

Step 3. Preparation of the Target Compound 74:

The 17α-hydroxy compound (66, 275 mg, 0.63 mmol) was dissolved in $CH_2Cl_2$ (10 mL) and cooled to 0° C. in an ice bath. In a separate round flask, trifluoroacetic anhydride (2.65 g, 12.6 mmol) and acetic acid (0.83 g, 12.6 mmol) were added to $CH_2Cl_2$ (10 mL), and the mixture was flushed with nitrogen and stirred at room temperature for ½ hr. The mixed anhydride was then placed in an ice bath and cooled to 0° C. The cold nixed anhydride solution was then added to the 17α-hydroxy compound (66) and treated _with p-toluenesulfonic acid (110 mg, 0.58 mmol). The reaction mixture was stirred for 1 hr at 0° C. The reaction was quenched with saturated $K_2CO_3$ (pH=10), diluted with $H_2O$ and extracted with $CH_2Cl_2$ (3×). The organic layers were washed with water (2×), brine (1×), dried over anhydrous $Na_2SO_4$, filtered and concentrated to yield 320 mg of 74 as a crude product. The 17α-acetate (74) was purified on a flash column (10% acetone in $CH_2Cl_2$) to yield 250 mg of 74. Crystallization from $CH_2Cl_2$ and ether gave 210 mg of the pure 74 as a white solid in 70.5% yield; m.p.=234–236° C. HPLC analysis on a Waters Nova Pak a C, 8 column eluted with MeOH:$H_2O$ in the ratio of 70:30 at a flow rate of 1 mL/min and at =260 nm indicated it to be 99.7% pure. FTIR (KBr, diffuse reflectance) $v_{max}$ 943, 1729, 1713, 1660, 1594, 1491, 1438, 1363 and 1258 $cm^{-1}$. NMR ($CDCl_3$) δ 0.38 (s, 3H, C18-$CH_3$), 2.10 (s, 3H, C17α-OAc), 2.15 (s, 3H, C21-$CH_3$), 2.45 (s, 3H, 11β-4-$CH_3$S-phenyl), 4.45 (d, 1H, C11α-CH), 5.8 (s, 1H, C4-CH═) and 7.0–7.35 (dd, 4H, aromatic-CH's). MS (EI) m/z (relative intensity): 478 ($M^+$, 28.2), 418 (28.2), 403 (28.2), 375 (100), 347 (11.3), 294 (15.5), 281 (8.5), 265 (18.3), 251 (42.3), 236 (15.5), 151 (18.3), 137 (60.6) and 91 (9.9). Anal. Calcd. for $C_{29}H_{34}O_4S$: C, 72.77; H, 7.16; S, 6.70. Found: C, 72.07; H, 7.07; S, 6.81.

Example 22

This example illustrates the preparation and properties of 17α-Methoxy-11β-[4-(N,N-dimethylamino)phenyl]-19-norpregna-4,9-diene-3,20-dione (97a) (FIG. 6):

Step 1. 17α-Hydroxyl-9-norpregna-4,9-diene-3,20-drone (92):

Under nitrogen, the diketal (50, 20.0 g, 49.7 mmol) was dissolved in a mixture of THF (333 mL) and $H_2O$ (333 mL) followed by trifluoroacetic acid (1 L, 13.46 mmol). The reaction mixture was then stirred at room temperature for 2 hr, after which time, TLC (10% acetone in $CH_2Cl_2$, overspotted with concentrated $NH_4OH$ indicated a complete reaction. The reaction mixture was cooled in an ice bath and neutralized by the dropwise addition of concentrated (29.5%) $NH_4OH$ (862 mL, ~13.46 mol) over a period of about an hour. The reaction mixture was diluted with $H_2O$ (500 mL) and extracted with methylene chloride (3×). The organic fractions were washed with saturated $NaHCO_3$ (1×) and $H_2O$ (1×), brine (1×), then filtered through anhydrous sodium sulfate, combined and concentrated in vacuo. Crystallization of the residue from acetone/hexanes gave 12 g of the pure product 92 as a white crystalline solid in 76.8% yield; m.p.=203–205° C. FTIR (KBr, diffusion reflectance) $v_{max}$ 3438, 2950, 1702, 1642 and 1593 $cm^{-1}$. $^1H$ NMR (300 MHz, $CDCl_3$) δ 0.857 (s, 3H, C18-$CH_3$), 2.289 (s, 3H, C21-$CH_3$) and 5.669 (s, 1H, C4-CH═). $^{13}C$ NMR ($CDCl_3$): δ 14.703, 23.901, 25.341, 25.714, 27.515, 27.615, 30.260, 30.765, 33.470, 36.971, 39.086, 47.846, 50.696, 89.565 (C17), 122.015 (C4), 125.440(C10), 145.632 (C9), 157.339 (C5), 199.824 (C3) and 211.201 (C20). MS (EI) m/z (relative intensity): 314 ($M^+$, 100), 296 (13.6), 271 (58.0), 213 (67.0) and 91 (35.9). Anal. Calcd. for $C_{20}H_{2603}$: C, 76.40; H, 8.34. Found: C, 76.23; H, 8.29.

Step 2. 17α-Methoxy-19-norpregna-4,9-diene-3,20-dione (93):

A suspension of the 17α-hydroxy dienedione (92, 19 g, 31.80 mmol) in $CH_3CN$ (167 mL) was stirred magnetically under nitrogen. Methyl iodide (134 mL; freshly opened) was added and a solution formed immediately. Silver oxide (8.1 g, 35.0 mmol) was added, the joints were well-greased to prevent evaporation of methyl iodide, and the flask was wrapped in foil to protect the contents from light. The mixture was brought to a gentle reflux and the reaction allowed to proceed overnight. The next morning, analysis by TLC (5% acetone in $CH_2Cl_2$) indicated virtually all the starting material had been converted to a single, less polar component. The reaction was allowed to cool to room temperature and filtered through a Celite filter cake on a sintered glass funnel. The filtrate was evaporated in vacuo to recover a thick syrup. Crystallization from boiling $CH_3OH$ afforded small white crystals. The crystals were collected on a Buchner funnel, triturated with cold $CH_3OH$, and dried under vacuum to recover 5.74 g. Flash chromatography of the mother liquors (5% acetone in $CH_2Cl_2$) afforded 1.69 g of additional material. The total purified product recovered was 7.43 g of 93 as white crystals in 71.1% yield; m.p.= 154–155° C. FTIR (KBr, diffuse reflectance) $v_{max}$ 2952, 1704, 1660, 1614 and 1583 $cm^{-1}$. $^1H$ NMR (300 MHz, $CDCl_3$) δ 0.739 (s, 3H, C18-$CH_3$), 2.164 (s, 3H, C21-$CH_3$), 3.141 (s, 3H, C177-$OCH_3$) and 5.672 (s, 1H, C4-CH═). $^{13}C$ NMR ($CDCl_3$): δ 14.264, 23.156, 23.431. 23.775, 25.547, 25.753, 26.431, 27.445, 30.755, 30.793, 37.054, 39.220, 47.243, 51.348, 52.258, 96.714 (C17), 122.057 (C4), 125.228 (C10), 145.588 (C9), 157.192 (C5), 199.637 (C3) and 210.479 (C20). MS (EI) m/z (relative intensity): 328 ($M^+$, 5.8), 285 (66), 253 (64) and 213 (100). Anal. Calcd. for $C_{21}H_{29}O_3$: C, 76.79; H, 8.59. Found: C, 76.64; H, 8.59.

Step 3. 3,3-Ethylenedioxy-17α-methoxy-19-norpregna-5 (10),9(11)-en-20-one (94):

Under nitrogen, a mixture of the 17α-methoxydione (93, 17.0 g, 51.76 mmol), triethylorthoformate (42.5 mL, 250 mmol), ethylene glycol (14 mL, 250 mmol) and p-toluenesulfonic acid monohydrate (0.5 g, 2.6 mmol) in dry $CH_2Cl_2$ (500 mL) was stirred at room temperature for 2 hr. After that time, TLC (2% acetone in $CH_2Cl_2$) indicated absence of starting material with formation of one major product. The reaction mixture was diluted with $CH_2Cl_2$ (200 mL) and washed with saturated $NaHCO_3$ solution (1×), $H_2O$ (1×) and brine. The organic fractions were filtered through anhydrous sodium sulfate, combined and concentrated in vacuo. Recrystallization of the residue from hot methanol containing a trace of pyridine gave 16.2 g of the pure 3-ketal 94 as a white solid in 84.1% yield; m.p.=123–125° C. FTIR (KBr, diffuse reflectance) $v_{max}$ 2927 and 1705 $cm^-$. $^1H$ NMR (300 MHz, $CDCl_3$) δ 0.553 (s, 3H, C18-$CH_3$), 2.147 (s, 3H, C21-$CH_3$), 3.147 (s, 3H, C17α-$OCH_3$), 3.983 (s, 4H, C3-ketal) and 5.568 br s, 1H, C11-CH═).

$^{13}C$ NMR ($CDCl_3$): δ 15.746, 23.123, 24.026, 24.570, 26.422, 27.972, 31.150, 31.298, 31.839, 38.233, 41.238, 46.079, 47.391, 52.318, 64.325, 64.448, 96.792, 108.131, 117.907, 126.081, 129.914 and 135.998 (signal/noise ratio obscured C20 at 210 ppm). Anal. Calcd. for $C_{23}H_{32}O_4$: C, 74.16; H, 8.66. Found: C, 74.16; H, 8.68.

Step 4. 3,3-Ethylenedioxy-5α,10α-epoxy-17α-methoxy-19-norpregn-9(11)-en-20-one (95):

Hydrogen peroxide (30% 3.0 mL, 29.3 mmol) was added to a vigorously stirred mixture of hexafluoroacetone trihydrate (4.0 mL, 28.7 mmol) in CH$_2$Cl$_2$ (70 mL) cooled to 0° C. in an ice bath. After stirring at 0° C. for 1/hr, solid Na$_2$HPO$_4$ (2.1 g, 14.8 mmol) was added followed by a solution of the 3-ketal (94, 7.0 g, 18.8 mmol) in CH$_2$Cl$_2$ (70 mL), precooled to 0° C. The mixture was then stirred at 5° C. overnight. The reaction mixture was diluted with CH$_2$Cl$_2$ (~200 mL) and washed with 10% Na$_2$SO$_3$ solution (1×) and H$_2$O (2×). The organic fractions were filtered through anhydrous Na$_2$SO$_4$, combined and concentrated in vacuo to give 7.29 g of 95 as a white foam in quantitative yield. Attempts to crystallize out the 5α,10α-epoxide by trituration with ether/pentane or mixtures of CH$_2$Cl$_2$ and pentane were unsuccessful. Analysis by NMR indicated a 4:1 mixture of the 5α,10α- and the 5α,10β-epoxides. NMR (300 MHz, CDCl$_3$): δ 0.554 (s, 3H, C18-CH$_3$), 2.139 (s, 3H, C21-CH$_3$), 3.8–4.0 (m, 4H, C3-ketal CH$_2$'s), 5.845 (m, 0.2H, C11-CH= of β-epoxide) and 6.034 (m, 0.8H, C11-CH= of α-epoxide).

Step 5. 3,3-Ethylenedioxy-5α-hydroxy-11β-[4-(N,N-methylamino)phenyl]-17α-methoxy-19-norpregn-9(10)-en-20-one (96a):

Magnesium (2.49 g, 102.45 mmol) was added to a 2.0 L, 3-neck flask with a mechanical stirrer, addition funnel and a condenser. The system was flushed with nitrogen and flame dried. After cooling, dry THF (100 mL) and 1,2-dibromoethane (0.2 mL) were added. The mixture was stirred under nitrogen and heated in a warm water bath until evidence of the reaction was observed. A solution of 4-bromo-N,N-dimethylaniline (18.81 g, 94 mmol) in dry THF (100 mL) was then added via the addition funnel and the mixture stirred and heated in a warm water bath until reaction initiated. Solid copper (I) chloride (1.86 g, 18.8 mmol) was added followed ½ hr later by a solution of the 4:1 epoxide mixture (95, 7.29 g, 18.8 mmol=assumed 5.47 g of the 5α,10α-epoxide (14.10 mmol)) in dry THF (125 mL). The reaction mixture was stirred at room temperature for 1.5 hr, then quenched by the addition of saturated NH$_4$Cl solution (250 mL). In order to oxidize Cu(I) to Cu(II), air was drawn through the reaction mixture for ½ hr with vigorous stirring. The mixture was then extracted with ether (3×). The organic fractions were washed with H$_2$O (3×), combined, dried over anhydrous Na$_2$SO$_4$, filtered and concentrated in vacuo to give 14.5 g of residue as a green-blue oil. This material was purified via Flash chromatography using CH$_2$Cl$_2$ followed by 4% acetone in CH$_2$Cl$_2$ to give 4.4 g of the pure compound 96a as a grey foam in 62.7% yield based on the 4:1 α:β ratio. FTIR (KBr, diffuse reflectance) $v_{max}$ 3526, 2944, 1707, 1613, and 1518 cm$^{-1}$. NMR (300 MHz, CDCl$_3$) δ 0.223 (s, 3H, C18-CH$_3$), 2.155 (s, 3H, C21-CH$_3$), 2.894 (s, 6H, N(CH$_3$)$_2$), 3.105 (s, 3H, C17α-OCH$_3$); 3.896–3.995 (m, 4H, C3-ketal CH$_2$'s), 4.255 (m, 1H, C11α-CH), 6.624 (d, 2H, J=9.0 Hz, 3',5' aromatic-CH's), and 7.03 (d, 2H, J=9.0 Hz, 2',6' aromatic-CH's). Anal. Calcd. for C$_{31}$H$_{43}$NO$_5$.⅓H$_2$O: C, 72.54; H, 8.52; N, 2.73. Found: C, 72.36; H, 8.52; N, 2.52.

Step 6 Preparation of the Target Compound 97a:

Under nitrogen, a solution of the Grignard adduct (96a, 3.73 g, 7.32 mmol) in THF (40 mL) was treated with H$_2$O (40 mL) and glacial AcOH (120 mL). After stirring overnight at room temperature, TLC (5% acetone in CH$_2$Cl$_2$) indicated incomplete hydrolysis. The mixture was heated to ~50° C. in a warm water bath for 1 hr, after which time TLC indicated a complete reaction. The mixture was cooled in an ice bath and neutralized with the addition of concentrated NH$_4$OH (141 mL). The mixture was then further diluted with H$_2$O (200 mL) and extracted with CH$_2$Cl$_2$ (3×). The organic fractions were washed with H$_2$O (2×), filtered through anhydrous Na$_2$SO$_4$, combined and concentrated in vacuo to give 4.0 g of residue as a yellow foam. This material was purified by flash chromatography (3% acetone in CH$_2$Cl$_2$) to give 1.6 g of the pure title compound (97a) as a foam along with 1.2 g of additional material contaminated with a by-product having a slightly higher R$_f$. Crystallization of the first fraction from boiling heptane afforded the pure title compound (97a, 1.2 g) as an off-white solid in 36.6% yield; m.p.=[164–166° C. FTIR (KBr, diffuse reflectance) $v_{max}$ 2953, 1707, 1666, 1614, 1601 and 1520 cm$^{-1}$. NMR (300 MHz, CDCl$_3$) δ 0.297 (s, 3H, C18-CH$_3$), 2.18 (s, 3H, C21-CH$_3$), 2.903 (s, 6H, N(CH$_3$)$_2$), 3.141 (s, 3H, C17α-OCH$_3$), 4.355 (d, 1H, J=7.2 Hz, C11α-CH), 5.745 (s, 1H, C4-CH=), 6.638 (d, 2H, J=9.0 Hz, 3',5' aromatic-CH's) and 6.994 (d, 2H, J=9.0 Hz, 2',6' aromatic-CH's). MS (EI) m/z (relative intensity): 447 (M$^+$, 72.8), 372(6.5), 251 (15.1), 134 (30.2) and 121 (100).

Analysis by HPLC on a Waters Assoc. NovaPak C$_{18}$ column eluted with MeOH/H$_2$O/Et$_3$N, 75:25:0.05 at a flow rate of 1 mL per min and λ=302 nm indicated compound 97a to be 98.33% pure with t$_R$ of 9.00 min. Anal. Calcd. for C$_{29}$H$_{37}$NO$_3$.1/12H$_2$O: C, 77.56; H, 8.34; N, 3.12. Found: C, 77.59; H, 8.34; N, 3.10.

Example 23

This example illustrates the preparation and properties of 17α-Methoxy-1-[4-(piperidino)phenyl]-19-norpregna-4,9-diene-3,20-dione (97b) (FIG. 6):

Step 1 3,3-Ethylenedioxy-5α-hydroxy-17α-methoxy-11β-[4N-piperidino)phenyl]-19-norpregna-5(10),9(11)-dien-20-one (96b):

Magnesium (845 mg, 34.7 mmol) was added to a 500 mL, 3-neck flask equipped with a reflux condenser, a magnetic stirrer and a rubber septum. A small crystal of iodine was added and the system flushed with nitrogen and flame dried. After cooling, dry THF (20 mL) and 1,2-dibromoethane (0.2 mL) were added. The mixture was stirred under nitrogen and heated in a warm water bath until evidence of the reaction was observed. A solution of N-(4-bromophenyl)piperidine (Veradro, et al., *Synthesis*, 447–450 (1991)) (8.35 g, 34.7 mmol) in dry THF (30 mL) was then added via syringe and the mixture stirred and heated in a warm water bath for 3½ hr. Solid copper (I) chloride (688 mg, 6.95 mmol) was added followed ½ hr later by a solution of the epoxide mixture (95, 2.7 g, assumed 6.95 mmol) in dry THF (30 mL). The reaction mixture was stirred at room temperature for 45 min, then quenched by the addition of saturated NH$_4$Cl solution. In order to oxidize Cu (I) to Cu (II), air was drawn through the reaction mixture for ½ hr with vigorous stirring. The mixture was then extracted with CH$_2$Cl$_2$ (3×). The organic fractions were washed with saturated NH$_4$Cl solution, H$_2$O and brine, combined, dried over Na$_2$SO$_4$, filtered and concentrated in vacuo to give 11.3 g of the residue as a dark oil. The material was purified via flash chromatography (5% acetone in CH$_2$Cl$_2$) twice to give 1.22 g of the Grignard adduct 96b as a white foam in 32% yield; m.p.=126–131° C. (dec). FTIR (KBr, diffuse reflectance) $v_{max}$ 3523, 2938, 1707, 1610, 1511 and 1447 cm$^{-1}$. NMR (300 MHz, CDCl$_3$) δ 0.207 (s, 3H, C18-Me), 1.682 (m, 6H, —(CH$_2$)$_3$— of piperidine), 2.147 (s, 3H, C21-CH$_3$), 3.103 (s, 3H, C17α-OCH$_3$), 3.05–3.2 (m, 4H, —N(CH$_2$)$_2$), 3.8–4.05 (m, 4H, C3-ketal), 4.23 (m, 1H, C11α-CH) and 6.78–7.05 (dd, 4H, aromatic-CH's). MS (EI) m/z (relative intensity): 549 (M$^+$, 59.7), 531 (18.1), 174 (20.8), 161 (100) and 99 (11.1). Anal. Calcd. for C$_{34}$H$_{47}$O$_5$N: C, 74.28; H, 8.62; N, 2.55. Found: C, 73.45; H, 8.51; N, 2.53.

Step 4. Preparation of the Target Compound 97b:

Under nitrogen, a solution of the Grignard adduct (96b, 1.0 g, 1.81 mmol) in THF (10 mL) was treated with $H_2O$ (10 mL) and glacial HOAc (30 mL). After stirring overnight at room temperature, TLC (5% acetone in $CH_2Cl_2$) indicated incomplete deketalzation and dehydration. The reaction mixture was heated to 50° C. in a warm water bath for 2 hr, after which time TLC indicated a complete reaction. The mixture reaction was cooled in an ice bath and neutralized with the addition of concentrated $NH_4OH$ (~35 mL). The mixture was then further diluted with $H_2O$ (~1001 mL) and extracted with $CH_2Cl_2$ (3×). The organic fractions were washed with $H_2O$, brine, combined, dried over $Na_2SO_4$, and concentrated in vacuo to give 900 mg of foam. The crude material was purified by flash chromatography (5% acetone in $CH_2Cl_2$) to give 630 mg of the target compound 97b as a foam. Recrystallization of the compound 97b from EtOH afforded 325 mg of the target compound 97b as an off-white solid in 35.7% yield. HPLC analysis of 97b on a Waters NovaPak $C_{18}$ column eluted with $MeOH/H_2O$ (80:20) with 0.05% $Et_3N$ at a flow rate of 1 mL/min and λ=260 nm indicated this compound to be 97.7% pure. FTIR (KBr, diffuse reflectance) $v_{max}$ 2934, 1708, 1665, 1610 and 1512 $cm^{-1}$. NMR (300 MHz, $CDCl_3$) δ 0.273 (s, 3H, C18-$CH_3$), 2.174 (s, 3H, C21-$CH_3$), 3.139 (s, 3H, C17α-$OCH_3$), 4.35 (d, 1H, C11α-CH), 5.746 (s, 1H, C4-CH=) and 6.8–7.0 (dd, 4H, aromatic-CH's). MS (EI) m/z (relative intensity): 487 (84.3), 412 (4.3), 318 (8.6), 251 (7.14), 206 (11.4), 174 (15.7) and 161 (100). Anal. Calcd. for $C_{32}H_{11}O_3N$: C, 78.85; H, 8.42; N, 2.87. Found: C, 78.00; H, 8.37; N, 3.00.

Example 24

This example illustrates the preparation and properties of 17α,21-Diacetoxy-11β-[4-(N-piperidino)phenyl]-19-norpregna-4,9-diene-3,20-dione (106a) (FIG. 7):

Step 1. 3,3-Ethylenedioxy-17β-cyano-17α-trimethylsilyloxyesttra-5(10),9(11)-diene (99):

Under nitrogen, pyridine (136.9 g, 1740 mmol) solution of the cyanohydrin ketal (98, 25 g, 73.22 mmol) was treated with chlorotrimethylsilane (44 g, 394 mmol). The mixture was stirred at room temperature overnight. The reaction mixture was poured into a 50:50 mixture of ice/saturated $NaHCO_3$ solution (1.2 L), stirred until the ice had melted, and extracted with hexane (3×). The organic extracts were washed with $H_2O$ (3×), brine (1×), combined, dried over anhydrous $Na_2SO_4$, and concentrated in vacuo. The remaining pyridine was azeotropically removed in vacuo with heptane. Crystallization of the residue from pentane gave 26.1 g of the pure silyl ether (99) as a white solid in 86.2% yield; m.p.=99–101° C. FTIR (KBr, diffuse reflectance) $v_{max}$ 2944, 2908, 2231 and 1253 $cm^-$. NMR (300 MHz, $CDCl_3$) δ 0.229 (s, 9H, C17α-$OSi(CH_3)_3$), 0.894 (s, 3H, C18-$CH_3$), 3.987 (s, 4H, 3-$OCH_2CH_2O$) and 5.615 (t, 1H, J=2.55 Hz, C11-CH=). MS (EI) m/z (relative intensity): 413 (M⁺, 100.0), 398 (5.5), 385 (24.0), 371 (6.4), 237 (33.9) and 69.3 (86.0).

Step 2. 3,3-Ethylenedioxy-5α,10α-epoxy-17β-cyano-17α-trimethylsilyloxyestr-9(11)-ene (100):

Hydrogen peroxide (30%, 12 mL, 117.12 mmol) was added to a vigorously stirred mixture of hexafluoroacetone trihydrate (20.20 g, 112.5 mmol) in $CH_2Cl_2$ (185 mL) cooled to 0° C. in an ice bath. The reaction mixture was stirred at 0° C. for ½ hr, and solid $Na_2HPO_4$ (11 g, 77.5 mmol) was added followed by an ice-cold solution of the silyl ether (99, 25 g, 60.44 mmol) in $CH_2Cl_2$ (185 mL). The mixture was then stirred at 0° C. for 5 hr, then at 5° C. overnight. Analysis by TLC (5% acetone in $CH_2Cl_2$) at that time indicated a complete reaction. The reaction mixture was diluted with $CH_2Cl_2$ (200 mL) and washed with 10% $Na_2SO_3$ solution (1×), $H_2O$ (1×) and brine (1×). The organic fractions were filtered through anhydrous sodium sulfate, combined and concentrated in vacuo. Trituration of the residue with ether afforded 16.66 g of the pure 5α,10α-epoxide (100) as a white solid in 64.16% yield; m.p. 156–160° C. FTIR (KBr, diffuse reflectance) $v_{max}$ 2955, and 2228 $cm^{-1}$. NMR (300 MHz, $CDCl_3$) δ 0.219 (s, 9H, $OSi(CH_3)_3$), 0.894 (s, 3H, C18-$CH_3$), 3.85–3.97 (s, 4H, C3-$OCH_2CH_2O$) and 6.082 (t, 1H, J=2.6 Hz, C11-CH=). MS(EI) m/z (relative intensity): 429 (M⁺, 18.5), 401 (2.8), 343 (11.1), 238 (9.5), 99 (100.0) and 86 (36.2).

Step 3. 3,3-Ethylenedioxy-5α-hydroxy-11β-[4-(N-piperidino)phenyl]-17β-cyano-17α-trimethyl-silyloxyestr-9-ene (101a):

Magnesium (0.95 g, 39.1 mmol) was added to a 500 mL, 3-neck flask equipped with a magnetic stirrer, rubber septum and a condenser. A crystal of iodine was added followed by dry THF (50 mL) and two drops of 1,2-dibromoethane. A solution of N-(4-bromophenyl)piperidine (see, EXAMPLE 23, Step 1) (10.24 g, 42.64 mmol) in dry THF (50 mL) was then added, and the mixture was stirred under nitrogen and heated to reflux for 1 hr. At the end of that time, all of the magnesium metal had reacted. The reaction was allowed to cool to room temperature, and solid copper (I) chloride (0.7 g, 7.07 mmol) was added followed ½ hr later by a solution of the 5α,10α-epoxide (100, 5.55 g, 12.92 mmol) in dry THF (50 mL). The mixture was stirred at room temperature for 1.5 hr. Analysis by TLC (5% acetone in $CH_2Cl_2$) of a small aliquot quenched with $NH_4Cl$ solution and extracted with EtOAc indicated a complete reaction. The reaction mixture was cooled in an ice bath and quenched by the addition of saturated $NH_4Cl$ solution (15 mL). The reaction mixture was allowed to warm to room temperature, and air was drawn through the reaction mixture for ½ hr to oxidize Cu(I) to Cu(II). The mixture was extracted wtih $CH_2Cl_2$ (3×) and the organic fractions washed with $H_2O$ (3×). The organic fractions were combined, dried over anhydrous $Na_2SO_4$, filtered and concentrated in vacuo. Trituration of the residue with pentane gave 7.37 g of 101a as an off-white solid in 97% yield.; m.p.=127–130° C. FTIR (KBr, diffuse reflectance) $v_{max}$ 3510, 2945, 2228, 1611 and 1510 $cm^{-1}$. NMR (300 MHz, $CDCl_3$) δ 0.241 (s, 9H, 17α-$OSi(CH_3)$ 3, 0.533 (s, 3H, C18-$CH_3$), 3.107 (t, 4H, J=5.6 Hz, piperidine α-$CH_2$'s), 3.884–4.043 (s, 4H, C3-$OCH_2CH_2O$) 4.284 (d, 1H, J=6.9 Hz, C11α-CH), 6.831 (d, 2H, J=8.7 Hz, 3',5' aromatic-CH's) and 7.060 (d, 2H, J=8.7 Hz, 2',6' aromatic-CH's). MS(EI) m/z (relative intensity): 590 (M⁺, 38.1), 572 (10.3), 320 (4.0), 174 (12.1), 161 (100.0), 100 (1.7), 99 (7.8) and 71 (7.0) Anal. Calcd. for $C_{35}H_{50}N_2O_4Si \cdot \frac{1}{3}C_5H_{11}$: C, 71.61; H, 8.85; N, 4.56. Found: C, 71.79; H, 8.89; N, 4.49.

Step 4. 17β-cyano-11β-[4-(N-piperidino)phenyl]-17α-hydroxyestra-4,9-dien-3-one (102a):

A solution of the Grignard adduct (101a, 7.27 g, 12.3 mmol) was dissolved in THF (25 mL) and the system was flushed with nitrogen. Glacial acetic acid (75 mL) and $H_2O$ (25 mL) were added and the mixture was heated to 65° C. for 3 hr. Analysis by TLC (5% acetone in $CH_2Cl_2$) at that time indicated a complete reaction. The mixture was cooled wt to 0° C. in an ice bath and the acetic acid was neutralized by slow addition of concentrated $NH_4OH$ solution (28%, 90 mL) to a final pH of 8 by pH paper. The mixture was diluted with $H_2O$ and extracted with $CH_2Cl_2$ (3×). The organic fractions were washed with $H_2O$ (3×), filtered through anhydrous $Na_2SO_4$, combined and concentrated in vacuo.

Trituration of the residue with ether gave 3.8 g of the cyanohydrin (102a) as a white crystalline solid. The mother liquors were concentrated and purified by flash column chromatography (5% acetone in $CH_2Cl_2$) to afford an additional 0.65 g of 102a after trituration with pentane. Total yield of the cyanohydrin (102a) was 4.45 g in 79.2% yield; m.p.=205–208° C. FTIR (KBr, diffuse reflectance): $\nu_{max}$ 3436, 3211, 2939, 2855, 2234, 1658, 1634, 1609 and 1512 $cm^{41}$. NMR (300 MHz, $CDCl_3$): δ 0.641 (s, 3H, C18-$CH_3$), 3.125 (t, 4H, J=5.7 Hz, piperidine α-$CH_2$'s), 4.427 (d, 1H, J=5.1 Hz, C11α-CH), 5.782 (s, 1H, C4-CH=), 6.862 (d, 2H, J=9 Hz, 3',5' aromatic-CH's) and 7.031 (d, 2H, J=9 Hz, 2',6' aromatic-CH's). MS (EI) m/z (relative intensity): 456 ($M^+$, 0.3), 429 (61.1), 401 (1.5), 174 (6.9), and 161 (100.0). Anal. Calcd. for $C_{30}H_{36}N_2O_2 \cdot \frac{1}{10}H_2O$: C, 78.60; H, 7.96; N, 6.11. Found: C, 78.64; H, 7.94; N, 6.11.

Step 5. 17β-cyano-11β-[4-(N-piperidino)phenyl]-17α-chloromethyldimethylsilyloxyestra-4,9-dien-3-one (103a):

Under nitrogen, a solution of the cyanohydrin (102a, 4.39 g, 9.61 mmol) and dimethylaminopyridine (0.4 g, 3.27 mmol) in dry THF (50 mL) and triethylamine (1.8 g, 17.79 mmol) was treated with chloromethyldimethylsilyl chloride (2.0 mL=2.17 g, 15.18 mmol). After stirring overnight at room temperature, TLC (2% acetone in $CH_2Cl_2$) indicated a complete reaction. The reaction was diluted with ether (50 mL) and stirred for an additional ½ hr. The resulting suspension was filtered through Celite and the filtrate concentrated in vacuo. The residue was taken up in ether/$CH_2Cl_2$ (9:1) and the solution/suspension was passed through a silica gel flash chromatography column using ether as eluent. Fractions containing the product were combined and concentrated in vacuo to give 5.4 g of the chloromethyl silyl ether (103a) as a white foam in quantitative yield. Attempts to crystallize or soldify the crude product using a variety of solvents were (n unsuccessful. This material was used in the subsequent reaction without further purification. NMR (300 MHz, $CDCl_3$): δ 0.403 and 0.410 (both s, 6H, OSi$(CH_3)_2$), 0.607 (s, 3H, C18-$CH_3$), 2.904 (s, 2H, $(CH_3)_2$Si$\underline{CH_2}$Cl), 3.123 (t, 4H, J=5.6 Hz, piperidine α-$CH_2$'s), 4.399 (d, 1H, J=6 Hz, C11α-CH), 5.775 (s, 1H, C4-CH=), 6.863 (d, 2H, J=8.6 Hz, 3',5' aromatic-CH's) and 7.027 (d, 2H, J=8.6 Hz, 2',6' aromatic-CH's).

Step 6. 17α-Hydroxy-11β-[4(N-piperidino)phenyl]-21-chloro-19-norpregna-4,9-diene-3,20-dione (104a):

Under nitrogen and anhydrous conditions, a solution of the chloromethyl silyl ether (103a, 5.1 g, 9.05 mmol) in dry THF (150 mL) was cooled to –78° C., and treated dropwise with a 2.0 $\underline{M}$ solution of lithium diisopropylamide (LDA) in THF/heptane (19 mL, 38 mmol). The reaction was stirred at –78° C. for 2 hr and then quenched at –78° C. by the slow addition of 4 N HCl (100 mL, 400 mmol). The mixture was allowed to warm and stirred at room temperature for 1 hr. The reaction was cooled to 0° C. and the excess acid was neutralized by slow addition of concentrated $NH_4OH$ solution (~25 mL). The reaction mixture was diluted with $H_2O$ (~100 mL) and extracted with $CH_2Cl_2$ (3×). The organic fractions were washed with $H_2O$ (2×), filtered through anhydrous $Na_2SO_4$, combined and concentrated in vacuo to give 5.6 g of a residue as a yellow foam.

This material was triturated with EtOAc to give 2.64 g of the pure 21-chloro product (104a) as a yellow solid. Concentration of the mother liquors followed by flash column chromatography (7.5% acetone in $CH_2Cl_2$) and trituration with EtOAc gave an additional 0.54 g of the product. Total yield of the 21-chloro intermediate (104a) was 3.18 g in 69.17% yield; m.p.=231–234° C. FTIR (KBr, diffuse reflectance): $\nu_{max}$ 3395, 2939, 1730, 1649, 1602 and 1512 $cm^{-1}$. NMR (300 MHz, $CDCl_3$): δ 0.382 (s, 3H, C18-$CH_3$), 3.104 (t, 4H, J=5.4 Hz, piperidine α-$CH_2$'s), 4.343 and 4.614 (dd, 25H, 3=16.5 Hz, C21-$CH_2$), 4.380 (d, 1H, J=6.0 Hz, C11α-CH), 5.762 (s, 1H, C4-CH=), 6.826 (d, 2H, J=8.9 Hz, 3',5' aromatic-CH's) and 6.981 (d, 2H, J=8.9 Hz, 2',6' aromatic-CH's). MS(EI) m/z (relative intensity): 507 ($M^+$, 23.7), 471 (18.0), 318 (6.5), and 161 (100.0). Anal. Calcd. for $C_{31}H_{38}ClNO_3 \cdot \frac{1}{6}CH_2Cl_2$: C, 71.06; H, 743; N, 2.66; Cl, 8.98. Found: C, 71.06; H, 7.55; N, 2.73; Cl, 8.78.

Step 7. 17α-Hydroxy-11β-[4-(N-piperidino)phenyl]-21-acetoxy-19-norpregna-4,9-diene-3,20-done (105a):

The 21-chloro intermediate (104a, 3.0 g, 5.9 mmol) and anhydrous potassium acetate (6.0 g, 61.14 mmol) in dry $CH_3CN$ (75 ml) was heated to reflux under nitrogen and monitored by TLC (10% acetone in $CH_2Cl_2$) which indicated a complete reaction after 3 hr. The reaction mixture was cooled to room temperature, diluted with $CH_2Cl_2$ (~50 mL), filtered and concentrated in vacuo to give 4.1 g of the residue as a yellow solid. This material was crystallized from $CH_2Cl_2$/acetone to give 2.63 g of the pure 17α-ol-21-acetate (105a) as an off-white solid in 83.8% yield; m.p.= 277–281° C. FTIR (KBr, diffuse reflectance): $\nu_{max}$ 3440, 2937, 1742, 1727, 1648, 1601 and 1513 $cm^{-1}$. NMR (300 MHz, $CDCl_3$): δ 0.379 (s, 3H, C18-$CH_3$), 2.174 (s, 3H, C21-OAc), 3.101 (t, 4H, J=5.4 Hz, piperidine α-$CH_2$'s), 4.376 (d, 1H, J=6.6 Hz, C11α-CH), 4.864 and 5.106 (dd, 2H, J=17.3 Hz, C21-$CH_2$), 5.762 (s, 1H, C4-CH=), 6.836 (d, 2H, J=9 Hz, 39, 5' aromatic-CH's) and 7.016 (d, 2H, J=9 Hz, 2',6' aromatic-CH's). MS(EI) m/z (relative intensity): 531 ($M^+$, 28.3), 513 (2.9), 501 (3.2), 471 (7.4), 174 (11.6) and 161 (100.0). Anal. Calcd. for $C_{33}H_{41}NO_5 \cdot \frac{1}{5}CH_2Cl_2$: C, 72.68; H, 7.61; N, 2.55. Found: C, 72.73; H, 7.53; N, 2.70.

Step 8. Preparation of the Target Compound 106a:

A mixture of trifluoroacetic anhydride (7.9 g, 37.6 mmol) and glacial acetic acid (2.21 g, 36.7 mmol) in dry $CH_2Cl_2$ (25 mL) was stirred at room temperature under nitrogen for 1 hr. p-Toluenesulfonic acid monohydrate (0.79 g, 4.15 mmol) was added, and the mixture was cooled to 0° C. in an ice bath. A solution of the 17α-ol-21-acetate (105a, 2.0 g, 3.76 mmol) in dry $CH_2Cl_2$ (35 mL) was added and the reaction mixture stirred at 0° C. for 2.5 hr. Assays by TLC (5% acetone in $CH_2Cl_2$) at that time indicated >90% of the starting material had been consumed. $H_2O$ (~10 mL) was added and the reaction stirred at 0° C. for 10 min. Additional $H_2O$ (~50 mL) was added and the reaction allowed to warm to room temperature. The pH of the reaction mixture was carefully adjusted to 9.0 with concentrated $NH_4OH$ and the mixture was extracted with $CH_2Cl_2$ (3×). The organic fractions were washed with $H_2O$ (2×), brine (1×), filtered through anhydrous $Na_2SO_4$, combined and concentrated in vacuo to give 2.3 g of a yellow foam. Purification of this crude 106a by flash chromatographies (7.5% acetone in $CH_2Cl_2$) followed by crystallization from ether gave the 17α,21-acetate 106a in two crops, both as white crystalline solids. Crop 1 (0.68 g), m.p.=188–189° C. Crop 2 (0.672 g), m.p.=186–188° C. Total was 1.352 g in 62.6% yield. Analysis of 106a by HPLC on a Water Associates NovaPak $C_{18}$ eluted with $CH_3CN/0.05$ $\underline{M}$ $KH_2PO_4$ [pH=3.0] at a flow rate of 1 mL per minute and λ=302 nm) indicated the first crop to be 99.1% pure and the second crop to be 98.1% pure. FTIR (KBr, diffuse reflectance): $\nu_{max}$ 2939, 2858, 2793, 1748, 1729, 1669, 1600 and 1509 $cm^{-1}$. NMR (300 MHz, $CDCl_3$): δ 0.417 (s, 3H, C18-$CH_3$), 2.125 (s, 3H, C17α-OAc), 2.168 (s, 3H, C21-OAc), 3.104 (t, 4H, J=5.35 Hz, piperidine α-$CH_2$'s), 4.386 (d, 1H, J=6.6 Hz, C11α-CH), 4.403 and 4.946 (dd, 2H, J=16.8 Hz, C21-CH$_2$OAc), 5.781 (s, 1H, C4-CH=), 6.832 (d, 2H, J=9H, 3',5' aromatic-CH's) and 7.011 (d, 2H, J=9 Hz, 2',6' aromatic-CH's). MS (EI) m/z (relative intensity): 573 (M$^+$, 46.3), 513 (11.5), 174 (10.4) and 161 (100.0). Anal. Calcd. for C$_{35}$H$_{43}$NO$_6$: C, 73.27; H, 7.55; N, 2.44. Found: C, 73.18; H, 7.60; N, 2.50.

Example 25

This example illustrates the preparation and properties of 17α,21-Diacetoxy-11β-(4-acetylphenyl)19-norpregna-4,9-diene-3,20-dione (106b) (FIG. 7):

Step 1. 3,3-Ethylenedioxy-5α-hydroxy-11β-[4-(2-methyl-1,3-dioxolan-2-yl)phenyl]-17β-cyano-17α-trimethylsilyloxyestr-9-ene (101b):

Under nitrogen and in flame-dried glassware, dry THF (240 mL) was added to magnesium turnings (2.3 g, 94.6 mmol). Solid bromoacetophenone ketal (see, EXAMPLE 20, Step 1) (20.79 g, 85.5 mmol) was added and the mixture heated to refux. After ½ hr of reflux, evidence of Grignard formation such as cloudiness and color change was observed. Heating was discontinued and the mixture stirred for 1 hr, after which time most of the magnesium had reacted and a substantial amount of the precipitated Grignard ragent was observed. Solid CuCl (4 g, 40.4 mmol) was added and the mixture was stirred at room temperature for 15 min, after which time the solid reagent went back into solution. A solution of the 5α,10α-epoxide (100, 17.5 g, 40.73 mmol) in THF (150 mL) was added and the reaction mixture was stirred at room temperature for 1 hr. After that time, TLC (5% acetone in CH$_2$Cl$_2$) of a small aliqout quenched with saturated NH$_4$Cl solution indicated a complete reaction. The reaction was quenched by the addition of saturated NH$_4$Cl solution (~50 mL). In order to oxidize Cu(I) to Cu(II), air was drawn through the reaction mixture for ½ hr. The resulting blue mixture was diluted with ether (500 mL) and washed with H$_2$O (2×), brine (1×), dried over anhydrous Na$_2$SO$_4$, filtered and concentrated in vacuo to give 41 g of the residue as an oil. Crystallization of this crude material from ether gave the pure 101b (23.0 g) as a white solid in 95% yield; m.p.=192–193° C. FTIR (KBr, diffuse reflectance): ν$_{max}$ 3515, 2951, 2884, 2230, 1619, 1505 and 1102 cm$^{-1}$. NMR (CDCl$_3$): δ 0.25 (s, 9H, Si(CH$_3$)$_3$), 0.5 (s, 3H, C18-CH$_3$), 1.67 (s, 3H, C11β-(acetophenone ketal CH$_3$), 3.67–4.17 (m, 8H, C3-OCH$_2$CH$_2$O), 4.37 (m, 2H, C11α-CH plus OH), 7.17 (d, 2H, J=9 Hz, 2',6' aromatic-CH's) and 7.37 (d, 2H, J=9 Hz, 3',5' aromatic-CH's). MS (EI) m/z (relative intensity): 593 (M$^+$, 3.6), 578 (6.0), 575 (9.1), 560 (2.5), 366 (5.2), 99 (27.3) and 87 (100.0). Anal. Calcd. for C$_{34}$H$_{47}$NO$_6$Si: C, 68.77; H, 7.98; N, 2.36. Found: C, 68.69; H, 7.87; N, 2.43.

Step 2. 17β-cyano-17α-hydroxy-11β-(4-acetylphenyl)-estra-4,9-dien-3-one (102b):

A solution of the Grignard adduct (101b, 23 g, 38.7 mmol) was dissolved in THF (100 mL) and the system was flushed with nitrogen. Glacial acetic acid (314.7 g, 524 mmol) and H$_2$O (100 mL) were added and the mixture was stirred overnight at room, temperature. At that time, TLC (10% acetone/CH$_2$Cl$_2$) indicated an incomplete reaction. The reaction mixture was then heated to reflux for 1 hr, after which time TLC indicated a complete reaction.

The volatiles were removed in vacuo at 50° C. and the residue diluted with H$_2$O (~250 mL) and saturated NaHCO$_3$ solution (~125 mL). The subsequent precipitate was extracted with EtOAc (5×) with some difficulty in that the crude product was relatively insoluble in most solvents used. The organic fractions were washed with H$_2$O (2×), brine (1×), combined, dried over anhydrous sodium sulfate, filtered and concentrated in vacuo. Trituration of the residue with ether gave the cyanohydrin (102b, 16.3 g) as a light yellow solid in 100% yield; m.p.=141–143° C. (dec). FTIR (KBr, diffuse reflectance): ν$_{max}$ 3362, 2966, 2946, 2232, 1619, 1730, 1658 and 1600 cm$^{-1}$. NMR (CDCl$_3$+d$_6$DMSO): δ 0.57 (s, 3H, C18-CH$_3$), 2.60 (s, 3H, C11β-(4-phenyl-C(O)CH$_3$), 4.57 (br s, 1H, C11α-CH), 5.80 (s, 1H, C4-CH=), 7.40 (d, 2H, J=9 Hz, 2',6' aromatic-CH's) and 7.97 (d, 2H, J=9 Hz, 3',5' aromatic-CH's). MS(EI) m/z (relative intensity): 415 (M$^+$, 0.5), 404 (0.4), 388 (100.0), 292 (65) and 97 (51.0). Anal. Calcd. for C$_{27}$H$_{29}$NO$_3$.⅓H$_2$O: C, 76.93; H, 7.09; N, 3.32. Found: C, 77.04; H, 6.99; N, 3.45.

Step 3. 11β-(4-acetylphenyl)-17β-cyano-17α-bromethytdimethylsilyloxyestra-4,9-dien-3-one (103b):

Under nitrogen, a solution of the cyanohydrin (102b, 15 g, 36.12 mmol), Et$_3$N (6.53 g, 64 mmol) and DMAP (2.6 g, 21.3 mmol) in dry THF (180 ml) was treated with bromomethyldimethylsilyl chloride (9.70 g, 54 mmol). The mixture was stirred overnight at room temperature, diluted with ether (500 mL), filtered through Celite and concentrated in vacuo. The relative insolubility of this material (103b) precludes chromatographic purification useing ether as eluent. The crude material (103b) was used directly in the subsequent reaction without further purification or characterization.

Step 4. 17α-Hydroxy-11β-(4-acetylphenyl)-21-bromo-19-norpregna-4,9-dien-3-one (104b):

Under anhydrous conditions and using a mechanical stirrer, a solution of the silyl ether (103b) (assumed 20.34 g, 36.12 mmol) in dry THF (500 mL) was cooled to −78° C. and treated dropwise with a 1.5 M solution of lithium diisopropylamide (LDA) in cyclohexane (100 mL, 150 mmol). After 1 hr, the reaction mixture became very viscous, almost a gel. The reaction was quenched at −78° C. by addition of 4.45 M HBr (500 mL, 890 mmol) and the mixture allowed to warm to room temperature. After stirring at room temperature for 1 hr, the excess acid was neutralized by slow addition of concentrated NH$_4$OH solution (~60 mL). The mixture was further diluted with H$_2$O (~200 mL) and extracted with CH$_2$Cl$_2$ (3×). The organic fractions were washed with H$_2$O (3×), combined, filtered through Na$_2$SO$_4$ and concentrated in vacuo to give 20 g of the residue as a foam. This material was purified via flash chromatography eluted with (10% acetone in CH$_2$Cl$_2$) to give 2.6 g of the 21-bromo product (104b) as a white solid in 14.1% yield. FTIR (KBr, diffuse reflectance): ν$_{max}$ 3340, 2946, 1723, 1693, 1679, 1645 and 1601 cm$^{-1}$. NMR (CDCl$_3$): δ 0.33 (s, 3H, C18-CH$_3$), 2.19 (s, 3H, 11β-(4-phenyl-C(O)CH$_3$), 4.30–4.70 (m, 3H, C11α-CH and C21-CH$_2$ Br), 5.83 (s, 1H, C4-CH=), 7.33 (d, 2H, J=9 Hz, 2',6' aromatic-CH's) and 7.93 (d, 2H, J=9 Hz, 3',5' aromatic-CH's). MS (EI) m/z (relative intensity): 512 (M$^+$, 24.1), 466 (100), 432 (48.5), 431 (48.5), 430 (86.4), 371 (71.9) and 91 (76.0).

Step 5. 17α-Hydroxy-11β-(4-acetylphenyl)-21-acetoxy-19-norpregna-4,9-diene-3,20-dione (105b):

A mixture of the 21-bromo drivative (104b, 2.5 g, 4.89 mmol), anhydrous KOAc (20 g, 203.8 mmol) in dry CH$_3$CN (100 mL) was heated to reflux under nitrogen. After 2 hr, TLC (10% acetone in CH$_2$Cl$_2$) indicated a complete reaction. The reaction mixture was cooled to room temperature, filtered and concentrated in vacuo to give 2.6 g as a foam. This material was purified via flash chromatography (12% acetone in CH$_2$Cl$_2$) followed by cyrstallization from EtOAc to give 1.5 g of the pure 17α-ol-21-acetate (105b) as a light yellow solid in 62.6% yield; m.p.=softens at 110° C. FTIR (KBr, diffuse reflectance): ν$_{max}$ 3467, 2948, 1749, 1727, 1727, 1681, 1380, 1664 and 1603 cm$^{-1}$. NMR (CDCl$_3$): δ 0.31 (s, 3H, C18-CH$_3$), 2.15 (s, 3H, C17α-OC(O)CH$_3$), 2.57 (s, 3H, 11β-4-phenyl-C(O)CH$_3$), 4.5 (br d, 1H, C11α-CH), 5.01 (dd, 2H, J$_1$=18.7 Hz, J$_2$=18 Hz, C21-CH$_2$OAc), 5.81 (s, 1H, C4-CH=), 7.34 (d, 1H, J=8.2 Hz, 2',6' aromatic-CH's), 7.35 (d, 1H, J=6.8 Hz, 2',6' aromatic-CH's) and 7.93 (d, 2H, J=8.2 Hz, 3',5' aromatic-CH's). MS (EI) m/z (relative intensity): 490 (M$^+$, 88.0), 430 (100.0), 344 (80.0), 236 (44.0), and 91 (55.0). Anal. Calcd. for C$_{30}$H$_{34}$O$_6$.⅕CH$_2$Cl$_2$: C, 70.99; H, 6.79. Found: C, 70.83; H, 6.65.

Step 6. Preparation of the Target Compound 106b:

Under nitrogen trifluoroacetic anhydride (11.15 g, 53.2 mmol), glacial acetic acid (3.25 g, 54.2 mmol) in dry CH$_2$Cl$_2$ (35 mL) were combined and stirred at mom temperature for ½ hr. p-Toluenesulfonic acid monohydrate (0.5 g, 2.63 mmol) was added and the reaction mixture was cooled to 0° C. in an ice bath. A solution of the 17α-ol-21-acetate (105b, 1.28 g, 2.61 mmol) in dry CH$_2$Cl$_2$ (10 mL) was precooled to 0° C. and then added. The reaction mixture was stirred at 0° C. After 45 min, TLC (10% acetone in CH$_2$Cl$_2$) indicated a complete reaction. The mixture was quenched at 0° C. with concentrated NH$_4$OH solution (~10 mL, ~148 mmol), allowed to warm to room temperature, and diluted with H$_2$O (~50 mL). The pH of the aqueous fraction was adjusted to 5 with concentrated NH$_4$OH solution and the mixture extracted with CH$_2$Cl$_2$ (3×). The organic fractions were washed with H$_2$O (3×), combined, dried over anhydrous Na$_2$SO$_4$, filtered and concentrated in vacuo to give 1.8 g of the crude product as a foam. The crude material was purified via flash chromatography (5% acetone in CH$_2$Cl$_2$) to give 1.1 g of the purified diacetate (106b) as a foam. Crystallization of this foam from EtOAc/heptane afforded 0.78 g of the pure solid (106b) as a white crystalline solid in 56.1% yield.; m.p.=197–199° C. Reverse phase HPLC analysis on Phenomenex Prodigy 5 ODS-2 column eluted with H$_2$O/CH$_3$CN, 1:1 at a flow rate of 1 mL/min and at λ=302 nm indicated this material to be >99% pure with a retention time (t$_R$) of 5.6 min. FTIR (KBr, diffuse reflectance): ν$_{max}$ 2951, 1757, 1678, 1664 and 1604 cm$^{-1}$. NMR (CDCl$_3$): δ 0.33 (s, 3H, C18-CH$_3$), 2.07 (s, 3H, C17α-OC(O)CH$_3$), 2.10 (s, 3H, C21-OAc), 2.50 (s, 3H, C11β-4-phenyl-C(O)CH$_3$), 4.43 (m, 1H, C11α-CH), 4.77 (dd, 2H, J$_1$=32.9 Hz, J$_2$=14.9 Hz, C21-CH$_2$OAc), 5.77 (s, 1H, C4-CH=), 7.23 (d, 2H, J=8 Hz, 2',6' aromatic-CH's), and 7.83 (d, 2H, J=8 Hz, 3',5' aromatic-CH's). MS (EI) m/z (relative intensity): 532 (M$^+$, 6.2), 472 (17.3), 412 (11.3), 371 (100.0) and 91 (14.3). Anal. Calcd. for C$_{32}$H$_{36}$O$_7$.½H$_2$O: C, 71.81; H, 6.83. Found: C, 71.89; H, 6.87.

Example 26

This example illustrates the preparation and properties of 17α-Acetoxy-11β-(4-acetylphenyl)-21-thioacetoxy-19-norpregna-4,9-diene-3,20-dione (106c) (FIG. 7):

Step 1. 17α-Hydroxy-11β-(4-acetylphenyl)-21-thioacetoxy-19-norpregna-4,9-diene-3,20-dione (105c):

A mixture of the 21-bromo derivative (104b, 5.746 g, 11.23 mmol), sodium iodide (16.84 g, 112.3 mmol), potassium thioacetate (12.83 g, 112.3 mmol) in dry acetone (600 mL) was heated to reflux under nitrogen. After 4 hr, TLC (50% EtOAc in hexanes) indicated a complete reaction. The reaction was cooled to room temperature, filtered, concentrated in vacuo, diluted with H$_2$O (~200 mL) and extracted with CH$_2$Cl$_2$ (3×). The organic fractions were washed with H$_2$O (1×) and brine (1×), combined, dried over anhydrous sodium sulfate, concentrated in vacuo to give the crude product as a yellow foam. This material was purified by flash chromatography (50% EtOAc in hexanes) followed by crystallization from EtOAc/hexanes to afford the pure 17α-ol-21-thioacetate (105c, 3.25 g, 57.1%) as a white crystalline solid; m.p.=159–160° C. FTIR (KBr, diffuse reflectance): ν$_{max}$ 3325, 2950, 1723, 1688, 1637 and 1590 cm$^{-1}$. NMR (CDCl$_3$): δ 0.33 (s, 3H, C18-CH$_3$), 2.4 (s, 3H, C21-SC(O)CH$_3$), 2.57 (s, 3H, C11β-4-phenyl-C(O)CH$_3$), 4.0 (dd, 2H, J$_1$=48.6 Hz, J$_2$=18 Hz, C21-CH$_2$SAc), 4.57 (br d, 1H, C11α-CH), 5.8 (s, 1H, C4-CH=), 7.37 (d, 2H, J=9 Hz, 2',6' aromatic-CH's), and 7.93 (d, 2H, J=9 Hz, 3',5' aromatic-CH's). MS(EI) m/z (relative intensity): 506 (M$^+$, 29.1), 488 (14.4), 474 (16.6), 431 (100.0) and 346 (78.1). Anal. Calcd. for C$_{30}$H$_{34}$O$_5$S.H$_2$O: C, 68.68; H, 6.92; S, 6.11. Found: C, 68.99; H, 6.73; S, 6.06.

Step 2. Preparation of the Target Compound 106c:

Under nitrogen, trifluoroacetic anhydride (17.43 g, 82.89 mmol), glacial acetic acid (7.17 g, 118.45 mmol), p-toluenesulfonic acid monohydrate (1.0 g, 5.3 mmol) and dry CH$_2$Cl$_2$ (100 mL) were combined and stirred at room temperature for ½ h. The mixture was cooled to 0° C. in an ice bath and a solution of the 17α-ol-21-thioacetate (105c, 3.0 g, 5.92 mmol) in dry CH$_2$Cl$_2$ (50 mL) was added. The mixture was stirred at 0° C. for 6 hr after which time TLC (4% acetone/CH$_2$Cl$_2$) indicated a complete reaction. The mixture was neutralized with cold saturated NaHCO$_3$ and extracted with CH$_2$Cl$_2$ (3×). The organic fractions were washed with brine (2×), combined, dried over sodium sulfate and concentrated in vacuo to give the crude product as a foam. Purification of this material by Flash chromatography eluting 4% acetone/CH$_2$Cl$_2$ followed by crystallization from EtOAc/hexanes gave 2.34 g of the pure compound 106c as a yellow crystalline solid; m.p.=204–205° C. FTIR (KBr, diffuse reflectance): ν$_{max}$ 2948, 1734, 1702, 1676, 1663 and 1602 cm$^{-1}$. NMR (CDCl$_3$): δ 0.30 (s, 3H, C18-CH$_3$), 2.15 (s, 3H, C17α-OC(O)CH$_3$), 2.33 (s, 3H, C21-SC(O)CH$_3$), 2.57 (s, 3H, C11β-4-phenyl-C(O)CH$_3$), 3.94 (dd, 2H, J$_1$=20.7 Hz, J$_2$=14.4 Hz, C21-CH$_2$SAc), 4.53 (br d, 1H, C11α-CH), 5.83 (s, 1H, C4-CH=), 7.37 (d, 2H, J=9 Hz, 2',6' aromatic-CH's), and 7.93 (d, 2H, J=9 Hz, 3',5' aromatic-CH's). MS (EI) m/z (relative intensity): 548 (M$^+$, 6.3), 488 (18.4), 413 (27.4), 371 (100.0) and 280 (24.0). Anal. Calcd. for C$_{32}$H$_{36}$O$_6$S.¹⁄₁₀H$_2$O: C, 69.82; H, 6.63; S, 5.82. Found: C, 68.83; H, 6.67; S, 5.59.

Example 27

This example illustrates the preparation and properties of 17α,21-Dimethoxy-11β-[4-(N,N-dimethylamino)phenyl]-19-norpregna-4,9-diene-3,20-dione (113a) (FIG. 8):

Step 1. 3,3-Ethylenedioxy-17α-methoxy-21-hydroxy-419-norpregna-5(10),9(11)-dien-20-one (107):

To a solution of the 17α-methoxy-3-ketal (94, 10.0 g, 27.1 mmol) in dry THF (150 mL) was added iodobenzene diacetate (Moriarty, et al., *J. Chem. Soc., Chem. Commun.*, 641–642 (1981); Velerio, et al., *Steroids*, 60:268–271 (1995)) (34.59 g, 4×) as a solid. The suspension was stirred under nitrogen and cooled to 0° C. H$_2$O (7.73 mL, 429.6 mmol, 16×) was added, followed by 0.5 M KO-tBu solution (1400 mL, 700 mmol, 26×) via transfer needle. (A 50:50 (v/v) mixture of freshly opened methanol (700 mL) and 1.0 M potassium t-butoxide in THF (700 mL; Aldrich) was prepared and cooled to 0° C. to give a 0.5 M base solution). Upon completion of addition the reaction mixture was removed from the ice bath and the solution alowed to warm to room temperature. The reaction was monitored every hour by TLC (5% acetone in CH$_2$Cl$_2$) and after 4 hr, virtually all of the starting material had been converted to approximately a 80:20 mixture of two more polar components. The reaction mixture was diluted with $H_2O$ (500 ml) and brine (500 mL) and extracted into ether (3×). Organic fractions were washed again with $H_2O$ and brine. Combined organic extracts were dried by filtration through $Na_2SO_4$, evaporated in vacuo, and further dried under high vacuum to recover 13.84 g of an orange oil. Purification by flash chromatography (5% acetone in $CH_2Cl_2$) gave 6.0 g of a pale yellow-white foam (107) in 57.5% yield. Trituration with pentane produced 107 which was dried under vacuum to recover 5.36 g of a white powder in 51.0% yield; m.p.=147–152° C. FTIR (KBr, diffuse reflectance): $v_{max}$ 3478, 2900, 2825, 1712, 1437, 1384 and 1372 cm$^{-1}$. NMR (300 MHz, CDCl$_3$): δ 0.550 (s, 3H, C18-CH$_3$), 3.159 (s, 3H, C17α-OCH$_3$), 3.981 (s, 4H, C3-OCH$_2$CH$_2$O), 4.251 and 4.471 (AB, 2H, $J_{AB}$=19.81 Hz, C21-$\overline{CH_2}$) and 5.544 (br s, 1H, C11-CH=). MS (Er) m/z (relative intensity): 388 (M$^+$, 54.8), 356 (13.8), 297 (100.0), 211 (65.0), 169 (51.1) and 99 (56.3). Anal. Calcd. for $C_{23}H_{32}O_5 \cdot \frac{1}{4}H_2O$: C, 70.29; H, 8.34. Found: C, 70.21; H, 8.12.

Step 2. 3,3-Ethylenedioxy-17α,21-dimethoxy-19-norpregna-5(10),9(11)-dien-20-one (108):

To a solution of the 3-ketal-21-hydroxy compound (107, 5.0 g, 12.87 mmol) in 500 mL of 1,2-dimethoxyethane (DME) was added Proton-Sponge® [1,8-bis(dimethylamino)naphthalene] (13.79 g, 64.35 mmol, 5×) as a solid. The solution was cooled to 0° C. in an ice water bath and trimethyloxonium tetrafluoroborate (9.52 g, 64.35 mmol, 5×) was added as a solid. The suspension was kept at 0° C. under nitrogen, for 3 hr. At that time, TLC (5% acetone in $CH_2Cl_2$) indicated all of the starting material had been cleanly converted to the slightly less polar 3-ketal-17α,21-dimethoxy compound (108). $H_2O$ and EtOAc were added, the mixture was transferred to a separatory funnel, and the layers allowed to separate. The organic fraction was washed with ice-cold 1 N HCl (2×), $H_2O$ (1×), saturated NaHCO$_3$ (1×), $H_2O$ (1×), and brine (1×). Combind EtOAc extracts (3×) were dried by filtration through $Na_2SO_4$ and evaporated in vacuo. The resulting colorless oil was dried overnight under high vacuum to recover a white foam (108, 5.28 g) in quantitative yield. Analysis by TLC and NMR indicated the crude material was sufficiently pure to carry directly on to the next reaction. A small amount was triturated with pentane and dried overnight under high vacuum to give 120 mg of 108 as a white solid; m.p=104–110° C. FTIR (KBr, diffuse reflectance): $v_{max}$ 2926, 2884, 2828, 1722, 1447, 1380, 1322 and 1252 cm$^{-1}$. NMR (300 MHz, CDCl$_3$): δ 0.585 (s, 3 Hs C18-CH$_3$), 3.175 (s, 3H, C17α-OCH$_3$), 3.442 (s, 3H, C21-OCH$_3$), 3.983 (s, 4H, C3-OCH$_2$CH$_2$O), 4.182 and 4.367 (AB, 2H, $J_{AB}$=18.01 Hz, C21-$\overline{CH_2}$) and 5.555 (br s, 1H, C11-CH=). MS (EI) m/z (relative intensity): 402 (M$^+$, 27.7), 370(7.2), 297 (100.0), 211 (62.1), 169(41.6) and 99 (62.7). Anal. Calcd. for $C_{24}H_{34}O_5 \cdot \frac{3}{8}H_2O$: C, 69.74; H, 8.58. Found: C, 69.82; H, 8.43.

Step 3. 3,3-Ethylenedioxy-17α,21-dimethoxy-19-norpregna-5(10),9(11)-dien-20-ol (109):

The 3-ketal 17α,21-dimethoxy-20-one (108, 5.0 g, 12.42 mmol) was dissolved in dry THF (100 mL) and 2 equivalents of LiAlH$_4$ (25 mL, 25 mmol, 1.0 M in ether) were added via syringe. The solution was stirred magnetically at room temperature under nitrogen. After 15 minutes, examination by TLC (5% acetone in $CH_2Cl_2$) indicated the starting material had been cleanly converted to a single, more polar product (109). The reaction mixture was cooled in an ice bath, and saturated $Na_2SO_4$ (~2–3 mL) was added dropwise via pipette. When the reaction was quenched, several scoops of $Na_2SO_4$ were added and the mixture allowed to stir 1 hr. Filtration through a sintered glass funnel, followed by evaporation in vacuo produced a concentrated syrup. The syrup was taken up in $H_2O$ and $CH_2Cl_2$, transferred to a separatory funnel, and the layers allowed to separate. The organic fraction was washed again with brine. Combined $CH_2Cl_2$ extracts (3×) were dried by filtration through $Na_2SO_4$ and evaporated in vacuo. The resulting white foam was dried further under high vacuum to recover 4.69 g of the crude 109. Purification of this crude product by flash chromatography (5% isopropanol in $CH_2Cl_2$) gave 4.24 g of 109 as a white foam in 84.4% yield.

The two purest fractions were combined and taken up in a minimum amount of acetone/hexane. After standing six days at room temperature, large, colorless crystals had formed. The crystals were collected by centrifugation, washed with several portions of hexane, and dried under high vacuum to recover 177 mg. Analysis by TLC (10% acetone in $CH_2Cl_2$) indicated the crystals were of the highest purity. Analysis of this material by NMR indicated a single isomer. No further work was done for identification of this single isomer. A second crop of 78 mg with only a trace of impurity was obtained from the mother liquors; m.p.=111–115° C. FTIR (KBr, diffuse reflectance): $v_{max}$ 3576, 3456, 2930, 2891, 2827, 1460 and 1372 cm$^{-1}$. NMR (300 MHz, CDCl$_3$): δ 0.824 (s, 3H, C18-CH$_3$), 3.298 (s, 3H, C17α-OCH$_3$), 3.392 (s, 3H, C21-OCH$_3$), 3.416 (dd, 1H, $J_1$=9.30 Hz, $J_2$=8.10 Hz, C21-CH$_2$), 3.490 (dd, 1H, $J_1$=9.30 Hz, $J_2$=3.30 Hz, C21-CH$_2$), 3.923 (dd, 1H, $J_1$=8.10 Hz, $J_2$=3.30 Hz, C20-CH), 3.980 (s, 4H, C3-OCH$_2$CH$_2$O) and 5.595 (br s, 1H, C11-CH=). MS (EI) m/z (relative intensity): 404 (M$^+$, 2.1), 372 (5.7), 329 (1.7), 297 (100.0) and 211 (35.7). Anal. Calcd. for $C_{24}H_{36}O_5 \cdot \frac{1}{8}C_6H_{14}$: C, 71.76; H, 9.27. Found: C, 71.83; H, 9.04.

Step 4. 3,3-Ethylenedioxy-5α,10α-epoxy-17α,21-dimethoxy-19-norpregn-9(11)-en-20-ol (110):

To a solution of hexafluoroacetone (2.01 mL, 14.39 mmol) in $CH_2Cl_2$ (50 mL), was added solid $Na_2HPO_4$ (1.36 g, 9.59 mmol) and 30% $H_2O_2$ (2.16 mL, 21.1 mmol). The mixture was transferred to the cold room and stirred vigorously for ½ hr at 4° C. A chilled solution of the 20-alcohol (109, 3.88 g, 9.59 mmol) in $CH_2Cl_2$ (25 mL) was added via pipette and rinsed in with additional $CH_2Cl_2$ (25 mL). After stirring overnight at 4° C., TLC (7.5% acetone in $CH_2Cl_2$) indicated virtually all of the starting material had been converted to one major, more polar product with only a trace of by-products. The reaction mixture was transferred to a separatory funnel and washed with 10% $Na_2SO_3$ (1×), $H_2O$ (1×), and brine (1×). Combined $CH_2Cl_2$ extracts (3×) were dried by filtration through $Na_2SO_4$ and evaporated in vacuo to recover a foam. NMR analysis of the crude material indicated the α and β epoxides were present in approximately a 9:1 ratio. Trituration with ether produced 2.27 g of the pure 5α,10α epoxide (110) as a white powder in 56.3% yield; m.p.=146–153° C. FTIR (KBr, diffuse reflectance): $v_{max}$ 3558, 2939, 1638, 1446, 1373 and 1247 cm$^{-1}$. NMR (300 MHz, CDCl$_3$): δ 0.824 (s, 3H, C18-CH$_3$), 3.273 (s, 3H, C17α-OCH$_3$), 3.389 (s, 3H, C21-OCH$_3$), 3.402 (dd, 1H, $J_1$=9.61 Hz, $J_2$=8.10 Hz, C21-CH$_2$), 3.476 (dd, 1H, $J_1$=9.1 Hz, $J_2$=3.30 Hz, C21-CH$_2$), 3.908 (m, 5H, C3-OCH$_2$CH$_2$O and C20-CH) and 6.053 (br s, 1H, C11-CH=). MS (EI) m/z (relative intensity): 420 (M$^+$, 1.7), 402 (6.0), 370 (6.2), 345 (20.0), 313 (77.8), 295 (100.0) and 99 (95.4). Anal. Calcd. for $C_{24}H_{36}O_5 \cdot \frac{1}{10}H_2O$: C, 68.25; H, 8.64. Found: C, 68.31; H, 8.71.

Step 5. 3,3-Ethylenedioxy-5α-hydroxy-11β-[4-(N,N-dimethylamino)phenyl]-17α,21-dimethoxy-19-norpregn-9-en-20-ol (111a):

A dry 50 mL 2-neck flask was equipped with a stirrer, a reflux condenser, and a rubber septum. Magnesium (191 mg, 7.85 mmol) was added and the entire apparatus was dried fruther, under a stream of nitrogen, with a heat gun. After cooling slightly, one crystal of iodine was added. The apparatus was allowed to cool completely and dry THF (4 mL) was added followed by one drop of 1,2-dibromoethane. A solution of 4-bromo-N,N-dimethylaniline (1.43 g, 7.14 mmol) in THF (2 mL) was added via transfer needle and rinsed in with additional THF (2.0 mL). The mixture was warmed gently with a heat gun to initiate reaction (as evidenced by bleaching of color) and then allowed to stir 1 hr at ambient temperature. Copper (I) chloride (78.2 mg, 0.79 mmol) was added as a solid and stirring continued for 20 min. A solution of the 5α,10α-epoxide (110, 1.0 g, 2.38 mmol) in THF (4.0 mL, heated gently to achieve a solution) was added via transfer needle and rinsed in with additional THF (2×2.0 mL). After stirring 2 hr at room temperature, the reaction was quenched by the addition of saturated $NH_4Cl$ (16 mL). Air was drawn through the mixture for ½ hr with vigorous stirring. The mixture was transferred to a separatory funnel, ether was added, and the layers allowed to separate. The organic fraction was washed again with $H_2O$ (1×), and brine (1×). Combined ether extracts (3×) were dried by filtration through $Na_2SO_4$ and evaporated in vacuo to recover an oily residue. Trituration with ether produced a solid 111a. The crystals were collected on a Buchner funnel, triturated with additional ether, and dried under high vacuum to recover 1.02 g of a beige solid (111a) in 79% yield; m.p.=195–199° C. FTIR (KBr, diffuse reflectance): $v_{max}$ 3534, 3418, 2938, 2875, 2820, 1868, 1614, 1560, 1519, 1443, 1353 and 1328 $cm^{-1}$. NMR (300 MHz, $CDCl_3$): δ 0.493 (s, 3H, C18-$CH_3$), 2.896 (s, 6H, —N($CH_3$)2), 3.289 (s, 3H, C17α-$OCH_3$), 3.362 (s, 3 H, C21-$OCH_3$), 3.340–3.448 (m, 2H, C21-$CH_2$), 3.747–4.075 (m, 5H, C3-O $CH_2CH_2O$ and C20-CH), 4.171 (br s, 1, C11α-CH), 6.635 (d, 2H, J=8.70 Hz, 3',5' aromatic-CH's) and 7.070 (d, 2H, J=8.70 Hz, 2',6' aromatic-CH's). MS (EI) m/z (relative intensity): 541 ($M^+$, 61.0), 523 (19.7), 416 (7.6), 134 (37.4), 121 (100.0) and 99 (20.2). Anal. Calcd. for $C_{32}H_{47}NO_6$: C, 70.95; H, 8.74; N, 2.59. Found: C, 70.92; H, 8.77; N, 2.65.

Step 6. 3,3-Ethylenedioxy-5α-hydroxy-11β-[4-(N,N-dimethylamino)phenyl]-17α,21-dimethoxy-19-norpregn-9(10)-en-20-one (112a):

(a) Preparation of o-iodoxybenzoic acid (Dess, et al., *J. Org. Chem.*, 48:4155–4156 (1983)): The initial preparation of IBX gave a material which appeared to be a mixture as evidenced by $^{13}C$ NMR. Although the oxidant was not homogenous, 3 equivalents of this material (assuming 100% IBX) cleanly converted the 20-OH (111a) to the 20-ketone (112a). The preparation of IBX has been since modified to obtain a homogeneous material with $^1H$ NMR and $^{13}C$ NMR identical to the reported spectra (Frigerio, et al., *Tet. Letters*, 35:8019–8022 (1994)). Only 1.5 equivalents are necessary for oxidation (Frigerio, et al., *Tet. Letters*, 35:8019–8022 (1994); Frigerio, et al., *J. Org. Chem.*, 60:7272–7276 (1995)). This new material was used for the preparation of 112b and 112c.

Potassium bromate (7.6 g, 45.5 mmol) was added over a 10 minute period to a vigorously stirred suspension of 2-iodobenzoic acid (8.52 g, 34.4 mmol) in 0.73 M $H_2SO_4$ (150 mL). Upon completion of addition, the mixture was warmed to 65° C. in a water bath. Over the next hour, bromine was evolved as was evidenced by a change in color from all orange to white. At that time, a second aliquot of potassium bromate (7.6 g, 45.5 mmol) was added and stirring continued at 65° C. for an additional 2 hr. The mixture was cooled to room temperature, filtered on a Buchner funnel, and washed with $H_2O$, followed by acetone. The resulting white solid was dried in vacuo to recover 7.74 g in 80.2% yield. $^1H$ NMR (300 MHz, DMSO): δ 7.845 (t, 1H, J=7.20 Hz), 7.96–8.06 (m, 2H) and 8.148 (d, 1H, J=7.80 Hz). $^{13}C$ NMR (300 MHz, DMSO): δ 125.011, 130.093, 131.398, 132.963, 133.406, 146.525 and 167.499.

(b) Oxidation of the 20-ol (111a) to the 20-one (112a): To a solution of IBX (2.42 g, 8.64 mmol) in DMSO (16.0 mL) at ambient temperature, under nitrogen, a solution of the Grignard product (111a, 1.56 g, 2.88 mmol) in DMSO (16.0 mL) was added via transfer needle. Additional DMSO (2×4.0 mL) was used to rinse in residual steroid. The resulting purple solution was stirred ½ hr. At that time, examination by TLC (10% acetone in $CH_2Cl_2$; aliquot was diluted in $H_2O$ and extracted into EtOAc) revealed all of the starting material had been cleanly converted to a single, less polar product. The reaction was transferred to a separatory funnel, $H_2O$ and $CH_2Cl_2$ were added, and the layers allowed to separate. The organic fractions were washed again with $H_2O$ (1×) and then brine (1×). Combined $CH_2Cl_2$ exracts (3×) were dried by filtration through $Na_2SO_4$ and evaporated in vacuo. The resulting residue was dried overnight under high vacuum to recover a brownish-purple gum (1.79 g). The gum was taken up in $CH_2Cl_2$ and filtered through silica (~250 mL) on a sintered glass funnel. After eluting with $CH_2Cl_2$ to remove DMSO (2×250 mL), the pure product was eluted with 10% acetone in $CH_2Cl_2$ (2×250 mL). Fractions containing the product were combined, evaporated in vacuo and dried briefly under high vacuum to afford 1.29 g of 112a as a colorless foam in 83% yield. A small sample (~100 mg) was reserved, triturated with pentane, and dried to give a white crystalline solid; m.p.= 160–165° C. FTIR (KBr, diffuse reflectance): $v_{max}$ 3514, 2938, 2824, 1724, 1616, 1521, 1520, 1447 and 1354 $cm^{-1}$. NMR (300 MHz, $CDCl_3$): δ 0.250 (s, 3H, C18-$CH_3$), 2.894 (s, 6H, —N($CH_3$)$_2$), 3.137 (s, 3H, C17α-$OCH_3$), 3.435 (s, 3H, C21-$OCH_3$), 3.998 (m, 4H, C3-O$CH_2CH_2$O), 4.231 and 4.363 (AB, 2H, $J_{AB}$=18.01 Hz, C21-$\overline{CH_2}$), 4.250 (br d, 1H, C11α-CH), 4.288 (br s, 1H, C5α-OH), 6.619 (d, 2H, J=8.85 Hz, 3',5' aromatic-CH's) and 7.016 (d, 2H, J=8.85 Hz, 2',6' aromatic-CH's). MS (EI) m/z (relative intensity): 539 ($M^+$, 71.4), 521 (34.8), 134 (52.9), 121 (100.0) and 99 (23.5). Anal. Calcd. for $C_{32}H_{45}NO_6$: C, 71.21; H, 840; N, 2.60. Found: C, 71.41; H, 8.60; N, 2.63.

Step 7. Preparation of the Target Compound 113a:

To a solution of the 3-ketal-5α-hydroxy-20-one (112a, 1.20 µm 2.22 mmol) in THF (15.0 mL), was added glacial acetic acid (45.0 mL, 783 mmol), followed by $H_2O$ (15.0 mL). The mixture was brought to reflux under nitrogen. After 1 hr., TLC (25% EtOAc in $CH_2Cl_2$) indicated the 3-ketal had been hydrolyzed to give the slightly less polar ketone. The reaction was allowed to cool to room temperature and left overnight under nitrogen. Concentrated $NH_4OH$ (53.0 mL, 783 mmol) was added to neutralize the reaction and additional $NH_4OH$ was added to bring the mixture to pH 7.0 (paper). The mixture was transferred to a separatory funnel and extracted into $CH_2Cl_2$ (3×). The organic fractions were washed again with $H_2O$ (1×) and brine (1×). Combined $CH_2Cl_2$ extracts were dried by filtration through $Na_2SO_4$ and evaporated in vacuo to give 1.21 g of a yellow oil. The crude product was purified twice by flash chromatography (7.5% acetone in $CH_2Cl_2$). Fractions containing the pure product were combined and evaporated to give a yellow gum. Trituration with heptane produced 350 mg of a pale yellow powder. All remaining material (impure fractions plus mother liquors) was combined and rechromatographed to give an additional 305 mg: Total yield was 655 mg of 113a in 61.7% yield; m.p.=132–136° C. HPLC analysis of 113a on a Waters Assoc. NovaPak $C_{18}$ column eluted with 300% 50 m$\underline{M}$ $KH_2PO_4$ (pH=3.0) in MeOH at a flow rate of 1 mL per min and at λ=302 nm indicated a purity of 97.9% with a retention time ($t_R$) of 7.87 min. FTIR (KBr, diffuse reflectance): $v_{max}$ 2946, 1724, 1665, 1599, 1518, 1445 and 1348 $cm^{-1}$. NMR (300 MHz, $CDCl_3$): δ 0.322 (s, 3H, C18-$CH_3$), 2.904 (s, 6H, —$N(CH_3)_2$), 3.173 (s, 3H, C17α-$OCH_3$), 3.453 (s, 3H, C21-$OCH_3$), 4.234 and 4.375 (AB, 2H, $J_{AB}$=17.86 Hz, C21-$CH_2$), 4.367 (s, 1H, C11α-CH), 5.750 (s, 1H, C4-CH=), 6.634 (d, 2H, J=8.55 Hz, 3',5' aromatic-CH's) and 6.979 (d, 2H, J=8.55 Hz, 2',6' aromatic-CH's). MS (EI) m/z (relative intensity): 477 ($M^+$, 83.2), 372 (10.3), 251 (17.1), 209 (20.4), 134 (35.3) and 121 (100.0). Anal. Calcd. for $C_{30}H_{39}NO_4$: C, 75.44; H, 8.23; N, 2.93. Found: C, 75.54; H, 8.14; N, 2.94.

Example 28

This example illustrates the preparation and properties of 17α,21-Dimethoxy-11β-[4N-pyrrolidino)phenyl]-19-norpregna-4,9-diene-3,20-dione (113b) (FIG. 8):

Step 1. 3,3-Ethylenedioxy-5α-hydroxy-11β-[4-(N-pyrrolidino)phenyl]-17α,21-dimethoxy-19-norpregn-9-en-20-ol (111b):

A dry 100 mL 2-neck flask was equipped with a stirring bar, a reflux condenser, and rubber septum. Magnesium (248 mg, 10.2 mmol) was added, and the entire apparatus was dried further under a stream of nitrogen with a heat gun. After cooling slightly, one crystal of iodine was added.

The apparatus was allowed to cool completely and dry THF (5.0 mL) was added followed by one drop of 1,2-dibromoethane. A solution of N-(4-bromophenyl)pyrrolidine (see, EXAMPLE 17, Step 3) (2.1 g, 9.27 mmol) in THF (2.5 mL) which was warmed gently to achieve solution, was added via transfer needle and rinsed in with additional THF (2.5 mL). The mixture was brought to reflux and after 2 hr, almost all of the magnesium had been consumed. The cloudy, dark gray mixture was allowed to cool to room temperature and copper (I) chloride (101 mg, 1.02 mmol) was added as a solid. After stirring 1.5 hr at room temperature, a solution of the 5α,10α-epoxide (110, 1.3 g, 3.09 mmol) in THF (5.0 mL) which was heated gently to achieve a solution, was added via a transfer needle and rinsed in with additional THF (5.0 mL). After stirring 1 hr at room temperature, the reaction was quenched by the addition of saturated $NH_4Cl$ (20 mL). Air was drawn through the mixture for ½ hr with vigorous stirring. The mixture was transferred to a separatory funnel, $H_2O$ and ether were added, and the layers allowed to separate. The organic fraction was washed again with $H_2O$ (1×), and brine (1×). Combined ether extracts (3×) were dried by filtration through $Na_2SO_4$, evaporated in vacuo, and dried further under high vacuum to recover a greenish-brown oil (2.47 g). Examination by TLC (15% acetone in $CH_2Cl_2$) revealed one major, slightly less polar product and a trace of impurities. Trituration with pentane or pentane/ether failed to produce a solid. Purification by flash chromatography (15% acetone in $CH_2Cl_2$) gave 978 mg of pure 111b as a white foam. Fractions containing 410 mg of the impure product were rechromatographed to recover 152 mg of an additional pure material 111b. The total yield of the purified product 111b was 1.13 g as a white foam in 64.4% yield. Trituration of this foam with pentane, followed by washing with heptane produced a white powder. The white powder was dried overnight in a drying pistol with benzene to give 727.1 mg of 111b in 41.5% yield.; m.p.=135–143° C. FTIR Kr, diffuse reflectance) $v_{max}$ 3469, 2945, 2820, 1614, 1517, 1487, 1462, 1442, 1371, 1239, 1192, 1122 and 1076 $cm^{-1}$. NMR (300 MHz, $CDCl_3$): δ 0.505 (s, 3H, C18-$CH_3$), 3.247 (m, 4H, pyrrolidyl α-$CH_2$), 3.288 (s, 3H, C17α-$OCH_3$), 3.364 (s, 3H, C21-$OCH_3$), 3.339–3.448 (m, 2H, C21-$CH_2$), 3.808 (m, 1H, C20-CH), 4.000 (m, 4H, C3-$OCH_2CH_2O$), 4.12–4.21 (m, 1H, C11α-CH), 4.392 (s, 1H, $\overline{C5α-OH}$), 6.460 (d, 2H, J=8.70 Hz, 3',5' aromatic-CH's) and 7.056 (d, 2H, J=8.70 Hz, 2',6' aromatic-CH's). MS (EI) m/z (relative intensity): 567 ($M^+$, 34.0), 549 (33.1), 442 (12.9), 160 (30.3), 147 (100.0) and 99 (14.9). Anal. Calcd. for $C_3$ $μL_9NO_6$: C, 71.93; H, 8.70; N, 2.47. Found: C, 72.03; H, 8.71; N, 2.46.

Step 2. 3,3-Ethylenedioxy-5α-hydroxy-11β-[4-(N-pyrrolidino)phenyl]-17α,21-dimethoxy-19-norpregn-9-en-20-one (112b):

To a suspension of IBX (EXAMPLE 27, Step 6(a)) (501 mg, 1.79 mmol) in dimethylsulfoxide (DMSO) was added a solution of the Grignard adduct (111b, 677 mg, 1.19 mmol) in DMSO (6.0 mL). Additional DMSO (2×2.0 mL) was used to rinse in residual 111b. Almost immediately upon addition of 111b, a green solution formed which rapidly changed to purple. After 1 hr, examination by TLC (15% acetone in $CH_2Cl_2$; aliquot was diluted with $H_2O$ and extracted into EtOAc) revealed all of the starting material had been cleanly converted to a single, less polar product. The reaction mixture was transferred to a 500 mL separatory funnel and diluted with $H_2O$ and brine. The product was extracted into EtOAc (3×). The organic fractions were washed again with $H_2O$ (1×), then brine (1×). Combined EtOAc extracts (3×) were dried by filtration through anhydrous $Na_2SO_4$ and evaporated in vacuo. The resulting residue was dried overnight under high vacuum to recover 0.85 g of a purple foam. Purification by flash chromatography (15% acetone in $CH_2Cl_2$) gave 494 mg of 112b as a pale yellow foam in 73.1% yield. A small amount was triturated with heptane and dried in a drying pistol with benzene to give 51 mg of a pale yellow solid for analysis; m.p.=120–125° C. FTIR (KBr, diffuse reflectance): $v_{max}$ 3540, 2946, 2830, 1722, 1666, 1613, 1517, 1488, 1462, 1445, 1372, and 1188 $cm^{-1}$. NMR (300 MHz, $CDCl_3$): δ 0.264 (s, 3H, C18-$CH_3$), 3.135 (s, 3H, C17-$OCH_3$), 3.242 (m, 4H, pyrrolidyl α-$CH_2$), 3.433 (s, 3H, C21-$OCH_3$), 3.997 (m, 4H, C3-$OCH_2CH_2O$), 4.232 and 4.381 (AB, 2H, $J_{AB}$=17.86 Hz, C21-$\overline{CH_2}$), 4.366 (br s, 1H, C11α-CH), 5.747 (s, 1H, C4-CH=), 6.463 (d, 2H, J=8.40 Hz, 3',5' aromatic-CH's) and 7.002 (d, 2H, J=8.40 Hz, 2',6' aromatic-CH's). MS (EI) m/z (relative intensity): 565 ($M^+$, 14.9), 547 (72.7), 503 (7.7), and 147 (100.0). Anal. Calcd. for $C_{34}H_{47}NO_6 \cdot ⅓C_3H_6O \cdot 1⁄20 C_7H_{16}$: C, 72.51; H, 8.34; N, 2.33. Found: C, 72.67; H, 8.13; N, 2.31.

Step 3. Preparation of the Target Compound 113b:

To a solution of the 3-ketal-20-ketone (112b, 443 mg, 0.78 mmol) in THF (5.0 mL), was added glacial acetic acid (15 mL, 261 mmol), followed by water (5.0 mL). After 5 hr, TLC (10% acetone in $CH_2Cl_2$; neutralized with concentrated $NH_4OH$ before developing) indicated that most of the 3-ketal had been hydrolysed to give the slightly less polar ketone. The reaction was allowed to continue overnight. The next morning, all of the starting material had been converted to the product with only a trace of impurities. The reaction mixture was neutralized by the addition of concentrated $NH_4OH$ (17.6 mL, 261 mmol, pH 7 by pH paper). The mixture was transferred to a separatory funnel and extracted with $CH_2Cl_2$ (3×). The organic fractions were washed again with H$_2$O (1×), and brine (1×). Combined CH$_2$Cl$_2$ extracts were dried by filtration through anhydrous Na$_2$SO$_4$ and evaporated in vacuo to give 450 mg of a yellow film. The crude product was purified twice by flash chromatography (10% acetone in CH$_2$Cl$_2$). Fractions containing highly pure product were combined and evaporated to give 311 mg of a pale yellow glass.

Trituration with heptane produced 264 mg of a pale yellow solid. At this point, inspection of this material by HPLC indicated a purity of 95.7%. The product was rechromatographed (7.5% acetone in CH$_2$Cl$_2$) and again triturated with heptane to produce 190 mg of a pale yellow powder. No additional purification was achieved.

Attempts to further purify the sample by normal phase HPLC were also unsuccessful. Finally, the sample was recrystallized from hot heptane and dried overnight in a drying pistol with heptane to give 97.1 mg of a beige powder in 24.4% yield; m.p. 122.5–126° C. Analysis by HPLC on a Waters Assoc. NovaPak C$_{18}$ column eluted with 30% 50 m $\underline{M}$ KH$_2$PO$_4$ [pH=3.0] in MeOH at a flow rate of 1 mL per min and at =302 nm, indicated a purity of 94.97% with a retention time (t$_R$) of 21.475 min. FTIR (KBr, diffuse reflectance): ν$_{max}$ 2944, 2826, 1726, 1667, 1614, 1518, 1488, 1465, and 1379 cm$^{-1}$. NMR (300 MHz, CDCl$_3$): δ 0.339 (s, 3H, C18-CH$_3$), 3.172 (s, 3H, C17α-OCH$_3$), 3.242 (m, 4H, pyrrolidyl α-CH$_2$), 3.450 (s, 3H, C21-OCH$_3$), 4.232 and 4.381 (AB, 2H, J$_{AB}$=18.01 Hz, C21-CH$_2$), 4.366 (br s, 1H, C$_1$]-CH), 5.747 (s, 1H, C4-CH=), 6.463 (d, 2H, J=8.55 Hz, 3',5' aromatic-CH's) and 6.962 (d, 2H, J=8.55 Hz, 2',6' aromatic-CH's). MS(EI) m/z (relative intensity): 503 (M$^+$, 59.3), 398 (4.9), 251 (8.6), 160 (17.6) and 147 (100.0). Anal. Calcd. for C$_{32}$H$_{41}$NO$_4$·⅙C$_7$H$_{16}$·⅙H$_2$O: C, 76.11; H, 8.47; N, 2.68. Found: C, 76.04; H, 8.40; N, 2.69.

Example 29

This example illustrates the preparation and properties of 17α,21-Dimethoxy-11β-[4-(N-piperidino)phenyl]-19-norpregna-4,9-diene-3,20-dione (113c) (FIG. 8):

Step 1. 3,3-Ethylenedioxy-5α-hydroxy-11β-[4-(N-piperidino)phenyl]-17α,21-dimethoxy-19-norpregn-9-en-20-ol (111c):

A dry 50 mL 2-neck flask was equipped with a stirring bar, a reflux condenser and a rubber septum. Magnesium (137 mg, 5.64 mmol) was added and the entire apparatus was dried futher under a stream of nitrogen with a heat gun. After cooling slightly, one crystal of iodine was added. The apparatus was allowed to cool completely and dry THF (4 mL) was added followed by 1 drop of 1,2-dibromoethane. A solution of N-(4-bromophenyl)piperidine (see, EXAMPLE 23, Step 1) (1.23 g, 5.13 mmol) in THF (2.0 mL) was added via a transfer needle and rinsed in with additional THF (2.0 mL). The reaction mixture was brought to reflux for 1 hr. At that time, the Grignard reagent had formed as evidenced by consumption of almost all of the magnesium and bleaching of the iodine color. The cloudy, dark gray mixture was allowed to cool to room temperature and copper (I) chloride (55.4 mg, 0.56 mmol) was added as a solid. After stirring 1/hr, a solution of the 5α,10α-epoxide (110, 1.0 g, 2.38 mmol) in THF (4.0 mL; heated gently to achieve a solution) was added via transfer needle and rinsed in with additional THF (4.0 mL). After stirring 2 hr at room temperature, the reaction was quenched by the addition of saturated NH$_4$Cl (16 mL). Air was drawn through the mixture for ½ hr with vigorous stirring. The mixture was transferred to a separatory funnel, H$_2$O and ether were added, and the layers allowed to separate. The organic fraction was washed with H$_2$O (1×), and brine (1×). Combined ether extracts (3×) were dried by filtration through anhydrous Na$_2$SO$_4$, evaporated in vacuo, and dried fisher under high vacuum to recover 1.73 g of an amber gum. Examination of the gum by TLC (15% acetone in CH$_2$Cl$_2$) revealed a single, slightly more polar product and trace of the epoxide. Trituration with ether failed to produce a solid. The crude product was purified by flash chromatography (15% acetone in CH$_2$Cl$_2$). Fractions containing the pure product ilic were combined and evaporated to give 0.36 g of a white foam. Fractions containing the product plus the epoxide were rechromatographed to give 0.43 g of additional pure product 111c. The total yield of the purified product obtained was 0.79 g of 111c as a white foam in 56.7% yield. A small amount was triturated with heptane and dried overnight in a drying pistol with acetone to give 73.8 mg of a white powder (111c) which was reserved for analysis; m.p.=162–171° C. FTIR (KBr, diffuse reflectance): ν$_{max}$ 3470, 2934, 2868, 2816, 1610, 1511, 1440 and 1380 cm$^{-1}$. NMR (300 MHz, CDCl$_3$): δ 0.475 (s, 3H, C18-CH$_3$), 3.091 (m, 4H, piperidyl α-CH$_2$), 3.285 (s, 3H, C17α-OCH$_3$), 3.361 (s, 3H, C21-OCH$_3$), 3.34–3.45 (m, 2H, C21-CH$_2$), 3.794 (m, 1H, C20-CH), 3.998 (m, 5H, C3-O CH$_2$CH$_2$O and C20-OH), 4.178 (br s, 1H, C11α-CH), 4.389 (s, 1H, C5α-OH), 6.810 (d, 2H, J=8.85 Hz, 3',5' aromatic-CH's) and 7.073 (d, 2H, J=8.85 Hz, 2',6' aromatic-CH's). MS (EI) m/z (relative intensity): 581 (M$^+$, 39.0), 563 (24.4), 456 (5.9), 174 (24.9), 161 (100.0) and 99 (12.1). Anal. Calcd. for C$_{35}$H$_{51}$NO$_6$: C, 72.26; H, 8.84; N, 2.41. Found: C, 72.31; H, 8.78; N, 2.36.

Step 2. 3,3-Ethylenedioxy-5α-hydroxy-11β-[4(N-piperidino)phenyl]-17α,21-dimethoxy-9-norpregn-9-en-20-one (112c):

To a suspension of IBX (0.49 g, 1.76 mmol) in DMSO (7.0 mL) was added a solution of the Grignard adduct (111c, 0.68 g, 1.17 mmol) in DMSO (6.0 mL). Additional DMSO (2×2.0 mL) was used to rinse in residual 111c. Almost immediately upon addition of 111c, a purple solution formed. The reaction was allowed to stir 2 hr at ambient temperature without any precautions against oxygen or moisture. At that time, the color had turned from purple to deep red. Examination of this solution by TLC (15% acetone in CH$_2$Cl$_2$; aliquot was diluted with H$_2$O and extracted into EtOAc) revealed all of the starting material had been cleanly converted to a single, less polar product. The reaction mixture was transferred to a separatory funnel, H$_2$O and CH$_2$Cl$_2$ were added, and the layers allowed to separate. The organic fraction was washed again with H$_2$O (1×) and brine (1×). Combined CH$_2$Cl$_2$ extracts (3×) were dried by filtration through anhydrous sodium sulfate and evaporated in vacuo. The resulting residue was dried overnight under high vacuum to recover 0.72 g of a purple gum. Purification by flash chromatography (15% acetone in CH$_2$Cl$_2$) gave 572 mg of a colorless gum. Trituration with heptane afforde 529 mg of 112c as a white solid in 77.8% yield. A small amount was reserved and dried further in a drying pistol with acetone for analysis; m.p.=107–111° C. FTIR (KBr, diffuse reflectance): ν$_{max}$ 3534, 2931, 2823, 1721, 1609, 1511 and 1450 cm$^{-1}$. NMR (300 MHz, CDCl$_3$): δ 0.234 (s, 3H, C18-CH$_3$), 3.089 (m, 4H, piperidyl α-CH$_2$), 3.134 (s, 3H, C17α-OCH$_3$), 3.429 (s, 3H, C21-OCH$_3$), 3.995 (m, 4H, C3-OCH$_2$CH$_2$O), 4.213 and 4.355 (AB, 2H, J$_{AB}$=18.01 Hz, C21-CH$_2$), 4.212–4.306 (m, 2H, C11α-CH and C5α-OH), 6.803 (d, 2H, J=8.70 Hz, 3',5' aromatic-CH's) and 7.021 (d, 2H, J=8.70 Hz, 2',6' aromatic-CH's). MS (EI) m/z (relative intensity); 579 (M$^+$, 38.7), 561 (16.1), 174 (23.7), 161 (100.0) and 99 (12.1) Anal. Calcd for C$_{35}$H$_9$NO$_6$: C, 72.51; H, 8.52; N, 2.42. Found: C, 72.47; H, 8.58; N, 2.35.

Step 3. Preparation of the Target Compound 113c:

To a solution of the 3-ketal-20-ketone (112c, 471 mg, 0.81 mmol) in THF (5.0 mL) was added glacial acetic acid (15 mL, 261 mmol) followed by H$_2$O (5.0 mL). The mixture was brought to reflux under nitrogen. After 3 hr, TLC (10% acetone in CH$_2$Cl$_2$; neutralized with NH$_4$OH before developing) indicated the 3-ketal had been hydrolyzed to give the slightly less polar ketone. The reaction mixture was allowed to cool to room temperature and neutralized by the addition of concentrated NH$_4$OH (17.6 mL, 261 mmol, pH 7 by a pH paper). The mixture was transferred to a separatory funnel and extracted into CH$_2$Cl$_2$ (3×). The organic fractions were washed again with H$_2$O (1×), and brine (1×). Combined CH$_2$Cl$_2$ extracts were dried by filtration through anhydrous Na$_2$SO$_4$ and evaporated in vacuo to recover 426 mg of a yellow glass. This crude product was purified by flash chromatography (5% acetone in CH$_2$Cl$_2$). Fractions containing highly pure product were combined and evaporated to give a pale yellow glass 113c. Trituration of 113c with heptane produced a pale yellow solid. The product was dried overnight in a drying pistol with benzene to give 189.6 mg of 113c as a pale yellow solid in 45.7% yield; m.p.= 108–112° C. Analysis by HPLC on a Waters Assoc. Nova-Pak C$_{18}$ column eluted with 30% 50 m$\underline{M}$ KH$_2$PO$_4$, pH 3.0 in MeOH at a flow rate of 1 mL per min and at =302 nm, indicated a purity of 97.22% with a retention time (t$_R$) of 3.73 min. FTIR (KBr, diffuse reflectance): $\nu_{max}$ 2935, 2822, 1723, 1664, 1609, 1511, 1488, 1451 and 1386 cm$^{-1}$. NMR (300 MHz, CDCl$_3$): δ 0.304 (s, 3H, C18-CH$_3$), 3.100 (m, 4H, piperidyl α-CH$_2$), 3.172 (s, 3H, C17-OCH$_3$), 3.450 (s, 3H, C21-OCH$_3$), 4.227 and 4.370 (AB, 2H, J$_{AB}$=18.01 Hz, C21-CH$_2$), 4.366 (br s, 1H, C11α-CH), 5.753 (s, 1H, C4-CH=), 6.821 (d, 2H, J=8.70 Hz, 3',5' aromatic-CH's) and 6.985 (d, 2H, J=8.70 Hz, 2',6' aromatic-CH's). MS (EI) m/z (relative intensity): 517 (M$^+$, 57.8), 412 (4.6), 318 (6.6), 174 (15.8), and 161 (100.0). Anal. Calcd. for C$_{33}$H$_{43}$NO$_4$: C, 76.56; H, 8.37; N, 2.71. Found: C, 76.45; H, 8.37; N, 2.70.

Example 30

This example illustrates the preparation and properties of 17α,21-Dimethoxy-11β-(4-acetylphenyl)-19-norpregna-4,9-diene-3,20-dione (113d) (FIG. 8):

Step 1. 3,3-Ethylenedioxy-Sa-hydroxy-11β-[4-(2-methyl-1,3-dioxolan-2-yl)phenyl]-17α,21-dimethoxy-19-norpregn-9-en-20-ol (111d):

Magnesium turnings (289 mg, 11.89 mmol) were weighed into a 100 mL round bottom two-neck flask equipped with a reflux condenser, a magnetic stirrer, and a rubber septum. A small crystall of iodine was added and the system was flushed with nitrogen and flame dried. After cooling to room temperature, freshly distilled THF (~10 mL) was introduced via syringe followed by a small amount of dry dibromoethane (~0.1 mL). After evidence of reaction was observed (disappearance of I$_2$ color, and bubble formation on metal), a solution of the ketal of 4-bromoacetophenone-(see, Example 20, Step 1) (2.89 g, 11.89 mmol) in dry THF (10 mL) was added via syringe. The mixture was then stirred in a hot water bath for 2 hr until the majority of the magnesium was consumed. After the reaction mixture was cooled to room temperature, solid copper (I) chloride (11.8 mg, 1.19 mmol) was added and the mixture was stirred at room temperature for ½ hr. The epoxide (110, 1.0 g, 2.38 mmol) in dry THF (10 mL) was added via syringe. The reaction mixture was stirred at room temperature for 1 hr then quenched with the addition of saturated NH$_4$Cl solution (~20 mL), and the mixture was stirred at room temperature for ½ hr while air was drawn through the reaction mixture to oxidize Cu(I) to Cu(II). The contents of the flask were diluted with water (~100 mL) and extracted with CH$_2$Cl$_2$ (3×). The organic extracts were washed with saturated NH$_4$Cl solution (1×), water (1×) and brine (1×), then dried over anhydrous sodium sulfate, filtered and concentrated in vacuo to yield 4.3 g of oil. This was purified on a flash column (10% acetone in CH$_2$Cl$_2$) to yield 850 mg of 111d as a white foam which was triturated with ether to produce a white crystalline solid in 61.2% yield; m.p.=145–150° C. (Material changed to amber gel) and gel melts at 173–177° C. FTIR (KBr, diffuse reflectance): $\nu_{max}$ 3461, 2946, 2877, 2812, 1663, 1602, 1540, 1505, 1457 and 1372 cm$^{-1}$. NMR (300 MHz, CDCl$_3$): δ 0.443 (s, 3H, C18-CH$_3$), 1.636 (s, 3H, CH$_3$ of acetophenone ketal), 3.289 (s, 3H, C17α-OCH$_3$), 3.358 (s, 3H, C21-OCH$_3$), 3.741–4.015 (m, 8H, C3- and C11β-4acetyl ketals), 4.244 (br s, 1H, C11α-CH), 7.165–7.327 (dd, 4H, aromatic-CH's). MS (EI) m/z (relative intensity): 584 (M$^+$). Anal. Calcd. for C$_{34}$H$_{48}$O$_8$: C, 69.86; H, 8.22. Found: C, 69.63; H, 8.28.

Step 2. 3,3-Ethylenedioxy-5α-hydroxy-11β-[4-(2-methyl-1,3-dioxolan-2-yl)phenyl]-17α,21-dimethoxy-19-norpregn-9-en-20-one (112d):

Under nitrogen, IBX (1.149 g, 4.104 mmol) was dissolved in DMSO (8 mL) over a period of 10 min. A solution of the Grignard product (111d, 800 mg, 1.368 mmol) in DMSO (8 mL) was added via pipette to the above solution and the reaction mixture stirred at room temperature for ½ hr. At that time, TLC (10% acetone in CH$_2$Cl$_2$; aliquot was diluted in water and extracted into EtOAc) showed the starting material had been converted to a single less polar product. The reaction was diluted with H$_2$O (150 mL) and extracted with CH$_2$Cl$_2$ (3×). The organic layers were washed with H$_2$O (1×) and brine (1×), dried over anhydrous sodium sulfate, filtered and concentrated in vacuo to give 820 mg of 112d as an off-white foam. This was purified on a flash column (10% acetone in CH$_2$Cl$_2$). The product was originally obtained as a foam and was triturated with pentane and dried in vacuo to yiled 540 mg of 112d as a white solid in 73% yield; m.p.=102–106° C. (shrinkage to an amber gel); 111–113° C. (gel bubbles); 123–133° C. (gel melts). FTIR (KBr, diffuse reflectance): $\nu_{max}$ 3526, 2939, 2884, 2825, 1722, 1665 and 1604 cm$^{-1}$. NMR (300 MHz, CDCl$_3$): δ 0.190 (s, 3H, C18-CH$_3$), 1.625 (s, 3H, CH$_3$ of acetophenone ketal), 3.146 (s, 3H, C17α-OCH$_3$), 3.445 (s, 3H, C21-OCH$_3$), 3.742 and 4.015 (m, C3 and C11β-4-acetylphenyl ketals), 4.310 (d, 1H, C11α-CH), 7.119–7.332 (dd, 4H, aromatic-CH's) MS (EI) m/z (relative intensity): 582 (M$^+$). Anal. Calcd. for C$_{34}$H$_{46}$O$_8$: C, 70.08; H, 7.96. Found: C, 70.11; H, 8.01. FTIR (KBr, diffuse reflectance): $\nu_{max}$ 3526, 2939, 2884, 2825, 1722, 1665 and 1604 cm$^{-1}$. NMR (300 MHz, CDCl$_3$): δ 0.190 (s, 3H, C18-CH$_3$), 1.625 (s, 3H, CH$_3$ of acetophenone ketal), 3.416 (s, 3H, C17α-OCH$_3$), 3.445 (s, 3H, C21-OCH$_3$), 3.742 and 4.015 (m, C3 and C11β-4-acetylphenyl ketals), 4.310 (d, 1H, C11α-CH), 7.119–7.332 (dd, 4H, aromatic-CH). MS (EI) m/z (relative intensity): 582 (M$^+$). Anal. Calcd. for C$_{34}$H$_{46}$O$_8$: C, 70.08; H, 7.96. Found: C, 70.11; H, 8.01.

Step 3. Preparation of the Target Compound 113d:

Nitrogen was bubbled through a mixture of EtOH (925 mL) and 8.5% sulfuric acid for ½ hr to remove oxygen. The 20-ketone (112d, 520 mg, 0.892 mmol) was added as a solid with stirring to the above solution. The mixture was put into an oil bath preheated to 95° C. and was refluxed under nitrogen for 1 hr. The reaction mixture was cooled in an ice bath and quenched with saturated K$_2$CO$_3$ solution (pH≅10), diluted with water (~125 mL) and extracted with CH$_2$Cl$_2$ (3×). The organic fractions were washed with water and brine, dried over anhydrous $Na_2SO_4$, filtered and concentrated in vacuo to give 460 mg of the crude product. Flash chromatography (10% acetone in $CH_2Cl_2$) gave 377 mg of an off-white pale yellow solid. This was crystallized from a mixture of distilled ether and $CH_2Cl_2$ to yield 360 mg of 113d in 81% yield as a white crystalline solid in two batches. The product 113d retained $CH_2Cl_2$ and required extreme drying: m.p.=133–136° C. (foams) and 172–178° C. (foam melts). FTIR (KBr, diffuse reflectance): $v_{max}$ 2942, 1719, 1681, 1665, 1600, 1409, 1359 and 1272 $cm^{-1}$. NMR (300 MHz, $CDCl_3$): δ 0.264 (s, 3H, C18-$CH_3$), 2.571 (s, 3H, $CH_3$ of acetophenone ketal), 3.185 (s, 3H, C17α-$OCH_3$), 3.449 (s, 3H, C21-$OCH_3$), 4.183 and 4.385 (dd, 2H, C21-$CH_2$—), 4.456 and 4.481 (d, 1H, C11α-CH), 5.90 (s, 1H, C4-CH=), 7.247–7.7883 (dd, 4H, aromatic-CH's). MS (EI) m/z (relative intensity): 476 ($M^+$, 35), 403 (93), 371 (100), 331 (67) and 91 (26). Anal. Calcd. for $C_{30}H_{36}O_5$: C, 75.63; H, 7.56. Found: C, 74.78; H, 7.58.

Example 31

This example illustrates the preparation and properties of 17α-Acetoxy-1113-[4-(N-piperidino)phenyl]-21-methoxy-19-norpregna-4,9-diene-3,20-dione (123a)

Step 1. 17α-Hydroxy-21-chloro-19-norpregna-4,9-diene-3,20-dione (115):

The 3-ketal cyanohydrin (28, 50 g, 73.22 mmol) was magnetically stirred with freshly distilled THF (550 mL) under nitrogen at room temperature. 4-Dimethylaminopyridine (DMAP) (4.47 g, 36.59 mmol) was added as a solid. Freshly distilled $Et_3N$ (27.60 mL, 197.68 mmol) followed by freshly distilled chloro-(chloromethyl)dimethylsilane (25.1 mL, 190.36 mmol) was added via syringe. The reaction was allowed to stir overnight at room temperature. The next day TLC on silica (2% acetone in $CH_2Cl_2$) showed all starting material had been converted to the silyl ether. The reaction mixture was cooled to −78° C. in a dry ice bath with isopropanol, and then diluted with THF (800 mL). Lithium diisopropylamide (LDA) (2.0 $\underline{M}$, 300 mL, 600 mmol) was added dropwise via an additional funnel over a period of 45 min. Once addition was complete, the reaction was stirred for 1.5 hr at −78° C. HCl (4 $\underline{N}$, 1250 mL, 5 mol) was added via the addition funnel. The dry ice bath was removed, and the reaction was allowed to stir overnight at room temperature. The reaction mixture was then cooled to 0° C. and neutralized by the addition of concentrated $NH_4OH$ (305 mL). The mixture was transferred to a separatory funnel and extracted with EtOAc (3×), washed with $H_2O$ (2×) and brine (1×). The organic fractions were combined, filtered through $Na_2SO_4$ and evaporated in vacuo. The resulting solid was triturated with ether (1000 mL), collected on a Buchner funnel, and washed with additional ether. After drying overnight in vacuo, 38.90 g of 115 as a dark yellow solid was recovered in 76.61% yield. Analysis by TLC on silica (5% acetone in $CH_2Cl_2$) showed the material was suitable to carry directly on to the next reaction; m.p.=204–207° C. FTIR (KBr, diffuse reflectance): $v_{max}$ 3465, 2946, 1729, 1664, 1599 and 1573 $cm^{-1}$. NMR (300 MHz, $CDCl_3$): δ 0.833 (s, 3H, C18-$CH_3$), 4.352 and 4.655 (AB, 2H, $J_{AB}$=16.8 Hz, C21-$CH_2$) and 5.687 (s, 1H, C4-CH=) MS (EI) m/z (relative intensity): 350 ($M^+$, 33.1), 348 (100.0), 253 (63.7), 213 (71.5) and 91 (62.6).

Step 2. 17α-Hydroxy-21-acetoxy-19-norpregna-4,9-diene-3,20-dione (116):

The 21-chloro compound (115, 37.90 g, 108.64 mmol), KOAc (111.83 g, 1139.63 mmol) and acetonitrile (927 mL) were mechanically stirred. The suspension was brought to reflux under nitrogen. After 2.5 hr, TLC on silica (5% acetone in methylene chloride) indicated the reaction had gone to completion. The reaction mixture was allowed to cool to room temperature, and precipitated KCl was removed by filtration through a sintered glass funnel. Acetonitrile was evaporated in vacuo, and the resulting residue was taken up in $CH_2Cl_2$ and $H_2O$. The mixture was transferred to a separatory funnel, extracted with $CH_2Cl_2$ (3×), and washed with $H_2O$ (2×) and brine (1×). The organic fractions were combined, filtered through $Na_2SO_4$ and evaporated in vacuo to give 36.26 g of 116 in 89.61% crude yield. The solid material was taken up in hot acetone (150 mL) and $CH_2Cl_2$ (150 mL). The solution was scratched, seeded and stored in the freezer for 4 hr. The crystals were then filtered through a Buchner funnel and dried in vacuo to recover 10.71 g of the 17α-ol-21-acetate (116) in 52.14% yield. The mother liquor was evaporated in vacuo and purified by flash column chromatography eluted with 10% acetone in $CH_2Cl_2$. Fractions containing the 17α-ol-21-acetate (116) were combined and evaporated in vacuo to recover 2.58 g of a golden yellow solid in 12.61%. The total yield of the purified 17α-ol-21-acetate (116) was 13.29 g of a golden yellow solid in 64.7% yield; m.p.=213–218° C. FTIR (KBr, diffuse reflectance): $v_{max}$ 3475, 2947, 2951, 1744, 1720, 1646, 1606, 1578, 1367 and 1235 $cm^{-1}$. NMR (300 MHz, $CDCl_3$): δ 0.841 (s, 3H, C18-$CH_3$), 2.182 (s, 3H, C21-OAc), 4.868 and 5.081 (AB, 2H, $J_{AB}$=17.4 Hz, C21-$CH_2$) and 5.683 (s, 1H, C4-CH=) MS (EI) m/z (relative intensity): 372 ($M^+$, 78.3), 354 (9.7), 312 (75.6), 253 (100.0) and 91 (69.3).

Step 3. 17α,21-Dihydroxy-19-norpregna-4,9-diene-3,20-dione (117):

The 17α-ol-21-acetate (116) (35.15 g, 94.37 mmol) was suspended in freshly opened MeOH (2870 mL) and deoxygenated by bubbling nitrogen through the mixture for 45 min. $KHCO_3$ (deoxygenated, 0.5 $\underline{M}$, 283 mL, 141.74 mmol) was added, and the suspension was mechanically stirred and brought to reflux under nitrogen. After 10 minutes at reflux, TLC on silica (5% isopropanol in $CH_2Cl_2$) showed the reaction to be complete. The reaction mixture was cooled to room temperature, neutralized by the addition of HOAc (8.15 mL), and MeOH was evaporated in vacuo. The reaction mixture was extracted with $CH_2Cl_2$ (3×), and washed with $H_2O$ (2×) and brine (1×). The combined organic fractions were filtered through $Na_2SO_4$ and evaporated in vacuo to recover 29.83 g of the solid in 95.7% yield. The solid was taken up in acetone with a small amount of $CH_2Cl_2$. The solution was scratched, seeded and stored in the freezer for 1 hr. The resulting crystals were collected on a Buchner funnel, rinsed with acetone and dried in vacuo to recover the first crop. The mother liquor was concentrated and stored in the freezer overnight to afford a second crop of crystals. The combined solid recovered was 16.15 g in 51.8% crude yield. The mother liquors were evaporated in vacuo and purified by flash column chromatography eluted with 5% isopropanol in $CH_2Cl_2$. Fractions containing the diol (117) were combined and evaporated in vacuo to recover 4.86 g. The total yield of 117 was 19.75 g of a light yellow solid in 76.7%; m.p.=197–204° C. FTIR (KBr, diffuse reflectance): $v_{max}$ 3917, 2954, 2869, 1715, 1635, and 1590 $cm^{-1}$. NMR (300 MHZ, $CDCl_3$): δ 0.827 (s, 3H, C18-$CH_3$), 4.323 and 4.690 (AB, 2H, $J_{AB}$=19.81 Hz, C21-$CH_2$) and 5.686 (s, 1H, C4-CH=). MS (EI) m/z (relative intensity): 330 ($M^+$, 100.0), 312 (10.1), 253 (61.7), 213 (64.5), 174 (26.1) and 91. (38.5).

Step 4. 3,20-bis-Ethylenedioxy-17α,21-Dihydroxy-19-norpregna-5(10),9(11)-diene (8):

The diol (117, 9.88 g, 29.89 mmol) and freshly opened ethylene glycol (750 mL) were magnetically stirred. p-Toluenesulfonic acid monohydrate (0.49 g, 2.60 mmol) was added to the suspension as a solid. The ethylene glycol was distilled in vacuo at 81° C. under 2 mm Hg. After distilling for 3 hr, the mixture was cooled to room temperature and poured into saturated $NaHCO_3$ (250 mL) and $H_2O$ (250 mL). The mixture was extracted with $CH_2Cl_2$ (3×), washed with $H_2O$ (2×) and brine (1×). The organic fractions were combined, filtered through sodium sulfate and evaporated in vacuo to recover a solid. Analysis by TLC on silica (5% isopropanol in $CH_2Cl_2$) showed all of the starting material to be converted to an 85:15 mixture of 3,20-diketal to 3-ketal with a small amount of by-product. The resulting solid was triturated with ether, collected on a Buchner funnel, washed with additional ether and dried in vacuo to recover 6.46 g of 118 in 51.64% yield. The mother liquor was evaporated in vacuo and purified through flash chromatography eluting with 4% isopropanol in $CH_2Cl_2$. This recovered 0.6 g of the light beige, solid diketal in 4.8% yield. The total yield of the solid diketal (118) was 7.06 g of a light beige solid in 56.44% yield; m.p.=173–176° C. FTIR (KBr, diffuse reflectance): $v_{max}$ 3452, 2892, 1652, 1436, 1370, 1223 and 1055 $cm^{-1}$. NMR (300 MHz, $CDCl_3$): δ 0.795 (s, 3H, C18-$CH_3$), 3.686 and 3.894 (AB, 2-H, $J_{AB}$=12.61 Hz, C21-$CH_2$), 3.987 (s, 4H, C3-O$CH_2CH_2$O—), 4.130 (m, 4H, C20-O$CH_2CH_2$O—) and 5.555 (br s, 1H, C11-CH=). MS(EI) m/z (relative intensity): 418 ($M^+$, 5.6), 400 (0.7), 387(3.9), 314 (3.5), 211 (4.6) and 103 (100.0).

Step 5. 3,20-bis-Ethylenedioxy-17α-hydroxy-21-methoxy-19-norpregna-5(10),9(11)-diene (119):

To a solution of the diketal (118, 0.5 g, 1.19 mmol) in $CH_2Cl_2$ (50 mL) was added 1,8-bis-(dimethylamino)naphthalene ("Proton Sponge", 1.28 g, 5.97 mmol) followed by trimethyloxonium tetrafluoroborate (0.88 g, 5.97 mmol). The mixture was mechanically stirred in an ice bath under nitrogen. The ice bath was allowed to melt to bring the reaction to room temperature. The reaction mixture was stirred for 3 hr, at which time TLC (5% isopropanol in $CH_2Cl_2$) indicated the reaction had gone to completion. The mixture was poured into a separatory funnel and washed with $H_2O$ (2×). The $CH_2Cl_2$ extracts (3×) were combined, filtered through $Na_2SO_4$ and evaporated in vacuo. The resulting residue was taken up in EtOAc, washed with ice-cold 1 N HCl (2×), $H_2O$ (1×), saturated $NaHCO_3$ (1×), $H_2O$ (1×), and brine (1×). Combined EtOAc fractions (3×) were filtered through $Na_2SO_4$ and evaporated in vacuo to give 0.5 g of 119 as a yellow foam in 97.14% yield. The material was of adequate purity to carry onto the subsequent epoxidation. The reaction was repeated to produce a total of 13.57 g of the 21-methoxy compound (119). NMR (300 MHz, $CDCl_3$): δ 0.798 (s, 3H, C18-$CH_3$), 3.415 (s, 3H, C21-$OCH_3$), 3.546 and 3.715 (AB, 2H, $J_{AB}$=10.51 Hz, C21-$CH_2$), 3.985 (s, 4H, C3-O$CH_2CH_2$O—), 4.05 (m, 4H, C20-O$CH_7CH_2$O—) and 5.54 (br s, 1H, C11-CH=). Decomposition of analytical sample precluded further analysis.

Step 6. 3,20-bis-Ethylenedioxy-5α,10α-epoxy-17α-hydroxy-21-methoxy-19-norpregn-9(11)-ene (120):

Hexafluoroacetone trihydrate (6.49 mL, 46.64 mmol) and $CH_2Cl_2$ (100 mL) were mechanically stirred vigorously at 4° C. Solid $Na_2HPO_4$ (3.67 g, 25.91 mmol) and 30% $H_2O_2$ (7.01 mL, 68.39 mmol) were added and stirred for 15 minutes at 4° C. A cold solution of the 21-methoxy compound (119, 13.45 g, 31.09 mmol) in $CH_2Cl_2$ (100 mL) was added to the mixture via an additional funnel over a period of 1 hr. The reaction mixture was allowed to stir overnight at 4° C. Examination by TLC (25% EtOAc in $CH_2Cl_2$) showed all of the starting material had been converted to a mixture of the α and β epoxides in about a 2:1 ratio. The mixture was transferred to a separatory funnel and washed with 10% $Na_2SO_3$ (1×), saturated $NaHCO_3$ (1×) and $H_2O$ (1×). Combined $CH_2Cl_2$ extracts (3×) were filtered through $Na_2SO_4$ and evaporated in vacuo to recover 14.06 g of the epoxide (120) as a white foam in quantitative yield. The 2:1 mixture of α- and β-epoxides was used directly for the subsequent Grignard reaction. NMR (300 MHz, $CDCl_3$): δ 0.700 (s, 3H, C18-$CH_3$), 3.407 (s, 3H, C21-$OCH_3$), 3.539 and 3.692 (AB, 2H, $J_{AB}$=10.51 Hz, C21-$CH_2$), 4.051 (m, 8H, C3- and C20-O$CH_2CH_2$O—), 5.819 (br s, 0.3H, C11-CH= of β-epoxide), and 5.997 (br s, 0.6H, C11-CH= of α-epoxide). Decomposition of analytical sample precluded further analysis.

Step 7. 3,20-bis-Ethylenedioxy-5α,17α-dihydroxy-11β-[4-piperidino)phenyl]-21-methoxy-19-norpregn-9-ene (121a):

Magnesium (1.27 g, 52.25 mmol), a crystal of iodine, dry THF (55 mL), and one drop of 1,2-dibromoethane were stirred together in dry glassware over nitrogen. A solution of N-(4-bromophenyl)piperidine (see, EXAMPLE 23, Step 1) (13.80 g, 57.48 mmol) in dry THF (45 mL) was added to the reaction flask, then rinsed in with an additional 10 mL of THF. The mixture was heated until all of the magnesium metal was gone. The reaction was allowed to reflux for 1.5 hr, and then cooled to room temperature. Copper (I) chloride (0.57 g, 5.75 mmol) was added and stirring continued for 1 hr. A solution of the epoxide (120, 4.69 g, 10.45 mmol) in dry THF was added to the reaction and rinsed in with an additional 10 mL of THF. The reaction was stirred under nitrogen, at room temperature, for 1 hr. The reaction was quenched with saturated $NH_4Cl$ (138 mL). Air was drawn through the mixture with vigorous stirring for 20 min. The mixture was transferred to a separatory funnel, extracted with ether (3×), washed with $H_2O$ (2×) and brine (1×). The combined organic fractions were dried with $Na_2SO_4$ for ½ hr, and evaporated in vacuo to recover 12.97 g of the crude product. Analysis by TLC (20% acetone in $CH_2Cl_2$) showed many impurities. The crude material was triturated with pentane to recover 4.45 g of a pale green solid. Analysis by TLC (20% acetone in $CH_2Cl_2$) showed a small amount of by-product still present. The precipitate was further purified by flash column chromatography (10% acetone in $CH_2Cl_2$). Fractions containing the pure Grignard adduct (1219) were combined and evaporated in vacuo to recover 2.56 g of an aqua-green solid in 40.17% yield. The mother liquors from the trituration were combined and evaporated in vacuo to recover 8.15 g of material. Purification of this material by flash column chromatography (20% acetone in $CH_2Cl_2$) afforded 0.29 g of a green gum. All recovered products were combined and triturated with ether to recover a total of 2.16 g of Grignard adduct (121a) in 33.9% yield; m.p.=218–220° C. FTIR (KBr, diffuse reflectance): $v_{max}$ 3508, 2940, 1609 and 1509 $cm^{-1}$. NMR ($CDCl_3$): δ 0.449 (s, 3H, C18-$CH_3$), 3.094 (t, 10H, —$NC_5H_{10}$), 3.437 (s, 3H, C21-$OCH_3$), 3.989 (m, 10H, C3 and C20-O$CH_2CH_2$O— and C21-$CH_2$—), 6.822 (d, 2H, J=8.85, 3',5' aromatic-CH's) and 7.067 (d, 2H, J=8.85 Hz, 2',6' aromatic-CH's). MS (EI) m/z (relative intensity): 609 ($M^+$, 29.1), 591 (46.6), 364 (8.6), 174 (29.2), 161 (100.0) and 117 (96.4). Anal. Calcd. for $C_{36}H_{51}N_7 \cdot \frac{1}{3} H_2O$: C, 70.22; H, 8.46; N, 2.27. Found: C, 70.10; H, 8.33; N, 2.40.

Step 8. 17α-Hydroxy-11β-[4-(N-piperidino)phenyl]-21-methoxy-19-norpregna-4,9-diene-3,20-dione (122a):

A solution of the Grignard adduct (121a, 2.10 g, 3.44 mmol) in THF (20 mL) was mechanically stirred under nitrogen at room temperature. Trifluoroacetic acid (60 mL, 764.26 mmol) and $H_2O$ (20 mL) were added, and the mixture was stirred under nitrogen for 3 hr. Examination by TLC (20% acetone in $CH_2Cl_2$) showed the reaction had gone to completion. The reaction mixture was cooled in an ice bath, and $NH_4OH$ (51.46 mL) was slowly added to neutralize the reaction to a pH of 7 by pH paper. The mixture was transferred to a separatory funnel, extracted with EtOAc (3×). The organic fractions were washed with $H_2O$ (2×) and brine (1×). The combined EtOAc fractions were dried with $Na_2SO_4$ and evaporated In vacuo to give 1.70 g of an amber foam. The crude product was purified by flash column chromatography (20% acetone in $CH_2Cl_2$) to recover 1.16 g of 122a as a bright yellow foam in 66.95% yield; m.p.= 211–216° C. FTIR (KBr, diffuse reflectance): $v_{max}$ 3429, 2941, 1721, 1648, 1601 and 1511 $cm^{-1}$. NMR ($CDCl_3$): δ 0.391 (s, 3H, C18-$CH_3$), 2.979 (t, 10H, —$NC_5H_{10}$), 3.454 (s, 3H, C21-$OCH_3$), 4.243 and 4.383 (AB, 2H, $J_{AB}$=17.71 Hz, C21-$CH_2$—), 5.762 (s, 1H, C4-CH=), 6.820 (d, 2H, J=8.55 Hz, 3',5' aromatic-CH's) and 6.980 (d, 2H, J=8.55 Hz, 2',6' aromatic-CH's). MS(EI) m/z (relative intensity): 503 ($M^+$, 57.9), 318 (5.8), 174 (12.3) and 161 (100.0). Anal. Calcd. for $C_{32}H_{41}NO_4 \cdot \frac{1}{3}H_2O$: C, 75.42; H, 8.24; N, 2.75. Found: C, 75.23; H, 8.04; N, 2.94.

Step 9 Preparation of the Target Compound 123a:

A mixture of $CH_2Cl_2$ (50 mL), trifluoroacetic anhydride (11.70 g, 55.65 mmol) and glacial acetic acid (3.35 g, 55.59 mmol) was stirred under nitrogen at room temperature for ½ hr. The mixture was cooled in an ice bath, and p-toluenesulfonic acid monohydrate (0.47 g, 2.45 mmol) was added. The 17α-OH (122a, 1.12 g, 2.22 mmol) dissolved in $CH_2Cl_2$ (7.5 mL) was transferred to the reaction flask and then rinsed in with an additional 8 mL of $CH_2Cl_2$. The reaction mixture was stirred at 0° C. for 2 hr. Examination by TLC (10% acetone in $CH_2Cl_2$) showed the reaction had gone to completion. The reaction was kept at 0° C. and diluted with $H_2O$ (30 mL), then neutralized by the addition of $NH_4OH$ (11.45 mL). Additional $NH_4OH$ was added until the pH of 6–7 by pH paper was reached. The mixture was transferred to a separatory funnel, the layers allowed to separate and $CH_2Cl_2$ fractions then washed with $H_2O$ (1×) and brine (1×). The organic fractions were filtered through $Na_2SO_4$ and evaporated in vacuo to give 1.21 g of a dark yellow foam. The crude product was purified by flash column chromatography (10% acetone in $CH_2Cl_2$) to give 1.08 g of 123a as a bright yellow foam. The purified product was then triutrated with pentane to give 0.92 g of 123a as a pale yellow powder in 76% yield; m.p.=142–144° C. FTIR (KBr, diffuse reflectance): $v_{max}$ 2941, 2360, 2338, 1737, 1664, 1608 and 1512 $cm^{-1}$. NMR ($CDCl_3$): δ 0.378 (s, 3H, C18-$CH_3$), 2.105 (s, 3H, C17α-OAc), 3.095 (t, 10H, —$NC_5H_{10}$), 3.413 (s, 3H, C21-$OCH_3$), 4.099 and 4.307 (AB, 2H, $J_{AB}$=17.11 Hz, C21-$CH_2$—), 4.377 (d, 1H, J=6.60 Hz, C11α-CH), 5.779 (s, 1H, C4-CH=), 6.810 (d, 2H, J=8.70 Hz, 3',5' aromatic-CH's) and 6.973 (d, 2H, J=8.70 Hz, 2',6' aromatic-CH's). MS (EI) m/z (relative intensity): 545 ($M^+$, 34.5), 485 (8.6), 412 (2.2), 174 (10.1), 161 (100.0) and 105 (2.5). Anal. Calcd. for $C_{33}NO_5 \cdot \frac{1}{10}H_2O$: C, 74.59; H, 7.95; N, 2.56. Found: C, 74.58; H, 7.89; N, 2.65.

Example 32

This example illustrates the preparation and properties of 17α-Acetoxy-11β-(4-acetylphenyl)-21-methoxy-19-norpregna-4,9-diene-3,20-dione (123b) (FIG. 9):

Step 1. 3,20-bis-Ethylenedioxy-5α,17α-dihydroxy-11β-[4-(2-methyl-1,3-dioxolan-2-yl)phenyl]-21-methoxy-19-norpregn-9-ene (121b):

A 3-neck 1 L flask was euipped with a mechanical stirrer, an addition funnel, and a reflux condenser and flame dried under a stream of nitrogen. Magnesium (3.90 g, 146 mmol) was added, followed by one iodine crystal, 150 mL of dry THF, and 1–2 drops of 1,2-dibromoethane. The mixture was stirred under nitrogen and heated in a warm water bath, but no reaction occurred. 4-Bromoacetophenone ethylene ketal (see, EXAMPLE 20, Step 1) (35.5 g, 146 mmol) was added as a solution in THF (100 mL) via the addition funnel and then rinsed in with additional THF (40 mL). Upon completion of addition, the mixture was heated to reflux to initiate formation of the Grignard reagent. Heating was discontinued and the mixture allowed to stir 1.5 hr as the water bath gradually cooled to room temperature. Copper (I) chloride (1.59 g, 16.06 mmol) was added as a solid and stirring continued for another ½ hr. The mixture of epoxides 120, 13.11 g, 29.2 mmol, ~66% α-epoxide) was added as a solution in THF (50 mL) via the addition funnel and rinsed in with additional THF (20 mL). After stirring 1.5 hr at room temperature, TLC (20% acetone in $CH_2Cl_2$; quenched with saturated $NH_4Cl$ and extracted into EtOAc) indicated the reaction was >95% complete. The reaction was quenched by the addition of 200 mL of saturated $NH_4Cl$ and air was drawn through the mixture for ½ hr with vigorous stirring. Ether was added, the mixture was transferred to a separatory funnel, and the layers allowed to separate. The organic layer was washed with 10% $NH_4Cl$, $H_2O$ and brine. Combined ether extracts (3×) were filtered through $Na_2SO_4$ and evaporated in vacuo to give 35.23 g of the crude product (121h). Purification by flash column chromatography (20% acetone in $CH_2Cl_2$) afforded 7.24 g of a pale foam. Trituration of this foam with ether and pentane produced 5.93 g of the product (121b) as a beige powder in 50.2% yield (based on 66% of the mixture as α-epoxide). NMR ($CDCl_3$): δ 0.4 (s, 3H, C18-$CH_3$), 1.63 (s, 3H, $CH_3$ of C11β-4-$C_6H_4C(O)CH_3$), 3.45 (s, 3H, C21-$OCH_3$), 3.57–4.40 (m, 15H, C3-O $CH_2CH_2O$—, C11β-$OCH_7CH_2O$— and C20O$CH_2CH_2O$—, C11α-CH and C21-$CH_2$—), 7.2 (d, 2H, J=9 Hz, 2',6' aromatic-CH's) and 7.83 (d, 2H, J=9 Hz, 3',5' aromatic-CH's). MS (EI) m/z (relative intensity): 612 ($M^+$, 0.1), 594 (3.3), 549 (15.0), 459(2.7), 117 (100.0) and 87 (74.7). Decomposition of the analytical sample precluded further analysis.

Step 2. 17α-Hydroxy-11β-(4-acetylphenyl)-21-methoxy-19-norpregna-4,9-diene-3,20-dione (122b):

The Grignard adduct (121b, 5.81 g, 9.48 mmol) was dissolved in THF (60 mL) and stirred magnetically, under nitrogen, at room temperature. Trifluoroacetic acid (180 mL) was added followed by $H_2O$ (60 mL). After 1.5 hr, examination by TLC (20% acetone in $CH_2Cl_2$; neutralized with $NH_4OH$ before developing) indicated all of the starting material had been converted to a slightly less polar product The reaction mixture was neutralized by the careful addition of $NH_4OH$ (165 mL) via an addition funnel. Enough additional $NH_4OH$ was added to bring the pH to 7.0 by pH paper. $H_2O$ was added, the mixture was transferred to a separatory funnel, and extracted with EtOAc. The organic fraction was washed again with $H_2O$ and brine. Combined EtOAc fractions (3×) were filtered through $Na_2SO_4$ and evaporated in vacuo to give 6.60 g of a foam. Purification of the crude product by flash column chromatography (20% acetone in $CH_2Cl_2$) afforded a yellow solid (122b). Crystallization from a minimum amount of hot EtOAc gave large, bright yellow crystals. The crystals were collected on a Buchner funnel and dried overnight under high vacuum at 70° C. to recover 2.84 g of 122b. A TLC of the mother liquors indicated they were pure enough to carry on to the subsequent reaction. The mother liquors were evaporated in vacuo and dried under high vacuum over the weekend to recover 0.46 g. The total yield of the 17α-OH (122b) was 3.3 g as bright yellow crystals in 75.25% yield. A small amount of the crystalline product was dried in vacuo at 110° C. over the weekend for purposes of characterization. The crystals were fused and pulverized with a spatula; m.p.=105–109° C. (softens). Analysis by HPLC on a Phenomenex Prodigy 5 ODS-2 column (150×4.6 mm) eluted with 50% $CH_3CN$ in $H_2O$ at a flow rate of 1 mL per min and λ=302 nm indicated a purity of >99% with a retention time ($t_R$) of 5.02 min. FTIR (KBr, diffuse reflectance): $v_{max}$ 3444, 2944, 1722, 1662, 1602, 1407, 1359 and 1271 $cm^{-1}$. NMR ($CDCl_3$): δ 0.33 (s, 3H, C18-$CH_3$), 2.57 (s, 3H, C11β-4-$C_6H_4$—C(O)$CH_3$), 3.47 (s, 3H, C21-$OCH_3$), 4.23–4.47 (AB, 2H, $J_{AB}$=18 Hz, C21-$CH_2$—), 4.52 (br d, 1H, C11α-CH), 5.48 (s, 1H, C4-CH=), 7.3 (d, 2H, J=9 Hz, 2',6' aromatic-CH's) and 7.92 (d, 2H, J=9 Hz, 3',5' aromatic-CH's). MS (EI) m/z (relative intensity): 462 ($M^+$, 100.0), 430 (11.2), 389 (27.0), 346 (97.9) and 91 (22.3). Anal. Calcd. for $C_{29}H_{34}O_5 \cdot \%_{20}C_4H_8O_2$: C, 73.66; H, 7.55. Found: C, 73.66; H, 7.29.

Step 3. Preparation of the Target Compound 123b:

A mixture of trifluoroacetic anhydride (32.78 g, 156 mmol) and acetic acid (9.38 g, 156 mmol) in $CH_2Cl_2$ (100 mL) was allowed to stir ½ hr at room temperature under nitrogen. The mixture was cooled to 0° C. in an ice $H_2O$ bath and p-toluenesulfonic acid monohydrate (1.30 g, 6.86 mmol) was added as a solid. The 17α-OH (122b, 2.89 g, 6.24 mmol) was added as a solution in 25 mL of $CH_2Cl_2$ and rinsed in with additional $CH_2Cl_2$ (25 mL). After 45 min, TLC (10% acetone in $CH_2Cl_2$) indicated the reaction had gone to completion. The reaction was neutralized by the careful addition of $NH_4OH$ (31.6 mL, 416 mmol). Additional $NH_4OH$ was added to bring the pH to 7 by pH papaer. Water was added and the mixture transferred to a separatory funnel. The organic fractions were washed with $H_2O$ and brine. Combined $CH_2Cl_2$ extracts (3×) were filtered through $Na_2SO_4$ and evaporated in vacuo to recover 3.13 g of crude material. Purification by flash chromatography (10% acetone in $CH_2Cl_2$) provided 1.56 g of a crystallizing oil. Additional fractions containing a small amount of a less polar impurity were also combined and evaporated to give 1.04 g of an oil. Pure fractions were crystallized from a minimum amount of boiling EtOAc, triturated with pentane and dried 3 nights in a drying pistol at 110° C. to give 0.99 g of 123b as pale yellow crystals. The crystals fused at this temperature, but were readily pulverized for analysis. Mother liquors were combined with the impure fractions and crystallized from EtOAc to give an additional 0.9 g. Total yield of 123b was 1.89 g as a pale yellow solid in 60.1% yield; m.p.=113° C. (softens).

Analysis by HPLC on a Phenomenex Prodigy 5 ODS-2 column (150×4.6 mm) eluted with 50% $CH_3CN$ in $H_2O$ at a flow rate of 1 mL per min and λ=302 nm indicated a purity of 99.7% with a retention time ($t_R$) of 7.69 min. FTIR (KBr, diffuse reflectance): $v_{max}$ 2942, 1730, 1680, 1602, 1432, 1408, 1368 and 1266 $cm^{-1}$. NMR ($CDCl_3$): δ 0.33 (s, 3H, C18-$CH_3$), 2.10 (s, 3H, C17α-OAc), 2.57 (s, 3H, C11β-C(O)$CH_3$), 3.42 (s, 3H, C21-$OCH_3$), 4.07 & 437 (AB, 2H, $J_{AB}$=18 Hz, C21-$CH_2$—), 4.50 (br d, 1H, C11α-CH), 5.83 (s, 1H, C4-CH=), 7.28 (d, 2H, J=9 Hz, 2',6' aromatic-CH's) and 7.92 (d, 2H, J=9 Hz, 3',5' aromatic-CH's). MS (EI) m/z (relative intensity): 504 ($M^+$, 3.3), 447 (17.9), 389 (28.4), 371 (100.0) and 91 (13.8). Anal. Calcd. for $C_{31}H_{36}O_6 \cdot \%CH_2Cl_2 \cdot \frac{1}{2}H_2O$: C, 70.92; H, 7.13. Found: C, 71.06; H, 6.91.

Example 33

This example illustrates the preparation and properties of 17α-Acetoxy-11β-{4-[2'-(N,N-dimethylamino)ethoxy]phenyl}-21-methoxy 19-norpregna-4,9-diene-3,20-dione (123c):

Step 1. 3,20-bis-(Ethylenedioxy)-5α,17α-dihydroxy-11β-4-[2'-(N,N-dimethylamino)ethoxy]phenyl}-21-methoxy-19-norpregna-4,9-diene-3,20-dione (121c)

Magnesium (0.58 g, 23.85 mmol), a crystal of iodine, distilled THF (27 mL) and one drop of 1,2-dibromoethane were stirred together in dry glassware over nitrogen. A solution of 4-[2-dimethylamino)ethoxy]phenyl bromide (Robertson, et al., *J. Org. Chem.*, 47:2387–2393 (1982)) (6.41 g, 26.24 mmol) in distilled THF was added to the reaction flask, then rinsed with an additional 5 mL of THF. The mixture was heated until all the magnesium was gone. The reaction was allowed to reflux for 2 hr., and then cooled to room temperature. Copper (I) chloride (0.26 g, 2.63 mmol) was added and stirring continued for 1 hr. A solution of the 5α,10α-epoxide (120, 14 g, 2.63 mmol) in distilled THF and rinsed with an additional 5 mL of THF. The reaction was stirred over nitrogen at room temperature for 1 hr. After cooling the reaction flask in an ice water bath, the reaction was quenched with water (79 mL). Air was drawn through the mixture with vigorous stirring for 20 min. The mixture was transferred to a separatory funnel, extracted with ether (3×), washed with water (2×) and brine (1×). The combined organic fractions were dried over sodium sulfate for ½ hr. and evaporated in vacuo to recover 3.21 g of a thick amber oil. Ether (50 mL) was added to this material, and a small precipitate was visible. The organic product was found to remain in the mother liquor. After removing the ether, the crude material was triturated with hexanes and a small amount of ether. A small precipitate formed, but once again the product was found in the filtrate by TLC (10% isopropanol in $CH_2Cl_2$). The crude material of 1.27 g recovered was a dark, amber oil. The material was further purified by flash column chromatography (10% isopropanol in $CH_2Cl_2$ with 0.1% $Et_3N$). All by-products were removed, and the product was flushed off the column with 10% isopropanol in $CH_2Cl_2$ with 1% $Et_3N$ to recover 0.76 g of a yellow gum. The material was triturated with ether and a small amount of $CH_2Cl_2$. After storing in the freezer overnight, a small precipitate formed, and the ether (containing the product) was decanted off to obtain 0.56 g of material. The crude product was further purified by another flash column (10% isopropanol in $CH_2Cl_2$ with 1% $Et_3N$) to recover 0.50 g of a yellow oil. This material was analyzed by HPLC on a NovaPak $C_{18}$ column eluted with 55% $CH_3CN$ in $H_2O$ with 0.05% $Et_3N$ at a flow rate of 0.5 mL/min and at λ=280 nm and indicated a purity of 17.83%. The material was then purified by prep HPLC on a Waters Assoc. Prep NovaPak HR $C_{18}$ (6µ) column (40×10 mm) eluted with 55% $CH_3CN$ in $H_2O$ with 0.05% $Et_3N$ at a flow rate of 25 mL per min and at λ=280 nm. Further analysis by HPLC on a Waters Assoc. NovaPak $C_{18}$ column eluted with 55% $CH_3CN$ in $H_2O$ with 0.05% $Et_3N$ at a flow rate of 0.4 mL per min and at λ=280 nm indicated a purity greater than 99.99% with $t_R$ of 10.21 min. $CH_3CN$ was removed from the fraction containing the product, and the aqueous layer with product material was extracted with EtOAc (3×). The organic fractions were then washed with $H_2O$ (x) and brine (x), dried over $Na_2SO_4$ and evaporated in vacuo to recover 0.35 g of white foam (121c) in 11.95% yield. A small amount of the material was triturated with pentane to use as the analytical sample, and the remainder of it was carried onto the hydrolysis; m.p.=179–183° C. FTIR (KBr, diffuse reflectance): $v_{max}$ 3508, 2942, 2894, 2818, 2772, 1610, 1580 and 1509 cm$^{-1}$. NMR (300 MHZ, CDCl$_3$): δ 0.443 (s, 3H, C18-Me), 3.435 (s, 3H, C21-OMe), 4.048 (m, 10H, C3- and C20-OCH$_2$CH$_2$O— and C21-CH$_2$), 6.803 (d, 2H, J=8.70 Hz, aromatic-CH's) and 7.099 (d, 2H, J=8.70 Hz, aromatic-CH's). MS (EI) m/z (relative intensity): 614 (M$^+$, 0.3), 595 (1.3), 568 (4.3), 550 (5.5), 117 (20.1), 71 (3.6) and 58 (100.0).

Step 2. 17α-Hydroxy-11β-{4-[2'-(N,N-dimethylamino) ethoxy]phenyl}-21-methoxy-19-norpregna-4,9-diene-3,20-dione (122c):

The Grignard product (121c, 0.30 g, 0.49 mmol) in THF (3 mL) was mechanically stirred under nitrogen at room temperature. Trifluoroacetic acid (9 mL, 121.14 mmol) and water (3 mL) were added, and the mixture was stirred for 2.5 hr under nitrogen. Examination by TLC (silica, 10% isopropanol in CH$_2$Cl$_2$ with 0.1% Et$_3$N) was difficult to analyze; therefore, the reaction was allowed to stir overnight at room temperature under nitrogen. Another TLC (silica, 10% isopropanol in CH$_2$Cl$_2$ with 0.1% Et$_3$N) was done, but the results were difficult to read due to the fact that the product was still very polar. The reaction was assumed to be complete and diluted with water (35 mL). The flask was then cooled in an ice bath, and a cold solution of 2M NaOH (61 mL) was slowly added to neutralize the reaction to a pH of 7 (y pH paper), although the mixture quickly went to a pH of 12. The reaction mixture was extracted with CH$_2$Cl$_2$ (3×) and washed with water (2×) and brine (1×). The combined organic fractions were filtered through sodium sulfate and evaporated in vacuo to recover 0.19 g (0.38 mmol) of a yellow oil (122c). The crude product was purified by flash column chromatography (20% isopropanol in CH$_2$Cl$_2$ with 0.2% Et$_3$N) to recover 0.15 g of a yellow foam (122c). A small amount of the material was triturated with pentane to use as the analytical sample, and the remainder of it was carried onto the acetylation; m.p.=78–82° C. FTIR (KBr, diffuse reflectance): $v_{max}$ 2944, 1722, 1665, 1607, 1509, 1461 and 1237 cm$^{-1}$. NMR (300 MHZ, CDCl$_3$): δ 0.376 (s, 3H, C18-Me), 3.454 (s, 3H, C21-OMe), 5.770 (s, 1H, C4-CH=), 6.821 (d, 2H, aromatic-CH's) and 7.099 (d, 2H, aromatic-CH's); MS (EI) m/z (relative intensity): 505 (M$^+$, 1.5), 473 (0.5), 436 (3.8), 72 (13.8) and 58 (100.0).

Step 3'. Preparation of the Target Compound 123c:

A mixture of CH$_2$Cl$_2$ (6 mL), trifluoroacetic anhydride (0.90 mL, 6.44 mmol), and glacial acetic acid (0.37 mL, 6.44 mmol) were stirred at room temperature under nitrogen for ½ hr. The mixture was cooled in an ice bath, and p-toluenesulfonic acid monohydrate (0.05 g, 0.28 mmol) was added. The 17-OH (122c, 0.13 g, 0.26 mmol) dissolved in CH$_2$Cl$_2$ (2 mL) was transferred to the reaction flask and then rinsed with an additional 0.5 mL of CH$_2$Cl$_2$. The reaction was stirred at 0° C. for 5 hr. Examination by TLC (20% isopropanol in CH$_2$Cl$_2$ with 0.2% Et$_3$N) showed the reaction had gone to completion. The ice bath was maintained and water (20 mL) was added. The reaction was neutralized by the addition of cold 2 M NaOH (14 mL) until the pH of 7–8 (by pH paper) was reached. The mixture was transferred to a separatory funnel, the layers allowed to separate, and CH$_2$Cl$_2$ fractions then washed with water (2×) and brine (1×). The organic fractions were filtered through sodium sulfate and evaporated in vacuo to recover 0.15 g of a dark, yellow foam. The crude product was purified by flash column chromatography (20% 20% isopropanol in CH$_2$Cl$_2$ with 0.2% Et$_3$N) to give 0.08 g of a bright yellow foam. These purified fractions were then triturated with ether to recover 0.02 g of a pale yellow powder (123c). The mother liquor was further triturated with pentane to give an additional 0.04 g of 123c. Analysis by NMR showed the material was contaminated with stop cock to grease; therefore all collected material was combined and further purified by flash column chromatography (20% isopropanol in CH$_2$Cl$_2$ with 0.2% Et$_3$N) to give 0.05 g of a yellow powdery foam in 33.78% yield. This material was then triturated with pentane to yield 0.03 g of a pale yellow powder (123c) in 19.10% yield; m.p.=115–127° C. (sintered at 73–78° C.). FTIR (KBr, diffuse reflectance): $v_{max}$ 2947, 1728, 1665, 1607 and 1509 cm$^{-1}$. NMR (300 MHZ, CDCl$_3$): δ 0.365 (s, 3H, C18-Me), 2.105 (s, 3H, C17-OAc), 2.332 (s, 6H, —N(CH$_3$)$_2$), 3.414 (s, 3H C21-OME), 5.793 (s, 1H, C4-CH=), 6.808 (d, 2H, aromatic-CH's) and 7.030 (d, 2H, aromatic-CH's). Anal. Calcd. for C$_{33}$H$_{43}$NO$_6$·⅛H$_2$O: C, 72.10; H, 7.88; N, 2.55. Found: C, 71.63; H, 7.91; N, 2.53.

Example 34

17α-Acetoxy-11β-{4-[2'-(N-piperidino)ethoxy] phenyl}-21-methoxy-19-norpregna-4,9-diene-3,20-dione (123d);

This procedure was similar to that employed for the production of 123c.

Step 1. 3,20-bis-(Ethylenedioxy)-5α,17α-dihydroxy-11β-{4-[2'-(N-piperidino)ethoxy]phenyl}-21-methoxy-19-norpregna-4,9-diene-3,20-dione (121d):

Magnesium (1.11 g, 45.59 mmol), a crystal of iodine, distilled THF (52 mL, distilled over Na and benzophenone), and one drop of 1,2-dibromoethane were stirred together in dry glassware over nitrogen. A solution of 4-[2-(N-piperidinophenyl)ethoxy]phenyl bromide (Lednicer, et al., J. Med. Chem., 8, 52–57 (1965) (14.26 g, 50.16 mmol) in distilled THF (50 mL) was added to the reaction flask, then rinsed with an additional 10 mL of THF. The mixture was heated until all of the magnesium was gone. The reaction was allowed to reflux for 2 hr., and then cooled to room temperature. Copper (I) chloride (0.50 g, 5.03 mmol) was added and stirring continued for 1 hr. A solution of the epoxide (120, 7.50 g, 16.72 mmol) in distilled THF (74 ml) was transferred C2 to the reaction vessel. The reaction was stirred over nitrogen, at room temperature, for one hour. The reaction was cooled in an ice water bath and quenched with water (186 mL). Air was drawn through the mixture with vigorous stirring for 20 minutes. The mixture was transferred to a separatory funnel, extracted with ether (3×), and washed with water (2×) and brine (1×). The combined, organic fractions were dried with sodium sulfate for %2 hr, and evaporated in vacuo to recover 17.32 g (26.49 mmol) of a thick amber oil. Analysis by TLC (silica, 10% isopropanol in methylene chloride with a few drops of Et$_3$N) showed a very polar, streaking product. The entire crude material was carried directly on to the hydrolysis. Due to the extreme polarity of the crude Grignard product, analytical work was not performed.

Step 2. 17α-Hydroxy-11β-{4-[2'-(N-piperidino)ethoxy] phenyl}-21-methoxy-19-norpregna-4,9-diene-3,20-dione (122d):

The Grignard product (121d, 10.93 g, 16.72 mmol) dissolved in THF (103 mL) was mechanically stirred over nitrogen at room temperature. Trifluoroacetic acid (307.10 mL, 4133.60 mmol, 13.46 M) and water (103 mL) were added, and the mixture was stirred over nitrogen, at room temperature, overnight. The reaction was diluted with water (750 mL) and cooled in an ice water bath. Ice cold 4 M NaOH (1030 mL) was slowly added to neutralize the reaction to a pH of 7–8 (by pH paper). The mixture was transferred to a separatory funnel, extracted with methylene chloride (3×), and washed with water (2×) and brine (1×). The combined methylene chloride fractions were dried with sodium sulfate and evaporated in vacuo to recover 15.33 g of the crude 122d as a gold foam in 16.8% yield.

Step 3 Preparation of the Target Compound 123d:

Treatment of the 17α-hydroxy compound (122d, 0.25 g, 0.46 mmol) in $CH_2Cl_2$ with a mixed anhydride (11.28 mmol) prepared from trifluoroacetic anhydride, acetic acid and p-toluenesulfonic acid monohydrate in $CH_2Cl_2$ at 0° C. for 4.5 hr and work up in the usual way followed by purification of the crude product (123d) by Preparative HPLC on a Waters Assoc. Prep NovaPak HR $C_{18}$, 6 µm, 4×100 mm) eluted with 50% $CH_3CN$ in $H_2O$ with 0.05% $Et_3N$ at a flow rate of 25 mL per min and at λ=302 run, provided 0.10 g of 123d as a light yellow powder in 9.4% yield; m.p.=85–89° C. (sintered at 74–78° C.). FTIR (KBr, diffuse reflectance): $v_{max}$ 2938, 1730, 1662, 1608 and 1509 cm$^{-1}$. NMR (300 MHZ, $CDCl_3$): δ 0.369 (s, 3H, C18-$CH_3$), 2.106 (s, 3H, C17α-OAc), 2.501 (m, 4H, piperidino α-$CH_2$), 2.748 (t, 2H, $OCH_2CH_2N$), 3.413 (s, 3H, 21-$OCH_3$), 4.055 (t, 2H, $OCH_2CH_2N$), 5.787 (s, 1H, C4-CH=), 6.783 (d, 2H, J=9.00 Hz, aromatic-CH's), and 7.010 (d, 2H, J=9.00 Hz, aromatic-CH's). MS (EI) m/z (relative intensity): 590 (M$^+$, 87), 445 (41), 371 (100), 355 (71), 299 (39) and 269 (26). Anal. Calcd. for $C_{36}H_7NO_6$·75/100$H_2O$: C, 73.15; H, 8.04; N, 2.37. Found: C, 72.96; H, 8.11; N, 2.27. Analysis by HPLC on a Waters Assoc. NovaPak $C_{18}$ column eluted with 50% $CH_3CN$ in $H_2O$ with 0.05% $Et_3N$ at a flow rate of 1 mL per min and at λ=302 nm indicated a purity of 99.16% of 123d with $t_R$ of 9.95 min.

Example 35

This example illustrates the preparation and properties of 17α,21-Diformyloxy-11β-[4-(N,N-dimethylamino)phenyl]-19-norpregna-4,9-diene-3,20-dione (139):

Under nitrogen, a solution of the diol (124, 1.0 g, 2.22 mmol) in formic acid (96%, 50 mL) was treated with perchloric acid (Oliveto, et al., *J. Am. Chem. Soc.*, 77:3564–3567 (1955)) (70%, 0.5 mL, 5.816 mmol) and the reaction mixture was stirred at room temperature overnight Analysis by TLC (10% acetone/$CH_2Cl_2$) of a small aliquot neutralized with cold $NH_4OH$ and extracted with EtOAc indicated absence of the starting material and formation of two less polar products in roughly equal proportions. The reaction was diluted with $H_2O$ (~200 mL), cooled in an ice bath, and carefully adjusted to a in pH of 7.5 with concentrated $NH_4OH$. The resulting suspension was extracted with $CH_2Cl_2$ (3×). The organic fractions were washed with $H_2O$ (2×), filtered through anhydrous sodium sulfate, combined and concentrated in vacuo to give 1.3 g of the residue as a yellow foam. Analysis by NMR indicated the crude mixture to consist mainly of the 17α-hydroxy-21-formate (140) and the desired 17α,21-diformate (139) in approximately a 45:55 ratio. Separation of the two products was accomplished by flash chromatography (8% acetone/$CH_2Cl_2$) to afford 0.62 g of the diformate (139) and 0.49 g of the monoformate (140). The diformate (139) was taken up in ether, blown down and triturated with pentane to give 0.53 g of a yellow solid inidcated by HPLC on a Waters NovaPak $C_{18}$ column elued with $CH_3CN$/0.05 $\underline{M}$ $KH_2PO_4$ (45:55) (pH=3.0) at a flow rate of 1 mL per min and λ=302 nm) to be only 97% pure. This material was rechromatographed using 7% acetone/$CH_2Cl_2$ and reprecipitated from $Et_2O$/pentane to give 0.235 g of the pure diformate (139) as a yellow amorphous solid in 20.9% yield; m.p.=softens at 110–112° C. Analysis by HPLC on a Waters NovaPak $C_{18}$ column eluted with $CH_3CN$/0.05 M $KH_2PO_4$ (45:55) [pH= 3.0] at a flow rate of 1 mL per min and λ=302 nm) to be 98.6% pure with a retention time ($t_R$) of 6.56 min. FTIR (KBr, diffuse reflectance): $v_{max}$ 2948, 1726, 1662, 1612, 1518, and 1169 cm$^{-1}$. NMR ($CDCl_3$): δ 0.460 (s, 3H, C18-$CH_3$), 2.908 (s, 6H, —N($CH_3$)$_2$), 4.407 (d, 1H, J=7.2 Hz, C11α-CH), 4.816 and 5.070 (dd, 2H, C21-$CH_2$—), 5.781 (s, 1H, C4-CH=), 6.651 (d, 2H, 3',5' aromatic-CH's), 7.006 (d, 2H, 2',6' aromatic-CH's), 8.029 (s, 1H, C17α-OC(O)H) and 8.165 (s, 1H, C21-OC(O)H). MS (EI) m/z (relative intensity): 505 (M$^+$, 21.0), 459 (8.6), 431 (7.6) 134 (13.1) and 121 (100). Anal. Calcd. for $C_{34}H_{44}N_2O_6$·⅛$H_2O$: C, 70.76; H, 701; N, 2.75. Found: C, 70.76; H, 7.01; N, 2.85. Trituration of the monoformate fraction from the chromatography afforded 0.265 g of compound 140 as a light yellow solid. NMR indicates the presence of 20-formate (140) at 8.172 ppm. NMR ($CDCl_3$): δ 0.39 (s, 3H, C18-$CH_3$), 2.902 (s, 6H, —N($CH_3$)$_2$), 4.384 (d, 1H, J=6.9 Hz, C11α-CH), 5.031 and 5.193 (dd, 2H, J=17.71 Hz, C21-$CH_2$—), 5.759 (s, 1H, C4-CH=), 6.656 (d, 2H, 3',5' aromatic-CH's), 7.015 (d, 2H, 2',6' aromatic-CH's), and 8.172 (s, 1H, C21-OC(O)H).

Example 36

This example illustrates the preparation and properties of 17α-Acetoxy-11β-[4-(N,N-dimethylamino)phenyl]-21-propionyloxy-19-norpregna-4,9-diene-3,20-dione (126a) (FIG. 11):

Step 1. 17α-Hydroxy-11β-[4-(N,N-dimethylamino)phenyl]-21-propionyloxy-19 norpregna-4,9-diene-3,20-dione (125a):

Under nitrogen, a solution of the diol (124, 1.0 g, 2.22 mmol) in dry benzene (20 mL) and pyridine (1 mL, 12.4 mmol) was treated with propionyl chloride (0.22 mL, 2.53 mmol). This addition caused an immediate precipitation of a large gummy mass, probably due to formation of a mixture of the hydrochloride salts of starting material and product Since the dimethylaminophenyl moiety is probably more basic than pyridine, any HCl formed during the reaction would protonate the 11β-(4N,N-dimethylaminophenyl) group rather than pyridine. Addition of triethylamine (1 mL, 7.11 mmol) resulted in dissolution of the precipitated mass with formation of a small amount of solid precipitate. The reaction mixture was then stirred at room temperature and monitored by TLC (10% acetone in $CH_2Cl_2$) which indicated about a 60% reaction after 1 hr. Additional propionyl chloride (0.22 mL, 2.53 mmol) was introduced and the reaction was stirred a futher 1 hr at room temperature. Analysis by TLC at that time indicated a complete reaction. The reaction mixture was concentrated in vacuo under a current of nitrogen and the residue was diluted with $H_2O$. The mixture was extracted with $CH_2Cl_2$ (3×). The organic fractions were washed with $H_2O$ (2×), brine (1×), then concentrated, dried over anhydrous $Na_2SO_4$, filtered and concentrated in vacuo to give 1.2 g of the residue as a yellow foam. This material was purified by flash chromatography (10% acetone in $CH_2Cl_2$) to give 1.1 g of the 21-propionyloxy-17α-ol (125a). Crystallization of this material from EtOAc/heptane afforded 0.43 g of the pure 125a in 67% yield. FTIR (KBr, diffuse reflectance): $v_{max}$ 3331, 2940, 1749, 1734, 1640, 1612 and 1518 cm$^{-1}$. NMR (300 MHz, $CDCl_3$): δ 0.37 (s, 3H, C18-$CH_3$), 1.17 (t, 3H, J=7.5 Hz, propionyl $CH_3$), 2.90 (s, 6H, —N($CH_3$)$_2$), 4.40 (br d, J=6 Hz, C11α-CH), 5.03 (dd, 2H, $J_1$=30, $J_2$=18 Hz, C21-

CH$_2$—O), 5.77 (br s, 1H, C4-CH=), 6.67 (d, 2H, J=9 Hz, 3',5' aromatic-CH's) and 7.07 (d, 2H, J=9 Hz, 2',6' aromatic-CH's).

Step 2. Preparation of the Target Compound 126a:

Under nitrogen, trifluoroacetic anhydride (11.18 g, 53.2 mmol), glacial acetic acid (3.26 g, 54.2 mmol) and dry CH$_2$Cl$_2$ (35 mL) were combined and stirred at room temperature for ½ hr. The mixture was cooled to 0° C. in an ice bathe and toluenesulfonic aicd monohydrate (0.5 g, 2.63 mmol) was added. A solution of the 21-propionyloxy-17α-ol (125a, 1.28 g, 2.61 mmol) in dry CH$_2$Cl$_2$ was then introduced and the mixture stirred at 0° C. and monitored by TLC (10% acetone in CH$_2$Cl$_2$) which indicated a complete reaction after 2 hr. The ice-bath was removed and the reaction was allowed to warm to room temperature. The mixture was then diluted with H$_2$O (100 mL), adjusted to a pH of 6.5 with concentrated NH$_4$OH solution and extracted with CH$_2$Cl$_2$ (3×). The organic fractions were washed with H$_2$O (2×), brine (1×), combined, filtered through sodium sulfate and concentrated in vacuo to give 1.1 g of the residue. Purification via flash chromatography (5% acetone in CH$_2$Cl$_2$) followed by trituration with heptane gave 0.49 g of the pure 21-propionyloxy-17α-acetate (126a) as a light yellow amorphous solid in 55% yield; m.p. softens at 86° C. NMR (CDCl$_3$): δ 0.43 (s, 3H, C18-CH$_3$), 1.11 (t, 3H, J=8 Hz, propionyl CH$_3$), 2.07 (s, 3H, OAc), 2.89 (s, 6H, —N(CH$_3$)$_2$), 4.43 (br d, C11α-CH, J=6 Hz), 4.85 (dd, 2H, J$_1$=28 Hz, J$_2$=17 Hz, C21-CH$_2$—O—), 5.77 (s, 1H, C4-CH=), 6.63 (d, 2H, J=7.8 Hz, 3',5' aromatic-CH's) and 7.0 (d, 2H, J=7.8 Hz, 2',6' aromatic-CH's). Anal. Calcd. for C$_{33}$H$_{41}$NO$_6$: C, 72.37; H, 7.55; N, 2.56. Found: C, 72.23; H, 7.71; N, 2.50.

Example 37

This example illustrates the preparation and properties of 17α-Acetoxy-1-[4-(N,N-dimethylamino)phenyl]-21-(2'-methoxyacetyl)oxy-19-norpregna-4,9-diene-3,20-dione (126b) (FIG. 11):

Step 1. 17α-Hydroxy-11β-[4-(N,N-dimethylamino)phenyl]-21-(2'-methoxyacetyl)oxy-19-norpregna-4,9-diene-3,20-dione (125b).

Under nitrogen, a solution of the 17α,21-diol (124, 1.0 g, 2.22 mmol), pyridine (1 mL, 12.41 mmol) and triethylamine (1 mL, 7.11 mmol) in dry benzene (40 mL) was treated with methoxyacetyl chloride (0.5 mL, 5.47 mmol). The reaction mixture was stirred at room temperature for 4 hr, after which time TLC (5% isopropanol in CH$_2$Cl$_2$) indicated a complete reaction. Solvents were removed in vacuo under a current of nitrogen and the residue was diluted with H$_2$O (~50 mL) and extracted with CH$_2$Cl$_2$ (3×). The organic fractions were washed with H$_2$O (3×), filtered through anhydrous Na$_2$SO$_4$, combined and concentrated in vacuo to give 1.4 g of the residue as a yellow solid. This material was purified by flash chromatography (3% isopropanol in CH$_2$Cl$_2$) to give 1.05 g of the product as a yellow foam. Crystallization from ether containing a small amount of CH$_2$Cl$_2$ gave 0.73 g of the pure 21-(2'-methoxy)-acetyloxy-derivative 125b as an off-white solid in 62.9% yield; m.p.=197–199° C. FTIR (KBr, diffuse reflectance): ν$_{max}$ 3329, 2948, 2888, 1754, 1729, 1637, 1602 and 1518 cm$^{-1}$. NMR (300 MHz, CDCl$_3$): δ 0.399 (s, 3H, C18-CH$_3$), 2.906 (s, 6H, —N(CH$_3$)$_2$), 3.488 (s, 3H, C21-OCH$_3$), 4.181 (s, 2H, C21-OC(O)CH$_2$—), 4.384 (d, 1H, J=4.384, C11α-CH), 4.975 and 5.234 (both d, 2H, J=17.4 Hz, C21-CH$_2$), 5.760 (s, 1H, C4-CH=), 6.654 (d, 2H, J=8.7 Hz, 3',5' aromatic-CH's) and 7.012 (d, 2H, J=8.7 Hz, 2',6' aromatic-CH's). MS(EI) m/z (relative intensity): 521 (M$^+$, 26.4), 431 (7.1), 134 (17.3) and 121 (100.0). Anal. Calcd. for C$_{31}$H$_{39}$NO$_3$: C, 71.38; H, 7.54; N, 2.69. Found: C, 71.48; H, 7.59; N, 2.64.

Step 2. Preparation of the Target Compound 126b:

Under nitrogen, trifluoroacetic anhydride (2.98 g, 14.16 mmol), glacial acetic acid (0.84 g, 13.98 mmol) and dry CH$_2$Cl$_2$ (5 mL) were combined and stirred at room temperature for ½ hr. Toluenesulfonic acid monohydrate (0.15 g, 0.79 mmol) was added and the mixture cooled to 0° C. in an ice bath. A solution of the 21-(2'-methoxy)acetyloxy-17α-ol (125b, 0.612 g, 1.173 mmol) in dry CH$_2$Cl$_2$ (2 mL) was added and the reaction was stirred at 0° C. and monitored by TLC (3% isopropanol in CH$_2$Cl$_2$) which indicated a complete reaction after 4 hr. The mixture was diluted with H$_2$O (~10 mL), stirred at 0° C. for another 15 minutes, then carefully neutralized with dropwise addition of concentrated NH$_4$OH solution (~3 mL). The mixture was extracted with CH$_2$Cl$_2$ (3×). The organic fractions were washed with H$_2$O (2×) and brine (1×), filtered through anhydrous Na$_2$SO$_4$, combined and concentrated in vacuo to give 0.72 g of the residue as an oil. This material was purified via flash chromatography (20% EtOAc in CH$_2$Cl$_2$) to give 0.34 g of 126b as a yellow foam. Trituration of this material with pentane gave 0.26 g of the pure title compound (126b) as a light yellow amorphous solid in 39.3% yield; m.p.= 110–113° C.

Analysis of 126b by HPLC on a Waters NovaPak, C$_{18}$ column, eluted with 0.05 M KH$_2$PO$_4$ buffer [pH=3.0]/MeOH, 35:65 at a flow rate of 1 mL per min and at λ=302 nm indicated this material to be >99% pure with a retention time (t$_R$=6.04 min). FTIR (KBr, diffuse reflectance): ν$_{max}$ 2947, 1766, 1737, 1663, 1612 and 1518 cm$^{-1}$. NMR (300 MHz, CDCl$_3$): δ 0.447 (s, 3H, C18-CH$_3$), 2.129, (s, 3H, C17α-OAc), 2.907 (s, 6H, —N(CH$_3$)$_2$), 3.473 (s, 3H, C21-OC(O)CH$_2$OCH$_3$), 4.176 (s, 2H, C21-OC(O)CH$_2$—), 4.392 (d, 1H, J=6 Hz, C11α-CH), 4.792 and 5.029 (both d, 2H, J=17.4 Hz, C21-CH$_2$), 5.777 (s, 1H, C4-CH=), 6.644 (d, 2H, J=9 Hz, 3',5' aromatic-CH's) and 7.002 (d, 2H, J=9 Hz, 2',6'-aromatic-CH's). MS (EI) m/z (relative intensity): 563 (M$^+$, 42.8), 503 (12.6), 134 (17.2) and 121 (100.0). Anal. Calcd. for C$_{33}$H$_{41}$NO$_7$: C, 70.32; H, 7.33; N, 2.48. Found: C, 70.14; H, 7.59; N, 2.41.

EXAMPLE 38

This example illustrates the preparation and properties of 17α-Acetoxy-21-hydroxy-11β-[4-(N,N-dimethylamino)phenyl]-19-norpregna-4,9-diene-3,20-dione-21-methyl carbonate (126c) (FIG. 11):

Step 1. 17α,21-Dihydroxy-11β-[4-(N,N-dimethylamino)phenyl]-19-norpregna-4,9-diene-3,20-dione-21-methyl carbonate (125c):

The 17α,21-diol (10) (124, 250 mg, 1.80 mmol) was dissolved in CH$_2$Cl$_2$ (10 mL) and pyridine (0.2 mL) was added followed by methyl chloroformate (0.245 g, 2.59 mmol). The mixture was stirred at room temperature for 20 min. TLC after 5 min showed the reaction complete. The mixture was evaporated in vacuo and dissolved in CH$_2$Cl$_2$. The dichloromethane was washed with H$_2$O (2×), brine and dried over anhydrous Na$_2$SO$_4$. The solvent was evaporated in vacuo. Benzene was added and evaporated to remove traces of pyridine. CH$_2$Cl$_2$ was added and evaporated to give 273 mg of the 17α-hydroxy-21-methyl carbonate (125c) in 29.9% yield.

NMR (CDCl$_3$): δ 0.381 (s, 3H, C18-CH$_3$), 2.899 (s, 6H, —N(CH$_3$)$_2$), 3.820 (s, 3H, C21-OC(O)OCH$_3$), 4.369 (m, 1H, C11α-CH), 4.914 and 5.178 (dd, 2H, C21-CH$_2$—), 5.747 (br s, 1H, C4-CH=), 6.644 (d, 2H, 3',5' aromatic-CH's) and 7.002 (d, 2H, 2',6' aromatic-CH's).

Step 2. Preparation of the Target Compound 126c:

$CH_2Cl_2$ (15 mL) was stirred at room temperature and trifluoroacetic acid anhydride (2.29 g, 10.9 mmol) and acetic acid (0.714 g, 11.8 mmol) were added. The mixture was stirred at room temperature in a nitrogen atmosphere for ½ hr. p-Toluenesulfonic acid monohydrate (1.90 g, 1.1 mmol) was added and the mixture cooled to 0° C. in an ice bath. The 17α-hydroxy-21-methyl carbonate (125c, 273 mg, 0.54 mmol) was dissolved in $CH_2Cl_2$ and cooled to 0° C. and then added to the stirred mixed anhydride. The reaction was complete in 6 hr. Saturated $NaHCO_3$ was added to neutralize the reaction and the mixture was extracted with $CH_2Cl_2$ (3×). The $CH_2Cl_2$ extracts were washed with $H_2O$, brine and dried over anhydrous $Na_2SO_4$. The solvent was evaporated, benzene was added and evaporated again. $CH_2Cl_2$ was added and evaporated again. Chromatography on flash column silica gel using $CH_2Cl_2$:acetone, 95:5 gave a product that was only 95% pure. Chromatography was run again using the same system followed by checking each fraction by HPLC on a NovaPak $C_{18}$ column eluting with $MeOH:H_2O:Et_3N$ (70:30:0.05) at a flow rate of 1 mL per min and at λ=260 rm. Good fractions were collected and combined to give 116.1 mg of the good product. The remainder of the product was rechromatographed using $CH_2Cl_2$:EtOAc (90:10) and checking fractions by HPLC as above gave an additional 38.1 mg of the good product. The good product was combined and dried in vacuo to a foam and dried at 45° C. A small amount of ether in the product was present. The foam was dried in a vacuum at 80° C. to give 131.6 mg of 126c as a yellow foam in 44.3% yield; m.p.=130–160° C. FTIR (KBr, diffuse reflectance): $v_{max}$ 2961, 1759, 1731, 1663, 1612, 1518 and 1278 $cm^{-1}$. NMR ($CDCl_3$): δ 0.436 (s, 3H, C18-$CH_3$), 2.125 (s, 3H, C17α-OAc), 2.907 (s, 6H, —N($CH_3$)$_2$), 3.828 (s, 3H, C21-OC(O)O$CH_3$), 4.391 (d, 1H, C11α-CH), 4.735 and 4.961 (dd, 2H, C21-$CH_2$—), 5.778 (s, 1H, C4-CH═), 6.638 (d, 2H, 3',5' aromatic-CH's) and 6.995 (d, 2H, 2',6' aromatic-CH's). MS (EI) m/z (relative intensity): 549 ($M^+$, 32), 489 (7.0), 134 (16.0) and 121 (100.0). Anal. Calcd. for $C_{32}H_{39}NO_7$: C, 69.92; H, 7.15; N, 2.55. Found: C, 69.62; H, 7.25; N, 2.61.

Example 39

This example illustrates the preparation and properties of 17α-Acetoxy-11β-[4-(N,N-dimethylamino)phenyl]-21-(1'-ethenyloxy)-19-norpregna-4,9-diene-3,20-dione (129) (FIG. 11):

Step 1. 17α,21-(1'-Ethoxyethylidenedioxy)-11β-[4-(N,N-dimethylamino)phenyl]-19-norpregna-4,9-diene-3,20-dione (127):

The 17α,21-diol (10) (124, 1.6 g, 3.56 mmol), triethyl orthoacetate (5.59 g, 3.45 mmol), and pyridinium tosylate (200 mg, 0.93 mmol) were dissolved in dry benzene in a nitrogen atmosphere and heated at reflux for 75 min using a Dean Stark trap to remove water. The reaction was complete at this time. Pyridine (1 mL) was added and the solvent was evaporated using nitrogen and vacuum. Water was added and the mixture was extracted with $CH_2Cl_2$ (3×). The $CH_2Cl_2$ extracts were washed with $H_2O$, brine and dried over anhydrous $Na_2SO_4$. The solvent was evaporated in vacuo. Purification by dry column chromatography, recrystallization and finally flash column chromatography using $CH_2Cl_2$:acetone (97:3) gave 1.028 g of the ortho ester (12) in 55.8% yield. NMR ($CDCl_3$): δ 0.334 (s, 3H, C18-$CH_3$), 1.620 (s, 3H, C17α,21-ethylidenedioxy-$CH_3$), 2.909 (s, 6H, N($CH_3$)$_2$), 3.55 (q, 2H, C21-ethylidendioxy-O$CH_2CH_3$), 4.404 (br d, 1H, C11α-CH), 5.769 (s, 1H, C4-CH═), 6.641 (d, 2H, 3',5' aromatic-CH's) and 7.003 (d, 2H, 2',6' aromatic-CH's).

Step 2. 17α-Acetoxy-11β-[4-(N,N-dimethylamino)phenyl]-21-hydroxy-19-norpregna-4,9-diene-3,20-dione (128):

The cyclic ortho ester (127, 1.028 g, 1.99 mmol) was suspended in methanol (60 mL) in a nitrogen atmosphere and NaOAc solution (8.2 mL, 0.1 M) and HOAc solution (16.4 mL, 0.2 M) were added. The mixture was heated at reflux for 3 hr. The solvent was evaporated using nitrogen and vacuum. $H_2O$ (~50 mL) was added and the mixture was extracted wtih $CH_2Cl_2$ (3×). The organic fractions were washed with $H_2O$, brine and dried over anhydrous $Na_2SO_4$ to give 1.0112 g of the 17α-acetoxy-21-hydroxy compound (28) as an off-white powder containing a trace amount of the 17α-hydroxy-11β-[4-(N,N-dimethylamino)phenyl]-21-acetoxy-19-norpregna-4,9-diene-3,20-dione compound (8). The crude product was chromatographed on flash column silica gel using $CH_2Cl_2$:acetone (8:2) as the solvent. Fractions were collected and each fraction was checked by TLC. Fractions #5–7 were essentially pure 128 and were combined to give 108.5 mg of good product The residue was crystallized from ether to give 75 mg of an additional pure 128. The total amount of the product 128 was 183.5 mg as an off white powder in 18.8% yield; m.p.=205–210° C. NMR ($CDCl_3$): δ 0.364 (s, 3H, C18-$CH_3$), 2.112 (s, 3H, C17α-OAc), 2.902 (s, 6H, —N($CH_3$)$_2$), 4.190–4.405 (br d and m, 3H, C11α-CH and C21-$CH_2$—), 5.779 (br s, 1H, C4-CH═), 6.629 (d, 2H, 3',5' aromatic-CH's) and 6.967 (d, 2H, 2',6' aromatic-CH's).

Step 3. Preparation of the Target Compound 129:

The 21-hydroxy compound (128, 682 mg, 1.39 mmol) was dissolved in $CH_2Cl_2$ (14 mL) in a nitrogen atmosphere and ethyl vinyl ether (5.27 g, 7.32 mmol) was added. Mercury (11) trifluoroacetate (25 mg, 0.059 mmol) was added and the mixture was stirred in a nitrogen atmosphere at room temperature for 22 hr. The mixture was poured onto dry column silica gel which had been washed with $CH_2Cl_2$ in a sintered glass funnel. The compound was eluted with EtOAc and the solvent was evaporated in vacuo. The residue (744 mg) was chromatographed on Flash column silica gel using $CH_2Cl_2$: acetone (95:5) as the solvent. A total of 141 mg of good product 129 was obtained as a yellow foam in 19.6% yield. The compound 129 was dried to remove ether, m.p.=114–116° C. Analysis of 129 by HPLC on a NovaPak $C_{18}$ column eluted with $MeOH:H_2O:Et_3N$ (70:30:0.05) at a flow rate of 1 mL per min and at λ=260 nm indicated it to be better than 99% pure. FTIR (KBr, diffuse reflectance): $v_{max}$ 2948, 1733, 1662, 1613, 1560, 1518, 1446, 1369, 1278 and 1235 $cm^{-1}$. NMR ($CDCl_3$): δ 0.408 (s, 3H, C18-$CH_3$), 2.118 (s, 3H, C17α-OAc), 2.901 (s, 6H, —N($CH_3$)$_2$), 4.096–4.662 (m, 6H, C21-Ovinyl H, C11α-CH and C21-$CH_2$—), 5.779 (br s, 1H, C4-CH═), 6.625 (d, 2H, 3',5' aromatic-CH's), and 6.967 (d, 2H, 2',6' aromatic-CH's). MS (EI) m/z (relative intensity): 517($M^+$, 73), 134 (18.0) and 121 (100.0). Anal. Calcd. for $C_{32}H_{39}NO_6 \cdot \frac{1}{3}H_2O$: C, 73.40; H, 7.64; N, 2.67. Found: C, 73.49; H, 7.62; N, 2.84.

Example 40

This example illustrates the preparation and properties of 17α-Acetoxy-1-[4-(N,N-dimethylamino)phenyl]-21-(2'-N,N-dimethylamino)acetoxy-19-norpregna-4,9-diene-3,20-dione (33) (FIG. 10):

Step 1. 17α-Hydroxy-21-(2'-chloroacetoxy)-11β-[4-(N,N-dimethylamino)phenyl]-19-norpregna-4,9-diene-3,20-dione (130):

The 17α,21-diol (124, 500 mg, 1.15 mmol) was dissolved in pyridine (7 mL) and cooled to 0° C. in an argon atmosphere. Chloroacetic anhydride (705 mg, 4.12 mmol) was dissolved in pyridine and added dropwise to the stirred diol (124) solution. The mixture was stirred at 0° C. for 2 hr. TLC showed very little reaction. The reaction was allowed to warm to room temperature. Additional chloroacetic anhydride (200 mg, 1.17 mmol) was added and the reaction was continued. When the reaction was complete, $H_2O$ (2 mL) was added followed by additional water (70 mL). The mixture was extracted with EtOAc (3×). The EtOAc extracts were washed with $H_2O$, brine and dried over anhydrous sodium sulfate. The solvent was evaporated in vacuo. The mixture was azeotropically evaporated with benzene (2×), dissolved in EtOAc, filtered through Celite and evaporated in vacuo to give 475 mg of the 21-chloroacetate (130) in 78.3% yield. It was used for the next reaction without purification. NMR ($DCl_3$): δ 0.381 (s, 3H, C18-$CH_3$), 2.908 (s, 6H, —N($CH_3$)$_2$), 4.201 (s, 2H, $CH_2Cl$), 4.999 and 5.271 (d, 2H, C21-$CH_2$—), 5.754 (s, 1H, C4-CH=), 6.669 (d, 2H, 3',5' aromatic-CH's), and 7.016 (d, 2H, 2',6' aromatic-CH's).

Step 2. 17α-Acetoxy-11β-[4-(N,N-dimethylamino) phenyl]-21-(2'-chloroacetoxy)-19-norpregna-4,9-diene-3,20-dione (131):

Trifluoroacetic anhydride (4.12 g, 19.62 mmol), and acetic acid (1.21 g, 20.15 mmol) were added to $CH_2Cl_2$ (35 mL) in an argon atmosphere and stirred at room temperature for ½ hr.

p-Toluenesulfonic acid monohydrate (155 mg, 5.26 mmol) was added and the mixture was cooled to 0° C. The 17α-hydroxy-21-chloroacetate 130, 475 mg, 0.97 mmol) was dissolved in $CH_2Cl_2$ (10 mL), cooled to 0° C., and added to the mixed anhydride solution. The mixture was stirred at 0° C. overnight. The reaction was complete. Saturated $NaHCO_3$ solution was added to neutralize the mixture and the mixture was extracted with $CH_2Cl_2$ (3×). The $CH_2Cl_2$ extract was washed with $H_2O$, brine and dried over anhydrous $Na_2SO_4$. The solvent was evaporated in vacuo. Chromatography on dry column silica gel using $CH_2Cl_2$:acetone (9:1) as solvent gave 286.2 mg of the 17α-acetoxy-compound 131 in 56% yield. NMR ($CDCl_3$): δ 0.437 (s, 3H, C18-$CH_3$), 2.130 (s, 3H, 17α-OAc), 2.923 (s, 6H, —N($CH_3$)$_2$), 4.201 (s, 2H, C21-OC(O)$CH_2Cl$), 4.395 (d, 1H, C11α-CH), 4.804 and 5.041 (d, 2H, $\overline{C21\text{-}CH_2}O$—), 5.779 (s, 1H, C4-CH=), 6.697 (d, 2H, 3',5' aromatic-CH's) and 7.017 (d, 2H, 2',6' aromatic-CH's).

Step 3. 17α-Acetoxy-11β-[4-(N,N-dimethylamino) phenyl]-21-(2'-iodoacetoxy)-19-norpregna-4,9-diene-3,20-dione (132):

The 17α-acetoxy-21-(2'-chloroacetoxy) compound (131, 286 mg, 0.47 mmol) was dissolved in $CH_3CN$ (50 mL) in an argon atmosphere. NaI (650 mg, 4.34 mmol) was added and the mixture was heated at reflux in an argon atmosphere for 45 min. After ½ hr, an aliquot was removed and checked by NMR. The reaction was complete after ½ hr. The mixture was cooled to room temperature and filtered. The solvent was evaporated in vacuo. The residue was dissolved in $CH_2Cl_2$ and filtered to remove solid salts. The solid was washed well with $CH_2Cl_2$ and the solvent was evaporated in vacuo to give 328.5 mg of the iodoacetoxy compound 132 in 73% yield. NMR ($CDCl_3$): δ 0.431 (s, 3H, C18-$CH_3$), 2.133 (s, 3H, C17α-OAc), 2.911 (s, 6H, —N($CH_3$)$_2$), 3.812 (d, 2H, C21-$CH_2O$), 4.394 (d, 1H, C11α-CH), 4.741 and 4.996 (d, 2H, $\overline{C21\text{-}CH_2}O$—), 5.777 (s, 1H, C4-CH=), 6.677 (d, 2H, 3',5' aromatic-CH's), and 7.008 (d, 2H, 2',6' aromatic-CH's).

Step 4. Preparation of the Target Compound 133:

The 21-iodoacetate (132, 328 mg, 0.52 mmol) was dissolved in THF (25 mL) and cooled to 0° C. in an argon atmosphere. Dimethylamine (2.5 mL, 2 M in THF) was added and the mixture was stilled at 0° C. in an argon atmosphere. TLC after 10 min showed the reaction complete. The solvent was evaporated in vacuo on the rotary evaporator at room temperature. $H_2O$ was added and the mixture was extracted wtih EtOAc (3×). The EtOAc extracts were washed with $H_2O$, brine and dried over anhydrous $Na_2SO_4$. The solvent was evaporated in vacuo to give 276.8 mg of the crude compound 133. The crude product was chromatographed on a flash column using EtOAc:$CH_3CN$ (70:30). Two fractions were obtained. The first fraction gave 84.5 mg which was 95% pure by HPLC analysis and the other gave 66.8 mg which was 90% pure by HPLC analysis. Total yield of 133 was 151.3 mg as a yellow foam in 58% yield. FTIR (KBr, diffuse reflectance): $v_{max}$ 2947, 1737, 1663, 1612, and 1518 cm$^{-1}$. NMR ($CDCl_3$): δ 0.440 (s, 3H, C18-$CH_3$), 2.126 (s, 3H, 17α-OAc), 2.386 (s, 6H, —C(O)$CH_2N(\underline{CH}_3)_2$), 2.906 (s, 6H, —N($CH_3$)$_2$), 3.308 (t, 2H, C21-OC(O)$CH_2NMe_2$), 4.393 (d, 1H, C11α-CH), 4.754 and 5.004 (dd, $\overline{2H}$, 21-$CH_2$—), 5.773 (s, 1H, C4-CH=), 6.643 (d, 2H, 3',5' aromatic-CH's), and 7.006 (d, 2H, 2',6' aromatic-CH's). Anal. Calcd. for $C_{44}N_2O_6 \cdot 1H_2O$: C, 68.69; H, 7.74; N, 4.71. Found: C, 68.66; H, 7.80; N, 4.70.

Example 41

This example illustrates the preparation and properties of 17α-Acetoxy-11β-[4-(N,N-diethylamino)phenyl]-21-thiocyanato-19-norpregna-4,9-diene-3,20-dione (138) (FIG. 11):

Step 1. 17α-Hydroxy-11β-[4-(N,N-dimethylamino) phenyl]-21-methanesulfonyloxy-19-norpregna-4,9-diene-3,20-dione (136):

Under nitrogen, a solution of the diol (124, 1.0 g, 2.22 mmol) and triehtylamine (0.72 g, 7.11 mmol) in dry pyridine (20 mL) was cooled to 0° C. in an ice bath treated with methanesulfonyl chloride (0.74 g, 6.46 mmol). The reaction mixture was stirred at 0° C. and monitored by TLC (10% acetone $CH_2Cl_2$) which indicated a complete reaction after two hours. The reaction mixture was diluted with $H_2O$ (~100 mL) and extracted with $CH_2Cl_2$ (3×). The organic fractions were washed with $H_2O$ (2×), filtered through $Na_2SO_4$, combined and concentrated in vacuo to give 1.3 g of the residue as a yellow oil. This material was purified by flash chromatography using 10% acetone/$CH_2Cl_2$ followed by trituration with ether to give 0.83 g of the 21-mesylate-17α-ol (136) as a yellow solid in 63.6% yield; m.p.=143–146° C. FTIR (KBr, diffuse reflectance): $v_{max}$ 3298, 2947, 1738, 1630, 1614, 1518 and 1174 cm$^{-1}$. NMR (300 MHz, $CDCl_3$): δ 0.375 (s, 3H, C18-$CH_3$), 2.899 (s, 6H, —N($CH_3$)$_2$), 3.190 (s, 3H, C21-$OSO_2CH_3$) 4.371 (br d, 1H, J=6.6 Hz, C11α-CH), 5.128 and 5.353 (dd, 2H, J=18 Hz, C21-$CH_2$—), 5.746 (s, 1H, C4-CH=), 6.645 (d, 2H, J=9 Hz, 3',5' aromatic-CH's), and 6.994 (d, 2H, J=9 Hz, 2',6' aromatic-CH's).

Step 2. 17α-Hydroxy-11β-[4(N,N-dimethylamino) phenyl]-21-thiocyanato-19-norpregna-4,9-diene-3,20-dione (137):

Under nitrogen, a solution of the 21-mesylate-17α-ol (136, 0.65 g, 1.23 mmol) and dry potassium thiocyanate (0.3 g, 3.09 mmol) in dry dimethylformamide (DMF) (15 mL) was heated to 95–105° C. After about 15 min of heating, a very fine precipitate was observed. The reaction mixture was cooled to room temperature, diluted with $H_2O$ (~100 mL) and extracted first with $CH_2Cl_2$ (3×) and then with EtOAc (3×) when it became apparent that the product was not very soluble in $CH_2Cl_2$. The organic fractions were washed with $H_2O$ (2×), filtered through anhydrous $Na_2SO_4$, combined and concentrated in vacuo to give a yellow solid residue. Trituration of this material with ether gave 0.598 g of the pure 17α-ol-21-thiocyanate (137) as a light yellow solid in 99% yield; m.p.=226° C. (dec). FTIR (KBr, diffuse reflectance): $v_{max}$ 3360, 2940, 2145, 1728, 1640, 1597 and 1518 cm$^{-1}$. NMR (300 MHz, CDCl$_3$): δ 0.356 (s, 3H, C18-CH$_3$), 2.907 (s, 6H, —N(CH$_3$)$_2$), 4.188 and 4.629 (dd, 2H, J=17.1 Hz, C21-CH$_2$), 4.403 (br d, 1H, J=6.0 Hz, C11α-CH), 5.762 (s, 1H, C4-CH=), 6.696 (d, 2H, J=8.4 Hz, 3',5' aromatic-CH's), and 7.023 (d, 2H, J=8.4 Hz, 2',6' aromatic-CH's). MS (EI) m/z (realtive intensity): 490 (M$^+$, 25.90), 465 (3.8), 414 (7.8), 389 (6.5), 134 (15.6) and 121 (100.0). Anal. Calcd. for C$_{29}$H$_{34}$N$_2$O$_3$S.⅓H$_2$O: C: 68.96; H, 7.10; N, 5.55; S, 6.35. Found: C, 68.90; H, 6.92; N, 5.58; S, 5.96.

Step 3. Preparation the Target Compound 138:

Under nitrogen, trifluoroacetic anhydride (5.20 g, 24.79 mmol), glacial acetic acid (1.57 g, 26.23 mmol) and dry CH$_2$Cl$_2$ (5 mL) were combined and and stirred at room temperature for 1 hr. p-Toluenesulfonic acid monohydrate (0.05 g, 0.26 mmol) was added, and the reaction mixture was cooled to 0° C. in an ice bath A solution of the 17α-ol-21-thiocyanate (137, 0.4 g, 0.815 mmol) in dry CH$_2$Cl$_2$ (2 mL) was added and the reaction mixture was stirred at 0° C. and monitored by TLC (10% acetone in CH$_2$Cl$_2$) which indicated a complete reaction after 2 hr. The mixture was diluted with H$_2$O (~10 mL), stirred at 0° C. for about ½ hr, then carefully neutralized with dropwise addition of concentrated NH$_4$OH solution (~5 mL). The mixture was extracted with CH$_2$Cl$_2$ (3×). The organic fractions were washed with H$_2$O (2×), filtered through anhydrous Na$_2$SO$_4$, combined and concentrated in vacuo to give 0.43 g of the residue as a yellow oil. This material was combined with product obtained from two previous batches (total amount of crude product=0.675 g from a total of 0.6 g of 137). This material was purified via flash chromatography (7.5% acetone in CH$_2$Cl$_2$) to give 0.3 g of 138 as a light yellow foam. This material was taken up in a minimum amount of CH$_2$Cl$_2$, blown down, and the residue triturated with ether to give 0.256 g of the pure title compound 138 as an off-white solid in 39.3% yield; m.p.=181° C. (dec).

Analysis by HPLC on a Waters NovaPak, C$_{18}$ column eluted with 0.05 M KH$_2$PO$_4$ buffer [pH=3.0]/MeOH, (35:65) at a flow rate of 1 mL per minute and at λ=302 nm indicated this material to be >99% pure. FTIR (KBr, diffuse reflectance): $v_{max}$ 2935, 2158, 1736, 1658, 1611 and 1518 cm$^{-1}$. NMR (300 MHz, CDCl$_3$): δ 0.401 (s, 3H, C18-CH$_3$), 2.153 (s, 3H, C17α-OAc), 2.914 (s, 6H, —N(CH$_3$)$_2$), 4.060 and 4.236 (dd, 2H, J=16.2 Hz, C21-CH$_2$) 4.407 (br d, 1H, J=6.9 Hz, C11α-CH), 5.783 (s, 1H, C4-CH=), 6.649 (d, 2H, J=9 Hz, 3',5' aromatic-CH's), and 6.985 (d, 2H, J=9 Hz, 2',6' aromatic-CH's). MS(EI) m/z (realtive intensity): 532 (M$^+$, 29.9), 134 (13.5) and 121 (100.0). Anal. Calcd. for C$_{31}$H$_{36}$N$_2$O$_4$S.⅓H$_2$O: C, 69.64; H, 6.83; N, 5.24; S, 6.00. Found: C, 69.63; H, 6.95; N, 5.12; S, 5.84.

Example 42

This example illustrates the preparation and properties of 17α-Acetoxy-11β-[(4-(N-piperidino)phenyl]-19-norpregna-4,9-diene-3,20-dione 3-oxime (141) (FIG. 4):

Under nitrogen, a solution of the dienedione (71, 200 mg, 0.38 mmol) in absolute EtOH (25 mL) was treated with a 10-fold excess of solid hydroxylamine hydrochloride (269 mg, 3.87 mmol). The reaction mixture was stirred at room temperature for 1¼ hr. At that time, TLC (10% acetone in CH$_2$Cl$_2$) showed no starting material and two major more polar spots. The reaction was diluted with saturated sodium bicarbonate solution (100 mL) and extracted with methylene chloride (3×). The orange fractions were washed with water and brine, dried over anhydrous sodium sulfate, filtered and concentrated in vacuo to yield 290 mg of off-white powder. Flash chromatography (10% acetone in methylene chloride) gave 177 mg of the material. Trituration with pentane with sonication gave 163 mg of 141 as an off-white solid in 80.8% yield after drying. HPLC analysis indicated a syn:anti ratio of 1:3.2; m.p.=167–172° C. FTIR (KBr, diffuse reflectance): $v_{max}$ 3237, 2932, 2855, 1735, 1714, 1610, 1512, 1452, 1369 and 1236 cm$^{-1}$. NMR (300 MHZ, CDCl$_3$): δ0.306 (s, 3H, C18-CH$_3$), 2.086 (s, 3H, C17α-OAc), 2.125 (s, 3H, C21-CH$_3$), 3.10 (m, 4H, —CH$_2$CH$_2$N— of piperidine ring) 4.33 (m, 1H, C11α-CH), 5.869 (s, 1H, C4-CH= of anti-oxime), 6.525 (s, 1H, C4-CH= of syn-oxime) and 6.805–6.975 (dd, 4H, aromatic-CH's). MS (EI) m/z (relative intensity): 530 (M$^+$). Anal. Calcd. for C$_{33}$H$_{42}$O$_4$N$_2$: C, 74.72; H, 7.92; N, 5.28. Found: C, 73.73; H, 8.16; N, 5.16.

Example 43

This example illustrates the preparation and properties of 17α-Methoxy-11β-[4-(N,N-dimethylamino)phenyl]-19-norpregna-4,9-diene-3,20-dione 3-oxime (142a) (FIG. 6):

Under nitrogen, a solution of the dienedione (97a, 0.4 g, 0.89 mmol) in absolute EtOH (25 mL) was treated with a 10-fold excess of solid hydroxylamine hydrochloride (0.62 g, 8.92 mmol). The reaction mixture was stirred at room temperature for 1 hr, after which time TLC (10% acetone/ methylene chloride, overspotted with con. NH$_4$OH) indicated a complete reaction. The reaction mixture was diluted with water (~100 mL), adjusted to a pH of ~8.0 with concentrated NH$_4$OH solution, and extracted with methylene chloride (3×). The organic fractions were purified via flash chromatography (10% acetone/methylene chloride) followed by trituration with pentane to give the purified oxime (142a, 0.22 g) as an off-white amorphous solid in 53% yield; m.p.=148–162° C.

Analysis by NMR indicated this material to consist of a mixture of 39:61 ratio of the syn and anti-isomers. HPLC analysis on a Waters NovaPak C$_{18}$ ODS column eluted with acetonitrile/0.05 M KH$_2$PO$_4$ [pH=3.0] 1:1 at a flow rate of 1 mL per min and at λ=276 nm indicated a purity of 96.5%. FTIR (KBr, diffuse reflectance): $v_{max}$ 3270, 2942, 1708, 1613 and 1517 cm$^{-1}$. NMR (300 MHZ, CDCl$_3$): δ 0.259 (s, 3H, C18-CH$_3$ of anti-isomer), 0.269 (s, 3H, C18-CH$_3$ of syn-isomer), 2.176 (s, 3H, C21-CH$_3$ of syn-isomer), 2.182 (s, 3H, C21-CH$_3$ of anti-isomer), 2.898 (s, 6H, —NMe$_2$), 3.150 (s, 3H, C17α-OCH$_3$), 4.298 (br d., 1H, J=7.2 Hz, C11α-CH), 5.840 (s, 0.64H, C4-CH= of anti-oxime), 6.490 (s, 0.37H, C4-CH= of syn-oxime), 6.638 (m, 2H, 3',5' aromatic-CH's) and 7.012 (m, 2H, 2',6' aromatic-CH's). MS (EI) m/z (relative intensity): 462 (100, M$^+$), 446 (43.4), 431 (15.9), 134 (38.5) and 121 (48.3). Anal. Calcd. for C$_{29}$H$_{39}$N$_2$O$_3$.⅓H$_2$O: C, 74.71; H, 8.30; N, 6.01. Found: C, 74.65; H, 8.31; N, 6.03.

Example 44

This example illustrates the preparation and properties of 17α-Methoxy-11β-[4-N-piperidino)phenyl]-19-norpregna-4,9-diene-3,20-dione 3-oxime (142b) (FIG. 6):

Under nitrogen, a solution of the dienedione (97b, 250 mg, 0.513 mmol) in absolute EtOH (25 mL) was treated with a 10-fold excess of solid hydroxylamine hydrochloride (38 mg, 5.13 mmol). The reaction mixture was stirred at room temperature for 1¼ hr. At that time, TLC (10% acetone in methylene chloride) showed no starting material and two major more polar products. The reaction was diluted with saturated sodium bicarbonate solution (100 mL) and extracted with methylene chloride (3×). The organic fractions were washed with water and brine, dried over anhydrous sodium sulfate, filtered and concentrated in vacuo to yield 260 mg of yellow foam. Flash chromatography (10% acetone in methylene chloride) gave 186 mg of the material. Trituration with pentane with scratching and sonication gave 172 mg of the product 142b after drying. HPLC analysis indicated this material to be 94% pure. Two additional flash column chromatography, trituration with pentane and drying again in vacuo yielded 143 g of 142b as an off-white solid in 55.5% yield; m.p.=157–162° C. (amber gel) and 195–200° C. (gel melts). HPLC analysis on a Waters Nova-Pak $C_{18}$ ODS column eluted with MeOH: water (80:20) with 0.05% $Et_3N$ at a flow rate of 1 mL per min and at $\lambda$=260 nm indicated a purity of 97.9%. FTIR (KBr, diffuse reflectance): $v_{max}$ 3183, 2934, 1707, 1610, 1511, 1450, 1385, 1349 and 1234 cm$^{-1}$. NMR (300 MHZ, CDCl$_3$): δ 0.239 (s, 3H, C18-CH$_3$), 2.175 (s, 3H, C21-CH$_3$), 3.07–3.150 (m, 4H, —N—CH$_2$CH$_2$— of piperidine ring), 3.13 (s, 3H, C17α-OCH$_3$), 4.28–4.30 (d., 1H, C11α-CH), 5.840 (s, 0.69H, C4-CH= of anti-oxime), 6.493 (s, 0.31H, C4-CH= of syn-oxime), 6.8–7.0 (dd, 4H, aromatic-CH's). MS (EI) m/z (relative intensity): 502 (M$^+$). Anal. Calcd. for $C_{32}H_{20}O_3N_2$: 76.46; H, 8.42; N, 5.57. Found: C, 75.38; H, 8.60; N, 5.39.

Example 45

This example illustrates the preparation and properties of 17α,21 dimethoxy-11β-[4-(N,N-dimethylamino)phenyl]-19-norpregna-4,9-diene-3,20-dione 3-oxime (143) (FIG. 8):

A solution of the 17α,21-dimethoxydienedione (113a, 0.3 g, 0.63 mmol) in absolute EtOH (20 mL) was treated with a 10-fold excess of solid hydroxylamine hydrochloride (0.44 g, 6.3 mmol). The reaction mixture was stirred at room temperature for 2.5 h, after which time, TLC (10% acetone in methylene chloride, overspotted with con. NH$_4$OH) indicated a complete reaction. The reaction mixture was diluted with water (100 mL), adjusted to pH of 8.0 with concentrated NH$_4$OH solution, and extracted with methylene chloride (3×). The organic fractions were washed with water (3×) then filtered through anhydrous sodium sulfate, combined and concentrated in vacuo to give 0.37 g of the crude product (143) as a yellow foam. This material was purified via flash chromatography (10% acetone in methylene chloride) followed by trituration with pentane to give 0.17 g of the purified oxime (143). Analysis by HPLC on a Waters Nova-Pak $C_{18}$ ODS column eluted with acetonitrile:0.05 M $KH_2PO_4$ buffer [pH 3.0]; 1:1 at a flow rate of 1 mL per min and at $\lambda$=276 nm indicated a purity of only 92%. This material was repurified via flash chromatography (10% acetone/methylene chloride) followed by precipitation from acetonitrile with water to give 0.11 g of 143 as a white powder in 35.5% yield for which HPLC analysis indicated it to be 96.2% pure; m.p. 129–135° C. FTIR (KBr, diffuse refelectance): $v_{max}$ 3290, 2938, 1722, 1613 and 1518 cm$^{-1}$. NMR (300 MHZ, CDCl$_3$): δ 0.288 (s, 3H, C18-CH$_3$), 2.898 (s, 6H, NMe$_2$), 3.165 (s, 3H, C17α-OCH$_3$), 3.454 (s, 3H, C21-OCH$_3$), 4.245 and 4.380 (dd, 2H, J=17.9 Hz, C21-CH$_2$) 4.301 (d., 1H, J=6.9 Hz, C11α-CH), 5.842 (s, 0.82H, C4-CH= of anti-oxime), 6.496 (s, 0.18H, C4-CH= of syn-oxime), 6.633 (m, 2H, 3',5' aromatic-CH's) and 6.997 (m, 2H, 2',6' aromatic-CH's). MS (EI) m/z (relative intensity): 492 (M$^+$, 100), 476 (12.9), 134 (59.8) and 121 (65.0). Anal. Calcd. for $C_{30}H_{40}N_2O_4 \cdot \frac{1}{10}H_2O$: C, 72.87; H, 8.19; N, 5.67. Found: C, 72.97; H, 8.18; N, 5.44.

Example 46

This example illustrates an unusual and novel oxidative N-demethylation method and properties of 17α-acetoxy-11β-[4-methylamino)phenyl]-21-methoxy-19-norpregna-4,9-diene-3,20-dione (145) (FIG. 3):

A mixture of the dimethylaminophenyl compound (38, 500 mg, 0.98 mmol) and calcium oxide (471 mg, 8.40 mmol) in THF (4 mL) and methanol (3 mL) was chilled in an ice bath. Iodine (1.255 g, 4.94 mmol) in THF (2 mL) was added. The reaction was stirred at 0° C. for 1.5 hr and diluted with CH$_2$Cl$_2$. The mixture was filtered and the filtrate sequentially yielded 591 mg of crude material. Flash chromatography using 10% acetone in CH$_2$Cl$_2$ gave 204 mg of 145 as an off-white solid in 49% yield. This was combined with material from other reactions (170 mg total) and purified as one batch. Two flash column chromatographies yielded 296 mg of material which was triturated with pentane accompanied with scratching and sonication. After drying in vacuo, 280 mg of 1 were obtained; m.p.=177–182° C. FTIR (KBr, diffuse reflectance): $v_{max}$ 3407, 2949, 1733, 1662, 1615, 1519, 1448, 1370 and 1236 cm$^{-1}$. NMR (300 MHZ, CDCl$_3$): δ 0.403 (s, 3H, C18-CH$_3$), 2.105 (s, 3H, C17α-OAc), 2.796 (s, 3H, —NCH$_3$), 3.412 (s, 3H, 21-OCH$_3$), 4.073–4:333 (dd, 2H, 21-CH$_2$OMe), 4.352–4.376 (d, 1H, C11α-CH), 5.775 (s, 1H, $\overline{\text{C4-CH}}$=), and 6.489–6.933 (dd, 4H, aromatic-CH's). MS (EI) m/z (relative intensity): 491 (M$^+$). Anal. Calcd. for $C_{30}H_{37}NO_5$: C, 73.29; H, 7.59; N, 2.85. Found: C, 73.22; H, 7.84; N, 2.87. Analysis by HPLC on a Waters Assoc. NovaPak $C_{18}$ column eluted with MeOH/H$_2$O (65:35) with 0.05% $Et_3N$ at a flow rate of 1 mL per min and at $\lambda$=260 nm indicated a purity of 98.1% of 145.

Example 47

This example illustrates an unusual and novel oxidative N-demethylation method and properties of 17α,21-diacetoxy-11β-[4-(N-methylamino)phenyl-19-norpregna-4,9-diene-3,20-dione (144):

This compound was prepared in a manner similar to that of the above Example 46. Our initial concern was whether the 21-acetate would undergo hydrolysis when exposed to the demethylation reaction conditions. Treatment of the dimethylaminophenyl compound (15) with iodine-calcium oxide in THF/MeOH proceeded similarly and smoothly to that of Example 46 without hydrolysis of the 21-acetate.

A mixture of the dimethylaminophenyl compound (15, 775 mg, 1.45 mmol) and calcium oxide (692 mg, 12.34 mmol) in THF (6.4 mL) and MeOH (4.8 mL) was chilled in an ice bath. Iodine (1.84 g, 7.25 mmol) was added as a solid and the mixture stirred under nitrogen in the ice bath for 2 hr. At that time the reaction was diluted with CH$_2$Cl$_2$ and filtered. The filtrate was washed with 15% sodium thiosulfate solution, H$_2$O, brine, and then dried over Na$_2$SO$_4$. Evaporation of the solvent yielded 1.38 g of the crude product (144). Flash column chromatography using 10% acetone in CH$_2$Cl$_2$ gave 490 mg of the product (144) as an off-white solid in 65% yield which was 90% pure by HPLC. This was combined with material from other batches (135 mg) and after two additional flash column chromatographies yielded 482 g which was 92% pure. An additional flash column chromatography was performed followed by trituration of the material with pentane, sonication and scratching. 330 mg of the demethylated product (144) were obtained; m.p.=135–142° C. FTIR (KBr, diffuse reflectance): $v_{max}$ 3394, 2942, 2883, 1737, 1662, 1613, 1519, 1370 and 1234 cm$^{-1}$. NMR (300 MHz, CDCl$_3$): δ

0.448 (s, 3H, C18-CH$_3$), 1.266 (s, 1H, —NH), 2.134–2.176 (s, 6H, C17α-OAc and C21-OAc), 2.810 (s, 3H, —NCH$_3$), 4.375–4.399 (d, 1H, C11α-CH), 4.670–4.981 (dd, 2H, 21-CH$_2$OAc), 5.787 (s, 1H, C4-CH=), and 6.523–6.980 (dd, 4H, aromatic-CH's). MS (EI) m/z (relative intensity): 519 (M$^+$). Anal. Calcd. for C$_{31}$H$_{37}$NO$_6$: C, 71.65; H, 7.18; N, 2.70. Found: C, 71.59; H, 7.31; N, 2.59. Analysis by HPLC on a Waters Assoc. NovaPak C$_{18}$ column eluted with CH$_3$CN/H$_2$O (50:50) with 0.05% Et$_3$N at a flow rate of 1 mL per min and at λ=260 nm indicated a purity of 98.8% of 144.

Biological Properties of the Compounds of Formula I

Materials and Methods

Statistical Analysis

Statistical analysis was performed using standard methods and a PROPHET data management system operating on SUN Microsystems OS 4.4.1 (Bliss, Cl., *The Statistics of Bioassay*, New York, Academic Press (1952); Hollister, C., *Nucleic Acids Research*, 16:1873–1875 (1988)). Raw data, statistical and regression analysis are available.

AntiMcGinty Test (McGinty, et al., *Endocrinology*, 24:829–832 (1939))

Immature female rabbits of the New Zealand White breed (approx. 1 kg body weight) were maintained under standard laboratory conditions and received a subcutaneous injection of 5 μg estradiol in 10% ethanol/sesame oil daily for 6 consecutive days. Twenty-four hours after the last injection of estradiol (day 7) animals underwent sterile abdominal surgery to ligate a 3–4 cm segment of both uterine horns. The experimental compound in appropriate solvent (usually 10% ethanol/sesame oil) was injected intraluminally into the ligated segment of one uterine horn and the vehicle alone into the ligated segment of the contralateral horn. Injection volume was limited to 0.1 ml, and care was taken to prevent leakage. A stimulating dose of progesterone (0.8 mg/day) was administered subcutaneously to each rabbit daily for the next three days (days 7, 8 and 9) for the purpose of inducing endometrial proliferation. All animals were sacrificed on day 10 when a segment central to the ligatures was removed and fixed in 10% neutral buffered formalin and submitted for histological processing. Five micron sections stained with hematoxylin and eosin (H&E) were evaluated microscopically for the degree of endometrial glandular proliferation according to the method of McPhail (McPhail, *J. Physiol.*, 83:145 (1934). The percent inhibition of endometrial proliferation for each rabbit was calculated and the mean of the group of five animals recorded.

AntiClauberg Test (Clauberg, C., *Zentr. Gynakol.*, 54:2757–2770 (1930))

Immature female rabbits of the New Zealand White breed (approx. 1 kg body weight) were maintained under standard laboratory conditions and received a subcutaneous injection of 5 μg estradiol in 10% ethanol/sesame oil daily for 6 consecutive days. Twenty-four hours after the last dose of estradiol (day 7) animals received progesterone by subcutaneous injection (0.8 mg/day) and the experimental compound in appropriate vehicle (usually 10% ethanol/sesame oil) orally or subcutaneously for five consecutive days. One group of rabbits received progesterone only. Twenty-four hours after the last dose all animals were sacrificed for removal of the uterus which was cleaned of all fat and connective tissue, weighed to the nearest 0.2 mg and placed in 10% neutral buffered formalin for subsequent histological processing. Five micron sections stained with hematoxylin and eosin (H&E) were evaluated microscopically for the degree of endometrial glandular proliferation according to the method of McPhail (McPhail, supra). The percent inhibition of endometrial proliferation at each dose level of the experimental compound was derived by comparison with the progesterone-stimulated animals alone.

Postcoital Test

Adult female rats of the Sprague-Dawley strain were maintained under standard laboratory conditions, 14 hours of light and 10 hours of darkness each day and cohabited with proven fertile males when in proestrus. Sperm-positive animals were randomly assigned to control and experimental groups. The day vaginal sperm were found in vaginal washings constituted day 0 of gestation. Rats received experimental compounds or vehicle (control) daily by the oral route on days 0–3 or 4–6 and were sacrificed between days 10 and 17 to record the number and condition of conceptuses.

Antiovulatory Test

Immature female rats of the Sprague-Dawley strain weighing 200 to 250 g were maintained under standard laboratory conditions, 14 hours of light and 10 hours of darkness each day. Vaginal washings were obtained daily and evaluated microscopically to establish the estrous cycle of each animal. Animals exhibiting two consecutive four-day cycles were used in the test. Each dose group consisted of eight rats and one group served as the vehicle control. Animals were dosed at noon on the day of proestrus and sacrificed 24 hours later when ova can usually be visualized in the distended ampulla of the oviduct using a dissecting microscope. The oviducts were excised, an incision made in the distended ampulla and the ova teased out in a drop of water on a microscope slide so that the number shed could be counted. Historically, control animals shed between 12 and 14 ova during each estrous cycle. Agents which inhibit ovulation usually exhibit an "all or none" effect; it is rare that ovulation is "partially" inhibited. Treatment groups were compared with the control group using a 95% contingency table or the ED$_{100}$ was established with additional dose levels.

Relative Binding Affinities for the Progesterone and Glucocorticoid Receptors

Uteri and thymus glands were obtained from estradiol-primed immature female rabbits of the New Zealand White strain for preparation of cytosols for the progesterone and glucocorticoid receptor assays, respectively. Tissues were excised and immediately placed in ice cold TEGDM buffer (10 mM Tris, pH 7.4; 1.5 mM EDTA; 10% glycerol vol/vol/; 1 mM dithiothreitol [DTT]; and 20 mM sodium molybdate). The tissues were dissected free of connective tissue and fat, weighed and minced finely. Minced tissues were homogenized in 3 volumes TEGDM/gm with four 10 second bursts of a VirTis Cyclone set at half maximum speed with a 30 second cooling period (in ice) between bursts. Homogenates were centrifuged at 109,663 g at 4° C. for 1 hour to yield the soluble cytosol fiction. Aliquots of cytosol were snap frozen and stored at −75° C.

All binding assays were carried out at 2–6° C. for 16–18 hours. The following radioactive ligands were used: [1,2-$^3$H(N)]-progesterone (50.0 Ci/mmole) for the progesterone receptor (PR). [6,7-$^3$H(N)-dexamethasone (39.2 Ci/mmole) for the glucocorticoid receptor (GR) and [2,4,6,7-$^3$H(N)]-estradiol for the estrogen receptor. For the progesterone receptor RBA assays 0.02 ml uterine cytosol or TEDGM buffer, 0.05 ml of various concentrations of test compounds or progesterone, 0.13 ml TEGDM buffer and 0.05 ml [$^3$H]-progesterone were added to duplicate tubes. For the glucocorticoid receptor RBA assays 0.1 ml thymus cytosol or TEDGM buffer, 0.05 ml of various concentrations of test compounds or dexamethasone, 0.05 ml TEGDM buffer and 0.05 ml [3H]-dexamethasone were added to duplicate tubes. For the estrogen receptor RBA assays 0.05 ml uterine cytosol, 0.1 ml TEGDM buffer, 0.05 ml of various concentrations of test compounds or estradiol and 0.05 ml [$^3$H]-estradiol were added to duplicate tubes. The concentrations of the test compounds, progesterone, dexamethasone and estradiol ranged from 0.05 to 100 nM and the concentrations of the competitors ranged from 0.5 to 500 nM. Total binding was measured at radioligand concentrations of 3.5 nM and nonspecific binding was measured in the presence of a 200-fold excess of unlabeled progesterone (PR), dexamethasone (GR) or diethylstilbestrol (ER), respectively.

In all incubations bound and free ligand were separated using dextra-coated charcoal (DCC). A 0.1 ml aliquot of DCC (0.5% charcoal/0.05% Dextran T-70) was added to each tube. The tubes were vortexed and incubated on ice for 10 minutes. Five-tenths ml TEG buffer (without DTT or molybdate) was then added to all tubes to improve supernatant recovery following centrifugation. The charcoal was pelleted by centrifugation at 2,100 g for 15 minutes at 4° C. The supernatants containing the [$^3$H]-steroid receptor complexes were decanted into vials containing 4 ml Optifluor (Packard Instrument Co.), vortexed, equilibrated in a liquid scintillation counter for 30 minutes and then counted for 2 minutes. This provided the quantity of receptor bound [$^3$H]-steroid at each competitor concentration.

The standard curves and the $EC_{50}$ (Effective Concentration) for each standard curve and curve for each test compound was determined by entering the counting data (receptor bound [$^3$H]-progesterone, [$^3$H]-dexamethasone or [$^3$H]-estradiol) into a four parameter sigmoidal computer program (RiaSmart® Immunoassay Data Reduction Program, Packard Instrument Co., Meriden, Conn. The RBA for each test compound LA was calculated using the following equation:

$$RBA = \frac{EC_{50}\text{Standard}}{EC_{50}\text{Test Compound}} \times 100$$

where $EC_{50}$ Standard=molar concentration of unlabeled progesterone, dexamethasone or estradiol required to decrease bound [$^3$H]-progesterone (PR), [$^3$H]-dexamethasone (GR) or [$^3$H]-estradiol to 50% of the respective buffer control (100% bound radioligand) and $EC_{50}$ Test Compound=molar concentration of test compound required to decrease bound [3H]-progesterone (PR), [$^3$H]-dexamethasone (GR) or [$^3$H]-estradiol to 50% of the respective buffer control (100% bound radioligand).

Results

Example 1

Results of the antiMcGinty and oral antiClauberg tests as well as the relative binding affinities of these compounds are shown in Table 1, infra. Compared to the lead compound (CDB-2914, 21-H), the 21-acetoxy (15) and the 21-methoxy (38) analogs exhibited 2.79 and 3.61 times, respectively, the antiprogestational potency as assessed by the oral antiClauberg test with a substantial reduction in glucocorticoid binding affinity. Further, the results of the antiMcGinty test of the 21-acetoxy analog (15) following intraluminal administration closely paralleled those observed in the antiClauberg test following oral dosing. Since mifepristone (CDB-2477) is frequently used as a reference standard, Table 2, infra, contains data comparing the antiprogestational activity and relative binding affinity for the progesterone and glucocorticoid receptors of CDB-2914 with this standard. Recent studies have shown a good correlation between relative binding affinity for the glucocorticoid receptor and a biological test based upon the antagonism of dexamethasone-induced thymus involution in adrenalectomized male rats.

The halogenated analogs (13, 14A, 14B) did not show significant differences in antiprogestational activity nor relative binding affinity to the progesterone receptor from the lead compound, CDB-2914. Other 21-substituted analogs generally exhibited reduced antiprogestational activity with the exception of the cypionate (40) which was about 50% more potent in the antiClauberg test. This may be due to hydrolysis to the corresponding 21-hydroxy compound. However, the presence of additional bulkiness at position 21 does not always favor an increase in biological activity (see 14B) and enhanced relative binding affinity for the progesterone receptor was not necessarily indicative of greater antiprogestational activity (see 12). Thus the window of opportunity for enhanced antiprogestational activity with a reduction in relative binding affinity for the glucocorticoid receptor for 21-substituted analogs of the lead compound (CDB-2914) is highly restricted and was identified only after numerous analogs had been synthesized and tested.

TABLE 1

ANTIPROGESTATIONAL ACTIVITY AND RELATIVE BINDING AFFINITY FOR THE PROGESTERONE AND GLUCOCORTICOID RECEPTORS

| COMPOUND | | ANTIPROGESTATIONAL[1] | | RELATIVE BINDING AFFINITY[2] | |
|---|---|---|---|---|---|
| Appln. No. | CDB No. | Anti-McGinty | Anti-Clauberg | Progesterone | Glucocorticoid |
| 69B | 2914 | 100 | 100 | 122 | 114 |
| 12 | 4062 | 26 | 29 | 261 | 32 |
| 13 | 4058 | 103 | 80 | 125 | 109 |
| 14A | 3876 | 75 | 68 | 127 | 90 |
| 14B | 4031 | 71 | | 130 | 175 |
| 15 | 4059 | 300 | 279 | 103 | 51 |
| 16 | 4102 | >2 | | 6 | 77 |
| 17 | 4101 | 65 | | 37 | 54 |
| 28 | 4030 | 32 | | 129 | 126 |
| 38 | 4124 | | 361 | 103 | 52 |
| 40 | 4125 | | 155 | 74 | 37 |
| 41 | 4152 | | 140 | 62 | 71 |
| 46 | 4167 | | 130–210 | 83 | 46 |

[1]Antiprogestational Activity
AntiMcGinty: see text; CDB-2914 = 100 (assigned)
AntiClauberg, oral: see text; CDB-2914 = 100 (assigned)
[2]Relative Binding Affinity
Progesterone receptor (estrogen-primed rabbit uterus) progesterone = 100%
Glucocorticoid receptor (estrogen-primed rabbit thymus) dexamethasone = 100%

TABLE 2

| | | BINDING AFFINITY[1] | | BIOLOGICAL ACTIVITY | | |
|---|---|---|---|---|---|---|
| CDB NO. | POUND NO. | Progester | Glucocortic | anti-Clauberg[2] | Post-coital[3] | Anti-ovulator[4] |
| 2914 | 69B | 122 (234) | 114 | 100 | 2 | 1 |
| 3875 | 69A | 164 | 30 | 97 | | |
| 3247 | 69C | 91 | 49 | ~10 | 2* | |
| 3248 | 69D | 40 | 89 | weak (subcu) | inactive @ 2* | |

TABLE 2-continued

| | | BINDING AFFINITY[1] | | BIOLOGICAL ACTIVITY | | |
|---|---|---|---|---|---|---|
| CDB NO. | COM- POUND NO. | Pro- gester | Gluco- cortic | anti- Clau- berg[2] | Post- coital[3] | Anti- ovulator[4] |
| 4243 | 91 | 171 | 59 | inactive | | |
| 4418 | 70 | 79 | /2 | ~25 | | |
| 4363 | 71 | 123 (203) | 20 | 253 | 0.5 | >16 |
| 4399 | 72 | 109 | 110 | 35 | | |
| 4176 | 74 | 131 | 32 | <10 | | |
| 4324 | 97a | 120 | 52 | 110 | | |
| 4398 | 97b | 47 | 38 | 99 | | |
| 4455 | 106a | | | | | |
| 4241 | 106b | 136 (172) | 14 | 34 | | |
| 4400 | 113A | 117 (237) | 62 | 229 | | |
| 4454 | 113B | 59 | 34 | | | |
| 4417 | 113c | 63 | 45 | 70 | | |
| 4239 | 123a | 174 (140) | 11 | 45–83 | | |
| 4416 | 123b | 64 | 45 | 77 | | |
| 4393 | 139 | 30 | 79 | inactive | | |
| 4247 | 126a | 95 | 43 | 170 | | |
| 4362 | 126b | 76 | 15 | 125 | | |
| 4374 | 126c | 68 | 67 | 224 | | |
| 4361 | 129 | 155 | 20 | 303 | | |
| 4306 | 133 | 82 | 13 | 95 | | |
| 4352 | 138 | 63 | 14 | 57 | | |

[1]Progesterone receptor (estrogen-primed rabbit uterus); progesterone = 100%
Figure in ( ) is relative binding affinity of the human isoform A progesterone receptor Glucocorticoid receptor (estrogen-primed rabbit thymus) dexamethasone = 100%.
[2]antiClauberg - oral except where indicated; CDB-2914 = 100 (assigned).
[3]Postcoital - oral, rat $MED_{100}$ (mg/day) days 0–3 or *days 4–6 subcu; day sperm in vaginal washings = day 0.
[4]Antiovulatory - oral, rat $MED_{100}$ (mg) single dose at noon on day of proestrus.

TABLE 3

RELATIVE BINDING AFFINITIES AND ANTIPROGESTION ACTIVITY OF CDB-2914 AND MIFEPRISTONE,(CDB-2477)

| | RELATIVE BINDING AFFINITY | | ANTIPROGESTATIONAL ACTIVITY | |
|---|---|---|---|---|
| DRUG | PROGES- TERONE[1] | GLUCO- CORTICOID[2] | ANTI- MCGINITY[3] | ANTI- CLAUBERG[4] |
| CDB-2914 | 114– (n = 18) | 127–24 (n = 12) | 0.56 | 3.27 |
| CDB-2477 | 150–17 (n = 11) | 221–35 (n = 16) | 1.0 (assigned) | 1.0 (assigned) |

[1]Progesterone = 100%; immature estrogen-primed rabbit uterus
[2]Dexamethasone = 100%; immature estrogen-primed rabbit thymus
[3]Intruluminal administration to estrogen-primed immature rabbits; CDB-2477 = 1.0 (assigned)
[4]Oral administration to estrogen-primed immature rabbits; CDB-2477 = 1.0 (assigned)

Example 2

AntiClauberg

Data from anti-Clauberg tests following oral administration are shown in Tables 1 and 2. Compounds 15, 38, 40, 41, 46, 71, 97a, 113a, 126a, 126b, 126c and 129 exhibited greater activity than the standard, 69B. Previous studies have shown that 69B is significantly more potent than mifepristone (3.27×; 95% C.I.=1.41–7.58) in this test. Compounds 15, 38, 71 and 129 represent four of the most potent antiprogestational compounds known, and their low binding affinity for the glucocorticoid receptor would predict minimal antiglucocorticoid activity.

Postcoital

Compound 71 exhibited about four times the postcoital contraceptive activity of the standard, compound 69B, following oral administration on days 0–3 of gestation.

Antiovulatory

Compound 71 was not fully active at a dose level 16 times the $MED_{100}$ for the standard, compound 69B, and compound 113a exhibited only about 6% of the antiovulatory activity of the standard.

Relative Binding Affinity for the Progesterone and Glucocorticoid Receptors

Relative binding affinities for the progesterone receptor (estrogen-primed rabbit uterine cytosol) and glucocorticoid receptor (estrogen-primed rabbit thymic cytosol) are shown in Table 1. Several compounds were also tested for binding affinity for the human isoform A progesterone receptor. Compounds 12, 13, 14A, 14B, 28, 38, 69A, 91, 71, 72, 73, 97a, 106b, 113a, 113d, 122b and 129 showed binding affinities greater than that observed for the standard, compound 69B. On the other hand, most of the compounds tested exhibited reduced binding affinity for both the progesterone and the glucocorticoid receptor.

Discussion

Many members of a series of derivatives of 19-norprogesterone possess potent antiprogestational activity following oral administration in experimental animals. They exhibit high binding affinity for the progesterone receptor (rabbit uterine) and only modest relative binding affinity for the glucocorticoid receptor (rabbit thymus). This is reflected in standard antiprogestational assays showing strong inhibition of progesterone-induced alterations of rabbit uterine endometrium. It is anticipated that the reduced binding affinity for the glucocorticoid receptor will reflect diminished biological antiglucocorticoid activity.

Table 3 compares the relative binding affinity for the progesterone and glucocorticoid receptors as well as the antiprogestational activity as measured by antiClauberg and antiMcGinty tests for the standard, compound 69B, and mifepristone (CDB-2477). Mifepristone exhibited greater binding affinity for both receptor proteins and was more potent than the standard, compound 69B, in the antiMcGinty test. However, the standard was 3 times as potent as mifepristone in the antiClauberg test following oral administration. This finding has not been satisfactorily explained, but may be due to the differential pharmacokinetics of these two steroids following oral administration. Higher blood levels of 69B have been observed following oral administration to several species, thus indicating a greater oral bioavailable for the standard.

Antiprogestational agents including mifepristone are known to prevent implantation in the rat (Dao, B., et al., Contraception, 54:243–258 (1996); Reel, J., et al., Contraception, 58:129–136 (1998)), guinea pig (Batista, M., et al., Am. J. Obstet. Gynecol., 165:82–86 (1991), and man (Baulieu, E., Clinical Applications of Mifepristone (RU 486) and Other Antiprogestins (Donaldson, M., Dorffinger, L., Brown, S. and Benet, L. (eds.), National Academy Press, pp. 72–119 (1993)). Compound 71 was four times as potent as the standard, compound 69B, in preventing pregnancy when orally administered on days 0–3 of presumptive gestation. Curiously, compound 71 was only about 5% as potent as the standard in inhibiting ovulation. Both compound 69B and mifepristone have been shown to inhibit ovulation in the rat (Dao, et al., supra), and mifepristone has been shown to affect ovulation in human subjects (Baulieu, et al., supra).

Compound 69B has been shown to affect both follicular development and ovulation as well as endometrial maturation in human subjects following a single oral dose (unpublished data).

Compound 113a exhibited high binding affinity for both the rabbit progesterone receptor (isoform B) and the human progesterone receptor (isoform A). This was reflected in potent antiprogestational activity in vivo where it was more than twice as active at the standard, compound 69B. It also showed reduced binding affinity for the glucocorticoid receptor and was about half as effective as compound 69B in preventing pregnancy in the postcoital test. Strangly, this compound was only 6% as active as the a, standard in inhibiting ovulation. Thus, compound 113a may represent an antiprogestational steroid with high tissue specificity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having the general formula:

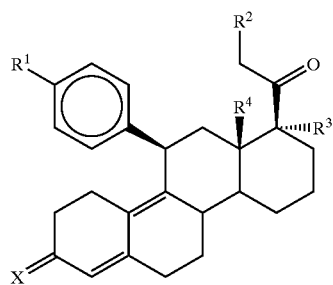

I wherein:
R$^1$ is a member selected from the group consisting of —N(CH$_3$)$_2$, —NHCH$_3$, —NC$_4$H$_8$, —NC$_5$H$_{10}$, and —NC$_4$H$_8$O;
R$^2$ is a member selected from the group consisting of hydrogen, halogen, alkyl, acyl, hydroxy, alkoxy, acyloxy, alkylcarbonate, cypionyloxy, S-alkyl, —SCN, S-acyl, and —OC(O)R$^6$, wherein R$^6$ is a member selected from the group consisting of alkyl, alkoxy ester and alkoxy;
R$^3$ is a member selected from the group consisting of alkyl-alkoxy, alkoxy and acyloxy;
R$^4$ is a member selected from the group consisting of hydrogen and alkyl;
X is a member selected from the group consisting of ═O and ═N—OR$^5$, wherein R$^5$ is a member selected from the group consisting of hydrogen and alkyl; and
wherein: if R$^1$ is —N(CH$_3$)$_2$ or —NHCH$_3$, R$^2$ is hydrogen R$^3$ is acetyloxy and R$^4$ is alkyl, then X is other than ═O and ═N—OR$^5$, wherein R$^5$ is methyl.

2. The compound in accordance with claim 1, wherein R$^1$ is a member selected from the group consisting of —N(CH$_3$)$_2$, —NC$_4$H$_8$, —NC$_5$H$_{10}$, and —NC$_4$H$_8$O.

3. The compound in accordance with claim 1, wherein R$^2$ is a member selected from the group consisting of hydrogen, acyloxy, alkoxy, —SAc, —SCN, —OC(O)CH$_2$N(CH$_3$)$_2$, and —OC(O)R$^6$, wherein R$^6$ is a member selected from the group consisting of alky, alkoxy ester and alkoxy.

4. The compound in accordance with claim 3, wherein R$^2$ is —OC(O)R$^6$ and R$^6$ is a member selected from the group consisting of —CH$_2$CH$_3$, —CH$_2$OCH$_3$ and —OCH$_3$.

5. The compound in accordance with claim 1, wherein R$^2$ is an alkoxy selected from the group consisting of methoxy, ethoxy, vinyloxy, ethynyloxy and cyclopropyloxy.

6. The compound in accordance with claim 1, wherein R$^3$ is a member selected from the group consisting of alkoxy and acyloxy.

7. The compound in accordance with claim 1, wherein R$^4$ is alkyl.

8. The compound in accordance with claim 1, wherein X is ═O.

9. The compound in accordance with claim 1, wherein X is ═N—OR$^5$.

10. The compound in accordance with claim 1, wherein:
R$^1$ is —N(CH$_3$)$_2$;
R$^2$ is hydrogen;
R$^3$ is acyloxy;
R$^4$ is methyl; and
X is ═O.

11. The compound in accordance with claim 10, wherein R$^3$ is acyloxy selected from the group consisting of —OC(O)H, —OC(O)CH$_2$CH$_3$ and —OC(O)C$_6$H$_{13}$.

12. The compound in accordance with claim 1, wherein:
R$^1$ is —N(CH$_3$)$_2$;
R$^2$ is hydrogen;
R$^3$ is methoxymethyl;
R$^4$ is methyl; and
X is ═O.

13. The compound in accordance with claim 1, wherein:
R$^1$ is —NC$_4$H$_8$;
R$^2$ is hydrogen;
R$^3$ is acetoxy;
R$^4$ is methyl; and
X is ═O.

14. The compound in accordance with claim 1, wherein:
R$^1$ is —NC$_5$H$_{10}$;
R$^2$ is hydrogen;
R$^3$ is acetoxy;
R$^4$ is methyl; and
X is ═O.

15. The compound in accordance with claim 1, wherein:
R$^1$ is —NC$_4$H$_8$O;
R$^2$ is hydrogen;
R$^3$ is acetoxy;
R$^4$ is methyl; and
X is ═O.

16. The compound in accordance with claim 1, wherein:
R$^1$ is —N(CH$_3$)$_2$;
R$^2$ is hydrogen;
R$^3$ is methoxy;
R$^4$ is methyl; and
X is ═O.

17. The compound in accordance with claim 1, wherein:
R$^1$ is —NC$_5$H$_{10}$;
R$^2$ is hydrogen;
R$^3$ is methoxy;
R$^4$ is methyl; and X is =O.

18. The compound in accordance with claim 1, wherein:
$R^1$ is —$NC_5H_{10}$;
$R^2$ is acetoxy;
$R^3$ is acetoxy;
$R^4$ is methyl; and
X is =O.

19. The compound in accordance with claim 1, wherein:
$R^1$ is —$N(CH_3)_2$;
$R^2$ is methoxy;
$R^3$ is methoxy;
$R^4$ is methyl; and
X is =O.

20. The compound in accordance with claim 1, wherein:
$R^1$ is —$N(CH_3)_2$;
$R^2$ is methoxy;
$R^3$ is ethoxy;
$R^4$ is methyl; and
X is =O.

21. The compound in accordance with claim 1, wherein:
$R^1$ is —$NC_4H_8$;
$R^2$ is methoxy;
$R^3$ is methoxy;
$R^4$ is methyl; and
X is =O.

22. The compound in accordance with claim 1, wherein:
$R^1$ is —$NC_5H_{10}$;
$R^2$ is methoxy;
$R^3$ is methoxy;
$R^4$ is methyl; and
X is =O.

23. The compound in accordance with claim 1, wherein:
$R^1$ is —$NC_5H_{10}$;
$R^2$ is methoxy;
$R^3$ is acetoxy;
$R^4$ is methyl; and
X is =O.

24. The compound in accordance with claim 1, wherein:
$R^1$ is —$N(CH_3)_2$;
$R^2$ is —$OC(O)CH_2CH_3$;
$R^3$ is acetoxy;
$R^4$ is methyl; and
X is =O.

25. The compound in accordance with claim 1, wherein:
$R^1$ is —$N(CH_3)_2$;
$R^2$ is —$OC(O)CH_2OCH_3$;
$R^3$ is acetoxy;
$R^4$ is methyl; and
X is =O.

26. The compound in accordance with claim 1, wherein:
$R^1$ is —$N(CH_3)_2$;
$R^2$ is —$OC(O)OCH_3$;
$R^3$ is acetoxy;
$R^4$ is methyl; and
X is =O.

27. The compound in accordance with claim 1, wherein:
$R^1$ is —$N(CH_3)_2$;
$R^2$ is —$OCH=CH_2$;
$R^3$ is acetoxy;
$R^4$ is methyl; and
X is =O.

28. The compound in accordance with claim 1, wherein:
$R^1$ is —$N(CH_3)_2$;
$R^2$ is —$OCH=CH_2$;
$R^3$ is methoxy;
$R^4$ is methyl; and
X is =O.

29. The compound in accordance with claim 1, wherein:
$R^1$ is —$N(CH_3)_2$;
$R^2$ is —$OCH=CH_2$;
$R^3$ is ethoxy;
$R^4$ is methyl; and
X is =O.

30. The compound in accordance with claim 1, wherein:
$R^1$ is —$N(CH_3)_2$;
$R^2$ is —SCN;
$R^3$ is acetoxy;
$R^4$ is methyl; and
X is =O.

31. The compound in accordance with claim 1, wherein:
$R^1$ is —$N(CH_3)_2$;
$R^2$ is —OC(O)H;
$R^3$ is —OC(O)H;
$R^4$ is methyl; and
X is =O.

32. The compound in accordance with claim 1, wherein:
$R^1$ is —$N(CH_3)_2$;
$R^2$ is —OC(O)H;
$R^3$ is hydroxy;
$R^4$ is methyl; and
X is =O.

33. The compound in accordance with claim 1, wherein:
$R^1$ is —$N(CH_3)_2$;
$R^2$ is —$OC(O)CH_2N(CH_3)_2$;
$R^3$ is acetoxy;
$R^4$ is methyl; and
X is =O.

34. The compound in accordance with claim 1, wherein:
$R^1$ is —$NC_5H_{10}$;
$R^2$ is hydrogen;
$R^3$ is acetoxy;
$R^4$ is methyl; and
X is =N—$OR^5$, wherein $R^5$ is hydrogen.

35. The compound in accordance with claim 1, wherein:
$R^1$ is —$N(CH_3)_2$;
$R^2$ is hydrogen;
$R^3$ is methoxy;
$R^4$ is methyl; and
X is =N—$OR^5$, wherein $R^5$ is hydrogen.

36. The compound in accordance with claim 1, wherein:
$R^1$ is —$NC_5H_{10}$;
$R^2$ is hydrogen;
$R^3$ is methoxy;
$R^4$ is methyl; and
X is =N—$OR^5$, wherein $R^5$ is hydrogen.

37. The compound in accordance with claim 1, wherein:
R¹ is —N(CH₃)₂;
R² is methoxy;
R³ is methoxy;
R⁴ is methyl; and
X is =N—OR⁵, wherein R⁵ is hydrogen.

38. The compound in accordance with claim 1, wherein:
R¹ is —NHCH₃;
R² is methoxy;
R³ is acetoxy;
R⁴ is methyl; and
X is =O.

39. The compound in accordance with claim 1, wherein:
R¹ is —NHCH₃;
R² is acetoxy;
R³ is acetoxy;
R⁴ is methyl; and
X is =O.

40. The compound in accordance with claim 1, wherein:
R¹ is —N(CH₃)₂;
R² is methoxy;
R³ is acetoxy;
R⁴ is methyl; and
X is =O.

41. The compound in accordance with claim 1, wherein:
R¹ is —N(CH₃)₂;
R² is acetoxy;
R³ is acetoxy;
R⁴ is methyl; and
X is =O.

42. The compound in accordance with claim 1, wherein:
R¹ is —N(C)H₃)₂;
R² is ethoxy;
R³ is acetoxy;
R⁴ is methyl; and
X is =O.

43. The compound in accordance with claim 1, wherein:
R¹ is —N(CH₃)₂;
R² is —OC(O)CH₂CH₂C₅H₉;
R³ is acetoxy;
R⁴ is methyl; and
X is =O.

44. The compound in accordance with claim 1, wherein:
R¹ is —N(CH₃)₂;
R² is hydroxy;
R³ is acetoxy;
R⁴ is methyl; and
X is =O.

45. A pharmaceutical composition comprising an effective amount of a compound in accordance with claim 1 and a pharmaceutically acceptable excipient.

46. A method of producing an antiprogestational effect in a patient, said method comprising administering to said patient an effective amount of a compound in accordance with claim 1.

47. A method of inducing menses in a patient, said method comprising administering to said patient an effective amount of a compound in accordance with claim 1.

48. A method of treating endometriosis, said method comprising administering to said patient an effective amount of a compound in accordance with claim 1.

49. A method of treating dysmenorrhea, said method comprising administering to said patient an effective amount of a compound in accordance with claim 1.

50. A method of treating endocrine hormone-dependent tumors, said method comprising administering to said patient an effective amount of a compound in accordance with claim 1.

51. A method of treating meningiomas, said method comprising administering to said patient an effective amount of a compound in accordance with claim 1.

52. A method of treating uterine fibroids in a patient, said method comprising administering to said patient an effective amount of a compound in accordance with claim 1.

53. A method of inhibiting uterine endometrial proliferation in a patient, said method comprising administering to said patient an effective amount of a compound in accordance with claim 1.

54. A method of inducing labor, said method comprising administering to a patient an effective amount of a compound in accordance with claim 1.

55. A method of contraception, said method comprising administering to a patient an effective amount of a compound in accordance with claim 1.

56. A method of postcoital contraception, said method comprising administering to a patient an effective amount of a compound in accordance with claim 1.

* * * * *

UNITED STATES PATENT AND TRADEMARK OFFICE
CERTIFICATE OF CORRECTION

PATENT NO. : 6,900,193 B1
DATED : May 31, 2005
INVENTOR(S) : Hyun K. Kim et al.

It is certified that error appears in the above-identified patent and that said Letters Patent is hereby corrected as shown below:

Title page,
Item [57], ABSTRACT, correct the formula to read:

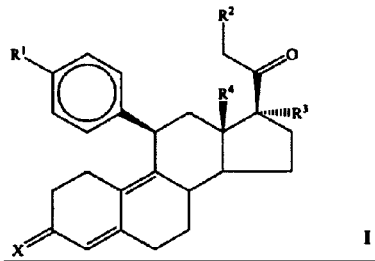

Drawings,
Fig. 1A, between formulas 1 and 2, replace "Me$_3$SiC" with -- Me$_3$SiCl --.
Fig. 1A, between formulas 2 and 3, replace "CF$_3$)$_2$CO" with -- (CF$_3$)$_2$CO --.

Column 2,
Line 22, correct the formula to read:

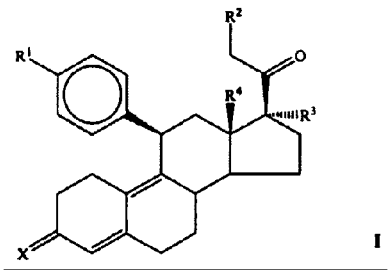

Column 3,
Line 38, correct the formula to read:

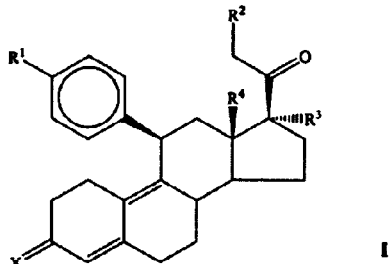

UNITED STATES PATENT AND TRADEMARK OFFICE
CERTIFICATE OF CORRECTION

PATENT NO. : 6,900,193 B1
DATED : May 31, 2005
INVENTOR(S) : Hyun K. Kim et al.

It is certified that error appears in the above-identified patent and that said Letters Patent is hereby corrected as shown below:

Column 101,
Line 25, correct the formula to read:

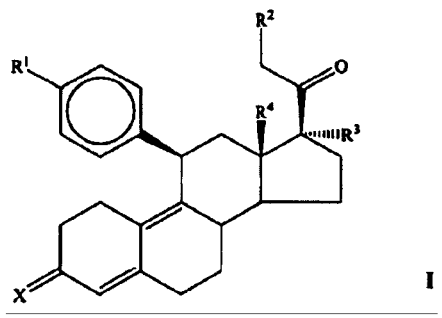

Signed and Sealed this

Sixth Day of June, 2006

JON W. DUDAS
*Director of the United States Patent and Trademark Office*